US010704100B2

(12) United States Patent
Devaux et al.

(10) Patent No.: US 10,704,100 B2
(45) Date of Patent: Jul. 7, 2020

(54) BIOMARKERS FOR HEART FAILURE

(71) Applicant: Luxembourg Institute of Health (LIH), Luxembourg (LU)

(72) Inventors: Yvan Devaux, Zoufftgen (FR); Mélanie Vausort, Hobscheid (LU); Lu Zhang, Metz (FR)

(73) Assignee: Luxembourg Institute of Health (LIH), Luxembourg (LU)

( * ) Notice: Subject to any disclaimer, the term of this patent is extended or adjusted under 35 U.S.C. 154(b) by 60 days.

(21) Appl. No.: 15/757,223

(22) PCT Filed: Sep. 15, 2016

(86) PCT No.: PCT/EP2016/071763
§ 371 (c)(1),
(2) Date: Mar. 2, 2018

(87) PCT Pub. No.: WO2017/046203
PCT Pub. Date: Mar. 23, 2017

(65) Prior Publication Data

US 2018/0265923 A1 Sep. 20, 2018

(30) Foreign Application Priority Data

Sep. 15, 2015 (LU) ........................................ 92830

(51) Int. Cl.
*A61K 48/00* (2006.01)
*C07H 21/04* (2006.01)
*C12Q 1/6883* (2018.01)

(52) U.S. Cl.
CPC ...... *C12Q 1/6883* (2013.01); *C12Q 2600/118* (2013.01); *C12Q 2600/178* (2013.01)

(58) Field of Classification Search
CPC ............ C12N 15/111; C12N 2310/531; A61K 31/713
See application file for complete search history.

(56) References Cited

U.S. PATENT DOCUMENTS

2014/0370502 A1* 12/2014 Brennan ............ G01N 33/6887 435/6.11

FOREIGN PATENT DOCUMENTS

| | | | |
|---|---|---|---|
| WO | WO 2012/050975 A2 | 4/2012 | |
| WO | WO 2014/083081 A1 | 6/2014 | |
| WO | WO 2016/124655 A1 * | 8/2016 | ........... C12N 15/111 |

OTHER PUBLICATIONS

Anonymous, "Agilent-069978 Arraystar Human CircRNA microarray V1," GEO (Apr. 2, 2015), retrieved from the Internet at https://www.ncbi.nlm.nih.gov/geo/query/acc.cgi?acc=GPL19978 on Nov. 23, 2016.
Devaux et al., "Long noncoding RNAs in cardiac development and ageing," *Nature Reviews Cardiology*., 12(7), 415-425 (Apr. 7, 2015).
Rybak-Wolf et al., "Circular RNAs in the Mammalian Brain Are Highly Abundant, Conserved, and Dynamically Expressed—Table S7: List of Primers and siRNAs Used in This Study," *Molecular Cell*, 58(5), Jun. 4, 2015.
Rybak-Wolf et al., "Circular RNAs in the Mammalian Brain Are Highly Abundant, Conserved, and Dynamically Expressed," *Molecular Cell*, 58(5), Jun. 4, 2015, pp. 870-885.
Vausort et al., "Myocardial Infarction-Associated Circular RNA Predicting Left Ventricular Dysfunction," *Journal of the American College of Cardiology*, 68(11), 1247-1248 (Sep. 5, 2016).
European Patent Office, International Search Report in International Patent Application No. PCT/EP2016/071763, 5 pp. (dated Dec. 13, 2016).
European Patent Office, Written Opinion in International Patent Application No. PCT/EP2016/071763, 9 pp. (dated Dec. 13, 2016).
Anonymous, "has_circ_0000585," circBase, retrieved from the Internet on Mar. 29, 2019 at http://circbase.org/cgi•bin/simplesearch.cgi (1 page).
Memczak et al., "Circular RNAs are a large class of animal RNAs with regulatory potency," *Nature*, 495(7441): 333-338 (Mar. 21, 2013), published online Feb. 27, 2013.

* cited by examiner

*Primary Examiner* — Amy H Bowman
(74) *Attorney, Agent, or Firm* — Leydig, Voit & Mayer, Ltd.

(57) ABSTRACT

The application discloses circRNAs as new biomarkers for the development of heart failure after myocardial infarction; methods for the prediction and diagnosis of heart failure are provided based on measuring said one or more circRNAs; and kits and devices for measuring said circRNAs and/or performing said methods. Further provided are methods for treating patients at risk of heart failure based on the evaluation of said one or more circRNAs.

14 Claims, 7 Drawing Sheets

Specification includes a Sequence Listing.

Figure 5 A-C

BIOMARKERS FOR HEART FAILURE

CROSS-REFERENCE TO RELATED APPLICATIONS

This patent application is a U.S. National Phase application of International Patent Application No. PCT/EP2016/071763, filed Sep. 15, 2016, which claims the benefit of Luxembourg Patent Application No. LU92830, filed Sep. 15, 2015, each application incorporated herein by reference in its entirety.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 121,149 Byte ASCII (Text) file named "738022_ST25.txt," created on Mar. 2, 2018.

FIELD OF THE INVENTION

The invention relates to biomarkers useful for the diagnosis and prediction of diseases and conditions in subjects, in particular heart failure, in particular in patients with myocardial infarction; and to related methods, kits and devices.

BACKGROUND OF THE INVENTION

Identification of patients at risk of developing left ventricular (LV) remodeling and dysfunction after acute myocardial infarction (MI) would represent a major step forward towards personalized healthcare. Indeed, these patients could benefit from improved treatment and follow-up, such as the treatment with anti-remodeling drugs which have shown some ability to reduce LV remodeling and dysfunction after experimental MI (von Lueder T G, et al. *Circulation: Heart Failure.* 2015; 8:71-78). However, predicting outcome after MI is a challenging task. Circulating biomarkers such as the markers of cardiac injury creatine phosphokinase (CPK) and cardiac troponins (cTn), or the stress markers brain natriuretic peptides (BNP) have proven to be useful in some circumstances but have serious limitations due to lack of specificity (Jaffe A S, et al. *J Am Coll Cardiol.* 2011; 58:1819-1824) and stability in the few hours following MI (Talwar S, et al. *Eur Heart J.* 2000; 21:1514-1521). Therefore, novel biomarkers are required.

The bloodstream is the reservoir of biomarkers. Biomarkers have been traditionally discovered in the cell-free compartment of the blood. In recent years, analysis of transcriptomic profiles of peripheral blood cells allowed the identification of candidate prognostic biomarkers of MI among the RNA family. Initial studies focused on protein-coding RNAs. More recent investigations revealed that non-protein coding RNAs, also known as non-coding RNAs, may also be useful in this prospect. Non-coding RNAs occupy a significant part of our genome. Indeed, while more than 80% of the human genome is transcribed, less than 2% is subsequently translated into proteins. MicroRNAs (miRNAs) have been the first class of non-coding RNAs reported for their biomarker value and for their ability to predict LV dysfunction after MI. Later on, non-coding RNAs longer than 200 nucleotides and named long non-coding RNAs (IncRNAs), either measured in peripheral blood cells or in plasma, have also shown some predictive value after MI (reviewed in Devaux Y et al. *Nat Rev Cardiol.* 2015; 12:415-425).

Circular RNAs (circRNAs) constitute another arm of the family of non-coding RNAs. Their origin is diverse. They can be produced by the formation of a covalent link between 5' and 3' extremities of exons (exonic circRNAs) or introns (intronic circRNAs). Furthermore, they can be formed by a back-splicing reaction linking exons of protein-coding genes. Exon-intron circRNAs are generated when introns are retained during the circularization of exons. Unlike most IncRNAs, circRNAs are abundant, conserved and stable. In the mammalian brain, circRNAs are dynamically regulated. The function of circRNAs is still poorly characterized and the role of circRNAs in the heart is unknown. One study has reported an association between a circRNA (a circular form of the IncRNA ANRIL—antisense non-coding RNA in the INK4 locus) and the risk of atherosclerosis (Burd C E, et al. PLoS Genet. 2010; 6:e1001233).

SUMMARY OF THE INVENTION

The inventors have found for the first time that the expression of non-coding circular RNAs in a patient is associated with the development of cardiac disease.

Accordingly, the inventors have identified myocardial infarction-associated circular RNAs (circRNAs) as new biomarkers advantageous for diagnosing and predicting the outcome of myocardial infarction (MI), more particularly the likeliness of developing heart failure (HF), more particularly HF due to left ventricular (LV) dysfunction (LVD) after MI.

Accordingly, the application relates to the use of one or more circRNAs for predicting and/or diagnosing the outcome of myocardial infarction in a patient and methods based on said use. More particularly, the invention envisages the use of one or more circRNAs selected from Table 1 as represented by SEQ ID NOs 1 to 12. Most particularly, the one or more circRNAs include ZNF609_hsa_circ_0000615 (MICRA).

In particular embodiments, the use or methods according to the invention comprise determining the expression level of said one or more of said circRNAs in a sample of said patient after myocardial infarction and optionally comparing the expression level of one or more circRNAs to the expression level of said one or more circRNAs in a control sample. For instance, the expression level can be determined by RT-PCR assay, a sequencing-based assay, a quantitative nuclease-protection assay (qNPA), or a microarray assay.

In particular embodiments, the use or methods according to the invention further comprise assessing one or more clinical factors in the patient and combining this assessment of said one or more clinical factors and the expression of the one or more circRNAs in said prediction or diagnosis. In particular embodiments, where the one or more circRNAs are used for predicting heart failure, the clinical factor is selected from the group consisting of: age, body-mass index, gender, white blood cell count, ischemic time, antecedent of MI, diabetes, hypertension, hypercholesterolemia, and smoking. In those embodiments, where the one or more circRNAs are used in the diagnosis of heart failure, clinical factors can be selected from breathlessness, exertional dyspnea, orthopnea, paroxysmal nocturnal dyspnea, dyspnea at rest, acute pulmonary edema, chest pain/pressure and palpitations or non-cardiac symptoms such as anorexia, nausea, weight loss, bloating, fatigue, weakness, oliguria, nocturia, and cerebral symptoms of varying severity, ranging from anxiety to memory impairment and confusion.

In particular embodiments, the use or methods according to the invention further comprise assessing one or more other biomarkers in the patient and combining the assessment of said one or more other biomarkers and the expression of the one or more circRNAs in the prediction or diagnosis. The detection of circRNAs can be combined with any biomarker which is associated with heart failure. In particular embodiments, the one or more other biomarkers is selected from the group consisting of CPK, cTnT, Nt-pro-BNP, MMP9. Most particularly, the use or methods as envisaged herein comprise detecting MICRA and Nt-pro-BNP and predicting the likeliness of said patient to develop heart failure based thereon.

In particular embodiments, the use or methods according to the invention comprise determining expression of at least two, more particularly three or more, four or more, five or more, six or more, seven or more such as ten or more circRNAs and basing the diagnosis or prediction of heart failure thereon. In particular embodiments, the use or methods according to the invention comprise determining expression of at least two, three, four, five, six, seven, eight, nine, ten, eleven or all twelve of said circRNAs in Table 1.

In particular embodiments of the use or methods according to the invention the sample is a whole blood sample.

The invention further provides a system for predicting the outcome of myocardial infarction in a patient, the system comprising: a storage memory for storing data associated with a sample obtained from the patient, wherein the data comprises quantitative expression data for one or more circRNAs and a processor communicatively coupled to the storage memory for analyzing the dataset to analyse the expression level of said one or more circRNAs. In particular embodiments, the one or more circRNAs are selected from Table 1.

The invention further provides a computer-readable storage medium storing computer-executable program code, which, when run on a computer allows storing of the data and the analysis of the data in the system described above.

The invention further provides kits for the diagnosis of heart failure or for predicting the outcome of myocardial infarction in a patient, comprising reagents for determining quantitative expression of one or more circRNAs in a sample of a patient and, optionally, instructions for using said reagents for determining said quantitative expression. Preferably said reagents are one or more pairs of primers or one or more probes. Preferably said kit comprises one or more pairs of primers or one or more probes capable of specifically amplifying and/or detecting a region in the circRNA comprising the junction point. In particular embodiments said kit comprises a pair of primers comprising the sequences as given in Table 2 (SEQ ID NO: 13 and SEQ ID NO: 14) for the amplification of MICRA. In further particular embodiments said kit comprises a probe comprising the sequence of SEQ ID NO: 17 for the detection of a region in MICRA, said region spanning the junction point, preferably said region comprises SEQ ID NO: 18.

The invention further provides methods for treating a patient at risk for heart failure, said method comprising determining the risk of heart failure in said patient using one or more circRNAs as described herein and selecting the treatment regimen for said patient based thereon.

The invention further provides methods for assessing the condition in a patient having suffered from myocardial infarction, said method comprising monitoring the expression level of one or more of circRNAs in a sample of said patient after said myocardial infarction and comparing said expression level to the expression level of said one or more circRNAs in a reference sample or in a sample of a control patient, wherein a sudden deviation of said level is indicative for the worsening of the condition of the patient. In particular embodiments, such method is a method for predicting the risk of left ventricular dysfunction leading to further heart failure in said patient. In particular embodiments, the sample used in these methods is taken from a patient who has suffered from a myocardial infarction within less than 5 days, for instance less than 3 days, particularly less than 48 hours or less than 24 hours before taking of the sample. In those embodiments where a expression levels are compared, wherein the deviation of said level corresponds to a decrease of the level of circRNA by at least about 20% (about 0.8-fold or less), or by at least about 40% (about 0.6-fold or less), or at least about 60% (about 0.4-fold or less), or at least about 80% (about 0.2-fold or less).

These and further aspects and preferred embodiments are described in the following sections and in the appended claims.

Figure 4:
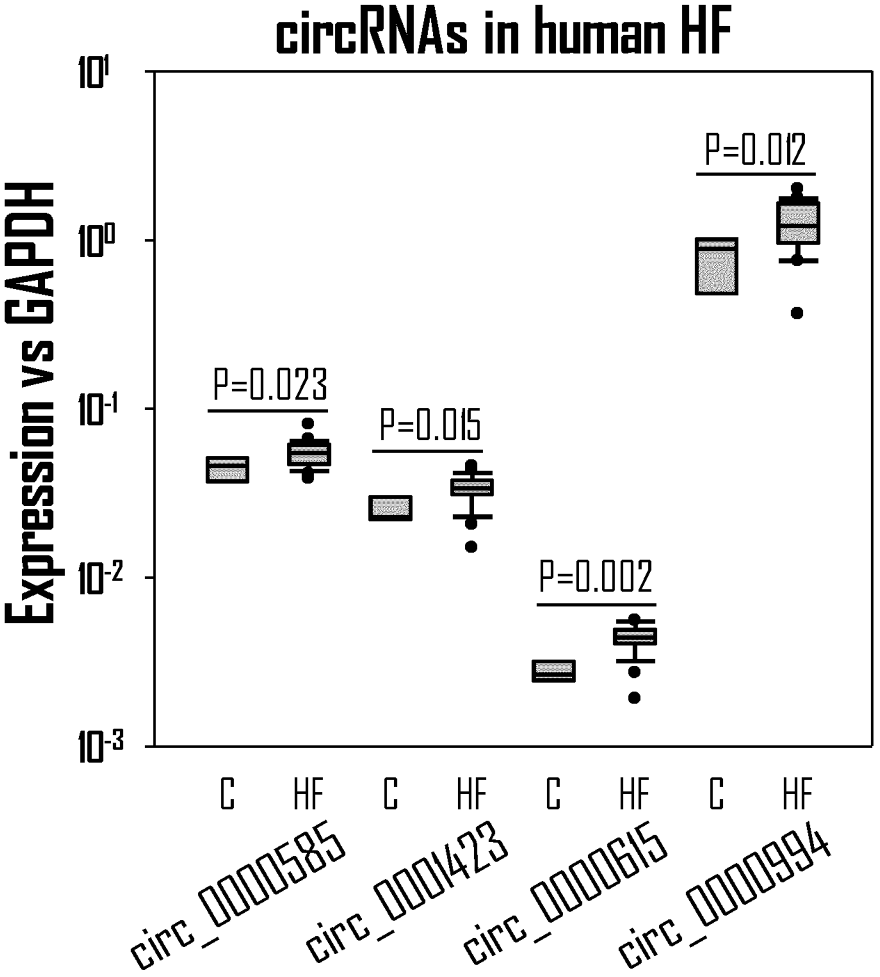

FIG. 4 provides exemplary expression levels of 4 circRNAs in human cardiac biopsies. Expression levels were measured by quantitative PCR in biopsies from the left ventricle of 5 control (C) donors and 22 patients with heart failure (HF) from either ischemic (n=11) or dilated (n=11) aetiology.

Figure 5:
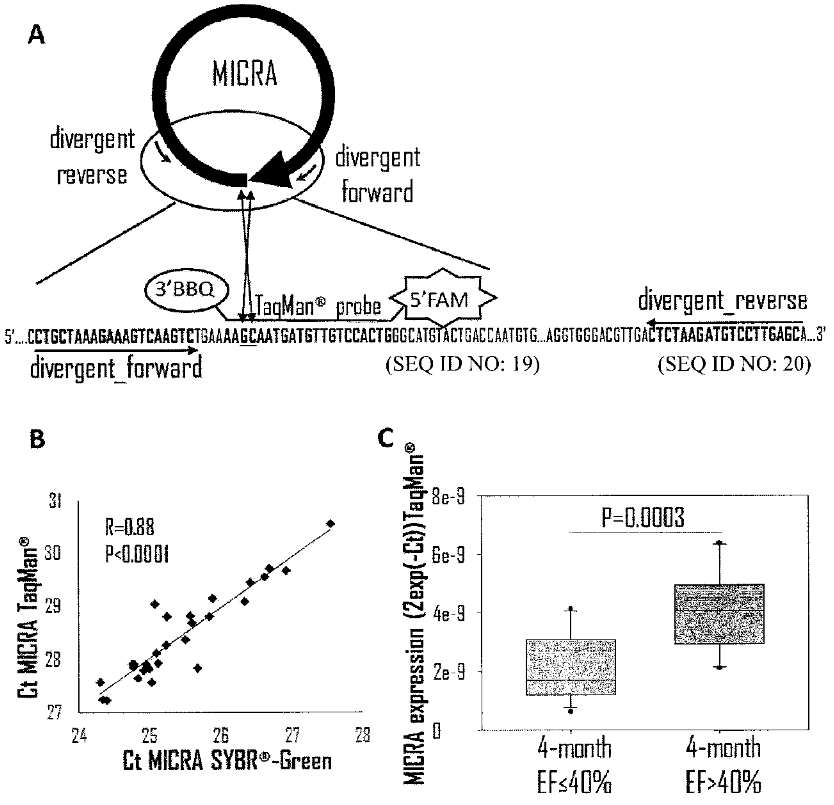

FIG. 5 provides the details of the amplification of MICRA by PCR. (A) The scheme shows the circular structure of MICRA with its junction point underlined in the sequence. The scheme represents the location of primers and probe used for amplification of MICRA by SYBER® Green PCR and TaqMan® PCR. The primers generate a PCR product of 162 bp and the TaqMan® probe spans the junction point. The localization of divergent primers used for quantitative SYBR® Green-based PCR is indicated as arrows both on the linear and circular representations of MICRA. The same primers are used in the TaqMan® PCR. Amplification products of MICRA by SYBR® Green PCR were sequenced using the forward and reverse divergent primers used for PCR. A part of the obtained sequence covering the junction point and thus attesting for the circularity of MICRA is shown. B) Correlation between MICRA expression values measured in 28 MI patients of the test cohort by SYBR® Green-based PCR and TaqMan® PCR. Spearman correlation coefficient with p value is indicated. C) Levels of MICRA as determined by TaqMan® PCR in a subgroup of patients from the test cohort with low EF (≤40%, n=12) and high EF (>40%, n=16). 2exp(−Ct) values are indicated. P value from t-test is shown. Diagrams were created with SnapGene software.

Figure 6:
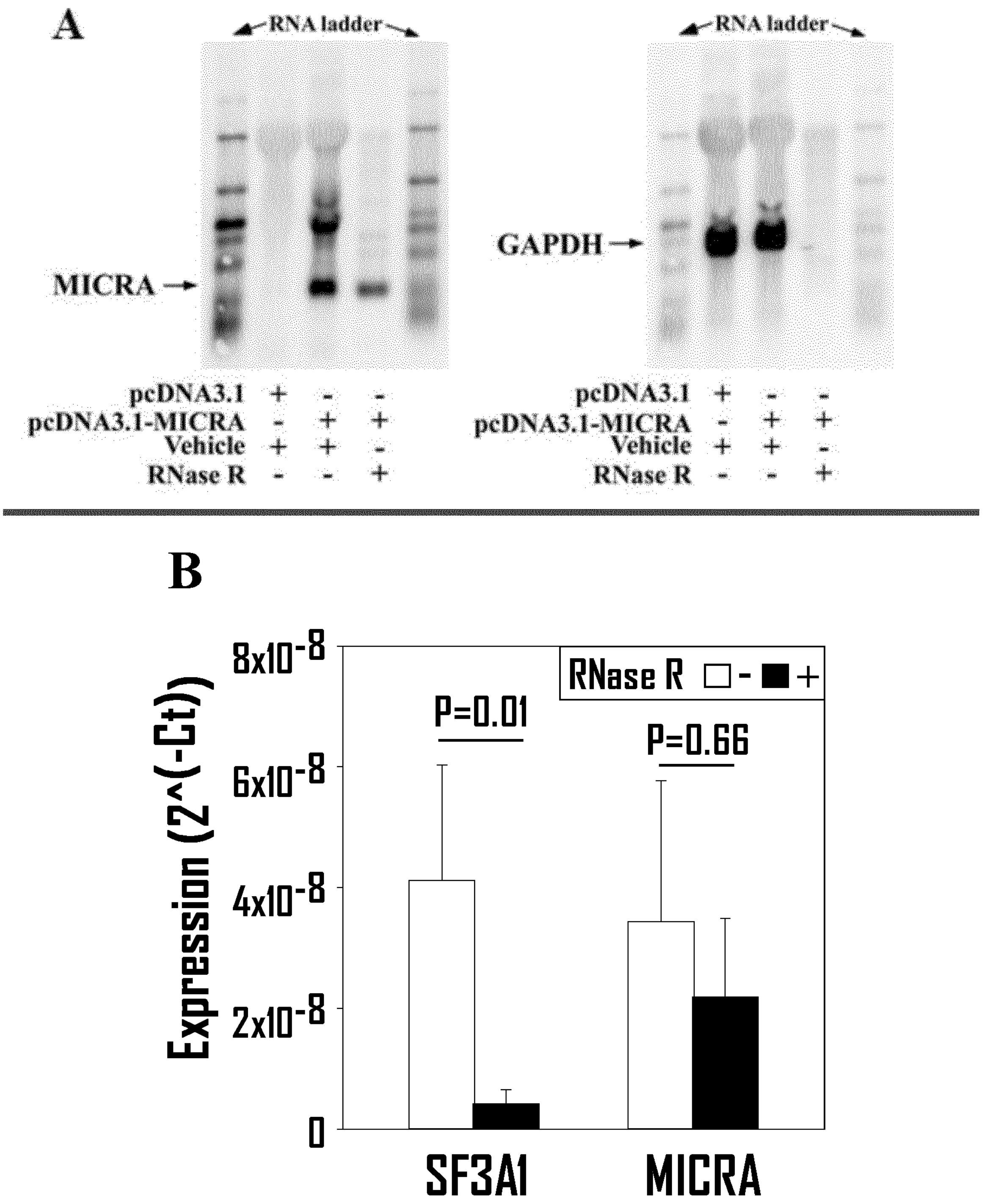

FIG. 6 provides verification that MICRA is a circular RNA in human samples. (A). Total RNA was isolated from a blood sample of a MI patient collected in PAXgene™ RNA tube. Amplification of insert fragments was performed with Q5® High-Fidelity DNA Polymerase kit. The PCR fragment was inserted as a HindIII-XbaI fragment into a pcDNA3.1 mammalian expression vector. A ~100-bp 5' flanking region was amplified and inserted in reverse orientation as an XbaI-PmeI fragment downstream MICRA, creating pcDNA3.1-MICRA. Purified pcDNA3.1-MICRA plasmid or empty vector were transfected in HEK 293 cells for 48 h. Total RNA was extracted and digested with RNAse R or vehicle. Digested RNA was purified and 20 microg was loaded per lane of a 1% agarose gel. After transfer and cross-linking to a nylon membrane, MICRA (left panel) and GAPDH (right panel) RNAs were revealed using DIG-labeled probes. In the left panel, the band for MICRA in the lane with RNA from cells transfected with pcDNA3.1-MICRA attests for the over-expression of MICRA. The band for MICRA in the sample transfected with pcDNA3.1-MICRA and treated with RNase R attests for the resistance of MICRA to RNAse R digestion. In the right panel, the absence of band for GAPDH after RNAse R treatment attests for the complete digestion of linear RNAs by RNAse R. The MICRA probe recognizes the 874 bp-long circular form of MICRA . . . (B) Total RNA was isolated from blood samples of healthy donors collected in PAXgene™ RNA tubes and was used as template for RNase R treatment. RNA was treated with 3 units of RNase R. Untreated RNA (mock) served as negative control. RNA samples were then reverse transcribed and amplified by quantitative PCR. The linear SF3A1 mRNA was used as positive control for RNase R degradation. A decrease in expression attests for a degradation of linear RNA (SF3A1) while a stable expression between mock and RNase R-treated samples (MICRA) attests for absence of linear RNA. CircRNAs are resistant to RNase R. Average expression values (±SD) of 3 independent experiments are shown.

Figure 7:
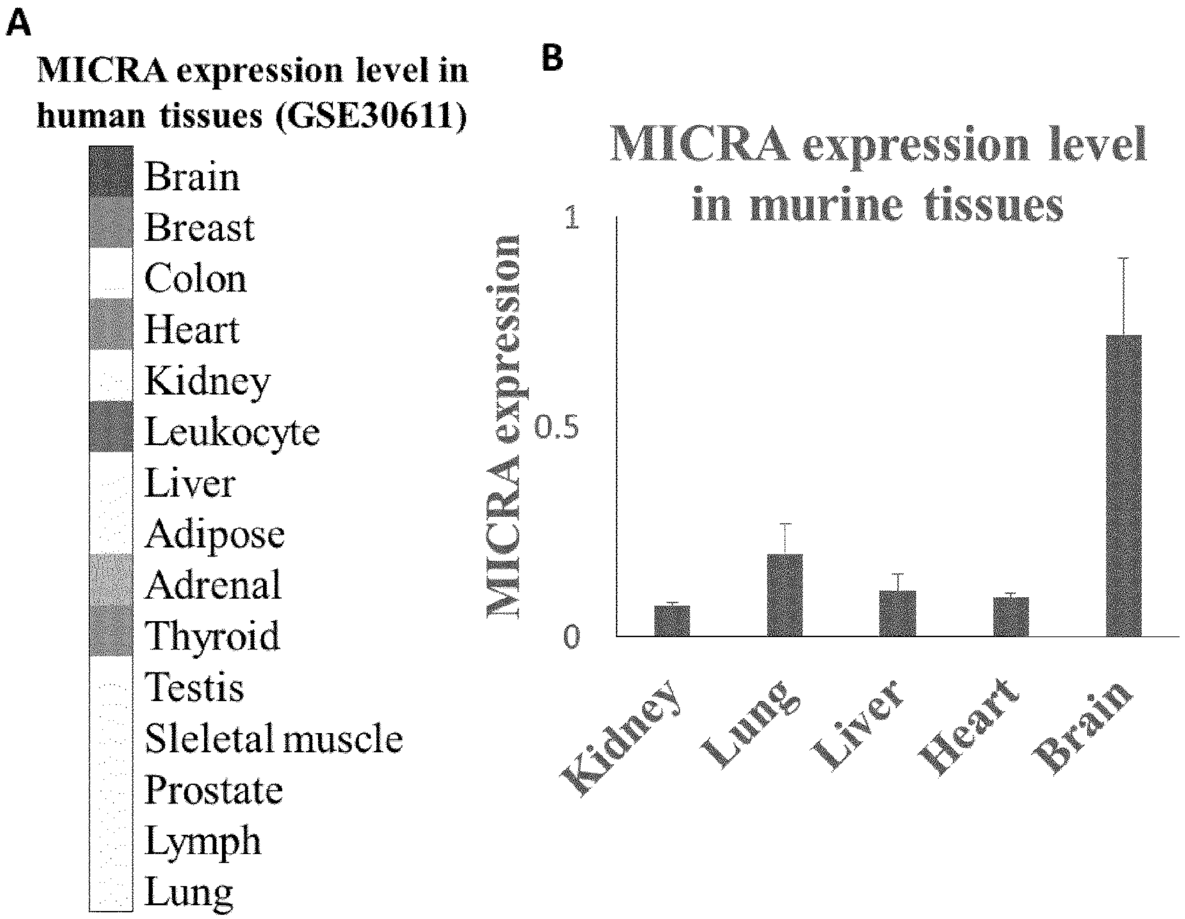

FIG. 7 illustrates the expression levels of MICRA in different human and murine tissues. (A) MICRA expression levels were retrieved from the human RNA-seq dataset deposited at Gene Expression Omnibus under the accession number GSE30611. The heat-map shows that MICRA was mostly expressed in the brain and in leukocytes. (B) MICRA expression levels determined by quantitative PCR in murine tissues show a high level of expression in the brain. MICRA expression was normalized to SF3a1 and data are means±SD of 2 mice.

DETAILED DESCRIPTION

As used herein, the singular forms “a”, “an”, and “the” include both singular and plural referents unless the context clearly dictates otherwise.

The terms “comprising”, “comprises” and “comprised of” as used herein are synonymous with “including”, “includes” or “containing”, “contains”, and are inclusive or open-ended and do not exclude additional, non-recited members, elements or method steps.

The recitation of numerical ranges by endpoints includes all numbers and fractions subsumed within the respective ranges, as well as the recited endpoints.

The term “about” as used herein when referring to a measurable value such as a parameter, an amount, a temporal duration, and the like, is meant to encompass variations of and from the specified value, in particular variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier “about” refers is itself also specifically, and preferably, disclosed.

All documents cited in the present specification are hereby incorporated by reference in their entirety.

Unless otherwise specified, all terms used in disclosing the invention, including technical and scientific terms, have the meaning as commonly understood by one of ordinary skill in the art to which this invention belongs. By means of further guidance, term definitions may be included to better appreciate the teaching of the present invention.

The term “biomarker” is widespread in the art and may broadly denote a biological molecule and/or a detectable portion thereof whose qualitative and/or quantitative evaluation in a subject is predictive or informative (e.g., predictive, diagnostic and/or prognostic) with respect to one or more aspects of the subject’s phenotype and/or genotype, such as, for example, with respect to the status of the subject as to a given disease or condition.

Reference herein to “disease(s) and/or condition(s) as taught herein” or a similar reference encompasses any such diseases and conditions as disclosed herein insofar consistent with the context of such a recitation, in particular left ventricular dysfunction associated with myocardial infarction.

The term “heart failure” a.k.a. “cardiac failure” or “cardiac dysfunction” as used herein refers to a condition in which the heart is no longer able to pump enough blood to the body’s organs and other tissues. As a result thereof, the organs and other tissues do not receive enough oxygen and nutrients to function properly. Cardiac dysfunction is defined as an alteration in the relationship between preload (often defined by left ventricular filling pressure) and stroke volume. This relationship is depicted by Frank-Starling curves, which identify a shift downward and to the right as cardiac dysfunction. One of the possible causes of heart failure is left ventricular dysfunction. The term "left ventricular (LV) dysfunction" or LVD relates to a condition whereby the ability of the left ventricle of the heart to contract is affected leading to heart failure, i.e. the heart is unable to pump sufficiently to maintain blood flow to meet the body's needs. One of the potential causes of left ventricular dysfunction is left ventricular remodeling, i.e. changes in ventricular thickness and size which occur as a result of myocardial stress. Left ventricular remodeling occurs at the subcellular, cellular, tissue and chamber level of the heart. Generally it results in a dilatation and thinning of the ventricular wall as a result of ventricular expansion, and a distortion of the shape of the heart may also occur.

The term "myocardial infarction" ("MI") as used herein refers to a condition whereby blood flow to a part of the heart stops causing damage to the heart muscle. MI may be associated with ST elevation (i.e. the trace in the ST segment in the electrocardiogram is abnormally high above the baseline) or can occur without ST segment elevation. The effects of myocardial infarction are diverse. Where the MI is limited, only minor symptoms such as chest pain may occur. Where the MI is significant the damage to the heart muscle affects the function of that part of the heart which, apart from its immediate effect on organ function, may also lead to remodeling of the heart in a way that is further detrimental to its function (e.g. left ventricular remodeling as described above).

The terms "predicting" or "prediction", "diagnosing" or "prognosis" are commonplace and well-understood in medical and clinical practice. It shall be understood that the terms "predicting and/or prognosticating" may be interchanged with "prediction and/or prognosis" of said disease or condition or "making (or determining or establishing) a prediction and/or prognosis" of said disease or condition, or the like.

By means of further explanation and without limitation, "predicting" or "prediction" generally refer to an advance declaration, indication or foretelling of a disease or condition in a subject not (yet) having said disease or condition. For example, a prediction of a disease or condition in a subject may indicate a probability, chance or risk that the subject will develop said disease or condition, for example within a certain time period or by a certain age. Said probability, chance or risk may be indicated inter alia as an absolute value, range or statistics, or may be indicated relative to a suitable control subject or subject population (such as, e.g., relative to a general, normal or healthy subject or subject population). Hence, the probability, chance or risk that a subject will develop a disease or condition may be advantageously indicated as increased or decreased, or as fold-increased or fold-decreased relative to a suitable control subject or subject population. As used herein, the term "prediction" of the condition as taught herein in a subject may also particularly mean that the subject has a 'positive' prediction of such, i.e., that the subject is at risk of having such (e.g., the risk is significantly increased vis-à-vis a control subject or subject population). The term "prediction of no" condition as taught herein as described herein in a subject may particularly mean that the subject has a 'negative' prediction of such, i.e., that the subject's risk of having such a condition is not significantly increased vis-à-vis a control subject or subject population.

The terms "diagnosing" or "diagnosis" generally refer to the process or act of recognising, deciding on or concluding on a disease or condition in a subject on the basis of symptoms and signs and/or from results of various diagnostic procedures (such as, for example, from knowing the presence, absence and/or quantity of one or more biomarkers characteristic of the diagnosed disease or condition). As used herein, "diagnosis of" the diseases or conditions as taught herein in a subject may particularly mean that the subject has such, hence, is diagnosed as having such. "Diagnosis of no" diseases or conditions as taught herein in a subject may particularly mean that the subject does not have such, hence, is diagnosed as not having such. A subject may be diagnosed as not having such despite displaying one or more conventional symptoms or signs reminiscent of such.

A good prognosis of the condition as taught herein may generally encompass anticipation of a satisfactory partial or complete recovery from the conditions back to before the condition was obtained, preferably within an acceptable time period. A good prognosis of such may more commonly encompass anticipation of not further worsening or aggravating the general health of the patient, preferably within a given time period.

A poor prognosis of the diseases or conditions as taught herein may generally encompass anticipation of a substandard recovery and/or unsatisfactorily slow recovery, or to substantially no recovery or even further worsening of such and more particularly resulting in death of the diseased subject.

As used herein, the terms "prevent" and "preventing" include the prevention of the recurrence, spread or onset. It is not intended that the present disclosure be limited to complete prevention. In some embodiments, the onset is delayed, or the severity is reduced.

As used herein, the terms "treat" and "treating" are not limited to the case where the subject (e.g., patient) is cured and the condition or disease is eradicated. Rather, embodiments, of the present disclosure also contemplate treatment that merely reduces symptoms, and/or delays conditions or disease progression.

The term "subject" or "patient" as used herein typically denotes humans, but may also encompass reference to non-human animals.

The terms "sample" or "biological sample" as used herein include any biological specimen obtained from a subject. Samples may include, without limitation, whole blood, plasma, serum, whole blood cells, red blood cells, white blood cells (e.g., peripheral blood mononuclear cells), saliva, urine, stool (i.e., faeces), tears, sweat, sebum, nipple aspirate, ductal lavage, tumour exudates, synovial fluid, cerebrospinal fluid, lymph, fine needle aspirate, amniotic fluid, any other bodily fluid, cell lysates, cellular secretion products, inflammation fluid, semen and vaginal secretions. The term "plasma" defines the colourless watery fluid of the blood that contains in itself no cells, but in which the blood cells (erythrocytes, leukocytes, thrombocytes, etc.) are suspended, containing nutrients, sugars, proteins, minerals, enzymes, etc.

The terms "binding," "binds," "recognition," or "recognize" as used herein are meant to include interactions between molecules that may be detected using, for example, a hybridization assay. When hybridization occurs between two single-stranded polynucleotides, these polynucleotides are described as "complementary". Complementarity or homology (the degree that one polynucleotide is complementary with another) can be quantified in terms of the proportion of bases in opposing strands that are expected to form hydrogen bonding with each other, according to generally accepted base-pairing rules.

The term "probe" refers to a molecule capable of hybridizing to a single-stranded nucleic acid target. The probes may target, e.g., comprise a sequence that is the reverse complement of, more than 7, 8, 9, 10, 11, 12, 13, 14, 15, 20, or more (optionally continuous) nucleotides of a given target. The probe may be single stranded nucleic acid sequence and may contain mismatches, additions, or deletions provided the probe retains the ability to bind to the target. In particular embodiments the probe is less than 100, more particularly less than 50 or less than 30 nucleotides.

The terms "quantity", "amount" and "level" are synonymous and generally well-understood in the art. The terms as used herein may particularly refer to an absolute quantification of a molecule or an analyte in a sample, or to a relative quantification of a molecule or analyte in a sample, i.e., relative to another value such as relative to a reference value as taught herein, or to a range of values indicating a base-line expression of the biomarker. These values or ranges can be obtained from a single patient or from a group of patients.

An absolute quantity of a molecule or analyte in a sample is commonly presented as a concentration, e.g., weight per volume or mol per volume.

A relative quantity of a molecule or analyte in a sample may be advantageously expressed as an increase or decrease or as a fold-increase or fold-decrease relative to said another value, such as relative to a reference value as taught herein. Performing a relative comparison between first and second parameters (e.g., first and second quantities) may but need not require first to determine the absolute values of said first and second parameters. For example, a measurement method can produce quantifiable readouts (such as, e.g., signal intensities) for said first and second parameters, wherein said readouts are a function of the value of said parameters, and wherein said readouts can be directly compared to produce a relative value for the first parameter vs. the second parameter, without the actual need first to convert the readouts to absolute values of the respective parameters.

Abbreviations and Acronyms Used Herein

AUC: area under the receiver-operating characteristic curve; BMI: body mass index; BNP: brain natriuretic peptide; CI: confidence interval; CPK: creatine phosphokinase; cTn: cardiac troponin; DCM: dilated cardiomyopathy; EF: ejection fraction; hsCRP: high-sensitivity C-reactive protein; HT: hypertension; ICM: ischemic cardiomyopathy; LV: left ventricular; MI: myocardial infarction; MICRA: myocardial infarction-associated circular RNA; miRNAs: microRNAs; MMP9: matrix metalloproteinase 9; NSTEMI: non-ST-segment-elevation myocardial infarction; NYHA: New York Heart Association; OR: odds ratios; PBMCs: peripheral blood mononuclear cells; PCI: percutaneous coronary intervention; ROC: receiver operating characteristic; STEMI: ST-segment-elevation myocardial infarction; TIMP1: tissue inhibitor of metalloproteinase-1; WBC: white blood cells.

The inventors have identified that the expression of circRNAs can be used to diagnose heart failure or to predict whether or not a patient will develop heart failure. More particularly, circular RNAs can be used as new biomarkers advantageous for predicting the outcome of myocardial infarction, more particularly the likeliness of developing left ventricular dysfunction leading to heart failure.

Accordingly, the application relates to the use of one or more circular RNAs (circRNAs) for predicting the outcome of myocardial infarction in a patient and methods based on said use. Based on the observation that the expression of circRNAs are appropriate for this use as described herein, further circRNAs can be identified which are suitable for the methods described herein.

In particular embodiments, the invention envisages methods which are based on determining the expression of one or more circRNAs selected from Table 1 below.

TABLE 1

| circRNAs | |
|---|---|
| Designation | Sequence |
| ZNF609_hsa_circ_0000615 (MICRA) | SEQ ID NO: 1 |
| CDK11A_hsa_circ_0000005 | SEQ ID NO: 2 |
| RSL1D1_hsa_circ_0000673 | SEQ ID NO: 3 |
| SNORD116-19_hsa_circ_0000585 | SEQ ID NO: 4 |
| FOXK2_hsa_circ_0000816 | SEQ ID NO: 5 |
| FOXK2_hsa_circ_0000817 | SEQ ID NO: 6 |
| GATAD2A_hsa_circ_0000917 | SEQ ID NO: 7 |
| AFF1_hsa_circ_0001423 | SEQ ID NO: 8 |
| FBXO34_hsa_circ_0000540 | SEQ ID NO: 9 |
| NFX1_hsa_circ_0001844 | SEQ ID NO: 10 |
| SLC8A1_hsa_circ_0000994 | SEQ ID NO: 11 |
| circNPPA | SEQ ID NO: 12 |

Each of these circRNAs is suitable for the methods described herein. For example, the circRNA ZNF609_hsa_circ_0000615 (termed "MICRA" herein) is associated with heart failure, cardiac hypertrophy and coronary artery disease, and is a 874 nucleotides-long circRNA formed from exon 1 of the zinc finger protein 609 (ZNF609) gene located on chromosome 15q22.

The methods provided herein involve determining expression of one or more circRNAs in a sample in vitro or ex vivo or in a tissue in vivo. In particular embodiments, the methods comprise detecting the expression of a combination of two, three, four five, six, seven, eight, nine, ten, eleven or all of the circRNAs of Table 1.

Methods for determining expression of a circRNA are known in the art and include sequencing assays, microarrays, polymerase chain reaction (PCR), RT-PCR, quantitative nuclease-protection assays (qNPA), and Northern blots. Additionally, it can be envisaged that circular RNAs can be detected using, antibody-binding assays, enzyme-linked immunosorbent assays (ELISAs), flow cytometry, protein assays, Western blots, nephelometry, turbidimetry, chromatography, mass spectrometry, or immunoassays, The information obtained by the detection method can be quantitative or can be a qualitative signal which can be translated into a quantitative measure by a user or automatically by a reader or computer system. In particular embodiments, the expression of a circRNAs is detected by RT-PCR.

In particular embodiments, the sample is selected from whole blood, plasma, serum, whole blood cells, red blood cells, white blood cells (e.g., peripheral blood mononuclear cells), saliva and urine. Most particularly the sample is a cell-containing sample. In particular embodiments, the sample is a whole blood cells sample. In a further embodiment, the sample has been enriched in white blood cells.

In particular embodiments, the methods comprise detecting the expression of one or more circRNAs in a tissue of a patient in vitro, ex vivo or in vivo. In particular embodiments, the methods comprise determining the expression of a combination of two, three, four five, six, seven, eight, nine, ten, eleven or all of the circRNAs of Table 1.

Methods for determining the expression of a circRNA in a tissue in situ or vivo are less straightforward but have also been described in the art. The most widely used method is fluorescent in situ hybridization (FISH) which makes use of short oligonucleotide probes (about 15-30 nts in length) complementary to a selected RNA sequence with a fluorophore tag. For in vivo detection the use of "quenched" probes i.e. to which quencher molecules are also attached to quench the emission of the fluorophore in unbound probes, is necessary. Molecular beacons are one type of such quenched probes whereby the design of the probe makes that a fluorescent signal is only generated upon binding to a target sequence (Silverman & Kool, 2005), but others have also been developed. The disadvantage of these probes is not only that their production is costly but more importantly, these conjugates are not able to diffuse directly into cells and thus perturbation or disruption of the membranes is still required. GFP and other auto-fluorescent proteins have also been adapted for detection of RNA molecules in vivo, including technologies involving split GFPs to avoid non-specific staining (Valencia-Burton et al., 2007). Finally, aptamers, i.e. functional single stranded RNA or DNA molecules, have also been developed which specifically bind RNA (Klussmann, 2006). Different strategies for developing aptamers which can be used as direct or indirect fluorescent tags have also been described (Ouellet, 2016).

In the methods as envisaged herein the expression of one or more circRNAs is determined in a sample of a subject in vitro or ex vivo or in a tissue in vivo. The subject is preferably a warm-blooded animal, more preferably a mammal, most particularly a human subject, but it can be envisaged that the methods provided herein are equally suitable for methods applied to subjects such as, e.g., non-human primates, equines, canines, felines, ovines, porcines, and the like.

The methods for predicting the outcome of myocardial infarction (MI) envisaged herein are particularly suitable when used on a sample obtained from a subject which has recently suffered from a myocardial infarction. Indeed, in particular embodiments, the methods envisaged herein involve determining the risk of a patient developing heart failure, through for instance left ventricular dysfunction and/or remodelling, after having had a myocardial infarction. It is of importance to take the sample as soon as possible after the myocardial infarction, preferably within a few hours and more preferably within 5 days after MI. In particular embodiments, the sample is from a patient who has suffered from a myocardial infarction within less than 5 days, such as less than 3 days, particularly less than 48 hours, such as less than 24 hours before taking of the sample.

Particular embodiments of the invention relate to the use of circRNAs for the diagnosis of heart failure. In these embodiments, the sample may be an unbiased sample or may be taken from a patient which is characterized by one or more clinical symptoms, such as breathlessness, Exertional dyspnea, Orthopnea, Paroxysmal nocturnal dyspnea, Dyspnea at rest, Acute pulmonary edema, chest pain/pressure and palpitations or noncardiac symptoms such as anorexia, nausea, weight loss, bloating, fatigue, weakness, oliguria, nocturia, and cerebral symptoms of varying severity, ranging from anxiety to memory impairment and confusion. It has been found that the circRNA are indicative of heart failure, irrespective of whether it is due to ischemic cardiomyopathy (ICM) or dilated cardiomyopathy (DCM). Accordingly, in particular embodiments, the invention provides methods for diagnosis of heart failure, wherein the patient may suffer either from ischemic cardiomyopathy ICM or DCM. In particular embodiments, the methods are of use for diagnosing heart failure in a patient having undergone ICM.

The methods as envisaged herein comprise determining the expression of one or more circRNAs in a sample of a subject and either predicting, based on the result of said determination, the risk of said subject to develop heart failure or using said information in the diagnosis of heart failure. In particular embodiments, the method may involve comparing the expression level of the one or more circRNAs in a sample of a subject with reference values for the expression level of said circRNAs, wherein the reference values represent a known prediction or diagnosis of heart failure.

For example, distinct reference values may represent the prediction of a risk (e.g., an abnormally elevated risk) of developing heart failure vs. the prediction of no or normal risk of developing heart failure. In another example, distinct reference values may represent predictions of differing degrees of risk of developing heart failure.

Similarly or alternatively, distinct reference values may represent the diagnosis of developing heart failure vs. the diagnosis of not developing heart failure (such as, e.g., the diagnosis of healthy, or recovered from MI). In another example, distinct reference values may represent the diagnosis of developing heart failure of varying severity.

In yet another example, distinct reference values may represent a good prognosis for myocardial infarction (MI) vs. a poor prognosis for MI. In a further example, distinct reference values may represent varyingly favourable or unfavourable prognoses for MI.

Such comparison may generally include any means to determine the presence or absence of at least one difference and optionally of the size of such different between values or profiles being compared. A comparison may include a visual inspection, an arithmetical or statistical comparison of measurements. Such statistical comparisons include, but are not limited to, applying an algorithm. If the values or biomarker profiles comprise at least one standard, the comparison to determine a difference in said values or biomarker profiles may also include measurements of these standards, such that measurements of the biomarker are correlated to measurements of the internal standards.

The term "threshold level or value" or "reference value" is used interchangeably as a synonym and is as defined herein. It may also be a range of base-line (e.g. "dry weight") values determined in an individual patient or in a group of patients with highly similar disease conditions.

Reference values for the quantity of circRNA expression may be established according to known procedures previously employed for other RNA biomarkers.

For example, a reference value of the amount of circRNA expression for a particular diagnosis, prediction and/or prognosis of heart failure or MI as taught herein may be established by determining the quantity of expression of circRNA in sample(s) from one individual or from a population of individuals characterised by said particular diagnosis, prediction and/or prognosis of said disease or condition. Such population may comprise without limitation ≥2, ≥10, ≥100, or even several hundreds or more individuals.

Hence, by means of an illustrative example, reference values of the quantity of circRNA expression for the diagnoses of heart failure vs. no such disease or condition may be established by determining the quantity of circRNA expression in sample(s) from one individual or from a population of individuals diagnosed (e.g., based on other adequately conclusive means, such as, for example, clinical signs and symptoms, imaging, ECG, etc.) as, respectively, having or not having heart failure.

Measuring the expression level of circRNA for the same patient at different time points may in such a case thus enable the continuous monitoring of the status of the patient and may lead to prediction of worsening or improvement of the patient's condition with regard to a given disease or condition as taught herein. Tools such as the kits described herein below can be developed to ensure this type of monitoring. One or more reference values or ranges of circRNA expression levels linked to the development of heart failure can e.g. be determined beforehand or during the monitoring process over a certain period of time in said subject. Alternatively, these reference values or ranges can be established through data sets of several patients with highly similar disease phenotypes, e.g. from subjects not developing heart failure. A sudden deviation of the circRNA levels from said reference value or range can predict the worsening of the condition of the patient (e.g. at home or in the clinic) before the (often severe) symptoms actually can be felt or observed.

In particular embodiments, the methods provided herein may include a step of establishing such reference value(s), more particularly a reference value for the expression of one or more circRNAs for the development of heart failure. In particular embodiments, the methods further comprise determining the difference between the quantity of circRNA expression measured in a sample from a subject and the given reference value for said circRNA(s). For example, the difference may represent in the sample of the subject, an increase of at least about 10% (about 1.1-fold or more), or by at least about 20% (about 1.2-fold or more), or by at least about 30% (about 1.3-fold or more), or by at least about 40% (about 1.4-fold or more), or by at least about 50% (about 1.5-fold or more), or by at least about 60% (about 1.6-fold or more), or by at least about 70% (about 1.7-fold or more), or by at least about 80% (about 1.8-fold or more), or by at least about 90% (about 1.9-fold or more), or by at least about 100% (about 2-fold or more), or by at least about 150% (about 2.5-fold or more), or by at least about 200% (about 3-fold or more), or by at least about 500% (about 6-fold or more), or by at least about 700% (about 8-fold or more), or like, relative to a the reference value with which a comparison is being made.

Alternatively, such a difference may comprise a decrease in the sample of the subject by, for instance, at least about 10% (about 0.9-fold or less), or by at least about 20% (about 0.8-fold or less), or by at least about 30% (about 0.7-fold or less), or by at least about 40% (about 0.6-fold or less), or by at least about 50% (about 0.5-fold or less), or by at least about 60% (about 0.4-fold or less), or by at least about 70% (about 0.3-fold or less), or by at least about 80% (about 0.2-fold or less), or by at least about 90% (about 0.1-fold or less), relative to a reference value with which a comparison is being made. The examples section shows that in the experiments done, the decrease in circRNA levels between subjects developing heart failure and subjects not developing heart failure is 0.4-fold, i.e. there is a 60% decrease of circRNA for patients with heart failure.

Preferably, the difference or deviation refers to a statistically significant observed difference. For example, a deviation may refer to an observed difference which falls outside of error margins of reference values in a given population (as expressed, for example, by standard deviation or standard error, or by a predetermined multiple thereof, e.g., ±1×SD or ±2×SD, or ±1×SE or ±2×SE). Deviation may also refer to a value falling outside of a reference range defined by values in a given population (for example, outside of a range which comprises ≥40%, ≥50%, ≥60%, ≥70%, ≥75% or ≥80% or ≥85% or ≥90% or ≥95% or even ≥100% of values in said population).

In a further embodiment, a deviation may be established if the observed difference is beyond a given threshold or cut-off. Such threshold or cut-off may be selected as generally known in the art to provide for a chosen sensitivity and/or specificity of the diagnosis, prediction and/or prognosis methods, e.g., sensitivity and/or specificity of at least 50%, or at least 60%, or at least 70%, or at least 80%, or at least 85%, or at least 90%, or at least 95%.

In the methods provided herein the observation of a deviation between the expression of a circRNA in the sample and the reference value representing the development of heart failure, can lead to the conclusion that the prediction of the condition in said patient is different from that represented by the reference value. Similarly, when no deviation is found between the quantity of expression of a circRNA in a sample from a subject and a reference value representing the development of heart failure, the absence of such deviation can lead to the conclusion that the prediction of the condition in said subject is substantially the same as that represented by the reference value.

The above considerations apply analogously to embodiments wherein different circRNAs are taken into consideration by determining a biomarker profile.

When two or more different biomarkers are determined in a subject, their respective presence, absence and/or quantity may be together represented as a biomarker profile, the values for each measured biomarker making a part of said profile. As used herein, the term "profile" includes any set of data that represents the distinctive features or characteristics associated with a condition of interest, such as with the development of heart failure. Biomarker profiles allow the combination of measurable biomarkers or aspects of biomarkers using methods such as ratios, or other more complex association methods or algorithms (e.g., rule-based methods). A biomarker profile comprises at least two measurements, where the measurements can correspond to the same or different biomarkers. A biomarker profile may also comprise at least three, four, five, 10, 20, 30 or more measurements.

In particular embodiments as described above, the methods envisaged herein comprise determining the expression level of two or more circRNA s for use in a biomarker profile. Additionally or alternatively other parameters may be used, in combination with the expression of one or more circRNAs as described herein, to diagnose heart failure or to determine the risk of developing heart failure as characterized by LVD or ventricular remodelling in a subject. More particularly, where the circRNAs are used in the prognosis of the outcome of MI, more particularly the prediction of heart failure, this may be in combination with the assessment of one or more clinical parameters, more particularly clinical parameters which are known in the art to be correlated with the outcome of MI. Examples of such clinical parameters include but are not limited to age, body-mass index, gender, white blood cell count, ischemic time, antecedent of MI, diabetes, hypertension, hypercholesterolemia, and smoking. Taking these additional features into account may further improve the reliability of the assessment. Accordingly, in particular embodiments, the invention provides methods for predicting the outcome of MI or the likeliness to develop heart failure, which methods comprise (i) measuring the expression of one or more circRNAs and (ii) assessing one or more clinical parameters associated with the development of heart failure and determining whether or not the patient is likely to develop heart failure based on the outcome of both (i) and (ii).

In particular embodiments, the methods involve taking into account all of these parameters in combination with one or more circRNAs for the assessment of the likeliness of the subject to develop heart failure. In particular embodiments, the methods involve combining the detection of expression of MICRA with that of one or more other parameters selected above.

Where the circRNAs are used in the diagnosis of heart failure, they may also be combined with one or more clinical parameters, more particularly parameters which are known in the art to be correlated with or indicative of heart failure. Examples of such parameters include but are not limited to breathlessness, Exertional dyspnea, Orthopnea, Paroxysmal nocturnal dyspnea, Dyspnea at rest, Acute pulmonary edema, chest pain/pressure and palpitations or noncardiac symptoms such as anorexia, nausea, weight loss, bloating, fatigue, weakness, oliguria, nocturia, and cerebral symptoms of varying severity, ranging from anxiety to memory impairment and confusion. More particularly the parameter may include the observation of the manifestation of one or more of these clinical parameters with progressively increasing severity. Accordingly, in particular embodiments, the invention provides methods for diagnosing heart failure, which methods comprise (i) measuring the expression of one or more circRNAs and (ii) assessing one or more clinical parameters associated with heart failure and determining whether or not the patient is suffering from heart failure based on the outcome of both (i) and (ii).

In particular embodiments, the methods involve taking into account all of these clinical parameters in combination with one or more circRNAs for the diagnosis of heart failure. In particular embodiments, the methods involve combining the detection of expression of MICRA with that of one or more clinical parameters described above.

Additionally or alternatively other biomarkers may also be used, in combination with the expression of one or more circRNAs as described herein, to determine the risk of developing heart failure through, for instance LVD or ventricular remodelling in a subject or to diagnose heart failure in a patient. Any biomarker known to be associated with the development of heart failure and/or with the occurrence of heart failure may be suitable in this context. Examples of suitable markers include but are not limited to CPK, cTnT, Nt-pro-BNP, MMP9. Taking these additional features into account, optionally also in combination with the clinical parameters described above may further improve the reliability of the assessment. In particular embodiments, the methods involve determining the expression of one or more circRNAs, such as MICRA, and one or more additional biomarkers from those recited above. In further particular embodiments, the methods involve determining the expression of MICRA and detecting levels of Nt-pro-BNP and predicting the development of heart failure based thereon.

It is envisaged that the methods provided herein which allow the identification of patients susceptible to the development of heart failure and the diagnosis of heart failure can be used to differentiate treatment options for these patients. More particularly it is envisaged that identification of patients at risk of developing heart failure after acute myocardial infarction would allow the treatment of these patients with drugs aimed at countering this. Similarly, the diagnosis of patients with heart failure can be used to decide on or confirm the selection of specific therapies aimed at countering heart failure.

Different types of medications have been described which attenuate remodeling, such as but not limited to Angiotensin-converting enzyme (ACE) inhibitors, drugs which directly or indirectly inhibit aldosterone, and certain beta blockers. Indeed, beta-blockers may reverse the remodeling process by reducing left ventricular volumes and improving systolic function. Examples of ACE inhibitors include but are not limited to perindopril, captopril, enalapril, lisinopril, and ramipril. Examples of beta-blockers include but are not limited to carvediol.

Accordingly, the application also provides methods determining the optimal treatment regimen for a subject at risk of developing heart failure and/or for patients potentially suffering from heart failure. These methods comprise determining the expression of one or more circRNAs as described hereinabove in a sample of said patient, wherein the selection of treatment is determined based on the expression level of one or more circRNAs so determined. In particular embodiments, these methods comprise selecting, when the expression of the one or more circRNAs is indicative of the development of heart failure (or confirms or establishes the diagnosis of heart failure), a treatment regimen aimed at countering heart failure, more particularly LVD and/or ventricular remodelling. In further particular embodiments, these methods involve determining whether or not the subject is likely to develop heart failure. In further particular embodiments, these methods include the selection of an anti-remodelling drug for the treatment of those subjects which are determined to be likely to develop heart failure and ventricular remodelling or patients diagnosed with heart failure. Similarly the application provides methods for determining whether or not to treat a patient with a drug which counters heart failure, such as drugs reversing tissue remodelling, such as but not limited to the drugs recited above.

The application further provides methods of treating a patient after myocardial infarction, said methods comprising determining the risk of heart failure in said patient using one or more circRNAs as described herein and selecting the treatment regimen for said patient based thereon. In particular embodiments the methods comprise selecting, where the risk of developing heart failure for said patient is high, one or more drugs that prevent and/or treat heart failure, such as those described herein above. In further embodiments, the methods may comprise the step of administering a drug aimed at countering heart failure to a patient for which it has been established that the risk of developing heart failure is high.

Additionally, the application provides methods for treating a patient after myocardial infarction, said methods comprising determining whether or not said patient is suffering from heart failure using one or more circRNAs as described herein and selecting the treatment regimen for said patient based thereon.

The present invention further provides systems for determining or predicting the outcome of myocardial infarction in a patient or for diagnosing heart failure in a patient, which systems are configured to carry out at least part of the methods described above. Typically, the systems comprise a combination of hardware and software adapted to carry out the determination step described herein.

In particular embodiments, the system comprises a storage memory for storing data associated with a sample obtained from the patient, and a processor communicatively coupled to the storage memory for analyzing the dataset to analyse the expression level of said one or more circRNAs. In particular embodiments, the data comprises quantitative expression data for one or more circRNAs as described herein. In particular embodiments, said circRNAs are selected from Table 1 above.

The system may further comprise hardware means for measuring a signal generated by a sample in a sample container, which signal is indicative of the expression of one or more circRNAs in the sample. In further particular embodiments, the system comprises a detection unit. In particular embodiments, the system further comprises means for separating and optionally identifying the one or more circRNAs from other components present in the sample such as, but not limited to, extraction chambers, chromatography columns, and/or sequencing means.

The application further provides computer-readable storage media storing computer-executable program code, which, when run on a computer allows storing of the data and the analysis of the data in the systems as described above.

The present invention further provides kits or devices for the diagnosis, prediction, prognosis and/or monitoring of the development of heart failure comprising means for detecting the level of one or more circRNAs in a sample of the patient.

In particular embodiments, such a kit or kits of the invention can be used in clinical settings or at home. The kit according to the invention may be used for diagnosing said disease or condition, for monitoring the effectiveness of treatment of a subject suffering from said disease or condition with an agent, or for preventive screening of subjects for the occurrence of said disease or condition in said subject.

Typical kits or devices according to the invention comprise means for specifically measuring the expression of one or more circRNAs in said sample. In particular embodiments, the kits further comprise means for visualizing whether the expression of the one or more circRNAs in said sample is below or above a certain threshold level or value, indicating whether the subject is likely to develop heart failure or not or, where the kit or device is envisaged for diagnosis of heart failure, whether the patient is suffering from heart failure or not. In particular embodiments, the means may be primers or probes selectively amplifying and/or detecting the expression of circRNAs. Typically these primers or probes are sequence specific, selectively detecting expression of a particular circRNA. In particular embodiments, the kits or devices comprise primers or probes selectively detecting the presence of one or more circRNAs in a sample of a patient, such as one or more circRNAs from Table 1. In particular embodiments the kit comprises at least one or more primer pairs and/or one or more probes to selectively amplify and/or detect the presence of a MICRA circRNA, based on the junction point of said circRNA. Indeed, the junction point of said circRNA will allow the identification of the RNA as circRNA and allow differentiation over non-circular RNAs which otherwise comprise a similar sequence. A schematic diagram exemplifying such primers is provided in FIG. 5A. An example of a set of primers (divergent forward and divergent reverse) that amplify MICRA comprise the nucleotide sequence of SEQ ID NO: 13 and SEQ ID NO: 14 and amplify a region comprising the junction point. Such region may span the sequence of the TaqMan® probe (SEQ ID NO: 17) as shown in FIG. 5A. Such region may comprise the sequence 5'-AAGCAATGATGTTGTCCACTG-3' (SEQ ID NO: 18). Preferably said sequence is an RNA sequence wherein T is replaced by U.

In particular embodiments the probes or primers are labelled, such as FAM fluorophore labelling, or are coupled to a quencher, such as a BBQ quencher. In particular embodiments, the probes or primers may be bound on a carrier.

In any of the embodiments of the invention, the kits or devices may additionally comprise one or more selected from means for collecting a sample from the patient, means for communicating directly with a medical practitioner, an emergency department of the hospital or a first aid post, indicating that a person is suffering from said disease or condition or not.

In any of the embodiments of the invention, the device or kit or kits of the invention can additionally comprise means for detecting the level of an additional marker in the sample of said patient. Non limiting examples of additional markers include but are not limited to CPK, cTnT, Nt-pro-BNP and MMP9. In particular embodiments, the kits are envisaged for use in the prognosis of the outcome of MI, more particularly to predict the likeliness of a patient to develop heart failure.

The invention further provides combinations of probes for use in the detection of the expression of one or more circRNAs in a sample of a patient, more particularly for determining the likeliness of the patient to develop heart failure or for the diagnosis of heart failure in a patient. More particularly, these probes can be used to selectively detect the expression of one or more circRNAs. In further particular embodiments, these probes are provided on a substrate. Examples of suitable substrate materials include but are not limited to glass, modified glass, functionalized glass, inorganic glasses, microspheres, including inert and/or magnetic particles, plastics, polysaccharides, nylon, nitrocellulose, ceramics, resins, silica, silica-based materials, carbon, metals, an optical fiber or optical fiber bundles, polymers and multi-well (e.g. microtiter) plates. Specific types of exemplary plastics include acrylics, polystyrene, copolymers of styrene and other materials, polypropylene, polyethylene, polybutylene, polyurethanes and Teflon™. Specific types of exemplary silica-based materials include silicon and various forms of modified silicon.

The above aspects and embodiments are further supported by the following non-limiting examples.

EXAMPLES

Patients and Blood Samples

Study 1

All 409 patients were enrolled from the Luxembourg Acute Myocardial Infarction Registry completed at the Institut National de Chirurgie Cardiaque et de Cardiologie Interventionnelle (INCCI) and the Department of Cardiology of the Centre Hospitalier de Luxembourg (CHL). All patients had acute MI and were treated with primary percutaneous coronary intervention (PCI). Acute ST-segment-elevation MI (STEMI) was the final diagnosis for 270 patients and 139 patients had non-ST-segment-elevation MI (NSTEMI). STEMI was defined by (1) clinically significant ST elevation (>1 mm); (2) occluded major coronary artery: thrombolysis in MI (TIMI) 0 flow in the left anterior descending, circumflex, or right coronary artery; (3) peak creatine phospho kinase (CPK) activity >600 U/L (3 times above the upper limit of the reference interval). NSTEMI was defined by (1) no significant ST-elevation but significant ST depression (>1 mm); (2) significant lesion in a major coronary artery requiring PCI; (3) positive cardiac troponin T (cTnT) concentration after 24 h (>0.03 μg/L). Most NSTEMI patients had a severe or sub-occlusive lesion in the left anterior descending, circumflex, or right coronary artery.

Blood samples were withdrawn at the time of reperfusion via an arterial catheter into PAXgene™ RNA tubes (BD Biosciences, Erembodegem, Belgium). Left ventricular (LV) ejection fraction (EF) and New York Heart Association (NYHA) score were determined after 4 months using echocardiography. Mortality status was recorded at 4 months and 1 year. The protocol has been approved by the ethics committee of Luxembourg. All patients signed an informed consent. In addition, arterial blood samples were collected from 86 apparently healthy volunteers, i.e. without apparent signs of cardiovascular disease.

Study 2

In a separate study, 233 patients from the Leipzig LIFE-Heart study were included. The study was designed to analyze genetic and non-genetic risk factors of atherosclerosis and related vascular and metabolic phenotypes. The study meets the ethical standards of the Declaration of Helsinki. It has been approved by the Ethics Committee of the Medical Faculty of the University of Leipzig, Germany (Reg. No 276-2005) and is registered by ClinicalTrials.gov (NCT00497887). Written informed consent including agreement with CMR imaging, and genetic analyses has been obtained from all participants enrolled in the study. All patients included in the present validation analysis were admitted for an acute MI as the first manifestation of coronary heart disease. STEMI was found in 184 (79%) patients. Peripheral venous blood was collected at median balloon-to-blood time 0.86 days (IQR 0.64-1.19) after angiographic reperfusion. The recruitment phase was conducted at a single tertiary care centre between July 2008 and October 2012. A follow up echocardiography was performed in each patient at median 100 days, inter quartile range (IQR) 91-134 including standardized planimetric assessment of the EF. Median age of MI patients was 60 and 73% were males. In this cohort, an EF<50% at median follow-up of 100 days (IQR 91-134) was used as a threshold for LV dysfunction. This threshold was used to compensate for the low proportion of patients with an EF<40% (10%) which significantly decreased the power of the study. 65 (28%) patients met this criterion of LV dysfunction. Compared to patients with preserved LV function, patients with LV dysfunction had higher blood cell counts at admission, higher levels of CPK, cTnT, CRP and proBNP, and had more often a prior MI.

Human Cardiac Biopsies

Cardiac biopsies were obtained from 22 explanted failing hearts and 5 non-failing control hearts. Among failing hearts, 11 had a dilated cardiomyopathy (DCM) and 11 had an ischemic cardiomyopathy (ICM). Donors of non-failing hearts had either a head injury (n=2) or a subarachnoid haemorrhage (n=3). Neither donors nor their relatives completed National Refusal List. The protocol has been approved by the Local Ethics Committee at Cardinal Stefan Wyszynski Institute of Cardiology under the approval number IK-NP-0021-48/846/13 (Apr. 9, 2013). Biopsies were obtained from the left ventricle, the right ventricle and the septum, were snap frozen separately, and were stored at −80° C.

Measurement of MICRA Expression

SYBR® Green-Based PCR

The expression of MICRA was assessed using quantitative PCR. Total RNA was extracted from PAXgene™ tubes with the PAXgene™ blood RNA kit (Qiagen, Venlo, Netherlands) as described by the manufacturer. Extracted RNA was further purified and concentrated using the RNeasy® MinElute™ kit (Qiagen). To extract total RNA from subtypes of leukocytes, cells were lysed in TriReagent® (Sigma, Bornem, Belgium) and RNA was extracted using the RNeasy® Micro kit (Qiagen). To extract total RNA from cardiac biopsies, tissues were homogenized using a Polytron®, homogenates were lysed in TriReagent® (Sigma) and RNA was extracted using the RNeasy® Mini kit (Qiagen). After extraction, total RNA was quantified with the ND-1000 spectrophotometer (NanoDrop® Technologies, Wilmington, USA). RNA quality was evaluated with the 2100 Bioanalyzer® apparatus (Agilent Technologies, Massy, France) and the RNA 6000 Nano chips. Reverse-transcription of 1 μg of total RNA was achieved using the Superscript II RT kit (Life technologies, Belgium). The absence of contaminating genomic DNA was ensured using controls with RNA but without reverse transcriptase. PCR was conducted in a CFX96 thermocycler with the IQ™ SYBR® Green Supermix (BioRad, Nazareth, Belgium). PCR primers design was performed with the Beacon Designer software (Premier Biosoft, USA). PCR primer sequences and PCR conditions are provided in Table 2.

TABLE 2

PCR primers

| Gene name | Access. Number | Forward primer (5'-3') | Forward primer (5'-3') | Convergent (C)/ divergent (D)* | T (° C.) | PCR efficiency (%) |
|---|---|---|---|---|---|---|
| MICRA | hsa-circ-0000615 | GCTAAAGAAAG TCAAGTC (SEQ ID NO: 13) | TCAAGGACAT CTTAGAGT (SEQ ID NO: 14) | D | 56 | 109.7 |
| SF3a1 | NM_005877 | GATTGGCCCCA GCAAGCC (SEQ ID NO: 15) | TGCGGAGACA ACTGTAGTAC G (SEQ ID NO: 16) | C | 60 | 96.6 |

* convergent primers allow the amplification of linear RNAs, divergent primers allow the amplification of circular RNAs.

The PCR protocol was: initial denaturation at 95° C. for 3 min, then 40 cycles of 95° C. for 30 s and 1 min annealing-extension (40 cycles). Annealing temperature was 56° C. for MICRA and 60° C. for SF3a1. SF3a1 was used as housekeeping gene for normalization of circRNAs in blood cells and GAPDH was used for human cardiac biopsies. A melting curve analysis and the sequencing of PCR products allowed attesting for the specificity of the PCR amplification. An inter-run calibrator was used to normalize the variations between PCR plates. Expression levels of MICRA were calculated by the relative quantification method (ΔΔCt) using the CFX Manager 2.1 software which takes into account primers efficacy (Bio-Rad).

TaqMan® PCR with a Probe Spanning the Splicing Site of MICRA

Expression levels of MICRA were determined in a subgroup of 28 MI patients using TaqMan® PCR. Sequences of MICRA PCR primers are the same for TaqMan® and SYBR® Green PCR assays and RNA extraction were conducted as described previously for leukocytes. In TaqMan® experiment, a hydrolysis probe was specifically designed to span the junction site of MICRA to increase the specificity of the detection of the circular form. The probe is labeled with FAM fluorophore at 5' and BBQ quencher at 3' (TIB Molbiol, Germany). Probe sequence is as follows: 5'-FAM-CAGTGGACAACATCATTGCTT-BBQ-3' (SEQ ID NO:17). The PCR reaction was performed with the TaqMan® Universal Master Mix II, no UNG (Life technologies, Belgium). The final concentrations of primers and probe were 900 nM and 200 nM, respectively. The PCR protocol was: initial denaturation at 95° C. for 10 min, then 45 cycles at 95° C. for 15 s and 1 min at 56° C. for annealing-extension of MICRA. The amplification was monitored by measuring the FAM fluorescence produced by the probe hydrolysis after every cycle.

Statistical Analyses

Mann-Whitney test was used to compare two groups of continuous variables. Chi-square test was used for qualitative data. One-way analysis of variance on Ranks followed by all pairwise multiple comparison procedures using the Holm-Sidak method was used for multiple group comparisons. The Spearman rank test was used to evaluate the correlation between two continuous variables. Multiple logistic regression and Kaplan-Meier survival analysis were conducted to address the ability of MICRA and other clinical variables to predict mortality. The SigmaPlot v12.0 software was used for statistical analyses. All tests were two-tailed and a P value <0.05 was considered significant.

Univariate and multivariable analyses with logistic regression were conducted to evaluate the ability of MICRA to predict heart failure, either alone or in combination with other clinical parameters. Odds ratios (OR) with 95% confidence intervals (CI) are presented. Analysis of deviance and reclassification analyses were implemented to address the added value of MICRA to a multi-parameter clinical model. A decrease of deviance after addition of a variable to a model attests for a better model fit and thus for an improvement of prediction. The Wald chi-square test was used to measure the statistical significance of the decrease in deviance. Computation of the integrated discrimination improvement (IDI) was used for reclassification analyses. All prediction analyses were performed on the R version 2.14.2 statistical platform using the packages Hmisc, Survival and Splines.

Example 1—Identification of circRNAs Associated with Heart Failure

Selection of circRNAs

Two databases were interrogated to identify circRNAs potentially associated with cardiac disease, the Circ2Traits database and the StarBase v2.0 database. In addition, the occurrence of the circRNAs in a public Heart RNA-seq dataset was considered. The circRNAs described in Table 1, among which ZNF609_hsa_circ_0000615 (termed "MICRA"), were consistently detected in the human heart in a public RNA-seq dataset. MICRA is a 874 nucleotides-long circRNA formed from exon 1 of the zinc finger protein 609 (ZNF609) gene located on chromosome 15q22.

MICRA is a Circular RNA

It was first confirmed that MICRA was indeed a circular and non-coding RNA, and not a linear protein-coding messenger RNA. Two approaches were undertaken to demonstrate this. First, the amplification product of SYBR® Green-based PCR performed with divergent primers were sequenced and a unique product corresponding to the circular form of MICRA was observed (FIG. 5 (A)). Second, TaqMan® PCR with a probe spanning the splicing site of MICRA yielded highly correlated results with SYBR® Green-based PCR data (FIGS. 5 (A) and (B)). Third MICRA was cloned into a pcDNA3.1 expression vector, which was sequenced and transfected into HEK293 cells. A robust over-expression of the circular form of MICRA was achieved. This circular form was resistant to RNAse R degradation (FIG. 6 A). In a further, total RNA extracted from the blood of healthy donors collected in PAXgene™ tubes was incubated in presence or absence of RNAse R (FIG. 6 (B)). This test is based on the ability of RNAse R to degrade linear but not circular RNAs. This demonstrated that MICRA is indeed a circular RNA.

Levels of circRNA are Lower in MI Patients Compared to Healthy Volunteers

Figure 1:
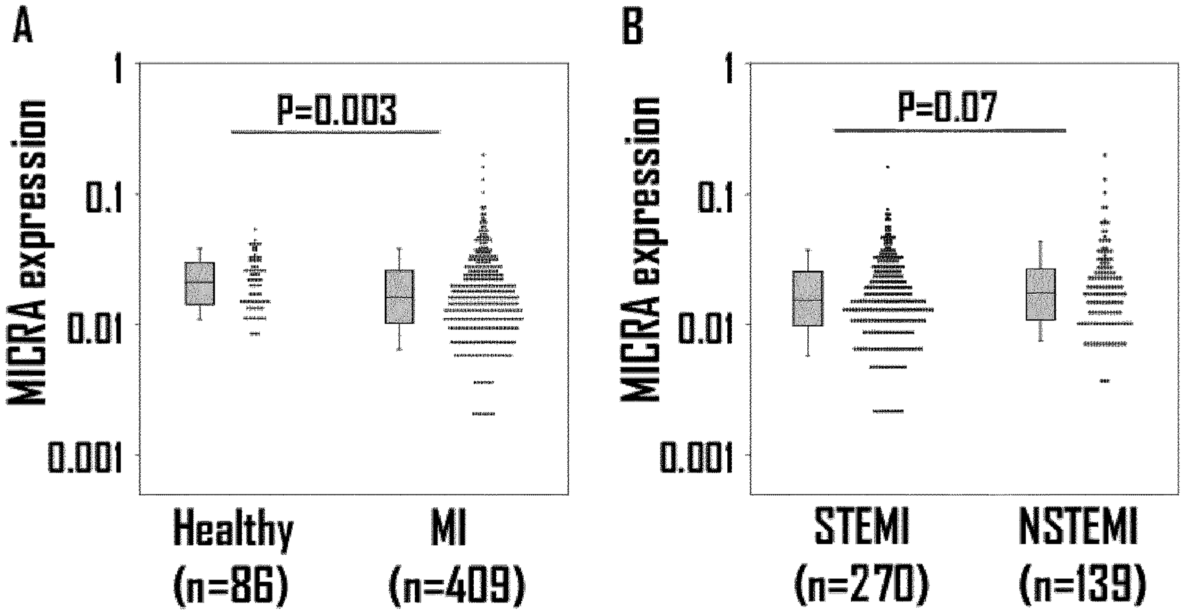
FIG. 1 illustrates exemplary normalized expression levels of a circRNA, named MICRA, in whole blood cells of MI patients and healthy volunteers as an illustrative embodiment of the invention. Blood samples were obtained from MI patients at the time of reperfusion. Expression levels of MICRA were measured by quantitative PCR normalized with SF3A1. (A) Comparison between healthy volunteers (n=86) and MI patients (n=409). (B) Comparison between patients with STEMI (ST-elevation MI; n=270) and patients with NSTEMI (non ST-elevation MI; n=139). P values for between-group comparisons are indicated.

To begin with the characterization of MICRA in MI patients, the expression levels of MICRA in whole blood cells harvested in PAXgene™ tubes obtained from the 409 MI patients from Study 1 and 86 healthy volunteers was determined. As shown in FIG. 1A, expression levels of MICRA were lower in MI patients compared to healthy volunteers. These levels were comparable between patients with STEMI (n=270) and patients with NSTEMI (n=139) (FIG. 1B).

The circRNA is Expressed by Circulating Lymphocytes

Next, it was sought to determine which blood cell type was responsible for the expression of MICRA. Expression levels of MICRA were not correlated with white blood cell count (Table 3), suggesting that variations of MICRA levels are not a simple mirror of the increase of white blood cell counts occurring after MI. Interestingly, there was a positive correlation between MICRA and circulating lymphocytes (Table 3). These data suggested that MICRA may be primarily expressed by lymphocytes.

TABLE 3

Correlation between expression levels of MICRA in 409 MI patients from Study 1, blood biomarkers, peak levels of cardiac biomarkers, and cardiovascular risk factors.

| | MICRA | |
|---|---|---|
| | Coeff** | P value |
| Blood biomarkers* (admission levels) | | |
| White blood cell count | 0.02 | 0.71 |
| Neutrophils, % | −0.22 | **<0.0001** |
| $10^9$/L | −0.08 | 0.14 |
| Lymphocytes, % | 0.25 | **<0.0001** |
| $10^9$/L | 0.26 | **<0.0001** |
| Monocytes, % | −0.08 | 0.12 |
| $10^9$/L | −0.07 | 0.15 |
| Platelet count | −0.04 | 0.46 |
| hsCRP | −0.08 | 0.18 |
| MMP9 | −0.16 | **0.001** |
| TIMP1 | −0.03 | 0.60 |

TABLE 3-continued

Correlation between expression levels of MICRA in 409 MI patients from Study 1, blood biomarkers, peak levels of cardiac biomarkers, and cardiovascular risk factors.

| | MICRA | |
|---|---|---|
| | Coeff** | P value |
| Cardiac biomarkers (peak levels) | | |
| CPK | −0.13 | **0.007** |
| cTnT | −0.13 | **0.008** |
| Nt-pro-BNP | −0.04 | 0.44 |
| Cardiovascular risk factors | | |
| Age | −0.04 | 0.46 |
| Gender | −0.01 | 0.85 |
| Body mass index | 0.06 | 0.25 |
| Diabetes | 0.04 | 0.42 |
| Hypertension | 0.07 | 0.18 |
| Hypercholesterolemia | 0.05 | 0.30 |
| Smoking | 0.08 | 0.12 |

*Neutrophils, lymphocytes and monocytes are expressed both as a percentage of white blood cell count and as absolute values in millions of cells per litre of blood.
**Coeff: correlation coefficient.
Significant P values are shown in bold.

Levels of the circRNA Inversely Correlate with Cardiac Biomarkers

An inverse relationship was found between the expression levels of MICRA and the cardiac biomarkers CPK and cTnT, as well as with the prognostic biomarker MMP9 (Table 3). However, MICRA was not correlated with Nt-pro-BNP levels. These data suggest that MICRA may provide useful prognostic information, complementary to that provided by cardiac enzymes and Nt-pro-BNP.

The circRNA Predicts Heart Failure, as Characterized by LV Dysfunction after MI

The value of MICRA measured at admission in whole blood cells was determined to predict heart failure as evident from LV dysfunction 4 months after MI. The log-transformed value of MICRA expression normalized with the house-keeping gene SF3A1 was used in prediction analyses. The demographic and clinical parameters included in multivariable models and reclassification analyses were age, body mass index, white blood cells count, CPK, cTnT, Nt-pro-BNP, ischemic time, gender, antecedent of MI, diabetes, hypertension, hypercholesterolemia, and smoking.

Figure 2:
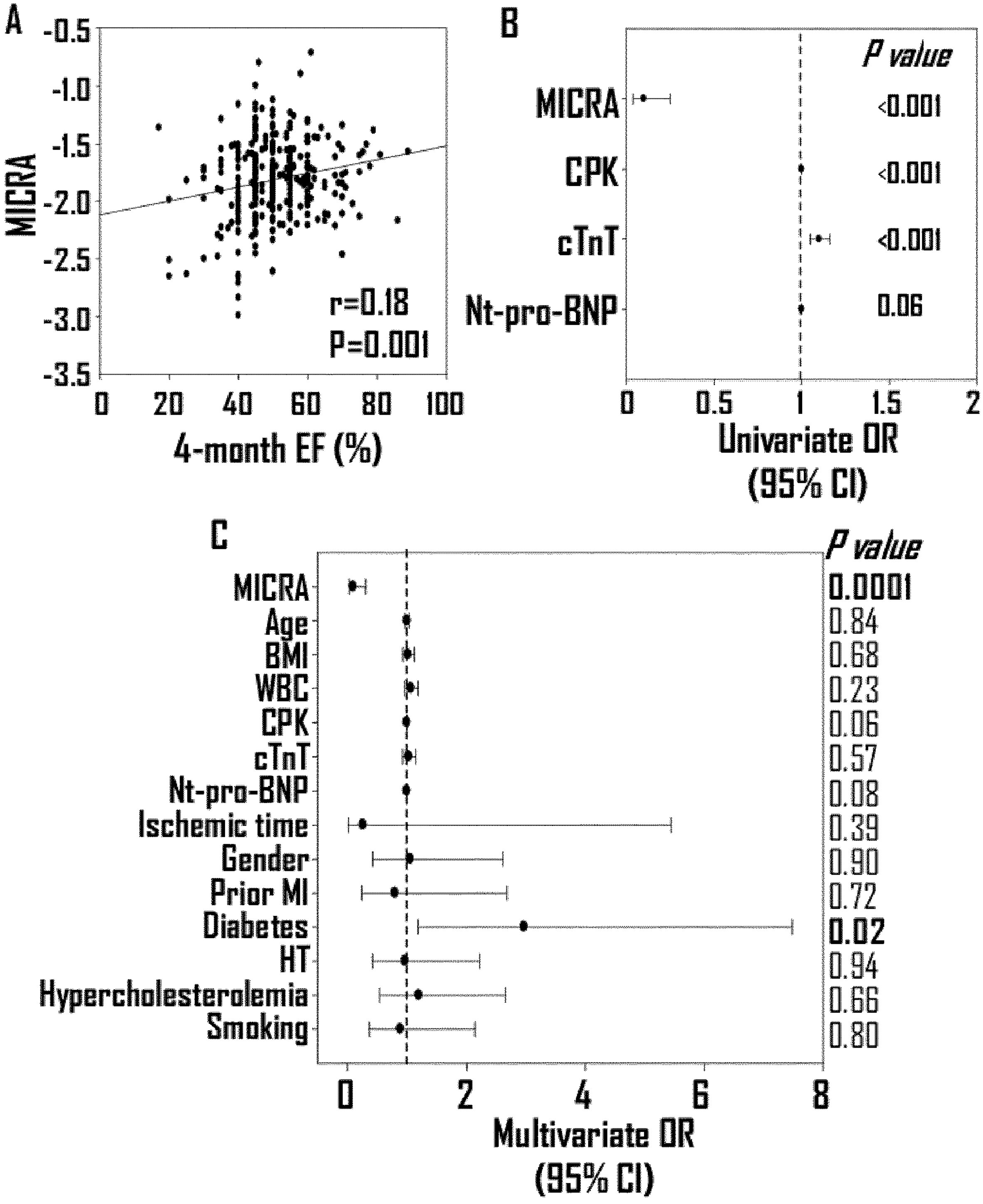
FIG. 2 illustrates the prognostic value of a circRNA, such as MICRA, after MI according to a particular embodiment of the invention. Expression levels of MICRA were measured by quantitative PCR in blood samples obtained from MI patients at the time of reperfusion. LV function and the EF were assessed at 4-month follow-up. MICRA was positively correlated with 4-month EF (A). The capacity of MICRA to predict heart failure as assessed by a 4-month EF ≤40% was evaluated using univariable analyses (B) and multivariable analyses (C). 327 patients from the First Study with 4-month EF available were included in these analyses. Demographic and clinical variables included in multivariable analyses: age, body mass index (BMI), white blood cells count (WBC), peak levels of creatine phosphokinase (CPK) and cardiac troponin T (cTnT), admission level of N-terminal pro-brain natriuretic peptide (Nt-pro-BNP), ischemic time (i.e. delay between chest pain onset and reperfusion), gender, antecedent of MI, diabetes, hypertension (HT), hypercholesterolemia, and smoking. The areas under the receiver-operating characteristic curves (AUC) and odds ratios (OR) with 95% confidence intervals (CI) are indicated. The log-transformed value of MICRA expression normalized with SF3A1 was used in these analyses.

First, a positive correlation, albeit modest but significant, was observed between the expression values of MICRA and the 4-month EF, taken as a continuous variable (Study 1: FIG. 2 A). Second, expression values of MICRA were used to predict heart failure taken as a dichotomized variable (4-month EF 540% attesting for LV dysfunction and 4-month EF >40% attesting for preserved LV function). Using univariate analyses, MICRA, CPK and cTnT were significant predictors of heart failure (Study 1: FIG. 2B). However, Nt-pro-BNP did not reach significance (P=0.06). In multivariable analyses, MICRA was the strongest predictor of heart failure (Study 1: FIG. 2C). Patients with low expression levels of MICRA were at high risk of heart failure (OR [95% CI] 0.09 [0.03-0.31]). Noteworthy, patients with diabetes had a 3-fold elevated risk of heart failure as compared to patients without diabetes (FIG. 2 C). The biomarkers CPK, cTnT and Nt-pro-BNP were not significant predictors of heart failure in multivariable analyses. Comparison of the deviance of the multivariable prediction models with and without MICRA revealed that addition of MICRA decreased the model deviance from 205.12 to 187.76 (difference 17.36, P=0.00003), attesting for an improvement of model fit and thus of prediction. In reclassification analyses, MICRA was able to correctly reclassify a significant proportion of patients misclassified by the multi-parameter clinical model (IDI=7%, [2-12], p=0.003).

MICRA was also assessed in a second independent study of 233 patients from the Leipzig LIFE-Heart study. Clinical and demographic features of these patients are comparable to the Luxembourg MI registry. In this study, an EF<50% at median follow-up of 100 days (IQR 91-134) was used as a threshold for LV dysfunction. This threshold was used to compensate for the low proportion of patients with an EF<40% (10%) which significantly decreased the power of the study. 65 (28%) patients met this criterion of LV dysfunction. In this group, MICRA predicted LV dysfunction with an OR of 0.53 [0.29-0.97], P=0.04) and provided an IDI of 0.02 [−0.01-0.05]. Gender and proBNP were also significant predictors of LV dysfunction (OR 0.3 [0.12-0.77], P=0.01 and OR 1.25 [1.11-1.41], P<0.001, respectively). Follow-up time and balloon-to-blood time had no confounding effects. These data confirm the ability of MICRA to aid in identifying patients at risk of developing LV remodeling and dysfunction after MI.

Even though white blood cell count was not correlated with MICRA (Table 3) and was not a significant predictor of heart failure (FIG. 2 C), a potential bias of white blood cell number in the prediction capacity of MICRA was evaluated. For this purpose, MICRA expression values were adjusted to the white blood cell count of each patient. This adjustment did not affect the predictive value of MICRA since the multivariable odds ratios was similar to that obtained without adjustment for white blood cell count (OR 0.10 [0.03-0.33], p=0.0001 and OR 0.09 [0.03-0.31], p=0.0001, with and without adjustment, respectively). Also, the improvement of model deviance and the reclassification value of MICRA were unaffected by adjustment to white blood cell count.

An association was observed between MICRA and the NYHA score evaluated at 4-month follow-up. Indeed, patients with low levels of MICRA at admission had more often a NYHA score at 4 months of 2, 3 or 4, as compared to patients with high levels of MICRA who had more often a NYHA score of 1 (OR 0.33 [0.14-0.74], p=0.007). This observation strengthens the finding of an inverse relationship between the expression levels of MICRA in white blood cells and heart failure after MI.

Taken together, these data support the value of MICRA to aid in identifying patients at risk of developing heart failure as evidenced by LV remodelling and dysfunction after MI.

CircRNAs are Up-Regulated in the Failing Heart

Figure 3:
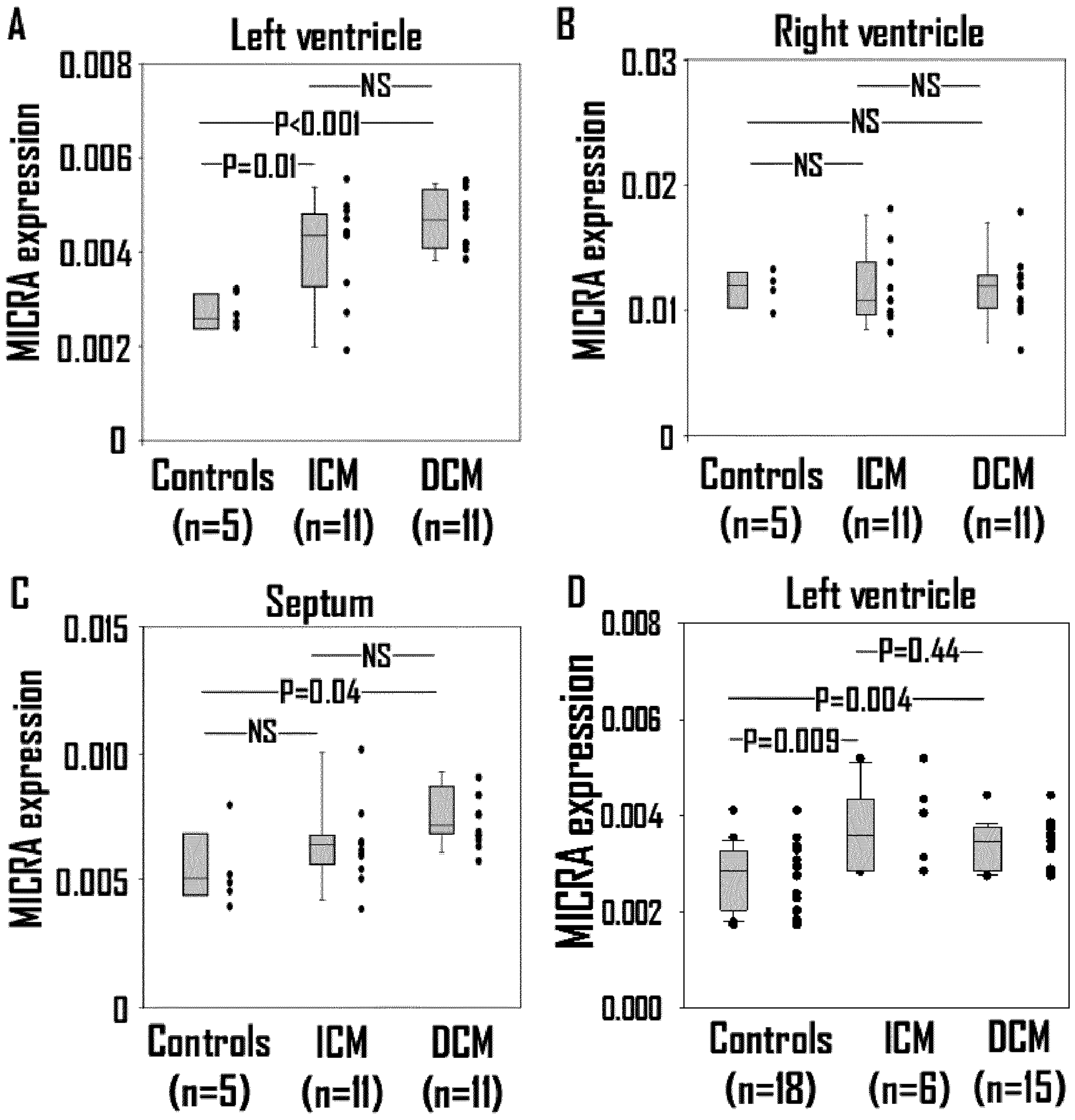
FIG. 3 provides exemplary expression levels of a circRNA, more particularly MICRA, in human cardiac biopsies. MICRA expression was measured by quantitative PCR in biopsies from the left ventricle (A), right ventricle (B) and septum (C) of 5 control donors, 11 patients with ischemic cardiomyopathy (ICM) and 11 patients with dilated cardiomyopathy (DCM). Normalized expression values (with GAPDH) are shown. NS: not significant. In (D) MICRA expression was measured in a second series of biopsies of 18 controls with no cardiac disease, and in the left ventricle of 6 patients with end-terminal heart failure of ischemic aetiology (ICM), and 15 patients with dilated cardiomyopathy (DCM).

To verify that MICRA is expressed in the heart and to test whether it is regulated during heart failure, biopsies from 22 failing human hearts (11 ICM and 11 DCM) and 5 non-failing control human hearts were used. MICRA was reliably detected in left ventricles (Ct values between 25 and 27), in right ventricles (Ct values between 22 and 24), as well as in the septum (Ct values between 24 and 25). In the left ventricle, MICRA was up-regulated in ICM and DCM as compared to control hearts (FIG. 3A). Expression levels of MICRA were comparable between the left ventricles of ICM and DCM patients. Noteworthy, all left ventricles from DCM donors had higher levels of MICRA than controls. MICRA expression was not regulated in the right ventricle (FIG. 3B), and slightly up-regulated in the septum of DCM donors (FIG. 3C).

Similar observations were made in additional human cardiac biopsies, independent from those used in FIG. 3A. FIG. 3D shows regulation of MICRA expression in 18 controls with no cardiac disease, in the left ventricle of 6 patients with end-terminal heart failure of ischemic aetiology (ICM), and 15 patients with dilated cardiomyopathy (DCM).

Therefore, in human hearts, MICRA is mostly up-regulated in the failing left ventricle regardless of the dilated or ischemic aetiology.

Accordingly, this demonstrates that MICRA is also a reliable marker for the diagnosis of heart failure.

FIG. 4 further illustrates other circular RNAs of Table 1 that are overexpressed in the failing heart and which can be used similarly to MICRA disclosed herein.

Expression of MICRA in Different Organs

FIG. 7 illustrates the expression levels of MICRA in different human (Panel A) and murine (Panel B) tissues. In human tissues, MICRA was mostly expressed in the brain and in leukocytes. In murine tissues, high expression of MICRA is observed in the brain.

| DNA Sequences encoding circRNA's of Table 1 |
|---|
| >GATAD2A_hsa_circ_0000917 (SEQ ID NO: 7)<br>TGACATGAAGTCCGAGAGGAGACCCCCCTCACCTGACGTGATTGTGCTCTCCGACAACGAG<br>CAGCCCTCGAGCCCGAGAGTGAATGGGCTGACCACGGTGGCCTTGAAGGAGACTAGCACC<br>GAGGCCCTCATGAAAAGCAGTCCTGAAGAACGAGAAAGGATGATCAAGCAGCTGAAGGAAG<br>AATTGAGGTTAGAAGAAGCAAAACTCGTGTTGTTGAAAAAGTTGCGGCAGAGTCAAATACAA<br>AAGGAAGCCACCGCCCAGAAGCCCACAGGTTCTGTTGGGAGCACCGTGACCACCCCTCCCC<br>CGCTTGTTCGGGGCACTCAGAACATTCCTGCTGGCAAGCCATCACTCCAGACCTCTTCAGCT<br>CGGATGCCCGGCAGTGTCATACCCCCGCCCCTGGTCCGAGGTGGGCAGCAGGCGTCCTCG<br>AAGCTGGGGCCACAGGCGAGCTCACAGGTCGTCATGCCCCCACTCGTCAGGGGGGCTCAG<br>CAAATCCACAGCATTAGGCAACATTCCAGCACAGGGCCACCGCCCCTCCTCCTGGCCCCCC<br>GGGCGTCGGTGCCCAGTGTGCAGATTCAGGGACAGAGGATCATCCAGCAGGGCCTCATCC<br>GCGTCGCCAATGTTCCCAACACCAGCCTGCTCGTCAACATCCCACAG |
| >NFX1_hsa_circ_0001844 (SEQ ID NO: 10)<br>GGACTGAATTGACTGTACCAAGAAGCATCTTCTGGGGGAACATGAGTGGGTTGAAGGGGAG<br>TATGCTTAATTTTTTCCACTTTGGGATTGTAGACCAGATTATAGAGGTTATGTATGGAAAACCC<br>AAAATATATTCCTAGGGGAAAGAGATGAAAACTAATACACTTATTAAGTACTATCTATGAAATC<br>ATATTTAAATTTCTCAGTAACCGTTGAAATAAGTATTGTCATCCTTTACCATAGACAAGGAAAC<br>TAAGGCTAAAAGCAGGCACGTGATATCCCTAAGTTCATACAATAAGTTGGACAGGTGGACTT<br>TAACCCATTTTGGCTTAGTCCAAAGCCTGTTTACTTGATATTACACAATGCTACTTTACTGTTT<br>TGAAAGAAGACCACATGGAACCTGATGATTGATACCCCTGAACTGTTAGCTGGCCTTAAATTT<br>TTGTAATAAAATGAATAGATGTATACATAGTACTTTATGGCCCAGGTGAGCATTTTTACTCGAC<br>AACACTTAGCTGTCATTGGCTATTGGTGTTTGGTTTTTGGACATGGAATAATGATTGATTAGT<br>CCTCCACAAGCACCTTGAACCCATCACCTTCACTGGAAACATAGTTCTTACTTAACAGCATGT<br>TTTATACAAAGTTCTAAGGAAAGTAATTTTTAGATTTGGCTTGGAGTCTATGAGTTTCATGGAT<br>GAAGTTTAATCTCTTTACTGGCATGTCTATTTTTTATGTCCTAGGTACTTTTAAATTCAATACAG<br>ATGCTGCTGAATTCATTCCTCAGGAGAAAAAAAATTCTGGTCTAAATTGTGGGACTCAAAGGA<br>GACTAGACTCTAATAGGATTGGTAGAAGAAATTACAGTTCACCACCTCCCTGTCACCTTTCCA<br>GGCAGGTCCCTTATGATGAAATCTCTGCTGTTCATCAGCATAGTTATCATCCGTCAGGAAGC<br>AAACCTAAGAGTCAGCAGACGTCTTTCCAGTCCTCTCCTTGTAATAAATCGCCCAAGAGCCAT<br>GGCCTTCAGAATCAACCTTGGCAGAAATTGAGGAATGAGAAGCACCATATCAGAGTCAAGAA<br>AGCACAGAGTCTTGCTGAGCAGACCTCAGATACAGCTGGATTAGAGAGCTCGACCAGATCA<br>GAGAGTGGGACAGACCTCAGAGAGCATAGTCCTTCTGAGAGTGAGAAGGAAGTTGTGGGTG<br>CAGATCCCAGGGGAGCAAAACCCAAAAAAGCAACACAGTTTGTATACAGCTATGGTAGAGGA<br>CCAAAAGTCAAGGGGAAACTCAAATGTGAATGGAGTAACCGAACAACTCCAAAACCGGAGGA<br>TGCTGGACCCGAAAGTACCAAACCTGTGGGGGTTTTCCACCCTGACTCTTCAGAGGCATCCT<br>CTAGAAAAGGAGTATTGGATGGGTATGGAGCCAGACGAAATGAGCAGAGAAGATACCCACA<br>GAAAAGGCCTCCCTGGGAAGTGGAGGGGGCCAGGCCACGACCAGGCAGAAATCCACCAAA<br>ACAGGAGGGCCACCGACATACAAACGCAGGACACAGAAACAACATGGGCCCCATTCCAAAG<br>GATGACCTCAATGAAAGACCAGCAAAATCTACCTGTGACAGTGAGAACTTGGCAGTCATCAA<br>CAAGTCTTCCAGGAGGGTTGACCAAGAGAAATGCACTGTACGGAGGCAGGATCCTCAAGTA<br>GTATCTCCTTTCTCCCGAGGCAAACAGAACCATGTGCTAAAGAATGTGGAAACGCACACAG |
| >FOXK2_hsa_circ_0000816 (SEQ ID NO: 5)<br>GTGCACATTCAGGTTCCCGAGCACAAACATCAAGATAACGTTCACTGCCCTGTCCAGCGAGA<br>AGAGAGAGAAGCAGGAGGCGTCTGAGTCTCCAGTGAAGGCCGTACAGCCACACATCTCGCC<br>CCTGACCATCAACATTCCAGACACCATGGCCCACCTCATCAGCCCTCTGCCCTCCCCCACG<br>GGAACCATCAGCGCTGCAAACTCCTGCCCCTCCAGCCCCCGGGGAGCGGGGTCTTCAGGG<br>TACAAGGTGGGCCGAGTGATGCCATCTGACCTCAATTTAATGGCTGACAACTCACAGCCTGA<br>AAATGAAAAGGAAGCTTCAGGTGGAGACAGCCCGAAG |
| >SNORD116-19_hsa_circ_0000585 (SEQ ID NO: 4)<br>GTGGTGTTGGCATGAGGAAAGGAGGTATCTTCGAGGGACAATCTTCTTCTTGTGCGATCCTT<br>GGAGATGCCATGAGGCCCCTGGACACATGTGGTGTGGGCTCCTTTGGAGGCTGTTGTATCC<br>CTTCTGAATGTAAGTGTCCACTTTCCAAAGTCCTGATTTTCCTCATTTTTGGGCATGAATAATG<br>TGCATGGATCGATGATGACTTCCATATATACATTCCTTGGAAAGCTGAACAAAATGAGTGAAA<br>ACTCTATACCGTCATCCTCGTCGAACTGAGGTCCAGCACACTGTTCATCAGGGGCTAGAGAG<br>AGAGACAACATCCATTTGTTGACACAGGCTGCATCAATGCTTGGGATGGGATCGTCTTTGGG<br>TGAAGTGGAGTAGCTGGGCATTTTGGACTTCTGTGGCTGAGAGACAGCTTGGTTGAAGCTCT<br>TCCCTCTGTGTGGCTATGTGTGTTATCGATTCATACCCCTTGGCTCCTGCACTCCCCAGAGG<br>AAGACAGTTACTGCTGCATGGGGACACAGCACAATGTTGTTCCCAGGCACTTCTTCGGCTCA<br>CTTTTATCCTAAGTCGGGGACATGGGAGTTCCTGTGGTGTATGGGTATCATCAAGGGCAGGC<br>AGTCGTGAGGAGGGTGGCAATACTGATTTGCTTTCTGCAGAGAAGCCCAGAGAGGGTATCC<br>ACGTTGAATTGTATGTCCATAGGAGGGGGAAACCCAAGTCCCGTGGCCCCTGAAGCATCCT<br>GGCAGTGGAAGGGGAGAGGGCCGTGCATGCGTGTACCACACAGCCTTCTGTCTGGGTCAC |

-continued

| DNA Sequences encoding circRNA's of Table 1 |
|---|
| AGAGCGACGACTGTGAGCCTCTTTCGGGCATTGTAGGGTGCCCATAGTCCATTTCATGATGA<br>CCTCAGGGTGCTGGGATGGGAATGTAATTGTAGGTCCACGTGCTCCTGCATCTCTGCAGACT<br>GACTTGGTTTGGAAGGTCTGTGTTGAGGAACCTCTGTGGGATACTTTTCCTTGGTGCATTTG<br>AGGTGTCTGATAATGAGTGTGTGGGTTTCTGTATCCTGGTGACTTCTACTCAGAAATGTGACC<br>CAGCAAGGTCTCTGTGCTTAAATACCTTAGTGGCTTGTGATGTTAGGTTATTTTCAAATTCCT<br>CCTAATTGTGTGTGACAATTCACACAAGTCTTTGTGAAATTGTCCTTGAATTGTATGACAGGG<br>CTAGTGTCTGTAGGCCAGTGATGGATAAGTTTTGGACTCCACAGCCATGTTCACAGCCAAGT<br>GGCTTAAGATGTATGGTGTTCTTAGTCATAGTGCCTTGGAAGCCCTGTAGGATTCAGCATGT<br>CTTGTGCTCTTCTGGGTCCCCGAGCTGTACCTTTGAGGAAAACCCAGAGGTGGAGGTTGATT<br>TGTGATTGAGCATGTTTCTCAGTGGGAAGAGTGTCAAAGGAGCCTGGGGTGAAAGTACTTCA<br>GGACCAAAGGAAAATTGCCCTTCACTCAAGAAGAGGCTTTCCTTGAACCTGTCCCCACTGAA<br>ATATCCTCATGGGCTTCATCTTCTCTGATGGCCAAAAGCAGGACTTTTGATTCAGAGGTGGC<br>AAATGAATGGTGTTGAGAGAGTTTGTTATGCTTGGTGCTCTGTAGCTGGAAGGAGCCCTCAA<br>AATTATTGTGTGCATGATAGCTTCATGCCTGCTTACACCCATGCACATGTCCCAGTAAGAGG<br>GGCTGCCTGTGGGAGATACATACACGATACACCACAGTGGGATGAATTGTATGGCCCTTGCA<br>ATGTGTGTACCTGCCTGCTGTTGTCAAACACACCTGTTTTTCCTCTGAACTTTCCAGGTGGCG<br>TGGGCATAGAAGGAAGGCCAGTGGCCACGAGGGACAATCTTGGTCTTGGGAGATCCTGGAA<br>ATGATAGGGAGTCCCTTGATATGTGTGGCATGGGCTCCTTCAGGTGCTAGTGGATTCCTTAG<br>GATGGTAAGTGTCCATTTCTCAGAAGCTCCAGATATTCCTCCTCTGCAGGGACAAAGACTGT<br>GCCTGGATCGATGATGACTTCCTTATATACATTCCTTGGAAAGCTGAACAAAATGAGTGAAAA<br>CTCTATACCGTCATCCTCGTCGAACTGAGGTCCAGCACATTGCTCTTACAGGGGCTAGAGAG<br>AGAGGGACAAATTTCATTTGATGATGCCCATTGCACCAAGGGGTTCTGTCCAGGCTTAGGAT<br>GGGGTCTCGTTTGGGCAAAGGAGAATGGCAGGGGAGTGGAGGCTATGTACACAGGAGATTC<br>CTTGTTTGAAGGACTCTATTTGTGAGGCCAGGGTACCACACATGCTGTCCGCAGGAGTAGGT<br>GAATGTGCAGTTGCCCAGGAAGAGTTAGCCTGTAGCCTGCCTCTGCATGGCAGTTTGTCCTT<br>GGGTCCTGGCTCTGGATTTCCATGTTCCTTGGAGGAGGATAGGTGATTTTGCTTGAGAAGAC<br>AGCACAGTACCATACTTTTGTTGTTTTTCTGCTCATTTCATCGTCCATTGAGGACAATGAAGTT<br>GTGGTCAGCAGGCATAGCTTTCAGGCCAGCGTGCCCATGTTGTGTCCCATGCATTGTGAGC<br>ACATGCATGTGGCATGAACACATAGGCTGCCACTCCAAGCTGAGTCTGATAGGCAATGAGAC<br>TCTGGCTTATCCTGATCCCGGTGTAGATCAAAGTCTTCCCAGTAGGATTGCATGGCCCCGAG<br>GCTATTGTGAGCTGCATTGCAGGTGTGGAAGCAAGGGTGTTGAGAGGGATGCTCAACATTA<br>GTGCTCTTTAGCGAGATGATGCACTATAAGGGCACCCTGAACCCAGACGTGCATCCCTATGT<br>ACGTGCATTTCTGTGTCCATAAATAGTTGAAGCCAGACAGCCAGATTCCAGATGTATCGCAG<br>GGGGCTGGATGACATGGCCCTTGTCACCTGTGTACCTGTCTGCCTTTCTGAAGCACGCTTGT<br>GTTTCCTCTACACCTCCCAGGTAGCATTGGCATGGAAGGCAGGCCCATGTTGGTGAGGGAC<br>AATTGTTATCTTGTGTGAGCCGCAGGGATACCAGGAAACCCCTGGACACAAATGGCAAAGGC<br>TTCTTTGGAAGTTGTTGGATCCCTTCTGCATGTAAGCAGTTCTTTCCCAGAGCGCTCTGATTT<br>TCCTCATTTGCAGGGACAAACACTGTGCGTGGATCGATGATGACTTCCATATATACATTCCTT<br>GGAAAGCTGAACAAAATGAGTGAAAACTCTATACCGTCATCCTCGTCGAACTGAGGTCCAGC<br>ACATTACTCCATCAGGGGCTAGACAGAGAGGGCCAACATTCGTTTGTTGATATGGGTTGCAT<br>CAAGGGGTCCATCCAGGCTTAGGATGGGGTCCCTTTGGGCAATTGGAAGTCACAGGGAAGT<br>GGGAGCTCCCATGCACAGGAAATTCCTTATTTGAAGGACTTCTTTCTCCCTGGGCGGGATAA<br>CTCACCTACTGTCTGAAGGACTAGGTGAATGGCAGGTGGCATGGAAAGAGTTTGTGGGTAG<br>TCTGCCTCTGGTGGCCAAGTTTGTTCTTGAGTCCAAGCTCTGGATTCCCAGAGGAAGACAGA<br>TCCCCTGGTTGCGGGGAGAGCACAAGCCTACACTATTCTCACTTGTTAGCTTGTTTTGTCCTT<br>GGCGGAGGACGTTGTATTTCCAGGCACCCAGCATAGCCTCTTTGCCGCATTTCCATGTCATA<br>TCCCATATGTTATGAGGATTTGTGTATTGCATGATCAGGCAGGCTTCTGCTCCAAGCTGGGG<br>CTGTCAGGCAAGGAGTCTCTGGGTTATTCCAAACCTGATTTAGGTCAGTGGCTTCCTCTTTCA<br>GGATTCATGGCCCCAAGGCTTTTGTGAGCACCATTGCAGGTGTTGAAGCAACGATGTTGAGA<br>GGGATGCCCAACATCAGTGCTCTTTAGCAGGATGGTGCACCTCGAGGGCCCCTGGCCCTGG<br>GACGAGCATCTGCGTGTCCATGCATTTCTGTGTCCATGAACAGGCGAGGCCATAGACAGGC<br>AAATAGCAGATGTGTCACAGGGGACTGGATAACATGGCCCTCGTGACGTGTGCAACCTGTCT<br>GCCTTTCTGAAGCACGCCTGTGTTTCCTCTGCACTTCACAGGTGGTGTTGGCATGAAAGGCA<br>GGCTTGTATCATGAGGAATGATTGTCATCTTGTCTGATTCTTGGAGATGGCAGGAAGCCCCT<br>GGAAACACATGGTGTGGACTCTTTCACAGGCTGTTGAAACCCTCCTGAATGTAAGTGATTTC<br>ATTCCAAAGCACCCTGAGTTTCCTCATTTGCAGGGATGAAACCTGTGTGTGGATCGATGATG<br>ACTTCCATATATACATTCCTTGGAAAGCTGAACAAAATGAGTGAAAACTCTATACTGTCATCCT<br>CGTCGAACTGAGGTCCAGCACATTACTCCAACAGGGGCTAGACAGAGAAGGCCAACATCCG<br>TTTGTTGACATGGGTTATATCAAGGCGTCTGTTCAGGCTTAGAATGTGGTCTCTTATGGGTGA<br>TGGGGGTCACAGGAGAGTGGTGGCTCCCATGTATAGGAAATTTCTTGTTTGAAGGACTGTCA<br>GTGAGGGTGGGTAACACATGCATTGTCTGCAGGACTAGGTGAATGTCCATGTGGCCTAGCA<br>AGAGTTAGCTGGTAGCCCGCCTCTGGTTGCCAATTTGTTCTTGAGTCCTTGTTCTGGGTTCT<br>CAGGTCCCACGGAGGAAAACAGATCTGTGTGGTTGAGAGGTGGGTACAAGGCCGCATCTTT<br>GTCATTTGTTGGCTAACTTTGTCCTTGGTTGAGGACATTAGAGTTTTGGTCACCAGGCATAGC<br>CTATGTGCCTTTGTGCCCGTGTTGTATCCCACGTGTTTTGAGGACATGTATTTTGCACGTAAA<br>GGTGAGCTCCTGCTCCAAGCTGGTTCTGATACCAAAGGAGTCCCTGGCTTATCCTAAACTCA<br>TGGTAGGTTAAAGCCTTCCTCCTTAGGGGTTCAGGGCCGCAAGGCTTTTGTGAGTGGCATTG<br>CAGGCGTTGAAGCAGTGATGTTGAGAGGGATGGTCAATGTCAGTGCTCTTTAGCAGGATGG<br>TGTACTGCAGGGGCCCCCAGCCCCGAGACGAGCATCCCTGCATCCATGCATTTCTGCCTCC<br>ATGAACAGGGGAGGCCAGAGACAGGCAGATAGTAGATAAATTGCAGGGGACTGGATGACAT<br>GGCCCTCGTGACCTGTGCACCTGTCTGTCTTTCTGAAGCACGCCTGTGTTAACTCTGCACCT<br>CCCAGGTAGCACTGGCATGGAGGGCAGGCACATGTTGGTGAGGGACAATTGTTACCTTGTG<br>TGAGCTGCGGAGATACCAGGAAGCCCCTGGACACAAATGGCAAAGGCTCCTTCGGAAGTTG<br>TTGGATCCCTTCTGAATGTAAGCACTTCTTTCCCAGAGCACTCTGAGTTTCCTCATTTGCAGG<br>GACAAATACTGTGCGTGGATCGATGATGACTTCCACATATACATTCCTTGGAAAGCTGAACAA<br>AATGAGTGAAAACTCTATACCGTCATCCTCGTCGAACTGAGGTCCAGCACATTACTCCAACA<br>GGGGCTAGACAGAGAGGGCCAACATCTGTTTTTTGACATGGGTTATACCAAGGCATCCGTTC |

-continued

| DNA Sequences encoding circRNA's of Table 1 |
|---|
| AGGCTTAGGATGGGGTCTTTTATGGGTGATGGGGGTCACAGGAGAGTGGTGGCTCCCATGT<br>ATAGGAAATTTCTTGTTTGAAGGACTGTCAGTGAGGGTGGGTAACACATGCATTGTCTGCAG<br>GACTAGGTGAATGTCCATGTGGCCTAGCAAGAGTTAGCTGGTAGCCCGCCTCTGGTTGCCA<br>ATTTGTTCTTGAGTCCTTGTTCTGAGTTCCTGGAAGGAAACAGATTTGTCTGGTTGGGAGGA<br>GAATACAAGGCCACATCTTTGTCGTTTGTTGGCTAACTTTGTCCTTGGTTGAGGACATTAGAG<br>TTTTGGTCACCAGGCATAGCCTATGTGCCTGTGTGCCCGTGTTGTATCCCATGTGTTTGGGG<br>GACATGTACATTGCATGAACTAGTGAGCTCCTGCTCATTGCTTCTGATACCCAAGGAGTCCC<br>TGGCTTATCCTAAACCCAATATAGGTTAAAGCCTTTCTCATTAGGGGCCCAGGGTCCCAAGG<br>CTTTTGTGAGTATCATTGTAGGTATTGAAGCAACGATGTTGAGAAGGATGCTGAACATGCTCT<br>TTAGTGGGATGACGTACTCTGAAGGCTCCTGACCCCCAGATGAGCATCCTTGTGTCCGTTAA<br>CTTCTGTGTTTATGAACAGGTGAGGCCAGAGACAGGCAGACAGCAGATGTATTGCAGGGAG<br>CTGGATGACATGGCCCTTGGAACCTGTGCACATGCCTGCCTTTCTGATGCACGTCCATGTTT<br>TCTCTGCACCTCCCCGGTGGTGTTGGTATAAAAAGCAGGCTTACATCAGCAAGGGATGATTG<br>TCGTCTCATGCGATCCTGGGAGATGGCAGAAGTCCCGGGACACATGGAGTGTGGGCTCTTT<br>CGGAGGCTGTTGGATCCCTCCTGAATGTAAGTGATTCCTTCTTAAAGCATGCTGATTTTCCTC<br>ATTTGCAGGGGCAAGGACTGGATCGATGATGACTTCCATATGTACATTCCTTGGAAAGCTGA<br>ACAAAATGAGTGAAAACTCTATACCGTCATCCTCGTCGAACTGAGGTCCAGCATACTGCTCAT<br>CAGGGGCTAGAGAGAGGGACAACATCCGTTTGTTGACAAGGGCTGTGTCAACACTTGGGAT<br>GGGGTCGTCTTTGGGTGAAGTGGAGTAGCTGGGCATTTTGGACTTCTGTGGCTGAGAGACA<br>GCTTAGTTGAAGCACTTCCCTCTGCGCAGCTATGTGTGTCCTTGATTCAAACTCCTTGGCTCC<br>TGCACTCCCCAGAGGAAGACAGTGGCTTCTGCATGGGGACACCACACAATGTTGTTCCTGT<br>GCACTTCTTTGGTTCACTTTCACCCTCATTTGGGGACGTGGCAGTTCCCATGGTGTTTAGGTA<br>GCATTGAGGGCAGGCAGTCCTCAGGAGGATGTTGATGCTGATTTGCTTTCTGCAGAGGAGC<br>CAGAGAGGGTATCCATGTTGAACTTGTATATCCATAGGAGGAAACCAGTCCCATGGCCCCTG<br>AAGGGTCCTGGCAGTGGGAAGGGGAGAGGTCTGCATGTGCATGTACTGGACAGCATATTCC<br>ATGTGGGTCATGGAGTGATGACTGTGGGCCTCTTTCGGGCATTGTAGCAGGCCCCCATTTCA<br>TTTCATGATGACCTCGGGGTGCTGGGACAGGAATGTGATTGCGGGTCCACGTGCTTCTGCA<br>ACTCCTCAGACTGACTTGGTTTGGAAGGTCTGTGTTCAGGACCCTCTGTGAGATGCTTGTCT<br>CCATTAGGCATTTGAGCTTATATCGGCCCAGGGTTTCTACCTATCGTAGGTTGTGCATACTTT<br>GCCTCTGAACCACTCAGGCACCTCGATGCAGTCAACGTGCCCGATTATAAGAGTGTGACTTC<br>CCATATCCTGGTGATCTCTACTCGGAAACATGGTCCAGGAAGGTCTCTGTGCTTAAATACCTT<br>AGTAGCTCGTGATGTTAGGTTATTTTCTAATTCCTCCTAATTCTTCCCAGGAGTCTTCTTTGTG<br>AAATAGTCATCTTGTTGTAGGACAGGGCTGGTATCCACAGGCAGTGATGCATAGGTTTTGCA<br>CTGCGCGGCCATGTTCAAAGGCAAGTGCCTTAAAATGTATGGTGTTCTCAGCCACAGTGCCT<br>TAGAAGCCATGTGGGATTCAGTGTGTCTGGTGGTCCTCTGAGCTGCACCTGTGAGGAAGAC<br>GCTGAGGTAGAGGTTAAGTTGTTATTGAACGTTTTTCTCAATCTGAAAAGTGTTCAAGCAGCC<br>CAGGGTGAAAAGTCTTCAAGACTGAAGGAAAATTGCCTTTTGTACTGGAAGAGTTTTTCCCCA<br>AAACTCTCCTCATTTAAATAGCCCTGTGGCTTGTGTCTTCTCTGATGACCAAGAGGAGGGCTT<br>TTGAGTCAGTGATGGCAAATGAGTGGTTTTGAGAGAGTTCTTACACTTAGGGCTCTGTAGCTT<br>GATGGTGCCTTCAAAATTAACACGTGCCTGCTATCTTCATTCCTGGGTAGACCCATACACCCA<br>TCCCAAAAGGGGAGTAGCCTGTGGGAAGCACATATGGGATATACCACAGTGAGTCGAGTGG<br>AATGGCCCTTTTGACATGTGTACCTGCCTCCCGTTCTTAAGCACACCCGTTTTTCCTCTGCAC<br>TTCCCAGGTGTTGTGGCCATGGAAGTAAGGCCAGTGGCTACGAGGGACAGTCTTCATCTTG<br>GGAGATCCCTAGAGAGGGCAGGGAGCCCCTTGACATGTGGAATGTGATCTCTGTTGGGTGC<br>TGGTGGATCCCACAGGTTGGTAAATGTCCATTTTCCAAAAGCCCCTGATGTTCCTTCTTTGCA<br>GGGATAAAGACTGTGCATGGATCGATGATGACCTCAATACATGCATTCCTTGGAAAGCTGAA<br>CAAAATGAGTGAAAACTCTATACCGTCGTCCTCGTCAAACTGAGGTCCAGCACGTGGCTCCA<br>ACTGGAGCTGGAGAGAGAGAGACAACTTCCATTGGTTGATGTGGGTTGCACTAAGCCATCCA<br>TCCAGGCTTAGGATGGGGTCCACTTTGGATCAAAGGGAGTCACAGGGCAGTAGGTGCTCCT<br>GTGCAGAGGAGATTCCTTGTGTGAAGGACTTCTCTTTGTGAGGCTGGGTAGCACGCACAATG<br>TCTGCAGGACTGGGTGAATGTGCAGGTGGCACAGAAGAGTTAGCCGGTAACCCGCCTCTGT<br>GTGGCCAGGTTTGTCCTTGAGTGCTGGCTCTGGGTTCCCTTGTTCCCCAGAGGTAGATAGCT<br>CCTTGTGGTTGGGAAGAGAGCCCAAGGCCACATCTTTGTTGTTCTTTGGCTCATTTTTTTTCA<br>TGGCTGAGGACTTTTAGTGCCCATGGTGTTTTCGTAGCAGCAGTGGAAGTCAGTTGTGAGG<br>AGGTTGGTGATGCTTATTTTCTTTCTGGAGAGTACCCTGTAGATCGGCTCCATTTATGATTTG<br>TGTGTCTCCAGGGAGAAACTGAAATCCCATGGCTGGTGATGGATACTCCAGGTGGGAATGA<br>GAAAGCGCCATACATGTGTTGACTTGGTACCCTAAGATGGGGATGGTCCGCCACATTTGCGC<br>GTCTGTTTTGCATGGTGTGTACTGCACATCACAAATGCCATGTTGGCCTTAGGGTGCTGGGA<br>ATGGAATATGATCTGATGTCTACATGGGAGGGCCTTTCAGCAGATTGCTTTTGTTTCCTGACA<br>GTCTTTGCTCCATCCCCAGTCACACGTGTTTTTCTCCAGGGAACATTTTATTGGAGTATATCA<br>GGTCGATATCAGAAAAAAAAATGTTGTGGTTATCCCAACATTAAGTGTGGTGATGTAACAGCA<br>GTGTGGATGGTAGCTCAAGTGAACAGTGGCAAAACCAAAATATATTGGTTTACGTAAGTGAC<br>CCTATTCTCTCCTATGTTTGAAGTCTGGTATGCATCTCTTTCTGCAATAATCTCAGTGATCTGG<br>AAACTTTCAGGAGGTCTTTTTTAGATATTTTATGTCCTTGTGGTTGTACTCATACTCCCTGCAG<br>TGCTAAGTCTGAGTCATTCTGCTATCCTAGTGCTACTGGAATTTCTATTGTTTTGGGGGCACT<br>GTCTGGTCATTGTGGATACCTCTCTTGGGGCCCTTTAATAAGAAGTATGTTAGAGGTCGGTTT<br>TGGGGCAGTGTTGACCTCCTGCCTAAGGTCAAAGGCAGTTTTCTTCCTAAATCTTATTGCAG<br>GATTCACTGCCTGGGGGTTGTGTGACAGGGAGAGCACAAAATTAGGGTATCCCATGTGGAC<br>TTGTGTCCAGTATCAAGGCAGTGTTGGATAATTTTCTATATCCACAAGGCTCCCACTGGACTC<br>TTTATGTCCAGCAGACATTCACAGGCCAACTTTTCTCTTACACAGGGGGCCTCATTCCTGCCA<br>TGTGTAGCTTCCATGGAACCATCCTTCAGGTTTTAAGTGCAAGGATTTCTCTCAAGAGTTTAA<br>TTTGTTTCTTTAAGACACCGTTTTCTTTTCTATAAATTCTGCTTTCTGTGGTTTGTAGCACAGAT<br>GAAATTGCCAGGTCATATTCTACATTTCTGCCCAATCTTGGATTAGTGAGCCTTTGAAATATG<br>TTCCTTGATCACTGGCAATGGTTCTTGGAATACCAGAACTTAGTTACAAGCATTGCAGACCTA<br>CAGAGGTTTGTTGTTATTTTTAACTGCATGAAGCAGTGGGTTTGTTTGTATCTTGTCACTCAC<br>GGCTGTCAGCAAAACTTAGGTGTTGCTAAACCAGACCACACCCATGAATTATAGTGCCTCTG<br>GTTCCTTCTGTAGTAGCCTGTGGGAAGTAGATACAGGATGCACCACAAGGGAATGAATGGCA |

-continued

| DNA Sequences encoding circRNA's of Table 1 |
|---|

TGGCCCTTGAGACCTGTGTACCTGCTTGCCTTTCTCAAGCACACCTGTTTTGCCTCTAATTCC
TAGGTGGTCTGGCATGGAAGAAGGCCAGAGGCTGCGATGGATCATCTTTGTCTTGGGAGAT
TCCTGGAGATGGTGGGGAGCCCCTGGGCACGTGCAGCATATGTGGCGTGGGCTTCTTCAG
GTGCTG

>FBXO34_hsa_circ_0000540 (SEQ ID NO: 9)
TGGTTGCAGGTTGTGAGGTATGGAGATACTGAGGGGTACGAGGCACTGTTTGTGGTGACAT
GAGAGCCACTAGCGGACAGAGACTGGGGAGAAGGATTGATCAGCTGGCGCATTAGCCCCAA
GATGCAGGTGAATTTGGGAACAGAAAGAGGGCCAAATGAGATGTTTGTGAAAATACTTTGTC
GATTTAAAACATTCCTTCCAGCTCAGGTGCTGTTATGTTTAGGGAAGATGTGCGTGTTTTCTC
TTTCTAGTGGGCTATTGTTAGCTACAAGGTGACCTTGCCTCCTGCTTTGAGGGAGAAGGAAA
AAGCTGGACCCACAAGACACAAATCCCAGCAGTCTGTGGTTACTGCTGGAATGATTACTGTT
CTTTATTTGTACTATTAGTTGTCTCTAAGATTGGTAACAGGAAAGTGAGAATAAGCTTACTCTC
AGAAATTTTTGTTGAGGGAGTTTTGTATAATTTCTGACTATTACCACATTCCCCTTTACTTCGA
CCCTCTTGGTTTTGCTGTTTGCTGTGCTCTAGTTTTACCATCTAATAACCCAGCACTAAAATCT
GATCTTGGGTATCAGATTCTCCTTTGTGGTTTGGTTTGTTAATAATTGAAGTACCTAATGGTTC
TGGGTGTGAACTGTGCATACTTGACAATCTAGAACCAGGGAAGTGAGTTTCCTATTGAAGTA
ATTAATAAAACCTTGTGGCTCTTAAAAATATATAAAAACTGTTACACAGAAATAACCAAAATGT
AAACTTAACAGGATATAGTTTAATTATGTTTTATAACATAAACCTTAAAGATAGAAGTATTTTT
AAGCTTGTTGGTGTCCTGTTCCTTTCTAGTTTGGGTGTGTAGGAGTCTTTTTTATCAGGAATTT
TGTTAGTGCTAATGCTGGGGTGGCTTTTTTTTTTTAAATCTATGTAAACATGACCCTATTAGAC
AGCTGTGTTTAATGTAGTAAAGACTCATGGGGAGACTTTATAGTGTTTCTTGTTGGGACTTAG
TGTCTGTATATTTTAGTATTTAAAGGATGTGGTTTGGTGCTTTGAAAATGAGAGGGAGGTCAC
CTAACTCATAGCTGAATGCCTGCGTGTCTAGATTGTTCCGTCCTGGAGGTTATTAACAACATG
AAAGTTGTTTTTATTCTAGTTAAACTGATAGTATTAAGTTAAATAACTTTATTGTGGAAGTGTTT
GTTTACACATGGCTGCTGAGTAGAATTTTCCTTAAAATCTGATTACATAGGAATGTTTTAGTAA
ATAGAGTGCTGGAAAAAAGCTGCTACACAAGCCAGAGCCTGTTGTGCTTTGCAGAACAGTAA
CCAAGATGAAGAGTGGCCTCTTTTTCTCCACCTTTTCCACCGCTCATCTCAGAGAAAGCAGG
GCGCTAATCAGGTGGAGCTGCTTAATTGCATTAAGTTCATGGGCTGCTCAAGGGTTGATTAG
TCAGACTCATAAACTTCCAGTTATGAGATGCTTGCTGACTGGCTGGTTTAAGTCCTTAGGGTT
TGATGCACATTCACTCTAATGAGTACTTACATGTACAGGGCACTGTGCTGTGTGCCCTGTGAT
GGACACAGAAAAGAATAAGATTACTTCTATCTTGAAGACAGGGTAGAACCTGGGAAGTGTCC
CAGGGTAGAAACTGGGAAGGCACAGTTCTGGGAATTCAACGGAGGCATGTAGTTAGTAGCC
ATTGGGTAATATTGATGGGGTGGGGGTGGGGCAGTAGATGTGATCTGGGCAACGAGGAGCC
AGTTGGAGAAGTGGTTTCAGTAGTTGCAGTGGGTAAAGCATGATAAAGATGCTCACAAAGCA
GAGAGGAAAAGTAAAATTGACAGGATCAGGCCACTGTGAACATGAAGGGCAAGTTAGAGGA
ACTCAGGCGGAAGCTCTTCATCAGGAGCCCTGGAGCTTTCCCCAAAATCCTACCAAAATCAC
TTATGTATGTGCTTTGGTATTTTTGGGTGGCAGAGAACTTAGACCTTTTCTCACATGTTCGGA
AGGGTCCAGCATCCAAAAAAGATTGACCACTGCTGCGCTGAGTTTTCATCCATTGGTGACAA
GATGGTCAGACTTCTAGAGAAATAAGGTAGTTTTGTGGTAGAACAAACTCTTCCTTGTGGGA
GGTATAGTGGGATTTGGGGAATAGGGTTTATGAAATGGTCCCCAGAGTGGGATGGCTTGCC
TTTTCAAACTGGGTTTCCCACCCAGCAAGTTAAGTTGACCCATTGCAGTGGATTGAGTGGAG
GGCAGGTGAAGGGCAGGTGTTTTCAAGTCAAAGGAGTTCAGGTGAAGGGCAGGTGCTTTTA
GTCAAAGGAGTTCCTTAGCATTATTTCCTCCTTTATTTGGAGATCAGATTGAAGATGTAGGGG
ACTAGAATGCAGTTGTAGTTTGTGGTGTTTACTTTTTATGGAAAAGTGCCTCTTATGTGAAAA
GTCTTCTGTGCTTGATCCTGGGGGTAGGGGGGTTATAAAAATGTCATACCTGGGATCCTGCC
CTTAAGGAGTTGATGGTAGGTAATGCTTTCCTTTGGCTTTTTGTTCATCTTGAGTCTGTGTAT
GTTCAGTTATCTTCAGCCATTTCCTGGGCAATGGGAAACATTTCTGTTAAAACAAACTTCTGA
CTTTGATCTGTGACTTATATTTCTTTTTAGATAATGAAGAACCACTGGGATTAGAGGGTGTATA
AAATACAATAATAAGTATAGTGTATGTAGGAACCTCTGTACAACCAATTTGGTGACTTTTAGG
CAACTCATTTGACTATTTGACTGTTTGTTACATGAGTGTGCATTTGGCTTTGTTTAAAATTCCT
CTATAAAGCACATTTTAAAAAATGACCCAGTACTTAGTATATAAGATGAACTGCCATTTGTATA
ATTGATCATTTAAAAATGCTTATTATACTTTTAATCAATCAGTTTCCATGTTTATGAAATGGGAA
TAATTATTATATCTAGCTCATAGAATTGTCCTGAAGATGAAATTTATATCCATATATACATAATG
AAGCTCTTTAGAGCAATGTATAACTACATGCCAACTGTTCAAAAAATATTAATGGCTACATCAC
TATTAATATTTTAAAATTAGTACTGTCATTTTCCCTTCCTACATGACTGAATGTAGGAGGTGAC
TATTTTTGTTATAAAAGGATTTCCAATGAGATACCTTTGAATGGTAAAATTTCCTATGCATTTAT
TTAAATGTTTATATATATATGTCTTTAAAGTATGAAAGTTAAGTGCACTTATACAAGGCAGATT
CAGGTACTAATTAAACTGCTCATTTAGATTACAGAATGAGGGACTGAAAATTATATGTATTTAA
TTAGGAATTGGATTGATTGGTCTTGACTGCTGTTGTCTTTCAGTTCTTTTTTATTGTTATACTTC
CCATGTGTTTGTCTCCTTTTCTTTTTATCTTTTAAAAATTGCTTTCTGATTTATTTCCTGTTCAG
TTTTCAGTAATGGGTGTAGAATAGGGCAAGAACTTATGTTGGTGCCCGTTGTTTGAACCAGG
AAGGAGCAACTGCATCAGACAGCCTGGGGCTCAGTTGGGAGGGACTTCAGATCAGTCCCTG
CAGAGCTGCCTGGCCCAGGGAACCACTGAATTCCAGTTTCCTAACTCCAAATCGGACAGTTT
GTGGGTCTACACTGTATGTACATAATGAACATTTTAAGGCTCATTCATCCAGTGTTTTCCACAT
GCTCCCATTTGTTTAGTTCTCCTTTTTAAAAACCAATAATTATGGAAAAATTTAGCTATGTACA
GAAATAGTAGTGAGAAACCCCCCACTTAGCCATCATGCAGCTTCAGCAGTTGATCATCTCATA
GCCAGTCTTGTTTGCTCAATACTCCCAACCATTTCTTTTCTCCCATTTTATTTTGCAGGAAATC
CCAGACATTATATCATTTAATCTAAAAGTATTTCAGGATGTATCTGTAAGAGATGAGGACTCAA
AAATGCATACACACATTTTGAGAACTTCCCAGAAATGTAAAAAAAAAAAATGCTATACACATAT
AGAATATATACATGCACGCACACACACACACACACACACACACATATATACTATTTTATGGTC
TGTCTGACTCAGAATCCTATGTGGTGTGTTTGGTTGGTAGGTCTCTTCACTCTTTTTTTTATTT
TATTTTTTTTTTTTTTTGAGACAGTCTCACTCTGTCGCCCAGGCTAGAGTGCAATGACACTAT
CTTGGCTCACTGCAACCTCCACCTCCTGGACTCGAGATCCTCTTGCCTTAGCCTCCTGAGTA
GCTGGGACCACAGATGTCCACCACTGTGCCTGGCTAATTTTTGTATTTTTAGTAGAGACAGG
GTCTCACCATGTTGCCCAGGCTGGTCTCTAACTCCTGAACTCAAGGGATTCACTCACCTTAG
CCTCCCAAAGTGCTGGGATTACAGGCATGAGCCACTGCACCTGGTCCATGCTTATGGTTATA -continued

| DNA Sequences encoding circRNA's of Table 1 |
|---|
| TTTTAATGCTATTTTCTTCTATTCTCTAGCATTTCTCATTCTATGGAACAATTTTTTGTAAATAAA<br>TCCGTTATAAATTGACACCACAACAGTATATCTGTGCATGTTCTCTTCCATGTGTTCTGTATAG<br>TTGTACCAGCCTTACTCTTTGATAATGTCATCGTCCTCAGGCCTCCGCTCAAGACTATCATAT<br>TCAATTTTTGAAGTCTCTTTTTGCCAAAAATAAAACTTGAATGTTTCTAATGATGGCTGCTTTTA<br>TTGCTAAGTTGATTTCAATACATTAGAAAATTACAGATTTGGAAATGAAAAGACTAAGGAATTG<br>ATGCATCTCTCTCAAATGTGCCTTGAGGGCAGAAATTCCTCAGTTTTGTTCATGCTGAAGCCG<br>CAGGCTAGCACAATATCCGACACTTAGAGGGAAGTTAAATATTTGATAAACAAATGAATTTAA<br>TTTTAAGTAAGGTGTCAAACTTGAGGCATCCAGAATTGAACCTGAAGCCACAGTTCTGCCTCC<br>TTTCACAGTCACACATCTTATACTCCACTTACCACTTGAAGATAAGCTTGCTGAGGAGTACCC<br>TGCCATGGGCCCTTCAGAATCTCCTTTCCTCATTGCATAGTGTAGTGGTAAGAGCGTAGGCT<br>TTGACTCCTGACCGCACACATATTGAGCTCTATGATATGCTTCCTGTGCGAACTTAGCAAGTT<br>TCTTAACTTGCCTCTGATTCAGTTTCTCCATCTACAATTGGAGATAAGAGTATGTACTTCTTTT<br>TTTTTTTTTTTTTTTGAGATGGAGTCTCGCTCTGTCGCCCAGGCTGGAGTGCAGTGGCACGAT<br>CTCAGCTCACTGCAACCTCTGCCTCCCGGATTCAAGCAATTCTCCTGCCTCAGTCTCCTGGG<br>TAGCTGGGACTACAGGCACGTGCCACCACACCCAGCTAATTTTTTGTATTTTTAGTAGAGAC<br>GGGGTTTCACTGTGTTAGCCAGGATGGTCTCGATCTCCTGACCCCATGATCTGCCCGCCTC<br>GGCCTCCCAAAGTGTTAGGATTACAGGCATGAGCCACTGCGGCCAGCGAGTATGGACTTCT<br>TTTATGGGTATTGTGACCTTGATCTTTGTAAGTTCCTTAAGCCATCTCTGATTCAGTTTCTTCA<br>TCTACAGTTGTAGATAAGAGTATGTACTTCTTGGGGTTTTATGGGTATTTTGAGCTTAAAACA<br>GTACCTGGCACATAGTAAACATTGTAGAGGTATTAGAGCTGTTATTATTCTAGAATAAAAACA<br>AGTTATTCTCCTCTTACTCATTTTTACCTTTTATCTCTAGCTCTACCTTGGTTTCTTTTCTTAGG<br>CCTAAAAACAGGCCAGGCGTGGTGCCTCACGCCTGTAATCCCAGCACTTTGGGAGGCCAAG<br>GTGGGTGCATCACAAGGTCAGGAGATCGAGACCATCCTGGCTAACACGGTGAAACCCCATC<br>TACTAAAAATACAAAAAATTAGCTGGGCATGGTGGCAGGCGCCTCTAGTCCCAGCTACTCGG<br>GAGGCTGAGGCAGGAGAATGGCGTGAATCTGGGAGGCGGAGCTTGCAGTGAGCTGAGATT<br>GCGCCACTGCACTCCAGCCTGGGCGACAGAGCGAGACTCCATCTCAAAAACAAAAAAAAAC<br>AAAAAAAAAAAAAGCCAAAAAAAACCCCCCAAAAAAACCAGTTCTCTAAGATACAAAATCCTTG<br>CCATAAAACTTGCACGCTTGTCTTGCTGGTAGCAGTGAAAATTAGCATTATCCCTTTGGAGAG<br>TGGTTGGGCAAGATATATCCAGTTGTGAAAATACACTCTGACTCAATAATTTCACTTTTGGAA<br>ATATTTTCTAAGGACATACCCTTAAATGCATAGGAGACAGTATTCATGAAAATGTTACAATGTC<br>CAGGTTTAGAGGGAATGGTTAAATATATTCTGGTACTTACACATTTACAATATTGGTTTTGAAG<br>ACTATGTAATATGGAAAATGTCTCCCTGTGATAAAAAGTACATTGTATGTACAATATGATCATA<br>ACCATATTAAGTAATATATACTGACATTCAGGAATTTCCCTAGGGTAGGACTTGTAACTGCTC<br>CTTTAATCACCTGCCCCCCCCCCCAATCCTGGATCTATGCTAACCTGGTTCCAAAGGCCCAA<br>ATTTTACCTTGAAACTAGGTGCTCTGTATCCTTTGTCGAAGCCATTATCCTTTTTATATGGCTT<br>TAGGAATTCCAAGTTTTGTCAGATTCTTGCAGAATAATACACAACAATGAAGATTCCCTCTGT<br>GTACTTAAGGAATAGTTGTGTTTGGAGGATAAGACAAATACACCAGATAACATTACAGTTTGG<br>GCTCTTGGTGCCCAATGATTGATTTATCTATAGTATAGATTTATTTCTCACAGTACCTCTTGGA<br>ATGCTCATTTTTAACCCCAATAGTTAAATTTGCCTTGGTAAGCTACAAAAACAGGCACCAAAG<br>CAGCAATGTTTTTTAGTTTTCTGTTGACCATAAATCTCGTTTCTTTACAAGTAGTAATTCTAAAC<br>AGAGTATACCTTAACCAGCCAGTGCACATACTGCTACTTCAGTCTTGGTTCAGCAGATCTTAG<br>AGGCATGTGGTAGAAGGAAGAATAGTTACTCAACAGGTGAGCAGGCAGGACAGTGGTTTTG<br>GCTTTCTTTGGTAAACACTATGGGGCCTATTTCTGAAGTAATTCCCCACCCCCTTCACTCCCA<br>CTCAGTATTGCTGACAGAAGTCTTAACTTGCCAAGTCTTTTGTCTACATTGATGCTATAAGCA<br>AACTATTATTTTTAGAGACCAGGTCTTGCTGTGTTGCTCAGGCTGGACTCAAACAACTGGGCT<br>TGTAGCTACCCTTCCACCTCAGCCTCCCAAGTTGCTGGGAGTACGGGGGTGTGCCACTGTG<br>CCTGGCTTGCAAGCAAACTCTTTTGCTTGGTGCACTAATACTTGTTATCCTGAATTTTTACCAA<br>CGTTTGCTTGCTTTTGAGACCAGGTCTCTCTGTTTCGCCCTAGCTGGAGTGCAGTGGCATGA<br>TCATAGCTCACTGCAACCTCTAACTCCTGGGCTCAGGCAATCCCATGGTCACCTCCCAAATA<br>GGACTACAAATACAGGCCATCATGCTTGGCTTTTTTTTTTTTTTTGAATGGGGGTGGTACATA<br>GGGAACCTCCCTGTATTGCTCAGTCTGATCTCGAACTTTTGTGCTCAAGTGATCCTCCTGCCT<br>TGGTATCCCAAAGTGCTGGGATTACACATGTGAGCCACCATGCCTGGCTGGCTCGTAATTTT<br>TATTTTAGCCTCTTTTTTTCTTTCCCTGGGGTCAAGCCATTTTAAAATTCAGTTACGTATAACT<br>GTGTTAATGGGCCAGCCTGTGCCCAGGTGGCATGTGTTAGGTACTTGGCCTAAGATCATTGT<br>CCAGCCAGGGATTTGTGTGTGTGGTGGCAGATGTGTGCGGTGTCAGGTTGCATTTATACTCT<br>AGAATTAGTAGCTGTACTCTTATTTTTCATATCAAATGTTATTTGACACATAATGGATTTTTGAA<br>CTGGATTCAAGGCTAGCCTTGGAATCTTGAATATTATCCCTTAAGAGAGAGCCTTTTGTTTGA<br>GTTACATTTTGGTCAAATAGGGCACATATTAAAGCACTGATCAACTCTTTGAAAGTACTGCAA<br>GTGATGTCAGAAATTGCTATTGCCTTAAAAATATTTTTAAAAAATTTATGTTTACATAAAAATAC<br>ATGTTAAAGAAAAAACTGATACTTGTTAAAGGTGGGCAAAAAAGACTATTCAGGACCATCGCG<br>ATAAGTATAGGGATCACTGCAGCGGGGTCTTGCAGCAAAGGAAAGAGGTTGGGCTCAACTC<br>CAAATACATCATGGGCAAGGAGCAGGATAGGGGTCAGTTGAAGGTAAACTACTAAGAGGAAA<br>CATTTGGAGTAAGGGGGATTCTGGCTAAACCCATCTAACAGGATTCTTGCTGAAGACAAGCC<br>AGGGTGATCAGACATCACCTGGGGGATGGTGGAAAATGAAGAACCTGATCAGATATTGAAGA<br>TGGGAGGGGGTCTTTTGCTAAAACTGGATTTTGTGAGAAAGTGCACAGATGGGCCTAGAAGA<br>AAGTTTAGAATCCTTACTCAAGTTTGGCCAAGCAAAGGATCTTTGTCATATGGAAAAATGATT<br>GGTTTCAAAGTAAAAGCAAGCATCAGCCCACTCAAGGAAGTAGTGGTTTGCTATGCAAAGGG<br>ATAGGAGTTTTATTTTCCTTCAGTTTCTGTAAAAAATATTAGAATAGGTAAAATATGCAAGAGA<br>GTTGTTAATAGGAACTCCGAATATCTGAAAATCCTTGGAAATTAAATTTTCCTGGTAATGCTCA<br>ATGTATTTTTCAAAATGTATTAATTTTTTTGGACTTTAACTTTTTATGAGGTTTCATCTGCATTTT<br>GTTGTTCATTCTAGTGGCATTTACCACTGGTAGGCTTTTCATTTGCCTGCTTAGCAGTAAATG<br>TGATATGCTGGAGTTTTGTGGGTGTTTGGCATTATGTCATAGGAGCAATAGGAAATGACTAC<br>GGATTAACTTAAACATCATTAAGTTTAACAAAATGGAATGCTTTATTTTGTCTCTATCCTGAAG<br>TGTTATTTAATAATTCACAACAGCTTAAGCAGAAGTTCTTTCCTCCAGGCCCTTCTCTTCCCTC<br>CCTACTCCAACAAAAGTGGGCTGGGGAACTGTGTAAATTTGCATAATATTACTAATTCACTAT<br>TTTGTAATACTGTCAAACTATTAGGTGTTGCATTTATTGCGAGCACAAAAGAAAACCAAAGTG<br>TAGTGGCTGTCATTCCCAACTTGTCAATATTCCTTTTTAATATGTTCTGGATACTTTGTTGTCC |

-continued

| DNA Sequences encoding circRNA's of Table 1 |
|---|
| CATCAAACTTATCATAGACCTTTCTCTACCTTCTGGAAGTTAGCTTCATTTGGTCAATATTATA<br>GATAACTTTGAAGCAGGTAGGTGCTGTATTTAAATCCCATTGTGAATTCTAAGATGGAAGCCG<br>TGAGCAGTTTTTGAAAACCATACATGTGTTTCCAAAGGCCATTCTATTACTCAGTATCCATTAA<br>CAGACAATAAAGGACTTTTCTGTCGTTCGCCACTAACCCTAACCACCCAGTCCTCATAAGGC<br>AAAATTAAGAAGTTACATGAATTGATTTTAGAGAATATTCCCTAAAAATAAAAGGGAGTGGACT<br>GCCTCCCCGAAAAAGTCATCCCCCAATATTTTGAAAGTTAATTTGAGAAATACTGCATTTTCT<br>GACCGATAGGGTTATTTTTTCTCCCTTTTTTCCTTTTTTAAAAAAGGCATGCTGTGGGAGTTG<br>GATGCATTTTTTCTGTCAGTGCTTAGAGACATGGAGGGGGAAGTCTTTTCTTGTGCCTCTGC<br>CTATATTCACACCCTCCTGGTCTTGGCATTTTTTCCAATTTAATAGCCATTGAAACAGCCTTTT<br>ATATGCTTTTAGATTAGTATGGTTTATGTGATCTGTCTGCCATAATGCATCACAGCTCTGTGTA<br>GTAGTTTTATGTGGCACTTATTAAAAACTGACCTAGTTTGAAAGATAAAAGCTCTTGGAATAGA<br>TGCTGTCAGAATTATTTAATTTTATTTGCGTCATAATTTATCGTAGGTTTTCGATATATCATCCT<br>TCATAGTGGGGAAAGTATAGATCCAGGAGACTGTATTTCCTATCTAATTCTAATCTTAATTTTA<br>CCACTGTCTAGCTGTGGGGCTTCAGAAGTCACTTTATTTGTGCTTCCTCATTTGTAAAAACAA<br>GGATTTCATTATATATATCTGCAGCACTTTGCTGAAGTTGCTAATCATTTGTACAATGGTCCAG<br>TGAAGAAGGCTGTCATAAGATGGTCTCTGGAAGCTTTTACAGTTTTTAAGACACAAATGATGA<br>ATTTTCTTACTGTATACTTTTTTCCTCTCTAAAGGTATTATATAATGAGAAGGGGCCTTTGTATA<br>CTATTCTATTTTTATTCCTCCGATTTTTTTTTTTTTTTTTTTGGTCTCCCAAGACGGAGTCTTGC<br>TCTGTCGCCCAGAACTAGAGTGCAGTGACGTGGCCTCAGCTCACTGCAACCTCTGCCTCCC<br>GCATTCAGCAATTCTCCTGCCTTAGCCTCCTGAGTAGCTGGGATTACAGGCGCATGCCACCA<br>CACCCGGCTAATTTTTATATTTTTAGTAGAGATGGTGTTTCATCATGTTGGCCAGGCTGGTCT<br>CGAACTCCTGACCTCGTGATCTGCCTGCCTCGGCCTCCCAAAGTGCTGGGATTACTAGCGT<br>GAGCCATGCCCCCAGCCATTATTCCTCCGATTTTTATAAATAAAGAGTGGCTCTTATGCTAAT<br>AAGTGACTCCTTTTTGGAATTAGCATTCCTGTGCCTTTACTGAAGCAGAAAGAAACATGAACT<br>GTCGTATCTTCTAACTTGTTTTGATAAGCAAGGCTGAAGACTAGCAAGTTAGAAAACTGGCAT<br>CTGCCTTTGATATTGTGGCTTCCTATTAGCACTAAGAGAAATATCGTCCTTTCTCCTTTTCTGA<br>CCACGTATTGTCATTCGATTCTTCATCAGGTTTACCCCTCTGTGGACAAGAGTTAGTATGACT<br>CTTTAGGTGTTAGGATTTATCCAAGTACATTTTTTAAAAAGGAAAGTTTAGTTGTCTTTTATGG<br>CTTCATTTTGGGGAGTGTATACTGTCTTTAGGTGAGAGTTTTCTTTTCTTTACTTTTTTAAGCT<br>GAACTTAGAGTCTAAAAGGAATACTGGAATTATTGAATGCAGGATTTGGGCCTTTACTGGAAT<br>AAAGTTGCTCAAATTATACCTGGTTCACTATTCTATCTCCCCATAGACCTGGAAAGGATTTAA<br>GCTGACAGGTATGTTGAGACTGTCCTTCATAGCCAAGCTTAGTGAGAGAGTCGCTGTAGTTG<br>GTGCTCACCCTCTCACCTTCTAGTCACCCCTCCATCATGAACTTTTGACTTCTTGTCCACTGT<br>ACTTCCTCACAGCAGGGTCACCAGGGGTCTTTATCACCAAGTGGGCACAATTCTTTATTTGA<br>CCTTGCTGCTGACTGTGCCTTCCTTTTACAGACTTTTTTTTTTTCCTGATTATGAAAGTAATAC<br>ATGGTCATTGTGAAAAATTTTGGAAAAAGAGTTGTTATCTCTATCCAGAAAACTTTCTCCTCAT<br>TGAAATGTTTCTGTGACAACTGTCTTCTTCCTTTCCTCCTGTTTCTCTTGACCAGACCTGAGTC<br>ATTTCGCCTCCTGGATATCTCTGTCTTGTAGGCACTCAAGCCCAATGTTAATTTTTGTGTATGT<br>GTATTTTTTTTTTTTTTTTTTACTTTAAGTTCTGGGATACATGTGCAGAATTTGCAGGTTTGTTAC<br>ACAGGTATACACGTGCCATGGTGGTTTGCTGCATCTATCAACCTGTCATCTAGGTTTTAAGCC<br>CTGCATGCATTAGGTATTTGTCCTAATGCTCTCCCTCCCCTTGTCCTCCACCCCCACCACCCA<br>CCAACATCCCCAGTGTGTGATGTTCCCCTCCCTGTATCCATGTGTTCTCATTGTTCAACTCCC<br>ACAGTGAGAACATGCGGTGTTTGGTTTTCTGTTCCTGTGTTAGTTTGCTCTCCCCATGGGCTC<br>TCACAGCACCCTGTGCTATCCTTCTGACACGTATAACATTTGTTGTAATTGTCTGTTTGCTTTT<br>CTGTCTCAAGGGCAGCAACGATGTTTTACTCATATTTATACCAGTGTCTAGCCCAGAGCGGC<br>TAGGACATTTCTGATAATAAACGGGTAGGGCTGGGTGTGGTGACTCACTCCTGTAATCCCAA<br>TACTTTGGGAGGCCAAGGTGGGAGGCTTACCTGAGTCCAGGAGTTCAGGATGATGATGGGG<br>TCAAATGATGACCCCAACATTTATTAAAGTGAATTTACCTCTGCCTCCCCTGCTCCAAGTATG<br>CTCAGCCACCTGTTGCCATCTCACTGGGAGGCATCACTCTTCATGTAGTTGCTGAAGCCATA<br>GATGAGGACCCATCCTTGACTCCTCTCCCTCATCCTCCATTTTCAGTCAGTAGTTAGAAACCT<br>TCTTGTTATTCCTGTGAACCCATTTACTTGTCATCTCTCTACTCTTAGCACCTTAACTTAGACT<br>CTCTTTATTTCCCACCTACCTGAATTTCCTAAAAGCATCATCCACTTTTGAAGGCTTAGGACTT<br>TGCGTATCTTCCCTCAGGGCTTAGCTTAGAAAATCAGGACTTCTCTGACCTGTTCCTATACCC<br>TCAGGTGAGCTTGGTGCTGATGTCCCCTTCTCCCTCTTCATCCATACCTCTTCCTTCTTCTCC<br>CCGTCTCCCCATGGGCTCTCACAGCACCCTGTGCTATCCTTCTGACACATATAACATTTGTTG<br>TAATTGTTTGCTTTTCTGTCTCAAGGGCAGCAACTATGTTTTACTCATATTTATACCAGTGTCT<br>AGCCCAGAGCGGTTAGGACATTTCTGATAATAAACAGGTAGGGCTGGGTGTGGTGGCTCAC<br>TCCTGTAATCCCAATACTTTGGGAGGCCAAGGTGGGAGGCTTACCTGAGCCCAGGAGTTCA<br>GGACCAGCCTGGGCAACTTAGTGAGACCCTGTCTCTACAAAAAATTTTTAAAAAGATTAGCTG<br>GCCATTGTGGCATGTGCTTGTGGTTGCAGCTACTTGGGAAGCTGAGGTAGGAGGATTGCTT<br>GAGCCTGGGAGGTTGAGGCTGCAGTGAGCCAAGATCACGCCACTCACTGTAGCCTGGGTGA<br>CAGAGGAAGGCCCTGCCTCAGAAAGAACGAAATTAAATAAATAAAAAATGAGTAGAAGGAAA<br>TGAACATTTGTAGGTTGGAGGTTAGTATAAAAAATCTGATGCTACATGTTTTATGGTCTTGGT<br>CTTGGCTGCCTTCAAATTGTATCTTAATATAATTGGCTTTCACTACCTAGTCTAGTAGTCATGG<br>TTCTGTGAACAAGCTTTCAAAGTGTGAAGTATGGTAGAGCAAAGCAGGAGTAAAGCTGTCAG<br>GTTGGCTGGAATGGGCCTCAGCACTTTGCTTGTATTGATAGAGGTTAGGTTTTCCAATAACTG<br>ATGACAGTGTAGCAGAGATGACTAGGGCAGTTGTGCTAGGGATAAAGAGTGGCACAGTTTA<br>GTGACTTGGCGATGAGATGTGGGGATCAGAAAGGAGGAATCTAAGTGACTCAAGCTTCTGG<br>CTTAATGGACTAGGTATACTTGAGGCTATCATTAACTAGTAGTGTTGATTTTGAGATTCTTTTT<br>GATATCCAGGTGAGTATGTCTACCAGGCTGTGGGATATGAAGTTGGGGAGAGTGTGTCACT<br>GGAAATGTTTGAGTTAAAACTACAAGAAATCACTTAGATATATAGCTTAAGAAGAGTAGTGGT<br>CTAGAAACAGAAAGAACTCTGAAGAACACTGATGTTTAGGGGCTGGGGAAGAAGAGAGCTG<br>GGAAGTCTATGTCAAAGAAACTGAGGAGCTGGTGGTTGAAGAGGGAATTTGGCAATAAAAAG<br>GCCATTTGACCTTCAGCTCTAGAAGCCAGGAAATTAAGAGAAAAAAGGCCGTTGAGTTTATT<br>GTGTTTTAAAAAGAAAATATCAAGAAAACGGGTGTGTTTTTACCCAGCCCTTAGATGAGATGC<br>TTCAGTATGGACTGTCTGCTTGGCATTTTGTTGGGCAGTTCCACCTTACCCGTTAGTAGCCCA<br>GCACCCCAGTCCACATCCAGAATCCTACTCTTACATTAGATCTAACACATGACCTCTAAAGTC |

-continued

| DNA Sequences encoding circRNA's of Table 1 |
|---|
| CCTTCCAATTTCAACCTAACATTAAAAACAGATTCTGGGCCCAGTCTGAGAAATTGTGATTCA<br>GCGGGCCTAGGGGATCTTAATTTCTTCTAAGGGCCTTTCTGAGAATCTGAAGAACATTGATG<br>TGTAGGTGCTATAAACCTGCATTTTACTTTATTGCAAGAGAGCAGGACTTTATTATAGCAACA<br>GTTTAAAATACAATTGTGATGAAGAGGTTGGCAACCATGGAAACCTAGCTGGAGCTTTACCC<br>CACCCATGCCTGCCTTTGTGTGTGGGGGTGACTTGGGGGTGGGAAAGTGCCACCATCTGTT<br>GTAATCTGTTGGAGATTTAAAGTTTTTGCTTTATGGATTTTTGCAGCAGATGCCCTTTGCTCCC<br>TGCATTATATCCTCTCAGGCCATCACTGGTTTCAAACAAAACTTAGATTTTTGTAGTTTCTCTG<br>TGTCTTGCCAACAGCTTTCTATTTTCTGCCTCAGGGCTCTCAAACCCAGCAAATGATGGGGA<br>AAGGCTAACCTCAGGCAACCTTCAACCAGTGAGGGATTGGAGCTGGTGCCTAAATGTCCTG<br>CTTCTTTCAGGGGTCTCACAGAATCACCCCACTTTGCAGCAGTCACCCTGTGTGTCCTTACT<br>GGCTATTTTCCTTCCCTCACGTCTGTTCCCTGGGATCACCTCCTATTTTAATCTTGCTAAAATC<br>TTGCACACAAAGTGTTAGTTGAGCTGACTTTAAAGCTGGAATGCAAATAAAAGCCTTCTGTAA<br>TTACATTAGTTTCTTTTTAATGTCCCTCTCTATCAATAATAGCACCTAAAATAATATATGGGGG<br>AAGAAGTCAAAGAGAACATATTGTGCAATGCACAATGGCGCACATATTGCTAAAGTTTAAATT<br>TATTCATAGATACTGTGTAATGAGATCATTATGTGAGAATTTATTGGGTTTTTCAACACTTCCA<br>TTTCTTTCATTTAGGAATGGGGTTGAACGGATATGAAAATGTAGAAAATAGTTGGCACAGAGA<br>GCACTAGGTGTGCCTCTTTTATTCATTTATATGTCATCCGTTCTTGAATTCTGGGTAGCTCTAT<br>TTGTAAGACTATACAGTATAATGATAGAAAGCTATTAAAAATGTCACAGTGCAGAAAGGGGGA<br>AGATCTCTACAGATGATTAGGCTATAAATTGCCAAAGATCAGAAAGACCCTGATAAGATCTGT<br>TTCAAAGGTTTTGTTTGGTTGGTTGGTTGGGTTTGTTTGGTTGGGTTTTTTTGTTGTTGTTGTT<br>TTTGGAGACAGGGTCTTGCTGTGTTGCCCAGGCTAGAGTATAGCAGTGTGATCATAGCTTAC<br>TGTAACCTTAAACTCTTGGGCTCAATAGATCCTTCTGCCTCAACCACCCCATTAGCTGAGACT<br>ACAGGCACGTGCCGTCACACCTGGCTAATTAAAAAAAAATTTTTTTTAGAGATGAGGTCTTGC<br>CGCGTTGCCCAGGCTTTCCTAGTTGAAGCATACATCTTGGACAGCTCAGTGTATTCATCCTC<br>GTTTGCTCCACATTTACTGAGTGCCTGCCATATGGCAGCCTCTATGGTAACTGTTTTCAGATA<br>CCAGTTTTAATCACTAGGAATAAACTTGGTCCCAAACTCCTGGCCTCAAAGGGTCCTCCCAC<br>CTATGCCTCCCAAAGCACTGGGATTATAGGTGTGAGCCACCATGCCTGGCTCCTATTTCAGG<br>GGTAACTTTTAAAAAACACTTTGTATGCTTTAAATGCAAAATTTCTCTTTATCTGGCTAGAAGA<br>TATCAATATCCATAATTCTTTTATCTGAGACTAGAATGTAGGATTTAAAAGTTGAAGGTGAAAG<br>GTAAACTTGTTCCAGACGATCACTTTCATTCTTGGTGATTAAAACTGATAACCTGAAATCAGTT<br>ACCACAGAGGCTGCCATATGGCAGGTACCCAGTAAATGTGGAGCAAAGGAGGATGAATATA<br>CTGAGCTGTCTGAGATGTATGTGTTCAGCTGCTGTCCCAGTGAGCAAGAGTAGGTGAAACTT<br>CACGTGCTTAGACCTGTAGGTACTATTGCCTCACTCCCACCAAACTGGGACTGCAGATCTTT<br>AGTTTCTAGGTTTATTTTGCAGGAGTCCAGCCATCCCTAGAAAACACTCTTTCCTCAATCCAG<br>GGTGTTTTGTGTAGCAGTGGGCTGTTTTATGTAAATTGTACATTGACAAGTTCATTAGGTTAT<br>CTAGTATTTCAGCCCCTCAGTTAACATTTCAGCTGAGACCGAGAGAGGAAGTGACTTGCCCA<br>AGGTAAAATCACCATGTCTAGATAATCACTGATATGGCAGGGACTGGAACACTAGTCTCTGC<br>ATGTAATCATCTTTTTGTCTCGTTTCTGAAATAGCTCCCATCTCTACCCCTGGCCAAGGACCA<br>AAACAAGGCACCATCTTTCTGAACTAGTTTAAAATGGTTTTAGAATTAATAAGGACTGTAGGG<br>TCTATATTTAAGATGGTTACAGGAAATTCGACAGTTAAATGTTTCTACACATAGATTATTTAGA<br>AAATCAAGACTAATAGATGGGCAAAGTACACAGGAAGCAAATGAAAAATTGTAAACATCTAAA<br>TATTCAGTATTCAGTGGTATGGGAATAGTTTAGGAAGCAATAATTTTCTTTTTTTTTTTTTTTTT<br>TGAGACAAAGTCTCGCTCTGTTGCCCAGGTTGGAGGGCAGTGGTGTGTGCGATCTTGGCTG<br>CAGCCTCTGCCCCTAGGTTAAAGCAATTCTTGTGCCTCAGCCTCTCGAGTAGCTGGGATTAC<br>AGGCACGCCCCACTACGCCCGGCTGATTTTTGTACTTTTAGTAAAGACAGGGTTTTCCCATG<br>TTGGCCGGGCTGGTCTTCAACTCCTGTCCCCACGTGATACGCCTGCCTTGTCCTCCCAAAGT<br>GCTGGGATTACAGACGTCAGTCACCATGCCCGGCCAGGAAGCAATAATTTTGATGGGCTGTT<br>TGCAACTAATAAAATGCGAATTGTGATGATTTAGAAAGGGTGTTTAAAAATCTAGTAGGGATC<br>TTGGAGGAGTTCTTTTTATACTTTCCTTTCTTCTGTACTATGCCTAATACTTAGTTGTTTTCAG<br>GAAGTTCAGATTTTTTTTTAATTTAAAAGGTTAAAGTTTACCAAATGTTAACTGAAGTCAGTTTC<br>TGAAGTTCTTCAGTCAAAACCAATTTATTTTCTGTAAAAAAAAAAAAAAAGTACTACACACCAT<br>ATAAACTGGTAGCTGTTTGTTATTCTTGATATGTGCAGTAAAAACTATCATGAGAGAGTTGGT<br>AAAGATTTAATGAACTGGTAGAACATGTTTTTCTTAGTTGCTAAGAACCATCTGAGCTTAAATT<br>TAAAAACATTTTTTTCTAAAAACAAAATTGGTTTCTGAATCAAATGTGTATTTCTTTCCTATAGG<br>GGCTTTGTTATGCACCTAAAGCCATATTGGAAGCTCCAGAAGAAAGAGCACCCCCCGGAAGT<br>CAGCAGGGAAACGCAGAGAACTCCTATGAACCACCAAAAGGCTGTAAATGATGAAACATGCA<br>AAGCTAGCCACATAACATCAAGTGTCTTTCCTTCAGCCTCTCTCGGTAAAGCATCATCTCGAA<br>AGCCATTTGGGATCCTTTCTCCAAATGTTCTGTGCAGTATGAGTGGGAAGAGTCCTGTAGAG<br>AGCAGCTTGAATGTTAAAACCAAAAAGAATGCACCATCTGCAACGATCCACCAGGGCGAAGA<br>AGAAGGACCACTTGATATCTGGGCTGTTGTGAAACCTGGAAATACCAAGGAAAAAATTGCAT<br>TCTTTGCATCCCACCAGTGTAGTAACAGGATAGGATCTATGAAAATAAAAAGTTCCTGGGATA<br>TTGATGGGAGAGCTACTAAGAGAAGGAAAAAATCAGGGGATCTTAAAAAAGCCAAGGTACAG<br>GTGGAAAGGATGAGGGAGGTTAACAGCAGGTGCTACCAACCTGAGCCTTTTGCATGTGGCA<br>TTGAGCACTGTTCTGTGCACTATGTGAGTGACAGTGGGGATGGAGTCTATGCTGGGAGGCC<br>TCTGTCAGTTATACAGATGGTTGCCTTCTTGGAGCAAAGAGCCAGTGCTCTGCTAGCTAGCT<br>GTTCAAAAAACTGCACAAACTCACCTGCAATTGTGAGGTTTTCTGGCCAATCCAGAGGTGTG<br>CCTGCAGTGTCTGAGTCCTATTCTGCCCCAGGAGCTTGTGAAGAACCCACAGAAAGGGGAA<br>ATCTTGAGGTTGGTGAACCACAGAGCGAACCAGTCCGTGTCCTTGACATGGTAGCCAAGTTG<br>GAGTCTGAGTGCCTGAAGCGGCAGGGCCAGCGTGAGCCTGGGAGCCTCTCAAGGAATAAC<br>AGCTTCCGTCGAAATGTGGGCAGAGTATTGCTTGCAAATAGCACTCAGGCTGATGAAGGCAA<br>AACAAAGAAAGGCGTCTTGGAGGCACCTGACACTCAGGTGAATCCTGTGGGGTCTGTATCT<br>GTGGATTGTGGCCCTTCAAGAGCTGATCGTTGTTCTCCTAAGGAGGACCAGGCCTGGGACG<br>GTGCTTCTCAGGACTGCCCCCCATTGCCAGCAGGAGTGAGTTTCCACATAGACAGTGCAGA<br>GTTAGAGCCGGGTTCGCAAACTGCCGTGAAAAACAGCAACAGATATGATGTGGAAATGACAG<br>ATGAACTCGTTGGGTTACCTTTTTCCTCTCATACCTATTCCCAAGCCTCTGAATTGCCCACAG<br>ATGCTGTTGATTGTATGAGCAGAGAGCTTGTGTCCCTTACTAGCCGAAATCCTGATCAAAGAA<br>AAGAATCTTTGTGCATTAGTATCACTGTGTCCAAGGTAGACAAAGACCAGCCTTCCATTTTAA |

-continued

| DNA Sequences encoding circRNA's of Table 1 |
|---|
| ACTCCTGTGAAGACCCAGTTCCAGGGATGTTGTTTTTTTTGCCACCTGGTCAGCACTTGTCA<br>GACTATTCCCAGTTGAATGAAAGCACAACAAAAGAGTCTTCAGAGGCCAGCCAGCTTGAAGA<br>TGCTGCTGGGGGTGACAGTGCATCTGAGGAAAAAGTGGGTCTGCTGAGCCATTTGTACTG<br>CCAGCCTCTTCTGTGGAAAGTACATTACCAGTGCTTGAGGCATCCAGTTGGAAGAAGCAGGT<br>GTCGCATGACTTCCTGGAGACCAGGTTTAAAATCCAGCAGCTTTTGGAGCCTCAGCAGTACA<br>TGGCTTTTCTGCCCCACCACATTATGGTAAAAATCTTCAGGTTACTTCCCACCAAGAGTTTAG<br>TGGCCCTTAAATGTACCTGCTGCTATTTCAAGTTTATCATTGAGTACTACAATATCAGGCCAG<br>CAGATTCTCGCTGGGTTCGAGATCCACGCTATAGAGAGGATCCTTGCAAACAGTGCAAGAAA<br>AAGTATGTGAAAGGGGATGTGTCCCTGTGCCGATGGCACCCCAAGCCCTATTGCCAGGCAT<br>TGCCCTATGGGCCAGGGTATTGGATGTGCTGCCACCGGTCTCAGAAAGGATTCCCTGGCTG<br>TAAGCTGGGGCTTCATGACAATCACTGGGTTCCTGCCTGCCACAGCTTTAATCGGGCAATCC<br>ATAAGAAAGCAAAAGGGACTGAAGCTGAAGAGGAATACTAAAGTCCATGTGAGAGGCAACAA<br>AAGGACCGGTTTCTAAAGCTGCAAAACACCTAGATACACCGTTCAAATGAGCGTAGCCCCCT<br>GAGTCATCACTCTAGAAGAATCTGTACATCATCAGGACTGCATTGCTCAGGCATTTTCTAAAC<br>TCTAAATTTACGAGCTGTACAAAAAAATTGGTCTTGTTGTTTATAGTGGCATCTCATGTTTGAA<br>CCCGGGTGGTATCCCACAGTTGGATTCAGTTGGCTGTGAATAACTGCCTGTTTTCCTAAATC<br>AAACCCATCCTCAAAGGATGAAGACTCACCACCATCCAGGACATTCAGAAGAGTTCACTGCA<br>GATGCTGCAGGTAGTCCTCAAAAATGGGTTCCAGAAATGTTTTGAGCACTGGCAACATATTT<br>GAAATAAGTGAATATTGTCCTGTGAAAAGAATAGCAGGACTTTTAGATGAAAAGTATTCTTAAA<br>AAGAAAAGTCAGGCACCCCACCTTAGACCTCGTATGCTTGATCCTGTGAGATTGATGTTTGT<br>GGCTGGAGGTGGATTTCATGCCCTGTGGTGTTTACAGTGTATATAATGGTTGTGTTTTCATGG<br>GGCTATGAAAGTGCACGTTAAACCTGAGCGCCTTTACCTTTAGATGAGTGCTTTGGCCCCTC<br>TGTGAATAGCACGATTAAAATCCAGTTGTATATAATGGACAGCTAACGGAACAATATAATCAC<br>CACAATGCAGCTAGGATAGTGTTGCGGCTATAATTTTGTGTTTTTTTTTTTTAATTGTCTAGTC<br>TTAAATTTGTACATCTTGTATAAAATATGAATGTTTCCCAAATAAACTATGAATGTTTCCTGTAT<br>AATATATGAATGTTTCTGAGAAGAAACTCTAAATAGTTGAAAGGCTAACCTGCTCAAAGGATA<br>CCAAATAATGGTTTAACTGGACAACCTGAAAATTAGCATAGAAAACAATCCTTTGTTATATTTT<br>AGTGATCCACAAGATTGAGAAAATATTATATAGTTAGATAATAACATTCTTGTCTACTTTATCC<br>TGTCTGGTTACAAAATTTTTTAAAACTTAAATAAAAACATGCATCTTAAATGGAACCCAAGTTTT<br>GCAAAGATTTTTTCTCCTGTTTTGATACAATGTTGAAGAAGGTTCTTGTGAATTGAATCATAAG<br>AATTTTTTAAATTGTTTTGAATTGTTGGAGATAAAGTGTTTTTTTCTGCCACGGAAGAGGCCAT<br>CTTCACTTAACATTGAAGTTTAAATTTTTGCAACCTGTCAGTTCTTCCGTTTGTTGTCTGTTCA<br>CAACCATTGTATTTCCTGTTCGAGTGACGTATTATCTAGGAGATTCTTACAGCTTATCTAGGC<br>GTCATCATTTGGGAGTCACTAAGGATCTATTCAAGCCTGTAGCTGCTTAGTGCTTGGTGGGG<br>TTGGGAGGTGTTGGACCCCAGAAAGCTGCTGTGGGTGGAAGATCTAAAAACTAGGCTGGCT<br>TGAAATCGAGTACCCACCAAAAAGCCTTGAGACCAGTGTCGGCTGCAGGCTGTGGAGAAGG<br>ATGGTACGTGCTCTAGGGGAGGCGCTGTGCTGGGCTGATGTGCTTGGTGACATGGTAGGCT<br>GCAGCCTCCAGGCTCATCAGATTTGTCTGTGACACGGGATCAAGAGGAGGCTGAGAATAGC<br>TTTTCCTTCAAGAGTGTTTTTCCTTATGACTCACCCAGGTGAGGCATGTTGGAAAATGCTTCT<br>AAATCCTAGCTGTCCCCTTGGTTGAGGTTTCCAGTGTTTGTCCTACTCCCCTTGTATTTGCTG<br>TAAACTGGCCATCTCAGTAGTGCCTTCTTAATTGGTTTGTTATGATTCATAATTTAGGTTTAAA<br>GGAGATCAACATAAAGGACCTAGAGTACAGCTTGCCTGTAGACGTCAGCTATGGCTGACATT<br>GACTATGGCTCTACACTGGCCCAGCCTGGACACTGGATAAACAACTCTCTTGGTTGGTTTTC<br>ACAGATCAGCCACTCTTGATCTGGTTTTCATGTGGGACACAAAGCTGTGACTGCGTGAGGGG<br>TTAAAGTGACCAAGAGCAGAGGGCACAGTAAGTATGTCCCAGCCCCAGTTGGCATGCAGTA<br>CTTGGGTCCCTCAGAAATCGCCGGTTATCTGTTTTGAACTATGTGGCAGGACCTGGTTCCCG<br>GTGCTGTCTGCATGAAAGGTGGAGGATTAGCAGGTGGCATCAGAGGACACCCCCTCCCAGG<br>GCTTCATTTCTAGGCAAGTGTAGCTTTCCTCTTAGGTGAAAGATGCTGTTCTTCAGGGCCCC<br>CTAGTGCCAAGCTGGTGAAAACAGCAGGCTTTTAAAATGTCTCCAGTAGTGTGCCGCACTAC<br>CTGCTTTCCTGCATTGCTGTAGGATCACAGAATTCAAGAAAGGACATGATAGTGTGTCAGTGT<br>GGGCACCAGCACCCTAGCCTCTCCCCACTGCACCCCTGCCCCCACCAAAAAAGAGAAAACC<br>TCCCCCCTCAGCTTTTCTTCAGGGACTCAGTACACCTGGCTTAGTTTTTTTCTCTCCTACCTC<br>CTACTTCAAGCCCTTACTTGATCATCTGAAGCAAAAACCAGAACCAGGGAAACTAGAGGAGG<br>AGTCAGGGAGCTGCTGCTCCTATTCCTGGAGTGGTTCACCTCTCCCCTGCCCAGTGGATGG<br>TCCAGACCCAAGGAAGGAGTGAATTGAAAGCTAAGGAGGGGCTCAG |
| >SLC8A1_hsa_circ_0000994 (SEQ ID NO: 11)<br>TAGGTTGTGACAGTTGGAAGTGTCATGTACAACATGCGGCGATTAAGTCTTTCACCCACCTTT<br>TCAATGGGATTTCATCTGTTAGTTACTGTGAGTCTCTTATTTTCCCATGTGGACCATGTAATTG<br>CTGAGACAGAAATGGAAGGAGAAGGAAATGAAACTGGTGAATGTACTGGATCATATTACTGT<br>AAGAAAGGGGTGATTTTGCCCATTTGGGAACCCCAAGACCCTTCTTTTGGGGACAAAATTGC<br>TAGAGCTACTGTGTATTTTGTGGCCATGGTCTACATGTTTCTTGGAGTCTCTATCATAGCTGA<br>TCGGTTCATGTCCTCTATAGAAGTCATCACATCTCAAGAAAAAGAAATAACCATAAAGAAACC<br>CAATGGAGAGACCACCAAGACAACTGTGAGGATCTGGAATGAAACAGTTTCTAACCTGACCT<br>TGATGGCCCTGGGATCTTCTGCTCCTGAGATTCTCCTTTCAGTAATTGAAGTGTGTGGCCATA<br>ACTTCACTGCAGGAGACCTCGGTCCTAGCACCATCGTGGGAAGTGCTGCATTCAATATGTTC<br>ATCATTATTGCACTCTGTGTTTATGTGGTGCCTGACGGAGAGACAAGGAAGATTAAGCATTTG<br>CGTGTCTTCTTTGTGACAGCAGCCTGGAGCATCTTTGCCTACACCTGGCTTTACATTATTTTG<br>TCTGTCATATCTCCTGGTGTTGTGGAGGTCTGGGAAGGTTTGCTTACTTTCTTCTTCTTTCCC<br>ATCTGTGTTGTGTTCGCTTGGGTAGCGGATAGGAGACTTCTGTTTTACAAGTATGTCTACAAG<br>AGGTATCGAGCTGGCAAGCAGAGGGGGATGATTATTGAACATGAAGGAGACAGGCCATCTT<br>CTAAGACTGAAATTGAAATGGACGGGAAAGTGGTCAATTCTCATGTTGAAAATTTCTTAGATG<br>GTGCTCTGGTTCTGGAGGTGGATGAGAGGGACCAAGATGATGAAGAAGCTAGGCGAGAAAT<br>GGCTAGGATTCTGAAGGAACTTAAGCAGAAGCATCCAGATAAAGAAATAGAGCAATTAATAG<br>AATTAGCTAACTACCAAGTCCTAAGTCAGCAGCAAAAAAGTAGAGCATTTTATCGCATTCAAG<br>CTACTCGCCTCATGACTGGAGCTGGCAACATTTTAAAGAGGCATGCAGCTGACCAAGCAAGG<br>AAGGCTGTCAGCATGCACGAGGTCAACACTGAAGTGACTGAAAATGACCCTGTTAGTAAGAT |

-continued

DNA Sequences encoding circRNA's of Table 1

CTTCTTTGAACAAGGGACATATCAGTGTCTGGAGAACTGTGGTACTGTGGCCCTTACCATTAT
CCGCAGAGGTGGTGATTTGACTAACACTGTGTTTGTTGACTTCAGAACAGAGGATGGCACAG
CAAATGCTGGGTCTGATTATGAATTTACTGAAGGAACTGTGGTGTTTAAGCCTGGTGATACCC
AGAAGGAAATCAGAGTGGGTATCATAGATGATGATATCTTTGAGGAGGATGAAAATTTCCTTG
TGCATCTCAGCAATGTCAAAGTATCTTCTGAAGCTTCAGAAGATGGCATACTGGAAGCCAATC
ATGTTTCTACACTTGCTTGCCTCGGATCTCCCTCCACTGCCACTGTAACTATTTTTGATGATG
ACCACGCAGGCATTTTTACTTTTGAGGAACCTGTGACTCATGTGAGTGAGAGCATTGGCATC
ATGGAGGTGAAAGTATTGAGAACATCTGGAGCTCGAGGAAATGTTATCGTTCCATATAAAAC
CATCGAAGGGACTGCCAGAGGTGGAGGGGAGGATTTTGAGGACACTTGTGGAGAGCTCGAA
TTCCAGAATGATGAAATTGT

>FOXK2_hsa_circ_0000817 (SEQ ID NO: 6)
GTGCACATTCAGGTTCCCGAGCACAAACATCAAGATAACGTTCACTGCCCTGTCCAGCGAGA
AGAGAGAGAAGCAGGAGGCGTCTGAGTCTCCAGTGAAGGCCGTACAGCCACACATCTCGCC
CCTGACCATCAACATTCCAGACACCATGGCCCACCTCATCAGCCCTCTGCCCTCCCCCACG
GGAACCATCAGCGCTGCAAACTCCTGCCCCTCCAGCCCCCGGGGAGCGGGGTCTTCAGGG
TACAAGGTGGGCCGAGTGATGCCATCTGACCTCAATTTAATGGCTGACAACTCACAGCCTGA
AAATGAAAAGGAAGCTTCAGGTGGAGACAGCCCGAAGGATGATTCAAAGCCGCCTTACTCCT
ACGCGCAGCTGATAGTTCAGGCGATTACGATGGCTCCCGACAAACAGCTCACCCTGAACGG
GATTTATACACACATCACTAAAAATTATCCCTACTACAGGACTGCGGACAAGGGCTGGCAG >CDK11A_hsa_circ_0000005 (SEQ ID NO: 2)
AGGAGAAGAAGATGATTCTTTGGCCATCAAACCACCCCAGCAAATGTCTCGGAAAGAAAAAG
TTCATCACAGAAAAGATGAAAAGAGAAAAGAAAAATGTAGGCATCATAGCCATTCAGCAGAA
GGGGGGAAGCATGCTAGAGTGAAAGAAAGAGAGCACGAACGTCGGAAACGACATCGAGAA
GAACAGGATAAAGCTCGCCGGGAATGGGAAAGACAGAAGAGAAGGGAAATGGCAAGGGAG
CATTCCAGGAGAGAAAGGGACCGCTTGGAGCAGTTAGAAAGGAAGCGGGAGCGGGAGCGC
AAGATGCGGGAGCAGCAGAAGGAGCAGCGGGAGCAGAAGGAGCGCGAGCGGCGGGCGGA
GGAGCGGCGCAAGGAGCGGGAGGCCCGCAGGGAAGTGTCTGCACATCACCGAACGATGAG
AGAGGACTACAGCGACAAAGTGAAAGCCAGCCACTGGAGTCGCAGCCCGCCTCGGCCGCC
GCGGGAGCGGTTCGAGTTGGGAGACGGCCGGAAGCCAGTAAAAGAAGAGAAAATGGAAGA
AAGGGACCTGCTGTCCGACTTACAGGACATCAGCGACAGCGAGAGGAAGACCAGCTCGGC
CGAGTCCTCGTCAGCGGAATCAGGCTCAGGTTCTGAGGAAGAAGAGGAGGAGGAGGAAGA
GGAGGAGGAGGAAGGGAGCACCAGTGAAGAATCAGAGGAGGAGGAGGAGGAAGAGGAAG
AGGAGGAGGAGGAGACCGGCAGCAACTCTGAGGAGGCATCAGAGCAGTCTGCCGAAGAAG
TAAGTGAGGAAGAAATGAGTGAAGATGAAGAACGAGAAAATGAAAACCACCTCTTGGTTGTT
CCAGAGTCACGGTTCGACCGAGATTCCGGGGAGAGTGAAGAAGCAGAGGAAGAAGTGGGT
GAGGGAACGCCGCAGAGCAGCGCCCTGACAGAGGGCGACTATGTGCCCGACTCCCCTGCC
CTGTTGCCCATCGAGCTCAAGCAGGAGCTGCCCAAGTACCTGCCGGCCCTGCAGGGCTGC
CGGAGCGTCGAGGAGTTCCAGTGCCTGAACAGGATCGAGGAGGGCACCTATGGAGTGGTC
TACAGAGCAAAAGACAAGAAAACAGATGAAATTGTGGCTCTAAAGCGGCTGAAGATGGAGAA
GGAGAAGGAGGGCTTCCCGATCACGTCCCTGAGGGAGATCAACACCATCCTCAAGGCCCAG
CATCCCAACATTGTCACCGTTAGAGAGATTGTGGTGGGCAGCAACATGGACAAGATCTACAT
CGTGATGAACTACGTGGAGCACGACCTCAAGAGCCTGATGGAGACCATGAAACAGCCCTTC
CTGCCAGGGGAGGTGAAGACCCTGATGATCCAGCTGCTGCGGGGGGTGAAACACCTGCAC
GACAACTGGATCCTGCACCGTGACCTCAAGACGTCCAACCTGCTGCTGAGCCACGCCGGCA
TCCTCAAGGTGGGTGATTTTGGGCTGGCGCGGGAGTACGGATCCCCTCTGAAGGCCTACAC
CCCGGTCGTGGTGACCCAGTGGTACCGCGCCCCAGAGCTGCTGCTTGGTGCCAAGGAATA
CTCCACGGCCGTGGACATGTGGTCAGTGGGCTGCATCTTCGGGGAGCTGCTGACTCAGAAG
CCTCTGTTCCCCGGGAATTCGGAAATCGATCAGATCAACAAAGTGTTCAAGGAGCTGGGGAC
CCCCAGTGAGAAAATCTGGCCCGGCTACAGTGAGCTCCCAGTAGTCAAAAAGATGACCTTCA
GCGAGCACCCCTACAACAACCTCCGCAAGCGCTTCGGGGCTCTGCTCTCAGACCAGGGCTT
CGACCTCATGAACAAGTTCCTGACCTACTTCCCCGGGAGGAGGATCAGCGCTGAGGACGGC
CTCAAGCATGAGTATTTCCGCGAGACCCCCCTCCCCATCGACCCCTCCATGTTCCCCACGTG
GCCCGCCAAGAGCGAGCAGCAGCGTGTGAAGCGGGGCACCAGCCCGAGGCCCCCTGAGG
GAGGCCTGGGCTACAGCCAGCTGGGTGACGACGACCTGAAGGAGACGGGCTTCCACCTTA
CCACCACGAACCAGGGGGCCTCTGCCGCGGGCCCCGGCTTCAGCCTCAAGTTCTGAAGGT
CAGAGTGGACCCCGTCATGGGGAGAACTCAGCCGGGACCACAGGCGTGGCTACTGCGGCT
GGAGCTGCGATGAGACTCGGAACTCCTCGTCTTACTTTGTGCTCCATGTTTTGTTTTTGTATT
TTGGTTTGTAAATTTGTAGAATTAAATCATTTTCCTTGTTGTGGAGGAAAGAGCTGTGTTTTCT
CCGTGACTTGCCAGGGCATCTTCGGGTGCCCACGTGGGGCAGCACAAACCTCCACACACCC
TCTCCCACTCTCGACACGCACGGGGCTGGCTGGGCCGTGATTTGGAAAGGAACTGGTGGGA
GCCGGGTGGATTGTTTAATCTTCGGAGCTGGAGACCTGTTTCTGTGTTGGGATGAGCGATGC
CCTCTTGCCCCAACCCACTCGTCCAGACCAGCCCTGTCCACACAGGCCCCCGGCCCCCAAC
CCCCAGCCCCAGCTGTGCCAGCAGACTCGACAGGTTTTTATACAAGGTTGTTGAGTTTTAAA
ATGTATTAAAATATTCTTCGAGGAAAGCTCCCCGTGTCGTCCTTTGAGTGACCCGGGACCAT
GTGTGGGAGGGGAGTCGCAGACCACCGGGCTCTAGGGGAAGAGGGTGGGGTGGGCGGCT
GTGGCCTCTGACCCCATGTGGGCCAGTGTCTTCCCCAGGCAGGAGGGGAGCTCCTACCTCC
TGGGGGGCCTCCACTCTGGCAAGGTGGTCCCCCACCCTGTGCCAGTCCTCCCAGCCCCCA
CCCACATCTCCTTGCAGAAGATCCTGGAGGCCCATCCCAGCCACATCTTTCAGGAAGCCCC
CTTTGCCTCCCTCCCCCAGCTCTGAGCAAGTCCTAGACAGAACCCAGGCTTCTGGGGCTAC
CCCAGGTGCTGCTCCACGTGCTGCCCCTGTCACTGGGGCCTCCTCTTATCCCACTTTCCCA
GGGGCCACCTTAGCAAAGCCCGTCCCGTCCTGTGCTGTACCTGTGGTCCGCTGTGCGGGG
AAGCAGGGGTGCCCAGCCCCGAGGACGCCCAGCTCTCGGTGGACCAGGGGCTGGGGTGT
CCACCTGCCCAGACTGGCTGCCCGCTGCCCTCCCAAGAATGAGCGAGGAGCCATCAGAGA
GAAAGTGCTTTATCAGCCGGGCTCAGCCCCGCACACGGACTCGCCAGGAGTAGGTGGTCAG
CACGCGCTGCTGGCGGCGCACCACGCAGGTGTAGGTGCCCTCATTGACGGCGTTGGCGAT -continued

| DNA Sequences encoding circRNA's of Table 1 |
|---|
| GATGCTCAGGTGCGCCTCGCCCAGGGCCAGGTAGCCGGGGTAGGAGAACTCCAGGGGCTC<br>CTGGTCCTTGTACCAGCTGCAGGGGGGCGGGGCGTCTCCTGCAGGCACAGCCCCCCCCCG<br>CTGCCTGCCCCGCACCCCTGCCCCAAGGCCGCCCGCGGGCTGCCCACCCCGAGGACCGC<br>CCGGGGCGCTCACTCACTACACTTTCCCTTTCTTGTGGAGGATCTTCTGGCCGCAGCGGAA<br>GGTCACGTTCCTGCCCTCGGGCACCAGCCTGGTTTTGGTCCTGGGGGGCGGTGGGGTGGT<br>GGCCACCGTGGGGAAGGGGAATTCTGCTCCGGGTGGGGGAAAGAGCCCCGTCAGTGCCCC<br>CTCAGCCCCGACCATGGCCAAGGCCCAGCTCCCACGCAGCCCTGTCCCGGCCCCGTGGGC<br>ATCACCGTAGCAGAAGTCGCAGCTGCTGGGGCAGAGCCTCTTCATGAGCCGCCGGCGAGC<br>GTCGCAGAAGCCCCTCCGCGCCCAGGACGCGCACACGAACAGCCTGTCGAGGCATCCTGT<br>CGGGAGCGTGGGGAGCACGGCCTGGCTCAGGACCGCCCGGTCCCCGCCCTCCCGCCCGA<br>CAAAGGGACTCACCGTAGAGCCGGTGCAGCCCCCACAGCTCGTCCTGGGACAACGCCTTCC<br>AGCCGCGCAGCGTGGCGTTCAGGTGCATGAGCGCCCGGCCGTGTTGTGAGTGCATCAGGC<br>CCAGCGCGTGGCCGATCTCGTGGGCCGCCACGTGCACCAGGTCCGTGAGCCACACGCCTG<br>CGGGCCCCGGGGGTCAGCGCCTGGGAGCCCCGGGCCCAGCCCCGCCGCCCGTGGGCCA<br>GCTCCCCGAGGCCCGGTGTATCTGCTGGAGCGCAGCCGCGGAGCCGCCCTCGGCCGCAG<br>CCACGGAAAGATAAGAATGTTCTGGGCCCAGGCGGTGAGCTCGGCCCCCAGGAATGCAGCT<br>CCAGCTCCCGCTCCAGAGGCGCAGGGGGATGGGAAAGGGAGTTCAGGGCTGCCGGGATG<br>GGGGCTCCCACGGGCTCCCCTCCTTGCCTGCTAGACTCCAGTGGCAGCCACCACCCCGGA<br>AGGTCCCTCCTGCCGTCTGCCCCAAAGCCCGACCGCGGCAGCCCACTGTGCTGCAGAGGA<br>GAGGCCTCCAGGAGGCCAGCCTGGACGGTCACCTTTCTTCCAGCTGTAGCGCGTGGGGCC<br>CAGGACCCAGTACTCGCTGTCGTCGAAGTGGATGCCGCCGTGCGGGGGGAAGAAGGCGTG<br>GGCCAGCTCCCCCGTGGGGCCGTCGAAGCAGTGGTGCAGCGCGGAGACCAGGCAGTCCG<br>TGTGGTTGATCGGGTAGAAGCCTGGGGGGAGCACGGGGCTGAGAGGCCGGGCGCGCAGG<br>GCCGGGCCGGGGCGGGGGCGGGCGCCCACCTATCCGGAGGTCGCTGGGCTGCTCGGGG<br>GCCACCTCGCGGAAGCTGAAGGGGGACACGTCGCTCCACATGCGGAAGGCGGCAGCTAGG<br>GCCCGCCGCGTCTCCCGCGGGCTCAGCAGGTTCCGCGGGAAGGAGAGGATCCTGCAGGG<br>AGAGTGAGCTCAGCGGGCGCCGGCCGCGCCCCCTCCCCCGGGGCCCAGCCAGGGCGCAC<br>CTGTAGGTGAGGTTGAAGTGGTCCCAGCGCAGCCTGGCTGGAGTCAGCGTGTAGCGGCGT<br>CTGCGGGGGGCCAGTGGGCCCGGGACCCGGGTGGGGGGGACCGCCGAGAGGCCCAGCG<br>CAGCGACGTCTCCCTTCAGGGAAGAAAGCGTGCGTGGGAGGCATCGGTGACGGTCCCCAG<br>GACCAAAAACTGCCGCGGAAAATGGACTGGAAGGAAACGGGGGTGGGGGTGCCCAGGGCT<br>GGGAGCGGGCGTGGCGGGTCCTGTCTGCCTGTGGTTTCGGGTCTCCTAACCTGAGCGCCC<br>TGTTGCACGTCCCTGGGAACGCGGCCCAGTGGAGGGGAAGGGGCTGAACAGCAGGGCGA<br>GGCCTCCCACCCCTCCCAACAACTGGACACAGGGGCGTCCAACCCTCCGACCTCGGGACG<br>CACATCCGGACCCTCAAACACCCCGCACACCCCGCACACCCTGCACACCCCGCACACGTCC<br>TGTGGGCCCCTTTTCTGAAGTGCTGATGTACATACTTTCTCGTACACACTTTTGTGAAGATTT<br>CAAGGGGAAGGGAGTCGTCTGCCATTCAATGTTTACATTTATGTTCTGCAAGACGCTGTCCT<br>CAGGGACCATTAGGGGACCATTCTGTTCAGTGCGATCCTGATGGTCCGGGAGATGAGGGTT<br>TCCGGGGCTAGTGATCGTGATCCCTTTTATTTGCAACTGTAATGAGAATTTTTCACACTAACA<br>CAGCGAGGGACTCAACACGCTGATTCTCCTCCTGCCTCTCCCGTGAGTCTCCAGCCTGCCC<br>AGCACCAGCAGCTGTGGAGCACGTGGATGCTGCCTACCCCGGCGCCCGCGTCTTCCACGG<br>GCACAGGTGTGTGGAGGCCGTGGTCGGACCCTGGTGTCCTGGTTACTGCTGCCCGGGTGT<br>CTTTTTTTTGAGTAACTGCTCTCTGAGTTTTGCACACAAAGTTGCCCTCATCTGCTGGAGATC<br>GATAAGGAAGGCACAAGACGTTCTCCTCTGCCCGTGAGGAGCTTCCCGCAGCCGCCTGGCC<br>CAGCCTGGGCACGTTCTCCGAGGCATGTGTCTCCCTGCTCACCCTCGTCTGGGCACCTCAG<br>CATCTGTGGACTTGAGCGTCCAAAAACCCTGAGTGTGATTCTGGGCAGCCGGCCTGGCTTG<br>AAGTCCGCCATGACCCTGGGCACAGGGGAAGCCCAGCCGTGGGCTTAGGAGAGAGGGACC<br>AGCGCCCAGCGTTAGGGCTGGAAGACGGCAGTGTTCAGAATTCCAGCCGCTCATCTGAACA<br>CAGAAGGTGTGAACTGACCTCTAAAGCAGCGTGAGATGGGAATGATCTAGAAAACTTTGGAT<br>TTTTGAAGTAAATTTTAATGTTTCATATTAATTTCTTGAAAATGTATTAAATGTCATTGAAAGCC<br>TTATTACGCTTTTCAGATCCTTTCAATAAACAAGACTTGTAGAAAATAAGCTGGGTTAATAACA<br>GCTTTCTTCTGACGCCGTGGAACCAACATAGAGGGGTCGGGCAGGGTCACCCCCATTAAAT<br>CCTAGCCCCAAAATGCCCATCCACCGAGTGTGGGGCCGGCAGGGCATCCTCCCCAAGGGG<br>CTGGGGGTGCCGCTGCCTCTTCCGGGCAAGGGGGCAGTGCCCTGGCGGGGGTAGGGGTA<br>GACAGAAGGGACTCAAACCCGAGGGGTGGTGTCGACTCGGGCAGGCTGTGTTGCTCCCGG<br>AAGAGCCACTGAGACCAGGGGGAGTTGAGTCCCTGCATTCCCGGGGCCAGCAGGGCTGGA<br>AGAGCCCCTCCATCCGGGCTGCCTAACAGGGGCAGCCACAAGCCAGGTGAGGACCCGCTG<br>GCCCCTGGGCCCAGCCTGGGCACCGATATCGGCCTCCCTCCCTCCACTGACGTGGTCCTG<br>CGCCCCGCAACCCCCCCACCCCGCACCGTCCCTGTTGTCCTAACAAGGCCCAGATGAATGT<br>GGCTCAGGGCTTTGCCGGCAGCCAGTCTGCACTACACGCGTGCAAGTCCAGGAGAGACCAA<br>AACGACCACCCTGTGGACACCTGCCCCTCCAGCACCCTGCCCCGTTTTGGGGACGTGAAAC<br>CCTGGGCTGTGGGCCCCGCCCTACCGACCTGGAGCGCCTCTGCCTCCCCGGCCTGGAAGA<br>GGCTGTGGGTCAAGCCTAACCTTCTTGGCTTTGGGGAGCACAGAGGCCCCAAGACATCCTC<br>GGGGGCTGCCGGGCTCAGGCTCTGGGGCATGGAAACCTTTTCGAGCCTGAAACGGCGGCA<br>TCCACGGTCCCTGCCGGGCCAGTGCCAGCCTGCACCCTGGGCACCTCTGTGCTGGGCCCG<br>GCACCCCCACCCTGCCTCCCACAGCCAGGGTGTCTCCTCAGGTCAGGTCCAAAGGGGCTG<br>CAGCCAGGCCCAAAGACCCAGCCCAAGTCCCACGGCTCCTGCGGGGTCTGGGTGAGGCCT<br>GTCCTGCTGGGAGCCCAGGAGGCTGCGACCCTGCCTGGAGCTGGAAGTCTGGTTGGGGGG<br>TAGTAGGGTCGGGGGAAAGCAGGGTGGGGCAGGTACAGGGTAGAGAAGCCAGCTGGAGGA<br>GCCCAGGGAAGGCTGGCGGTGCTGGGGATGTAGGGGACAGCAGGAGCTGGTACATCACCA<br>CATGTTTCAGCTGCTTCCAGCACATCCTGCCCCAGAAGGATCTCAGCCAGGGCATGGGCTG<br>CCTTCAGGGTCTGGCAACACCAAGGAGCCAAGGCAGGTGGTAAACCGAGGCCACAACCTCC<br>TTAGGAGCCTCCACAACCAGGGCGCACAGCTGAAAGAGGAAGGAGGCCCCTGCGGAGAGC<br>AGGGTGGGCAGGAGTGGGTGGCCAGGACAGGTGGTGCCCAGTGACCGGCGGTGGGGACC<br>CGGGAGCCACAGAGGAGCCGGCTCAGCCACCCCTGTGCAGGAGGCACCTGGGGCCTGTAC<br>TCAGGCCTCACCCAGGGCTGCCCCACGCCCACATCCTGCTGACAAGCCCCCAGGACCAGC<br>ATCCCCACCCAGCTGCTCTGTGCAGAGGGGACAGGAGGCCAGACAAAAAGATGGACAAACA |

-continued

| DNA Sequences encoding circRNA's of Table 1 |
|---|
| CCCACGTAGATTCACACACACACAAACAGACACACCACACAGAAAAATATGCATGGACACCA<br>CTGAGACACACGCAGGCACCACACACTCAGAGACACACACACAGACACATCACACAGAAAA<br>ATATGCATGGACGCCACTGAGACACACGCTAACACCACACACTCAGACACAAACACACCACA<br>CACACAGACTCACACAGATACACACACAGAAAAATACACATGGACGCCACTGAGACACATAC<br>ACTCAGAGACAGGCAGTGCGCTCTGGGAAACAGGATGGTTCCTCCAAACCAGTGAAGGGCC<br>CAGGAAAGCATGAGCGGCCCTGACATGTATGGAGGGTCCAAAGGCTGCGGGAACTTGCCC<br>GTGAGTGACCTTGGCCTGGAGAACTCCCCGGCCTCAGTTTCCCCACCTGCTGATGAGGACA<br>AATTGCAGGGGCATGAGCGGCTGCTGCTCCCCTACCTCTGCGCAGGTGGCCGAGTGGCCT<br>GCAGGCTGGGTCTCCAGGTGGGGACCCTTCCCTCTTCCTCCCCACCCACTCTATCCCCTTC<br>CGGCGTCATGTGGATAGAAATTCATTAATATGCACAACAAATGACTACATGCAAGCAGGAAAA<br>CATTTGCAATAATACAGCAGGTCGATGTTCTCAACTAGCAAAACAGATGCAATAATACAATTC<br>GTGGATGTTCTCAATACAGACAAAGCTCATATAATCGACACAAAACATTCACAGAAAAATTGT<br>CAAAGGGCAGAAACCGATGACTCAAGGAAGAATATAAATAGCTAAGAAGTAAATGATCAATAA<br>TCAAACTAGAACATAATCAAAGAACTTTAAAATTAAAATTATTAATACACTCCTCCCAGGCAAA<br>ATAGCAAAGAGAGGGGACATGGTGGCTCACACCTGTAATCCCAACACTTTGGGAGGACGAG<br>GTGGGAGGTCCTTCTGGGGAGAGGAAGAGAGGAAAGCACACAGGCTTCCAGACACTATTCC<br>AAAATCATTAATACGCACACCCCAGGCCCAGCACGGTGACAGCCACCTGCAGACCCAGCTA<br>CTCGGGAGGCTGAGGCCAGAGAGCCCTGAGTTTGAGCCCAGCCTGGGCAAAGTAGCGAGA<br>TCCCCCATCTCAAAAATAAAATAAAATGCATGGTTCCTCATGAAATGTAAGGCTTTGCTATAAA<br>AACTTTGAGAGGCCAGGCGTGGTGGCTCACACCTGTAATCCCAGCACTTTGGGAGGCCAAG<br>GTGGGTGGATCATGAGGTCAGGAGTTCAAGAGCATCCTGGCTAACAACGGTGAAACCCCGT<br>CTCTACTAAAAATACAAAACAATTAGCTGGGCATGGTGGCGGGTGCCTGTGATCCCAACTCC<br>TCGGGAGGCTGAGGCAGAAGAATCTCTTGAACCTGGGAGGTGGAGCTTGCAGTGAGCCGA<br>GATCGCGCCACTGCACTCCAGCCTGGGCGACAGAGTGAGACTCCGTCTCAAAAAAAAAATAA<br>AGGCCGGGCGTGGGGTAGCTCACGCCTGTAATCCCAGCACTTTGGGAGGCTGAAGCGGGC<br>AGATCACAAGGTCAGGAGATGGAGAACATCTTGGCCAACATGGTGAAACCCTGTCTCTACTA<br>AAAATATAAAAATTAGCTGGGCGTGAGGGCACACATCTGTAATCCCAGCTACTCAGGAGGCT<br>GAGGCAGGAGAATCACTTGAACCCGGGAGGCGGAGGTTGCAGTGAGCTGAGATCGTGCCA<br>CTGCACTCCAACCTGGGCGATGAGAGCGAAATTCCATCTCAAAAAAAAAAAGGAGTACTTTTTA<br>TAAATCTGCTTTTGAAATCATTTGGATACCACAGCGGCCCTGCTGACCACAACAGCTGAGAC<br>TGTTGGGCAAATCACCAGACATTTCTGGGTTTCCTGGAAAGTAGGAGAATCTACTTTGTAAAC<br>TGCTCTCAAATTTATGAACTCCGTGTGGATAGTGAACTCAGGCAGCAGGCAGGTGGCACTCC<br>ACTGCGTTAATTTCACTTCATTTTATAATTTTCTTTCTTCCTTTTTTTTTTTTTTTTTTTTTTGACG<br>GAGTCTCACTCTGTCGCCAGGCTGGAGTGCAGTGGCCCAATCTTGGCTCACTGCAAGCTCT<br>GCCTCCTGAGTTCAAGTGATTCTCCTGCCTCAGCCTCCCAAGTAGCTGGGATTACAGGCACG<br>TGCCACCATGCCCGGCTAATTTTTTTTCGTATTTTTTGTAGAGACGGGGTTTCATCGTGTTAG<br>CCAGGATGGTCTCGATCTCCTGACCTCGTGATCCGCCCGCCTCGGCCACCCAAAGTGCTGG<br>GATTACAGGCGCGAGCCAACGCACCCAGCCTTTTTTTTTTTTTTTTTTTTTTTTTTTTTTTTTTT<br>GTGAGACAAGGGTCTCACTCTGTCGCCCAGGCTGGAGTGTGGTGCTGTGATTCTAGCTCAC<br>TGCAGCCTCAAGCTCCCAGGCTCAAGCCATCCTCCCACCTCAGCCTCCCGAGTGGTTGGAA<br>CCACAGACACCATCGCTGCGCTCTGACCGGCTCCCGGGGGCGCTCCGTGCCCCTCCTCCT<br>GCCCCACTCCTCTGGGGACATCCCCACCAAAGACCCCACGGGAGGAAACAGTCCCAGCCTC<br>TGGCCCAACCCGGCTGCGGGCGCCACGGGGAAGCCTGGGGAAGGAGGCTGCCATCAGCC<br>TCCTGAAGCTTTACGAAGGTTCATGCAACGGAAACAAAAACAAGTGGAAGTTTAACAAAACGT<br>AAAAGTAATATTTATTTATTTATTTATTTATGAGATGAAGTCTCCCACTGTCGCCCAGGTCGGA<br>GAGCAGCGGCGCTATCTCGCCTCACTGCAACCTTCAACTCCAAGGTTCAAGCGATTCTCCTG<br>CCTCAACCTCCCGAGTAGCGGGGACCACAGGCACGCGCCACGAGACCCGGGTAATTTTTTT<br>TTGTATTTTTAGTAGAGATGGGGGGGGGTTCACTATGTTGGCCAGGCTGGTCTCGAACTCCT<br>GACCTCAGGCGATCCGCCCGCCTCAGCCTCTCAAAATGCTGGGATTACAGACGTGAGCCAC<br>CTCGCCCGGCCAAAAGTAATCTTTTCTTTTTTCTTTTGACAGGGAGTCTCGCTCTGTCGCCAG<br>GCTGGAGTGCAGTGGCGCCATCTCGGCTCACTGCAACCTCCGCCTCCCGGGTTCAGGTGAT<br>CCTCCTTCCTCAGCCTCCGGAGTAGCTGGGATTACAGGCGCCCGCCACCACGCCCGGCCAA<br>TTTTTGTATTTTTAGTAGAGACGACGTTTTACCACGTTGGCCATACCAGGCTGGTCTCAAGCT<br>CCTGACCTCGTGATGCGCCGGCCTCGGCCTCCCAAAGTGTTGAGATTACAGGCGTGAGCCA<br>CCGGGCCCGGCCCAAAAGTAATCTCTAAAGAGCCCTTTAGCCGTAACTTCATTCCTGAAAAT<br>TATTTGGGAAAGTAACGCTAGGAAAACGCTCGACGAAGCTCCGGAGCCGGGGGTCCTCGGG<br>GCCGCAGGCGCGCCCGCGGGTGTCTGCTCCGGATGTCCCGCGGCAGCCCCGACGCCAGC<br>CTGGATACGAAGGCCCCGCCCCGGAGCGCGCCACCAGCCAATCAGCGCCCTGAGGCGAGT<br>CCTCACCCCGCGCGGCGGCCCCGCCCCCCGCAGCTCCGGGCCCAGCTGTCAGAGCAGCTT<br>TCCCTCAGGCTGGGCGGAGCGTGGCCACTTCCGCCAGGAGGCGCCTTTGTGTCTTCTAAGT<br>TAAGCCTATTCAGTGGATTTCTTATTCCTGGAACCCAAACCTGGGCAGTAAACCCTCCGGGG<br>CTTAGAGGCCGCTGCCTCCACAGACTGGCCGATCCCGCCCTGAAGTGCCGCTGGTGGAACA<br>GCCCGGGCGGAACCGCCCGGGCGGAACCAACGGGCTGCCGCGGGGGGTGGGGCCACGG<br>TCCCCCCCCTTCTGCCTTCAGTGGAACGGCCCCGGCGGAACCAACGGGCCACGGGGATGC<br>ACTACGCGCACCGTCGTCCTCTCCCTCTGCCTGCAGTGGAACGGCCCGGGCGGAACCAAC<br>GTGCGGCCGCCCGGAGCACTCGGCGCGCCGTGTCCCTCCCCGTGTGGCTGCACTGCAACG<br>GCCCGGGCTGGACCACCAGGCGGCAGCGGAGAGGCACTTAAAAGCCCCGTGTTACCCTAG<br>ACCTTAAAAAAAAAAAAAAAACTGCGTGTTTCCACCCCCGTCGGCCTGCAGTGGAAGGGCCC<br>GAGCAGAACCAACGGGGGAGGGGACGCTGAGCGCGCCGTGTTTCTCCTCCCGTCTGCCTG<br>GAGTAGAACGGCCCGGGCGGAACCAACGGGCAGCCGCGGGGGCGTTGTGGGCCGCGGCG<br>CGTTTCCCCGGCTCCGTGGCTCTGGGGCACTGAGGAGCGGCGCCCGCGGGGCAGCGAGG<br>AGCCCGATGCAGGGTTCTGCGCGTCATTTCCGGTCCCGCGGGCGCCCCGTGAAGCCCACC<br>TGGATCCGCCAGCGCTGTGCCACTCCCCAGTGCCGAGCTCCGAGCTGTCTCCGCGGCCTC<br>GCGCCCGGCCCCTCCACCGCGCGCCTCTCAGGCCCCGCCCGCCAGCGTCCCTTTGTTGTG<br>AAGGCGCCGGGGCCTAGCGCTATGCCTGCGGCGGAGACTGCATCAGGCTCTCGGTGGGTT<br>CTGCGTGCGGGGTGCTCTGCTCGGTGATCGGTGCTGGGTGCTGCGTGCTCGGTGCTCGGT<br>GCTGGGTGCTGGGTGCCGGTACTGATGCTGAGTGTGCGGGCGTCCGGGGTTTCCCTGCCC |

-continued

| DNA Sequences encoding circRNA's of Table 1 |
|---|
| GGATTCGCTCCTGGGGGTCCTTTCCTATGGCTGGCGCTGTGCGCGGAAAACGCTGGTGGG<br>GTTTTCCCAGCTGGCTTTAAGCGTTTTCACGTCCGGGAGTCCACGGCGACCCCCACGCCCT<br>GAAGCCTGGGAACGCGGTGTGCGTGGCCGCAAAAAGAACAACAACAACAAAAAAACACAAA<br>ACAAAACACGCAAAAAACTAAAGCAAAACTCCCGACAGCCGAGCCCCGTTCGGTGCCTTTTC<br>TTTTTTTTTTCTTTAATGGAGTGAAATCTACTTTGCTCAGGAAGCCTGCAAATCACATTTTCA<br>GGCCAAACGAGGCAGTATTTTAGAAGGGGTCGCTGAGGCAGGAGTAGGAAGGCTTTCCACT<br>CCACTCACGCATTTTCAGTGTAGGCGAATCGTAAAACGGAGGGCAGAACGAAAATGAGCGG<br>ATCTGGGAGTGCAGGCTGCGCTTCGTCCACATCGATAACAGATGTTTCCTGGTGAAGATGTG<br>TAGGGCGCAGCGGGTCACCTGGTCGGGGGAGGGCACAGGGCGTCCCTCCACGGGGTGCC<br>TTTGGCGTTGGGCACTTGTGTGGTCTCCAGCTTCCGGGTTTTGGAAGCGGAGTGTCCCCTG<br>CAGCCTGAGCCTCTTGCAGGTGGTTTCCTTGGGACGAACTCCCAGGGGGAGGTCTGAGTTC<br>TGGGGCATGGTTTGAAGATTTGGGACACATTTTGCCTGAAATTCCCTGCTGGCCGTTTGAAC<br>CCACCTGGACTTCCTGACCAGGGGCACGGATTCTTAACCTCTGGTGCAGGGGCCTGGCTAG<br>GAGAGGTCTGCACAGTTGGACGAGGTGCAAAGTGACGCTTTGTCAGTAACCCGGCGTTGAG<br>ATTCCTGTGGTGGGACGAGCAGCTCCTATGGCTTTATCCCATTTTAAATCCAAGTTTTCTTTT<br>CCTTCTAGTCCTCGGGCTCCACCCGGGGAGCTGTGCCCAGACAGCAGAAGGGAAGGATGT<br>CACTTCTGAGATGAGGTTCAGAAAGGTCTGGGCTCCTGTCCTGGCTGCTCTCTCCCACTCCC<br>TGATGAGCTTGCTGGATGAAAGCTCCTGTCAGGCTGTGGGGCGTCCTGTGGAGAAGCTGGC<br>AAGAAACTGGTGGGGGCCCTTTCCACCTATAGCCAGCAAGGAACTGAACCCAGCCAGCGTC<br>CACCTGAGTGAGCTCAGAGGTGGGCCTCAGCCCCAGTTGAGCCTTCGGATGAGGTCACAGC<br>CCTGGTCCATGGTGTGACTGCAGCTTCAGGAGGGACCTTAAGCCAGAGGTGCCTGGCTAAG<br>CTTCCCGCAGATTGCTGCCCCACAGGAGCCAACATCAAAAGCATTTGTTGTTTTGAGGTGGT<br>AAGTGTGGAATGACTGTTACAGGGCAGTAGAGAAGGAGCATGCACCCTTCCTGCTTCTTATT<br>TGCCTTTTAGAAATTGTCCTCTGTGAATCGCTTGAACCTGGGAGGTTGAGGTTGCAGTGAGC<br>TGATATCTCACCACTGCACTCCAGCCTGGGCGACAGGAGCGAAACTCCTTCTCCAAAAACAT<br>AAATTCTTCTCTGTGAAATATGTTGTTTTGTTTTTTTTTTTTCTTTACTTTTTGAGACGGAGTCT<br>TGCTGTGTCACCCAGGCTGGAGCAGGCGCAGTCTCAGCTCACTGCAACCTCCGCCTCCCAG<br>GTTCAAGTGATTCTGCTGCCTCAGCCTCCTGCGTGGCTGGGATTACAGGCGCCTGCCACCA<br>CGCCTGGCTAATTTTTGTATTTTTGGTAGAGACGGAGTTTCATCATGTTGGCCAGGCTGGTCT<br>CGAACTCCTGACCTCAGGTGATCTGCCCGCCTTGGCCTCCCAAAGTGCTGGGATTACAAGC<br>ATGAGCCACCATGCCCCGCCAACATTTTTTTTTTTTTGCCTGTTTTTCTACTTGGTTTGTAGGA<br>ATTCTTTATACTTTCTGGATATTAATCCTTTGCCATGTTGCAAGTATTTTTTCCCAGGTTGTGG<br>CTGTTGATTTCACTTTATGGTATGTATATATATATATATATTTTTTTTTGTTTCTTTTTTTTTTTTT<br>TGAGACAGAGTTTTGTTCTTATTGCCCAGGCTGTTGTGCAATGGCGCGATCTTGGCTCATCA<br>CAACCTCTGCCTCCCGTGTTCAAGTGATTCTCCTGCCTCAGCCTCCTGAGCAGCTGGGGTTA<br>AAGGCATGTGCCACCATGCCGGCCAACTTTGTATTTTTAGTAGAGATGGGGTTTCTCCATGTT<br>GGTCAGACTGATCTGGAACTCCCAACCTCAGGTGATCCACCCACCTCAGCCTCCCAAAGTG<br>CTGGGATTACAGGCGTGAGCCAAGTCTGGCCTTTTTTTTTTTTTTTTGAGACAGGGTCTCACC<br>CTGTTGCCCAGGCTGGAGTGCAGCGGCGCAGTCTGGGCTCACTGCAACCTCCCCGTCCTG<br>GGTTCAAGCAATTCTCCTGCCTCACCCTCCCGAGTAGCTGGGATTACAGGTGCATACCACCA<br>CACCTGGTTAATTTTTGTATTTTTAGTAGAAACAGGGTTTCACCATGTTGGTCAGGCTGGTCT<br>CGAGCTCCCGACCTCAAGTGATCCGCCCACCTTGGCCTCCCAAAGTGCTAGGATTACAGGC<br>ATGAGCCACTGCGCCCGGCCCACTTTGTGGTGTACTTTGGTGAAACAGAATTCTTCATTTAG<br>CCAAGTTAGTCCACCTGACCCTTTTTTTAATGGGTCATGCTTTTGGGGTTTGGTTAGAGAAAT<br>TATTGTCCTACCCCAAAAAGGGTCAGGAAGACATTCTCTTATATTTTCCTGAGCATAAAGTTTT<br>ACACATTTAAGTTTATCATAAGAGCAGGCCACCTGGGTTCGAATCGTGACCCTGCTGCTGCA<br>AAGCCGTGTCTTTCCTTCGTGTGTCTCACGTGGGTGATAACAGCACCTTCCCCAGAGGGCTA<br>TTGTGGGGATTCACCGCTGTGCAGAGAGTGCTTCGGACCCTCCAGCAGCACAGTCAGGGCT<br>GTGTCAGTGTTACTAATTGTCGCTGTTTGTGTACTGATAATGAGATCAGAATCCAGTTTTTCTT<br>TTTGCCTGGCAGCATGGACAACTGTCCTGGTATCATAGACTGAATAAAGTTTCCTTCTTCAGC<br>AACTCGTGGTGCCTCCATTCTGGGTACACCAGACCTGTTTGTTTGTTTTTTTTTGAGACAGTC<br>TCGCTCTGTCAGCCAGGTTGGAGTGTAGTGGTGCAATCTCAGCTCACTAAAGCCTCCGTCTC<br>CCAGGTTCAAGTGATCCTCGTGCCTCAGCCTCCTGTGTAGTTGGGACTACTGGCACCCACCA<br>CCACGTCCAGCTAAGTTTTTTGTATTTTTGGTAGAGACGGGGTTTCACTGTGTTAGCCAGGAT<br>GGTCTCAATCTCCTGACCTCGTGATGCGCCCACCTCGGCCTCCCAAAGTGCTGGGATTACA<br>GGCTTGAGCCACCGCGCCCGACCTCGAGGTCCTTATTCTTTTGCATTTGTTTACTCGCCCAG<br>CCCTGCACCAAGGTCTCAGACTGAACTAGAAGTCCTCATGTCTTGGGAGGACGGCTGCCGC<br>CCCCTCCCTGCGCCTCCGTCTCCTTGCAGGACGTGTTTGTCTTCTACTCATCGTGCGTGCAT<br>AGCTTTCTCTCTGATTCACACATGCTTTGTGCGTGCATAGCTTTCCCTCTGTGATTGACATGT<br>GCCTCATAGGGCTGGATCTATCTCGAGACTACATAGCCTCTTGTTTCTAAGCTTTATTTTTTTC<br>TGGGACAGAGTTTCGCTCTGCCGCCCAGGCTGGAGTGCAATGGCGCGATCTCCGCTCACTG<br>CAGCCTCCACCTCCTGGGTTCAAGCGATTCTCCTGGCTCAGCCTCCTGAGTAGCTGGGATTA<br>CAGGCACGCGCCATCATGCCCGGCTAATTTTTTGTAGTAGAAATGGGGTTTGACTGTGTTGG<br>CCAGGAGGATCTCGATGTCCTGACCTTGTGATCCGCCCACCTCAGCCTCCCAAAGTGCTGG<br>GATGGCAGGTGTGAGCCAGCGCGCCCGGCCGTTTCTAAGCTTTTACTCAGTAGTTTTAGTCT<br>CTTGGTGACTCGTCGTGATTGTGATGATGATCGTGATGGTGGCCAGATGGTGGCTTCTCATT<br>CTGTCACTCTGATGATCATGGATTGACTTTGTGCTGGGAAGAAAGACTTCCCCTCCTTTGCCA<br>TTCGTTCATCAGCATGGCCTTGTGGGCTGTTGTTTTACTGGGGGTTCTGATCCTTTACTGTGT<br>TACGTACTCTGCCTTTCAAGCCCCCTGCGCCCTCCCTCGGCCAACCCTGAGTTCATTCCTAG<br>ATCACAAACTTTCGGCGCAGCCAACATGACCGCTCCTCTGGTGTCTTTCCCACCACAGCCCG<br>AGAGTCAGTCATTTTTCAAAGAAGCCTGGTTGGCTTTGTGGAGAATGATATATGTTATTATTAT<br>TTTTTGTTTTGTTATGTTGTGTTTTTTAGACAGTCTCGCTCTTTGCCCAGCCTGTAGTACAGTG<br>GTGCAATCTTGGTTCCCTGCAACCTCCGCCTCCGGGTTCAAGCGATTCTCATGCCTCAGCCT<br>CCTAAGTGGCTGGGACTACAGGCACCCGCCAGGATTAATCTTTTTTTTTTTTTTTTGAGATGG<br>AGTCTCCCTCCATCACCCAGGCTGGAGTGCAGTGGCCCGATCTAGGCTCACTGCAACCTCC<br>GCCTCCCGGGTTCAAGAGATTCTCCTGCCTCAGCATGCCAAGTAGCTGGGACTACAGGCGC<br>CTGCCACCATGTCTGGCTAATTTTTTTTGTATTTTTAGTAGAGATGGGGTTTCATTATGTTGGC |

-continued

| DNA Sequences encoding circRNA's of Table 1 |
|---|
| CAGGCTGGTCTCCTGACCTCATGATCTGCCCGTCTCGGCCTCCCAAAGTGCTGGGATTACA<br>GGCGTGAGCCACCACGCCCGGCCTAATTTTTTGTTTTTTAGTAGAGACTAATTTTTTGTATTT<br>TTAGTAGAGACAGGGTTTCGCCACATTGCCCAGGCTCGTCTAGAACTCCTGAGCTCGGGTAA<br>TCCGCCTGCCTCAGCCTCCCAAAGTGCTAGGATTACAGGCGTGAGCCATTGCGCCCAGCCC<br>CTTTAGTGGAGAATGATATTTAGAAACCAAGGTTAGGGCGCTGGGAGCGCGCTGTGCAGGT<br>GTGACTGTCTCTGGGCAGATGTGCTGTGTTGGGGTGTGTGTGTGCGTGCGTGTCGCCCGTC<br>CGCCCATCCGTTCAAGCCTGTGCGCTCGGGCCCGACAGCACCCTCACAGGCCGACACCGC<br>GGGGGTCATTCCATCCATCTTCTTTCTTCTTTTTATTTATTTATTTATTTGTTTTTGAGACGGAG<br>TCTCACTCTGTGGCCCAGGCTGGAGTGCAGTGGCACGATCTCAGCTCACTGCAAGCTCCGC<br>CTCCTGGGTTCTCGCCCTTCTCCTGCCTCAGGCTCCTGAGTAGCTGGGAGTACAGGTGCCC<br>GTCACCACGCCCGGCTAATTTTTTGTATTTTTAGTAGAGACAAGGTTTCACAGTGCTAGCCAG<br>GATGATCTCGATCTCCTGACCTCATGATCCGACCCCCTTGGACTCCCAAAGTGCTGGGATTA<br>CAGGCGTGAGCCTCCGTGCCTGGCCTTTTTATTTTTTTGAGACAGAGTCTCTGTCGCCCAGG<br>CTGGAGTGTGGTGGCATGATCTCGGCTCACTGCGACCTCCGTCTTCTAGGTTCAAGTGATTC<br>TTCTGCCTCAGCCTCCCGAGTAGCTGGGATTACAGGCGCATGCCACTGCACCCAGCTAACTT<br>TTGTATTTTTACTAGGGATGGGGTTTCACCATGAACTCCTGACCTCAGGTGATCCACCCGCC<br>TCGGCCTCCCAAAGTGCTGGGATCACAGGCGTGAGTCACCGTGCCCAGCCTCTTTTTTTCAT<br>TTTTATTTTTATTTTTTCACTACAAGACTGCCCTGAAGGACTTCCTTTCGTGTTTGCATCTCGC<br>TTCACTCACATGATGAAATCTGCCTCCCGTCATGTACAAAATATTTATGTATTTGCCCAATCCG<br>GAATTCTAACCCATGAGTCAGCAAAAAAAAAAAAAAAAAAAGAAAAAAAAAAGAAAAGGGAGGCT<br>GGGCGCAGTGGCTGATGCCTGTAAATCCCAGCACTTTGGGAGGCCGAGGCAGGCAGATCA<br>CGAGGTCAGGAGTTCGAGACCAGCCTGGCCAACATGGTGAAAACCCGTCTCTACTAAAAATA<br>CAAAATCAGCAGGGTTTGGTGGCACGTGCATGTAATCCCCACTACCCGGGAGGCTGAGGCA<br>GGAGAATCGCTTGAACCTGGGAGGCGAAGGTTGTGGTGAGCCAAGATCGTGCCATTGCACT<br>CCAGCCTGGGCAACAAGAGTGAAACTCCATCTAAAAATGAAATGAAAATACAAAAATTCACTG<br>GGCGTGGTGGCGGGTGCCTGTAATCCCAGCTACTCAGGAGGCTGAGGCAGGAGAATCACTT<br>GAACCCGGGAGGTAGAGGTTGCAGTGAGCTGAGATCGCGCCATTGCACTCCAGCCTGGGC<br>GACAGAGCGAGACTCCGTCTCAAGAAAAGAAAAGGGAAAAAAGCATGTTTAGAACTCGGTAT<br>TTGTTTGGAGCTCCTGTGTCTGGAGCTACTTGTGTGTCTGGAGCCCTTGTGTCCATCACCTG<br>CGTACCCACATCCAGCGTCCATGCACCCGAGTTCCCAGGGCTTGTTCTGCTTCTCCCCTCAG<br>GGTGATTGTGTCGTTTGTTTGATCTGTGGTGTGGTTCATGCATTCGTGTTCGTGTTCCATTTC<br>AGAGACCCTTTTCCCCTACCCTTGTTGATTTAATTATTTTTGCTTTTTAAGCAAGCGACATATT<br>TTCATGGTTCTGAAAGTCAGACCTGGAGCCGCCCCCACCTCACTGCACTGCACTCCTGCCTG<br>CCCTGTCACTGAAGAGTCTCCTTATTCTTGGGTATATCCTTCCTGTATTTCTTTTTCCTTTTCT<br>TTTTTTTTTTTTTTTTTCTGAGAAAACGTTTCACTGTGTCGCCCAGGCTGGAGTGCAGTGGTG<br>AGATCACGGTCACTGCAGGCTCATCCTCCCAGACTCAAGCAGTCCCCCCACCTCAGCTGGG<br>CACACAGGCGCACACCACCGTGCCCAGGCCTAATTTTTGTACTTTTTTGGTAGAGATGAGGT<br>TTCGTCATATTACCCAGGCTGGTATTGAACTCCTGGGCTCAAGCAATCCTCCTGCCTCGGTC<br>TCCCAAAGTGCTAGGATTACAAGCATGAACCAACACACCTGGGCAAAAAATGCTCCAACTTTT<br>TTTTTTTTTTTGAGACGGAGTTTTTGCTCTTGTTGCCCAGGCTGGAGTGCAATGGCGCAATC<br>TTGGCTCACTGCAACCTCCACCTCCCAGGTTCAAGTGATTCTCCTGCCTAAGCCTCCCAAGT<br>AGCTGGGACTACAGGCATGCGCCACCACGCCCGGCTAATTTTGTATTTTTTTAGTAGAGACA<br>GGGTTTCTTCATGTTGATCAGGCTGGTCTCGAACTCCCAACCTCAGGTGATCTGCCCGCCTT<br>GGGCTCCCAAAGTGCTGGGATTACAGGTGGGAACCACTGCACCCGCTGGCTGTCCTGTTTT<br>TTTTTTTTTTTTTTTTTTTTGAGATGGAGTCTCGCTCTGTTGCCCAGGCTGGAGTGCAATGGC<br>GCGATCTCGGCTCACTGCAAGCTCTGTCTCCCAGGTTCACGCCATTCTTCTGCCTCAGCCTG<br>CCAAGTAGCTGGGACTGCAGGCACCCACCACCACGCCCAGCTAATTTTTGTATTTTTAGTGG<br>AGACGGGGTTTCACCATGTAGGCCAGGATGGTCTCAATCTCCTGACCTTGTGATCCACCCGC<br>CTCGGCCTCCCACAGTGCTGGGATGACAGGCGTGAGCCACTGTGCCCAGCCTCCTGGGAT<br>GACAGGCGTGAGCCCCCGCGCCCGGCCTCCTATTCTTAATTTCCAAGGCCCACTTGGGTTG<br>TGGGTGGTCCCCACTTACCATGGTCTGAGTTGTGATTTTCTGACTTTATGATGGTGGGAAAG<br>CAAACGCCTTCAGCAGAAACGCTGCCCTGAGCTCACAGCCGTCCTCTCTCTCACTTCCGGTG<br>GGGTTGTCTGAATTTCACGAGCGGCTCAGCGCGCTTATAGCCACTCTGCATTAGGCGGCTTA<br>GCCCAAATGTCACTGATGTGGGTGTCAGCACGCGGAGGTGGATGAGGCACATTAAGAGCCA<br>AAGGACGGGCTGGGGGCTGTCTGTGGAGATGTCAGTGGCCTTGAAAAGACAGTGCACTGG<br>GGCAAGCGTCTCACGACTGCTGAGTGTCTACCCTGCGGCCCACGGGTCTCCTGGGCTGTGC<br>CCCAGACGTGAGTGGACAGCAAGCGATCCTCCCTCCTCGGCCTTCCAAAGTACTGGGGTTC<br>TAGGTGTGGGCCACCGCCGCTGGCCAAACATGAAGGTTTGACTTACAACTTTGTGGTCTCTG<br>GTCTGAACAGGCACCTGCACCTGGAGGACTCTGAGACCCTGTTTCCAACCATGATGTTTTGC<br>ACTTGTGCTCTGATATGAAATGTGTTTGGTCTTTGTTCCTGGTTCCTGGCACAGAAGCTCCTC<br>GAAGCCTTGGAATTTCCTGAGTGACAGGAGTGGTTCAGATCACCCCGGAGCTTATGCTGATC<br>ACACCTGAGCTTATGCTGATGAGGCAGGGGGTGGGGCCCTGGAGAGCGGGGGTAGGGGG<br>GACTGGTCGCCAGAACACCAGGTGACCCCAGGATTGGAGGCTGGGAGCTTTGAGCCCCAC<br>CCGCCAACCTCAGGGACGCAGCGAGCGAAGGTGGAGATTAAACGCTGTAAAAACCCGTGAA<br>TGAGAGATGAAAGAGTGGGATGGTCTTCGGATTGTGGTGCTGGGGGCAGGGGGTGGCGCC<br>CAGAGAGGGCCTGAAACCCAGCACCTGCCCAGGCCTTGCCTGCGCGTCTCTGCGGCCGGC<br>TGCTCCTCTGTTTTCTTTTAACGTAAGTGCTTTCTGCAGTTCTGTAGGGCAGTCCTGTCAAAC<br>TCATTGATCCTCAGGAGGGTGTCGTGGGAACCCCGATGTATAGCTGCCGGTCAGAAGCACG<br>GCCCACAGGCTGACCAGCATCTGAGGAGGGGGCAGTCTTGTGGGATCCAGCCCTCGCCGC<br>AGGGGACCTGGCACTCTCCCCAGGGGGACGGCTTCGGGAGGGAATTGAACCAGAGGACAC<br>ACAGCTAGTGTCTGTGGAGAATTGCTCAACGTGGAAATAACCTGCATCTCCTGTGGGAAGTG<br>TTGTGTGGGAGTGCAGAGAAACTGTGCATTCCTCACAGGACTTTATTTATTTGCTTGTTTATTT<br>ATTTGTTTGTTTTTGGAGACAGAGTCTCGCTCTGTCCCCCAGGCTGGAGTGCAATGTCTCGA<br>TGTCGGCTCACTGCGATTTCCACCTCCAGGGTTCAAGCAATTCTCCTGCCTCAACCTCTTGA<br>GTAGGTGGGATTACAGGTGCCCACAACCACACCTGGCTAATTTTTATATTTTTAGTAGAGACG<br>GGGTTTCACCTTGTTGGCCAGATTGGTCTCGAACTCCTGACCTCAAGTGATCCACCTGCCTC<br>CAAAGTGCTGGGATTACAGGCGTGAGCCACCAAGCCCGGCCTCCCCCATGTAAACCTTGAA |

-continued

| DNA Sequences encoding circRNA's of Table 1 |
|---|
| CTCTCGGAACTACTTAGGAAGGACCCCGGGCTGTGATCTCTCACAACTACTTAGGGAGGAC<br>CCCGGAACCCCCTGGCTGCTCAGCTGGGTTCCAGCACCTGAAGGTGCTGTTGCTTTCCCCT<br>GGGGCCCGTCCCCGAGATGAGAGGAGCACGTGCTGGAATTCCCTCTTTCAGGCACTTTCAT<br>GCTTTTATTTCTACACGTGGTGCTTCCCGCACAGCTGACAGCGCATGGTGGAGCCGAGTCGT<br>GCGTTTCTGTCTGTGATTCGTCCCTCAGTCTTCCCCCGCTCCGGTGGGTTTGGGCTTGGGGT<br>CCGTCCCTTTGACACTGGGACTGAGCCCCTCATTTCCATCGTAGCTTCAGCTCCATCAATAA<br>GGTGTTTGTTTCTACTGTTGACAGGCACGTAGGTTGGCATTCTTTTGGTGTTTGCTTTGTCTT<br>GTTTTGCTACTAACAAAAAATGCTCATTAAACACCCACCTCCAAGACTTCTATGAGAAGGTGT<br>GAAGAGCCCACCCATTTTCCCGGGACCGTTTGGCCCTCTGTGACCCAAGTCAGCCTCGGCG<br>AAGTGCTTTATTTTCTTGTTTTTGTCGCTCCCTGTCACCCGCATGACCTCTGAAAGGTTGCA<br>CCCAGCCGGGCACGGTCACTCATGCCTGTAATCCCAGTTCTATGGGAGGCCAAGGCGGGC<br>GAATCACATGAGGTCAGGAGATTGAGACCAACCTGGGCAACATGGTGAAACCCTGTCTCTTC<br>TTTTTTTTTTTTTTTTTTTTTTTTTTTTTTTTTTTTTTTTTTTTTTTTTTTGAGACAGAGTGTTGCT<br>CTGTCGCCCAGGCTGGAGTGAGTGCAGTGGCGCGATCTCGGCTCGCTGCAAGCTCCACCT<br>CCCGGGTTCACACCGTTCTCCTGCCTCAGCCTCCTGAGTAGCTGGGACTACAGGCGCCCGC<br>CACCACGCCTGGCTAATTTTTTGTATTTTTAGTAGAGACAGAATTTCACAGTGTTAGTCAGGA<br>TAGTCTCCATCTCCTGACCTCGGGATCCCTCTGCCTCAGCCTCCCAAAGTGCTGGGATTACA<br>GGCGTGAGCCACCACGCCCGGCCTAAATCCTATCTCTTCTAAAAGTACAAAAATTAGCCAGG<br>CTTGGTGGCGCATGCCTATAATTCCAGCTGCCCGAGAGGCTGAGGCATGCGAATCCCTTGA<br>ATCCAAGAAGTGGGGGCTACGGTGAGCTGAGATTGTGCCACTGCACTCTAGCCTGGGCGAC<br>AGAGTAAGAGTCCCTCTCAAAAAAGAAAAGAAAAGAGGCCGGGCGCGGTGGCTCACGCCTG<br>TAGTCCCAGCACTTTGGGAGGCCTAGGTGGGTGGATCACGAGGTCAGGAGATCGAGACCAT<br>CCTGGGTAACATGGTGAAACCCTGTCTCTACTAAAAAAATACAAAAAAAAACAAAATTAGCCA<br>GGCGTGGTGGCGGGCGCCTGTAGTCCCAGCTACTTCAGAGGCTGAGGCAGGAGAATGGTG<br>TGAACCCAGGAGGCAGAGCTTGCAGTGAGCCAAGATCATGCCATTGCACTCCAGTCTGGCT<br>GACAGAGCGAGACTCTATCTCGAAAAAAAGAAAAGGAAAAGGAAAGAAAGGTCTCACTAGAC<br>AGTTTCAGGCCGGAATCTGTTTGCATTTGTACCGTCAGGAATTTCCAGCCTGGGAACAGTCA<br>GTGACAGGAACGAACCGTGGGTGCCTCTGCAGGGGTGGCTCCTGCCTGGCTGCCCTTGAG<br>TTGGCTGAGGAGCTGAGAACTTGGACTTCAGGATTCTCTGACTTCACTGGTCTGACGTGGAG<br>CTCCCAGTGTTTGAATAAGAAGCGGCTGGGCGTGGTGGCAGGCGCCTGTAATCCCAGTTAC<br>TCGGGAGGCTGAGGCAGGAGAATCCCTTGAACCTGGGAGGTGGAGGTTGCAGTGAGCCGA<br>GATTATGCCACTAAACTCCAGCCTGGGCGACAGATCGAGATTCCATCTAAAAAAAAAAAAAA<br>AGAATAAGCAGCCAGCCTCAGGCATTTACGCAGGGACAGGTGTTTACGTGGGGGGAAGATT<br>AGATATCGCCTCCTCCTGCGGCCTTGGAGCTGTGGGGACAGGGATGCTGGGGGTGAGGAC<br>GGTTCATGGTAGTGAAGTCCTGCAGATTGGGAGGGGAATGGAGACCCCGGGACCACGTGG<br>GCTCAACTGCAGGGACGGGACAGTCACCCACACAGAGCCGGGGCAGGGCTGTGGGAGCAC<br>AGGTCGGTGTGACGTTGGCTGGGGCTCAGCATGCGTGTCCCAGGGCTGGGCAGTTCCACT<br>CCTGCACGTAGACACAGACGAGGATGCTCCTAGTAGCCCGTCCCAAGTGCTTCTTGCCAGA<br>ATGGGTCCATTTGTCCAGTGGGCTGCTGTGCAGTGATCGGACAGAGAACCCGCGTCCCAGC<br>GCAGCTGCATGGAGAGGCCTTTGTTTGCAGTCGGCTTCTTGTTTAAGCTCTTTTAATTTTTTTT<br>AACTTTTTTTTAATTTTTAGAGTCAGGGTCTTGCTCTGTTGCCCAGGCTGGAGTTCAGTGGCA<br>CAATCACGGCTCACTGCAGCCTTGACCTCTCTTGTTCAAGCAATCCTCCCACCCCAGCCTCC<br>TAAGTAGTTAGGACTACAGACATGCACCACCATGCCCGGCTACATTAAAAAAAAATTTTTTTTT<br>TTTGAGACGGAGTTTCACTCTTGTTGCCCAGGCTGGAGTACAACGGTGTGATCTCGGCTCAC<br>CGCAACCTCCGCCTCCCGGGTTCAAGCGATTCTCCTGCCTCAGCCTCCTGAGTAGCTGGGA<br>TTACAGGCATCCACTACGCCCGGCTAATTTTGTATTTTTAGTAGAGACGGGGTTTCTCCACGT<br>TGGTCAGGCTGGTCTTGAACTCCTGACCTCATGATCCACCCTCCTCGGCCTCCCAAAGTGCT<br>GGGATTACAGGTGTGAGCCATCGCGCCCAGCATTTTTTTTTTTTTTTTTTTTGACGGGAGTCT<br>CGCTCTGTTGCTCAGGCTGGGGTGCAATGGCGCGATCTCAGCTCACTGCAAGCTCTGCCTT<br>CCAGGTTCAAGTGATTCTCCTGCCTCAGCCTCCCGAGTAGCTGGGATTACAGGTGCCAGCC<br>ACCACACCCGGCTGATTTTTTTTTTTGTACTTTTAGTAGAGACGGGGTTTTGCTGTGTTTGCCA<br>GGCTGGTCATGAACTCCTGAGCTCAGGTGATCCGCCCACCTTGGCCTCCCAAAGTGCTGGG<br>ATTCCAGGTGTGAGCCACGGCGCCTGGCCCAGAACCTTAAGTTCTTGATGTACAGAGAACG<br>GCAGCGTCAGTGAAGTGTGATTTCTGTTTTTTTGTTTCCACTAATTGTGAGCAAACATTAGGG<br>TGGGGACTGGGCTGCTTGTGTGGGTCCCACAGGCTTCTTGGAGCACAGTGTCAGCAGAGAA<br>GGGGAATGGGGGTCCTCATTGCGGGGAGCAGTTTTGCCTGGGATGCTGTGAGTTTCTCAGA<br>GGGAAGCTAAGTGGACAGACTGTTCTGGCAAGAGGGAGATGCTTGCCTTTTGAATTCCAGGT<br>TTGCCTCGACGTCAGGTGGGACGTGACTGGCGTCGTCTGCACACGCCCGAGCCCACGTGC<br>TGTTCCTTGCTCCTGGAGGGGTTTCTTGAGCGTGGCCTCCTTGCCATGTAAATGAATTTGGT<br>TTTAGAAACTCGCTGGTGGTGGCAGAGCCTGTGTAGCGGGTGCTGTGACAGCGTCCCCAGC<br>CAGGGGGCAGCCTTCGAGGTGGGAGGGAGAGGTCAAGGGCCGTGAGGCCTAGTGAGGTG<br>GGGAGTGAGATCCACGCCTGCCATGAGCTCCACCCCTGCCTTGCGGAGCCCTGTCGCGAG<br>TGCTCTGTCCTTTTGCTCTGCCGCACCCTTTGTTGTTGGATTTTCACCTCAGGAAAGCCAGGT<br>AGCTGCTCCACCCCCAGCCAGGGCCCATCAGTCCGGGAAACTGGCACAAAGTCTCCTAGCT<br>CCCTGGCTCAGGGCCCAGCCAGTCCTAGCTCCAGGGAGGCTGCAGCCCATGGAGGTTTAG<br>CTCCCAGCTTGTTGTCACCCCAGGCTAAGCAGTGGGACTGTGCTGCTGAACAGGAAGAAGG<br>GAATGGTGTCTTTGTGGAGATCTGGCACTGTCAGTGGCCCGAGGAGTGGATGAGTCCTTTG<br>TTATTCCGAGGCTGTGGGAACTGGTGGAGGGGTCGGCCTTCTCCTCACTGAGGCCTGGGGT<br>GCCCTTGGAGGCAGCTGTCCTGGTGCACCGAGGGGTCAGGGCACACATGGGTGGCCTGGG<br>AGCGTCTGGGTGGCACTGAGCTGGCGGTGTGATGGGCAGACGGGGAGACCTGGGTGCACA<br>GACACACACAGCAGGGGGAGGGGAGGAGAGAGAGGAAGGCTGCAGAGGCCCTGGCATTG<br>CCGCCACTGGGGAGAGGGCAGAAGCGCCTGTTCCCGGGTATGGGGAGGCCAAGTTTCAGG<br>CACCTCTGAGCACTGCTGGGCAGGTGAGCTGGGGGAGAGGCCGGCCTGAGCACCCAGGC<br>GAGGTCTTCATGGGGGAGGGGGTGGCGTGCGTCCCTCAGTGTGAACACAGAATATTTATGT<br>ATACATATGGCACGCACGCAAGTGCATAAACATAAACACAGAAGGAGGTCACGAATGAGGTG<br>GGAACCCCAGTTTCCCGGGGGAGAAGTGAGACGAGGAGGGGTACTGGGTCGGGCAGCACG<br>GCCGGCACCACACGCTCCCAGAGCGCCTTGGTGAGACAGGATGGGCGCCCCTTCAGATGC |

-continued

| DNA Sequences encoding circRNA's of Table 1 |
|---|
| ACAGCCTCCCCCGAAGCAGGAAGAGAAACCCAGGTGTGAGAAACAGGAAATCGGGCTGCCT<br>GAGCGCTGGGATTGAGACCTGGGGGAGGTGGGGTCTCGGTGCTGCGGAGTCACAGTGGCG<br>TCTGTGCAAAGCCCCAGCTGGGGGGATGATTCCCACTGGACCTCAGGAGGAAACGGCTGTT<br>CTGACCTTCCTGGAGCTCGTGGGAAGGGAGGGGGTGTCTCGCCCCGAAGCCACAGTCGCC<br>TGAGCGTGAAGCGGGTGTAAGTGTGGTTTTATACCACGGAGTCTGTCTAGAAAGTAGCATGG<br>AACTTTAGGAGGCCGAGGTGGGCGGTTCACGAGGTCAGGAGATCGAGACCATCCTGGCTAA<br>CACGGTGAAAACCCGTCTCTACTAAAAAAAAAAAAATTACAAAAAATTAGCCGGACGTGGTG<br>GCGGACGCCTGTCGTCCCAGCTACTCGGGAGCCTGAGGCAGGAGAATGGCGAGAACCCGG<br>GAGGCGGAGCTTGCAGTGAGCCCAGATCACGCCTCTGCACTTCAGCCTGGGCGACAGAGC<br>AATACTCCGTCTCAAAAAAAAAAAAAAAAAAGGAAAAAGAAAGTAGCATGGAATTAGTCCTGGG<br>CACCCGACAGCGGCAGCCACAAAGCCCATCGAGAAGGTGCAGCTGCCAGGCAGGGCGTGA<br>AGGACCCACAGCCCCAGGTCTGCCAGGACGACAGTCAAGTGTGCCAGGAGACCGTCTCTCA<br>AGAGCAAGGATCCGCCAACACGCGCAGAGAAAAACGGGATTCAATTGCTAAAAATCTTTGGA<br>CAGTGAACGATTGCATTTTCTTTTTTTCTTTTCTTGAGACAGAGTCTCACTCTGTCACTGAGGC<br>TGGAGTGCAGTGGTATCATGTCGGCTCACTGCAACCTCCGTCTCCTGGGTTCAAGCAATTCT<br>TCTGCCTCAGCCTCCCGAGTAGCTGGGATTACAGGCGCCGGCCACCATGCCCTGCTAGTTT<br>TTATATTTTTAGTAGAGACGGGGTTTCGTCATGTTGGCCAGGGTGGTCTCGAACTCCTGACC<br>TAAGGTGATCCACCTGCCTCGGCCTCCCAAAGTGCTGGGATTACAGGTGTGAGCCACCGTG<br>CCCGGCCCAATTGCATTTTCAAAGTGATTTTAAATTGGTGGTTGAAACCTTTGAGGACATTAA<br>ATGTTCAAAACGGGTGATGTGTTTCCTTTTCTTAATATTTTAGCGTCTGCTTCTGCGCTTTGCC<br>TGGGAGAGGCCCTGGTGGCCTCGTTCCTGGCGCCCGGAGTCCCTGCTGCGGCCCCACCCC<br>CGGGCGGTCACGGTGACCCATGCTGCCCAGCCTGGAGGTAAAATCGTTCGTGGCTGTGGCT<br>TCAGCATGTCGTCCTCGGTGAAAACCCCAGCACTGGAAGAGCTGGTTCCTGGCTCCGAAGA<br>GAAGCCGAAAGGCAGGTCGCCTCTCAGCTGGGGCTCTCTGTTTGGTCACCGAAGTGAGAAG<br>ATTGTTTTTGCCAAGAGCGACGGCGGCACAGATGAGAACGTACTGACCGTCACCATCACGG<br>AGACCACGGTCATCGAGTCAGACTTGGGTGTGTGGAGCTCGCGGGCGCTGCTCTACCTCAC<br>GCTGTGGTTCTTCTTCAGCTTCTGCACGCTCTTCCTCAACAAGTACATCCTGTCCCTGCTGG<br>GAGGCGAGCCCAGCATGCTAGGTAGGCGGCGGCTCGGGCAGGGTGGAAGCCGGCCACCT<br>GCCACCCCACAGGGAGCAGCCAGCAACCACCCGGGAGGGCCGGGGGAGCCCAGGTCAGG<br>ATGGGAGGCCGGGGGTGGAGCCCACTGCAGGCATGGGAGGGGTGATTCTCCCTCTTGTCT<br>TCGGCCCCCTCCCTCCCGCAGGTGCGGTGCAGATGCTGTCCACCACGGTTATCGGGTGTGT<br>GAAAACCCTCGTTCCTTGCTGTTTGTATCAGCACAAGGCCCGGCTTTCCTACCCACCCAACT<br>TCCTTATGACGATGCTGTTTGTGGGTCTGATGAGGTAAAGAATCTCCTGGTTTTGGTTGAGTG<br>TCTCTTTTTCTTTAAATGTAAAGTCCCTCTCGTTACTAGAGCGGGGACTCTGCTGGCTGGTGA<br>GTTTTCAGTGCAGACTTTATAAAAGCACCAGGGCTGTCCAGATTTCAGGACACCAAATGAAT<br>GTGGCTTCGTGGCTCTCACTGCCACGTGTGTTCAGTCAGCTTCTTTCCGGGCTGGTGGTCTC<br>AGGACAGGGTGCCTCCTTGTCTCTGGGACGTTTTCAAGGGGTGGCAGAAGTCACTTCCCATT<br>GGACGCAGTGCCGTTTCCTGGGGGCTCGACCTAAAGCGTCACAGAAGCGGGTCCAGGCAC<br>CATGTTGGTGATGAGGAGGTGGGCGGAGAGGGGCCGACGTGCCAACCGAGCGAGCGAGC<br>CCCTTGGAGAGCCTGCCCGGTGGGTGCAGGCAGACAGACTCGTTCTAAGGTGATGGTGCTT<br>TTGGCTCATTTTTAGGTTTGCAACTGTGGTTTTGGGTTTGGTCAGCCTGAAAAATGTGGCGGT<br>TTCGTTTGCTGAGACGGTGAAGAGCTCCGCCCCCATCTTCACGGTGATCATGTCTCGGATGA<br>TTCTGGGGGAGTACACAGGTGAGGCCCCCGGGCCCCGCCCCTCCGCCTGCGCCCCACCAT<br>CCCAGGCCTCCATCCGTGGTGCCCGTCTCTGCTGCCTGCCATGGGGCTCTGCCGCGAGGA<br>CCACTCAGAGTGGTGCCCACACTGGCAGTGCCTTCACTTCTCTCACGGTCACATGTGCGGG<br>GGTGTCTTGGAGCCTGGCGTCTGCCAGGTATTCTCACACTGGCATGCGGAGGTCAGGGCAG<br>GGTTGTGTCTGTGGCCCTAACTGGGTGGGGAGACAGGTGGGGGCTGGGCAGATTCCTGGC<br>AAGCAAGATTACTGCAGGTGCCAATCACTGATCCGAAGAGGACGGGTGGGGGCCGCCTTCG<br>GCCAGCACCACACAGGCGGCCGTGGCTCCTGGTCCGTGGGCCCTCCTGTGCCAGCACCCC<br>ACAGCCTCTCCAGCACCCGCCACCACAGGCCTGTCCTGGGCCCCAGCCCCTGACCTCAGCT<br>GCAACCCAGGCTCCTGCCTCTCCCACCTCTTAATGACTCACAGGCGATTTCCAGCGACATGT<br>CAGCCCCATGTCGCGTACCCAGTGTGGCTGCATGAAAACCAGCGAGGAGCAGAGGCGCCC<br>ACAGAGCGCGGCGTCTTGAACGGAGTCGGGGGGTGCACACGTGTTCGCTTATTTAAGAAAC<br>TACAAGATCTTAAGGCCGAGGGAAGTGTCTGTCTGCCTTTGGGGACGGGAGGAGGCCGAG<br>GGTCCAGGATGGGGTTGGGCTTGCCCCACATGCACTTGAGACCCGCACACACGTTTAGGTG<br>ATTATAACAAAATCAAAGCCTAAAAGTCAACTCTGGTTTTTTTTTGTTTTTTTTTTTTTGTTTTTT<br>TTATGTTTTTGAGACAGGGTCTTGCTCTGTCGCCCAGGCTGCAGTGCAGTGGCGAGGTCAC<br>GACTCACTGCAACCTCGGCCTCCCAGGCTTAGGCAATCCTCCCACCTCAGCCTGTTGGGTA<br>GCTGGGACCTCAGGCATGTGCCACCATGCCCAGCTAATTTTTGTATTTTGTGTGTCTTTTTGT<br>TTTTTCACTGTGAATATACGTTAGTCATTTTTCTTAACAATTGAAACTTGGAACTCTGGGGATT<br>CAGAATTAACAGCCTTGGCTGTGAGCTTATCGATACCAGAAAAAGTTTGGACCTTGCGTTCC<br>ACGTTATTCTGCTGGGCTTTGTCCGAATGAACCCTTGTGAGCTGCTGTGTCCATTTCACGCC<br>GATTCTCCTGCCCACAATTTCACCTGGGAAGACCGAGTCCTCGAGGATTGCGACGTGCGCA<br>GCTGTCGGAGCGTGGATCCTGGGACGCTTTTGCTTATTTTTTGTACACCTTTTTTGAGTTGGT<br>TTAGGCAGAATTTTCCTCTAAGCAATAGACGACATACTTACCAGTGAACTTTTTCTCCAATTCA<br>CGTACTAGCCAGACTTGGATGTTCTGGAATTATTTCAGTGGCAGAACAGGAACAAAGATTAT<br>GATAACTTCCTTTTTTTTTTCTTTTTTTTTTTTTCTTTTTTGAGAGGAGTCTTGCTCTCTCGCC<br>CAGGCTGGAGTGCAGTGGCACGATCTTGGCTCACTGCAAGCTCCATCTCCCGGGTTCTCGC<br>CATTCTCCTGCTTCAGCCTCCTGAGTAGCTGGGACTACAGGCGCCCACCACTGCGTCCGTC<br>TAATTTTTTGTATTTTTAGTAGAGACTGGGTTTCACCGTGTTAGCCAGGATGGTCTCGATCTC<br>CTGACCTCGTTGATCCGCACGCCTCAGCCTCCCAAAGTGCTGGGATTACAGGTGTTAGCCA<br>CCACAGCCGGCCCTCTTTTTTTTGAGATGGAGTCTCGCTTTGTTGCCCAGGCTGGAGTGCAG<br>TGGCGCAATCTTGGCTCACTGCAGCCTCTGCCTCCCGGGTTCAAGTGATTCTCCTGCTTCGG<br>CCTCCTCTGAGTAGCTGGGATTACAGGCATGTGGCCCCACACCCAGCTAATTTTTGTATTTTT<br>AGTAGAGATGGGGTTTCACCATGTTGGCCATGCTGGTCTTGAGCTCCTGACCTCGTGATCTG<br>CCCGCCTCAGCCTCCCACAGTGCTGGGATTCCAGGCGTGAGCTGCTGCACCTGCCCATAAT<br>AACTTTCTCACCACCACCAACTTCAGTTTCCCTCACTGCTGTAATATTCAGCTCCCTGAGCTG |

-continued

| DNA Sequences encoding circRNA's of Table 1 |
| --- |
| GGCCTTGAGGTCCGAGTTCATCTCCAGCTCCAGAAGAATCTAAGAAGGCAAGAACACCAGG<br>GTCAACCCTCAGTGCGTGTATGAGCACCCCCAGCCTCATTTTTGTGTTTTCTATAGAGATGG<br>GGTCTCGCTGTGTTGCCCATGCTGGTCCTGAACTCCTTATCTCAAGTGATCCTCCTGCCTCG<br>GCCTCCTAAAGTGCTGGGATTACAGCCATCAGCCGCCGTGTCCGGCTTTAAAAAGCAATCCT<br>AAAAATCGTAAACAAAATGACACAGAGGAACCTTATTGCGCATCGAGCCATGCAAGAAAGGA<br>GCCGTTTATTTCCAGCAAGTTTAAACATCGATTTGACCTCCAGCCATGGTCGATGAGATGTTA<br>GAAAACCAACTCTCTTGCTGACAACAATGAGAAAATCTTGATACCATTTAGCAAAAAGAAGTC<br>TGTGGGGGAGGCGTTGGAGAGTGACGGAACTGCCAGGGCCTGAGGCACCCGGCTTCCGGT<br>GCCTCTGGCAGCCCAGAGAAGTGACTCTGTCTGTCTTAAGGCACCACCCTCCCCGGTGCAT<br>TTGCTGATGGTTTCTGAGCAGAGCAGTCTCCTGGGGCTGGAGGGGCACAAGCTGGAATGGG<br>CGCCCCACCATGGGGACCCCCAGATGCCAGACCTTCAACTGAGATAGGAATCTGGTGCTGG<br>ATATAGGCGTCTATGGCACCCCAGCTGCATGTCAACAGCAGCAGCAAGCCCTCCTTGAAGG<br>GTGAAACGGCATTCACAGTCTCCAGTTTTCTCTACAATTTTCATAAATGTTGTCCGTGATTCAA<br>CCAGAGTTTCCAGCAGAGGCCGAGACCAGGTGACGGCAGACGAGAGGACGCCCCTCTGGC<br>TGGAGCCTCCCCGCACAGACTCGGGTCCCTCTGCTACGCCAGGGTCTCGACTGGGCAGTAT<br>CTGTGGGTTTCCCACGTTAACTTGTCTCAGGTTTCTCTTTCTTCTTTTGAGACAAGGTCTCAC<br>TCTATCGTCCAGGCTGGAGCGCAGTGGCATGGTCACAGCCCACTGCAGCCTCGGCCTCCCC<br>CGTGCAGGTGATCTTCCCACCTCAGCCTCCCCAGTAGCCGGGACACACACCCAGCTAATTTT<br>TGTATTGTTTGTAGAGGCGGGGTCTCACCTTTGCTCAGCCCTGTTCTTGAACCCCTGGGCTC<br>AAGTGATCCTCCTGCCTCAGCCTCCCAAAGTGCTGGGATTACAGGTGTGAGCGGTGTTCCAT<br>AGATTTTTTAAAAATCCTTCACGTAAAAGTTTTTTGTTACATTTCAGAAGGAAACAGAAAAGCA<br>TAAATTCAATGTGGGCATCCCCCTCCCGGCCCACAGGGCCTCTTTCTCTGCAGTTCCCTGGG<br>GACCATCTCCTTCACACTCACCGTTTCACAGGAGCGTTCACAGAATCAGGAAGGTTTCTGTG<br>GCTCACCTGCCCATGGCTGGGGCTCAGTCTCTGGGGGACGCATCTCATGTAGAGTGAAAGG<br>CGCCACCTTTGCCGTGGGGACGGGACTTATTTGCAGACACGGACTTTGATTTGCTTTATCTC<br>ACAATGTGAAGAAACTGACAAGTATTGTTTTTGAATTGAAGGAAGCATCCGTTCCTTTCATAA<br>GAGGGGATGGAAACAGCCTGGCCCTCGGGAGGGAGCGTCCGCCCGGCGGGTCAGCCACT<br>CACAGGGGCTGTCCTCTCGCCAGGGCTGCTGGTCAACCTCTCCCTCATCCCAGTCATGGGC<br>GGGCTGGCGCTGTGCACGGCCACTGAGATCAGCTTCAATGTCCTGGGGTTCTCGGCCGCAC<br>TGTCCACCAACATCATGGACTGGTGAGTCACAGAGAAGGTGGGCGTGAGGGGGACGAGAC<br>CCGGTGCTCACCTGCATCTGGGTGTGCAGATTCTCAGGTGAGCTGAGAATTCCTCCCGTGA<br>GCCAAAGCAGGTGCGTCCAATGCTGCCCTTTCCTAAAGAGCAAAACAACAGGTATCCCCGG<br>CAGGTAAGTTTCTCAAAAATAAGCCGAAATTTCAGGATGGACGGTCTTGGTACTTAAAATGCT<br>AACCATGGAGACACGGTTAGCTGACAAATGCTGAAATACGCAGATACGCTCAGCAGTGTGTC<br>TCGCTCGGTGTGTCTTCATGCGGCTGCCAGAGCAGGGACAGTCCCCCAGCGGCAGGTTCTG<br>CCTGTTTGGGAGCTGCGCGGCCTCCAGGTCGGGCGGATCCTCTGCTTCCTTGTGGCCATCT<br>GTGTCCTGGTGTCACGATGGCAGGAAGGATGAGAGGCCGACTCCCACAGCGAGGACAGCG<br>CGTGGCAGGCTCCCAGAGGAGAGGGCCCTGTTATTTACGTCTTTGTCACTCGGTAGAGAAG<br>AGCGGTGGACGCTGCACTTCGGGGGCCGTTCAGATTCACCCAGAATTGGGCGTCCACCTCC<br>CTGCCGTGCTGTTAATGGCCACACTCCAGCCCCGGCAAAACCTGCCCTTTGAGAATGACCG<br>GCTTCTAGGCTTTTCCTGCTTTTGAGGAAAGAAAGGAAAAGACACCACCACTGGTGTCTGAG<br>AGTTTATCATTATTACTGATAATCAAAACAGGTTTGTGGTGAGATTTTGAATAATACAGAAGTA<br>AAAATAAAAATATGTTGGGCACAGTGGCTCACGCCTGTAATCCCAGCACTTTGGGAGGCCAA<br>GGCGGGTGGATCACGAGGTCAGGAGATCGAGACCATCCTGGCTAACATGGTGAAACCCCGT<br>CTCTACTAAAAATACAAAAGATTAGTCGGGCATAGTGGCGGACGCCTGTAGTCCCAGCTACT<br>GGGGAGGCCGAGGAAAGAGAGTGGCGTGAACCTGGGAGGCGGAGCTTGCAGTGAGCCGA<br>GATTGCGCCACTGCACTCCAGCCTGGGCGACAGAGCCAGACTCTGTCTCAAAAAAAAAAAAA<br>AAATCTGTTGGGCGTGGTGGCTCACACTTGTAATCCCAGCACTTTGGGAGGCTGAGGCGGG<br>TGGATCACTTGAGGTCAGGAGTTGGAGACCAGCCTGGCCAACACGGTGAAACCCTATCTCT<br>ACTAAAAATAAAAAAGTAACCAGGCGTGGTGGCGGGCACCACTGAGGTCTGGTCATTGTCG<br>CCATCGCTCCGTGTGAGCGCAGACACCTTCTCCCCCTGATGTTCCGTGCCGAGGACTAGTA<br>TTGATGCATAACCTCTTTTCTTTATTCTAGTTTGCAAAATGTTTTTTCAAAAAAGCTGCTCAGC<br>GGGGACAAATACAGGTTCTCGTAAGTATTATTCGTCAGTGAAATCTCCAAGTCATAAGACGAA<br>GAGGACTTCCTGCTCACTGTAAGAGTCAGAACACCCCACAGGCCTGACTCCCTTCCTGTCTG<br>GCTTGGGTGGCCTTTACAAGTACCCTGTCTAAGCTCGGGAGGGACCCGCCCGTTTCTCAGC<br>TACTCCCTTGAGCCCCTCAGCCAGCCTGGTGTGCGTTTGCGTTTTCATTTCTGGGAAGCTGC<br>AGCACCCTAGTCCTGTCTAGAGAGAATGAACGTCTTCTGGGCTGGGGTGCCTGGGTGTTCTT<br>GCTGTGAGGGAGCTGCGTGTGAACTCGGCCTGTCCCGACACGGGGGGCCCAGCGTGTTCT<br>GTCACCCACAGGGCCCCGGAGCTGCAGTTCTACACCAGCGCCGCTGCGGTGGCCATGCTC<br>GTCCCGGCCCGGGTTTTCTTTACGGTGGGTTTCAGACACAGGCGTCCCGTCCTTACTTGCC<br>GGGCTGCCTTCTCCGGTGATTCAGGAGCAGAATGACTTCCGTTTCCAGGCCGTGTGCTGGC<br>TGGTTGGGCCCAGCTCCGCTGCGGGTCCTGCTTAGCTGAGTTGCCCTGGGAGCCACTCGG<br>GGTTTGCAGCTCAGATTTCTGTGTGAAGACTTTTATTTTGTTTATTGTTTGTTTGTTTTGTTTTG<br>ATTCTTCATCATTCAACTTGAGATGACTTTTAGGTTAGCTTAATTTCTTTTTTTTATTAGAAAAA<br>CTTTTTTTTTTTATTTTTATAAAGAGTCTCGCTCTGTATCCCAGGCTGGAGTGCAATGGTGTGA<br>TCTCTGCTCACTGCAAAGTCTGCCTACCAGGCTCAAGTTATTCTCCTGCCTCAGCTTCCCAA<br>GTAGCTGGGACCTGCAATTTGTAGACTTCCCTAGAGTCCCCCACACAGAGGGTTCTCTGTGT<br>GAGATGCAGTTTCAAGTTCTTATTGCGGTTTTCTGGATTTTAATCCATTAGCTGTCAAGGCTG<br>ACTGACTTGGCCATTCTCCCTGCAGGGAAGTTGTGGTTGCCGGCCAGGGCCATCAGTTCTT<br>GTGCGTGTATACCCAGCAGTGGAAGTGCTGGATTATATAATAATTCTATATTTAATTTTTTTTT<br>TTTTTTTTGGAGATGATATCTCACTCTGTTGCCCAGGCTGGGGTACAGTGGTGCGATCTCAG<br>CTCACTGCAACCTCTGCCTCCCGGGTTTAAGTGATTGTCCTGCCTCAGCCTCCCGAGTAGCT<br>GGGATTACAGGCGCCCACCACCACGCCTGGCTAGTTTTTATGTTTTTAGCAGAGACGAGGTT<br>TCACCGTGTTGGCCAGACTGGCCATGCCCGGCCCCGCATTGGGGTTTCTGTTGCATTTTCCT<br>GATGATGGTGACGTTCAGCCTCTTTCATGTGCTTGTTGTCCATTTGCATCTGCATGGTGAAAA<br>TTAATTAGTGCAAAAAATAATAAAAACAAACAAACAAAAAAAACAGAAAATGGATGAGTGCAC<br>AGTCCAGCTGTCCGCTCGAGGCATTTTCAGGGCTGTCCTCAGTGGCAGCAGCTTTACCCAG |

-continued

| DNA Sequences encoding circRNA's of Table 1 |
|---|
| TTTCTGGGCAGGAGTGGCGCTGGGCGTTTTGGTGGATGATTAGTAAATGGAAAATGGAAAC<br>CGATAGAGTACCCTTTTGTTTGCCACATAGGACGTCCCAGTGATCGGGAGGAGTGGGAAGA<br>GCTTCAGCTACAACCAGGACGTGGTGCTGCTGCTTCTGACAGACGGAGTCCTGTTCCACCTT<br>CAGAGCGTCACGGCGTACGCCCTCATGGGGAAAATCTCCCCGGTGACTTTCAGGTGAGCAG<br>AGGAACTTCCCAAGAGTTGAGTGTGTCCAGGTTGTTTACAAAGGAGACCAGAAATCTAGGTA<br>TTTTTATAAGGGACACATGTGATTCTCTTCCACGGGGATGAGTGTGGCTATGCAGTGTAATTA<br>CTAGGCTATTTTATACCCATGCTGTTTGAAATGCAAACGATAGGCCGGGCCCAGTGGCTCAT<br>GCCTGTAATCCCAGCACTTGAGAGGACAAGGCAAGTGGATCACTTGAGGTCAGTAGTTCAAG<br>ACCAGCCTGGCTAACATGGTGAAACCCCATCTCTACTAAAAATACAAAAATTAGCCGGGTGT<br>GATGCTGGGCACCTGTAATCCCAGCTACTCGGGAGGCTGAGGCAGGAGAATCACTTGAATC<br>CAGGAGCCGGAGGTTACAGTGAGTTGAGATCTCACCACTGCACTCCAGCCTGGGGGATGGG<br>AGCGAGAGTCCTTCTCAAAAAAAAAAAAACAGAAAAACAAATGAGAAACTGTAAAATAAACCG<br>TAAACTGTGTGAAATAGGTATTTAGGGAAATCTCCACTAGAAGTCTCTGCGTTTGAAGGTTTT<br>TGAAATTGAGTGCTTTTCTGTCTAGAATAGTCGGGCGTTGCGACTAGTCTTGTCTGCAGGAAT<br>GGAATGGTCTCTTCTGGGCTGTCCAGTGCAGGAGCCACTGGCCACATACAGCTTCTGAGCA<br>CTTGAAATGTGGAGAATATAACAAGAACCAGATTAGGAATTCAAGCTGATTGCTGTCAGTTTG<br>AACTTGAACAGACACCTGTGGCCACTGCTTCCTGTGCCGTGCGGTGCAGCTCTAGAAACGG<br>GGAGGATCCTTCAGCTTCTTTCCACTTCTGTAACTGGGCAGATTGAATGAAGCTGCAATTTAT<br>TTGTTTATGTATTTTATTTTATTTATTTATTTTTTTGAGACAGAGTCTCACTCTTTCACCCAGGC<br>TGGAGTTCAGTATCGCAGTCTCGGCTCACTGCAAGCTCCGCCTCCCGGGTTCACGCCATTCT<br>CCTGCCTCCGCCTCCCGAGTAGCTGGGACTACAGGCGACTGCCACCACGCCCGGCTAATTT<br>TTTTTTTTGTATTTTTAGTAGAGACAGGGTTTCACCGTGTTAGCCAGGATGGTCTCGATCTC<br>CTGACCTTGTGATCTGCCCGCCTCAGCCTCCCAAAGTGCTGGGATTACAGGCGTGAGCCAC<br>CGCGCCCTGCCTATGTATTTTATTTTTCCCGAAACAGAGTCTTGCTCTGTCACCCAGAGCTG<br>GATTTCTCTGGTTTGATCTCGGCTCACTGCAACCTCCGCCTCCCGGGTTGAAGTGATTCTCC<br>TGCCTCAGCCTCCCAAGTAGCTGGGATTACAGGCGTGTGCCACCATGCCCGGCTAATTTTTG<br>TATTTTTAGTGGAGACGGGGTTCACCATATTGGCCAGGCTGGTCTCAAACTCCTGACCTCAG<br>GCGATCCGCCCGCCTCGGCCTCCCACAGTGCTGGGATTACAGGCGTGAGCCACGGCGCCC<br>GGCCTCCACAGTGCTGGGATGACAGGCTGAGCCCCCGTGCCCGGCCTCCCACAGTGCTGG<br>GGTTACACACATGAGCCCCCACGCCCAGCCTCCCACAGTGCTGGGGTTACAAGCATGAGCC<br>CCCACACCCAGCCTCCCACAGTGCTGGGGTTACAGACATGAGCCCCCACGCCTAGCCTCCC<br>ACAGTGCTGGGATTCCAGGCTAAGCCGCTGCGCCCGGTGATGTTCTTGTTCTTTAGAGAGCA<br>GGCTGAAGTACTCAGGGGTGAGATGTCATGATACCTGTAATTTACTTAAAAATATTTCATCTG<br>GGTGTGGTGGCTCACGCCTATGATCCCAGCTCTGTGGGAGGCCCAGGTGGGAAGATCACTT<br>GAGCCCAGGATTTGAAGACCAGCCTGGGCTACATAGTGAGACCCACCTCGATTGGATGAAG<br>CTGATGAGGCGGATGTCATGAATTCCTGCGTCTAGATCACAGGACGTGGCCGTTACTTAGGT<br>TTCTCCTCCTCTGCCTTTTTTAATAATGAAAAGTACCCCTCAAAAAAGAAGGGACGAGGGAGC<br>AGGCAAGCCCCGCTGAAAGCTCCCAAACCCCTGGGCTGATCTCACCACCACCGAGGTCCCG<br>TTGAGCACCCCCGCCCCATCCTGGCCTCCAGACCCGGGGTCAGCCGAGCTGCTGGCCGCA<br>GGGCTGATGTCACCGTGACGCTGAGTCCCCCAACCCCACCCAGCCTCCAGACCCAGGCTCA<br>GCCGAGCTGCTGGCCACGGGCTGAGGAGACCATAGCCCTGAGCGCCCCTGCTGCCTCCCC<br>TTGCCTCCGCAGCGTCGCCAGCACCGTGAAACATGCCTTGTCCATCTGGCTCAGCGTAATC<br>GTTTTCGGCAACAAGATCACCAGCTTGTCGGCCGTTGGCACAGCCCTGGTGACCGTTGGGG<br>TCCTGCTCTACAACAAAGCCAGGCAACACCAGCAGGAGGCGCTGCAGAGCCTGGCTGCAGC<br>CACTGGCCGGGCCCCAGACGACACAGTGGAGCCGCTGCTTCCACAGGACCCCAGGCAGCA<br>TCCCTGAGAGCAGGAAGCTGCCAGCTGCTGCTGTCCTCGTGACACTGCATCCCCCAGAAAT<br>GGGCAGGGACGCCCTCCTCCATGGCCCTGCTGGGGTGCAGGACATGGGGAGCTAAGTTGG<br>CCATTGCCTGCGGCTTTCTCGGTTTGTCGGTGAAGACCAGCAGAAACTCAAACTGGGGATTC<br>CAGGTATCAGCTTCCTGGAGTAGAGACCAGACCAGTAGCTGACTGTGTCCGCCGAGCCCAT<br>CCCCGTGTAGTGTGAAAACAGCCTCTGAGGCTCCCATGCTGGGGGTGCCCACTTCCTCTCT<br>GGGCGACACCCCAGGGTCCACCGGGAGCCAGAGGTGGGTCCAGTGCCAACGAGAGCCGC<br>TCCCTGCCACAGCCAAGAGAGCCCTCGGCTTCCCACACCAGCCATCGAAGGCCCTGAGGCC<br>CTGGACCGGCGGCAGACTGGCCCTGGGCATGAGGCCACAGAGCAGGGCCGAAGGGAGGG<br>GACAGAGGGCCCTGGAAGGAAGGGTCTCCTGCTGCCACGGTGGGCACTCAGAACTTCTCC<br>CCACCTGACCCAGGGCTGTGGGCATCCTCAGACTATCCCAGAGGCATCGCAAGCCTCAAGC<br>TGCAGCATTGCACGGCACTCAAGGGCTATGACCACGGAGGCCGTTCAGTCGCTTCTGTTTA<br>GAGGAAGGCCCCCTACCTCTTCCACACCCTGCCCTCCTATCCCTTCCACACCCTGGGCTGC<br>GTGAGCTCCCCGCAACCCCAGGGCACCCTGCCCTCCTACCTGTGGGGGTTTCCAGCCCTGA<br>GGTTGAGGACAAACCTCTCGTGTTTAACTTGGGAGGAGATGTGTACGTTCCTTTTCTTTTTTG<br>GACTCTGAGTATGAGGCAGGCTGTTCTGAGGTCCCCGTGGGGTGAGCCTGTCTGTCCTCCC<br>TCAGAGCCCACCGTTCCTATCATCATCTAGCACCTGTCCGGTTCCCCACGTGAGCCTTGGGC<br>AGGACGCTGCAGTGTTGATGGTTTGGGTTACGTGGCGTTTACCTGGGCGCCGTCCTTGCTG<br>AAAAAGGAAACGTCCACACTGAATGTTTCTGGGGCGCGTGGTGTGTGTCAGGCGCCCACCC<br>TGTCCCACTCTCCCCAAGGGACAGTAGTACGGCACACTGGGGCCACCAGCCAGCTCAACTC<br>ATCCTCCTGTGTCACGCACCCCCGAGGGCGCAGGAGGCCTGAGGAGTGGCTACTGGAGCC<br>GTGTGTTAGGCAGAGGCTTCTGACCATGTCTGAGCTCTTTACCCCCAATCTCGCAGCTGGCG<br>GATTCCCATGCCCGGTGCAGCCTGTTGCCAGCCAGCCTTTGAGACCCAGAGCTCCAGGGCT<br>TGTCAGAGGCAGCATGGGGCGCCAGTGGTCCTGAGTCTCATTTCCCTGCCTGCTCTTTAGG<br>CCTTTGGCACCCATGGTCACTTCACTGGCTTTCCATTTGGCTTCTCACCTGGGAAATACAAAA<br>ATAGCCCCTCCTGAAGATAAAATCATTCAGAAACAGAGCAATAATTCTGACTCATTAACTTCTA<br>CCTACTCAAAAAAGTCTGCCATGATGATGGACCGAAGTGAGGCTTTTTAACCCACAAGTAAC<br>CTTTTTATTTTTTTGAGACAGTCTTGCTCTGTCTGTCACCCAGGCTGGAGTACAGTGGCATGA<br>TCTTGGCTCACTGCAGCCTCGACTTCCTGGGCTCAAATGATCCTCCCACCTCAGCCTCCCAT<br>GTGGCTGGAACCACAGGCACGTGCCACCATGCCTGGCTATTTTTTTGTTGAGCTGGGCTCTC<br>GCTTTGTTGCCCAGGCTGGTCTTGAACTCCTCGGCTCAAGCAATCCTTCCTACTCAGCCTCC<br>TGTAGTGTCGAGAATATAGGCGTGGGCTACTACACCTGCTTCAGCCGCTTCTATAAAACCGC<br>TGACCTGTGTGTGGAGGACAGGCCAGGTGTGTGCTCACTGCGCTGCGAAGATGTTTTGTCA |

-continued

DNA Sequences encoding circRNA's of Table 1

CGTGACTTTCCCCGGATTTCCATTTCTTTTTTTCTGCTTTCCTCAAAAACTAATAGAAGACTGG
GTGTGGTGGCTCACGCCTCTAATCGCAGCACTTTGGGAGGCAGCAGCTGGCGGATCACAAG
GCCAGGAGTTCGAGACCAGCCTGGCCAACATGATGAAACCCTGTCTCTACCAAAAATACAAA
AATTAGCTGGGTGCGATGGTGGGTGCCTGTAATCCCAGATACTCAGGAGGCTGAGGCAGGA
GAATTGTTTGAACCCCGGAGATGGAGGTTGCAGTGAGCCAAGATCGTGCCATTGCACTCCA
GCCTGGGCAACAGGGCAAGATTCCGTCTCAAAAACAAACACTATTAGAAAATGCCCTGGAGG
TGGCGGGGAGTTGTTGATTTGTGAGGACAGATTGAAAGCAACTCCCAGGGTGGTAATGTGG
CTGCCGGCCTCTTTGAAGATTGTGGTCTGGCATAAGGAGAGGTGCAGGCGCCTGGTTCTGA
GCACCTTGGAATTTCCAGCCGCACAGCATCTGGTGCCCTCCCCTCCACCCTCACAAGGAGC
TGCCATCCTGTTTGGATTTTCTGTTTGTGGACCAGAAACAAACGTTTTTCCAAAGGATTAGCA
AATAGGGTAATTTCCTGTGTAACGCTGCTCTGGGGCCTCTTCCTCATCCTGGCAGAAGGAGC
CTGGAGCCCATGAGGCAGCCAGCACTGTGCCCTTGCTCAGTCGTGCTGTCCCCTCCCTCTC
CCTCAGTCTCCTCTCCATGCCCAAGTCGGTTTCCAGCCGCTGGTCTTCATGGCATTCCCAGC
ACAGCCGGGCACCAAGAGGCAAAACCCAAGGCCTGGCTTGGCCGTGTTAACGATTGTACAG
ACATTTTTTAAAATAACTTTGTGTAATACTTTTCTGGAATAGTAAGTTCTTGTTGAACTGTCACA
GGTGAGCTTCTAGGAACACACCGGGTGTGGTTACTTCCACTGGGTGTGTCCATGGTCGTGG
TCTGTGCTTTTGTAAACGAACAGAACACTTGAACCACCTCCCGAATTGGGTCATCGGCTTCTT
TACGTTGATACTTAGAGATTTGCAGCTCTCTTTCAAGGAAACTTCCCCTACTGAAAGGCATAA
AAAGGTTAAAAAAGAAAATCCGAGAGTCCCAATTCCCTGTATAACAGCATTAAAATAATCTGC
CTGCCTGGAAAGATGAGAACACTGTTGCACAACCCAAAATGTGTCTTTAATTTGTGAAAAATT
ACCATGGTGAGTCAGACAGTCATTTTAAACAGCTGAACAGAGACTATCATCAGCAAATAGAG
CTCAGCTTTGTAGCTGCCTTTAAAATCCTTGTCCCAAATCCGGTGAGCTCTGCTTGCTGCCG
CCGCGCTCCTGGGTGATCACTCAGACGGGTCAGTGGGAATAACAGGCCAACAAGACAGCTT
TTTACATGTGTCCAAAGGATGGCCTTTCGAAGGCCTGGAAGTATTTCACTGTTGGAAGAAGT
AAACAAGAATGACATTCCAGATGGAAATAGAATTCTCTCTCTTGCCTTTGACCAACATGGTAC
TAAGGGGTTTCTTCTTTCCCAATGTATGTACGTGCCCTGCTGGGGGCCTTACTTTATAGAATG
AGAGCATCCGAGCTTCCCTAATGAATCTGGCTAGTTCTGTGTCTGGCTGAGGATACAGGAGT
GGGACATCCACTCTCGGATCCCTCAGAGCACAGAAACCTTCAGCTTTGCTGTCTCTGAAGTA
TTTCCTCCAGTTTCCCTGCGGGCCCCTATGTTTGAGTTTGATGGCTGCTGGATCCTCACTCA
ACGAAAACTCGGTTGGAAACTGTTCCGCCTGGCAGTCCTTTTTTGTTGTTTTCCATCTCATTT
CCCTTCCATCTGAAAGTGGCATTCAGCTGACTTGCTCATTTAGACTGTTCACGGAGTCTGAAT
CTGCCAACGTGGTGTTGGAGGCTCCACCTTGAAAAGGGCCACAGTCAGGGCAACTTTCCCC
ATACAGGAAAACTTGAAAATTACATCAACAGTCTACGTCACAGCCAAATTATATTTCCTTTATA
CCAAACAAAACTATGGAGAACTAAAAGTACATCACACAAAACGTTTATAGTGTTTTGCATGTG
ACCTATTTCAGTATTTATATAACTAGATTAGTGCTTTCTAGCAAACGGTTCTGTTAATTAGCGA
GTCACTGTTGATTCTGCTGTGGTGGTAAGTTGATACCGTGTAACTAATCCCGTGGATGCCTC
CTCGTTATTTTTGTCCAAACGAAGCAGCCGTGGTAGTAGCTGTCTATGATTCTTGCTCAGCAA
AGTAAAATAAATGTTAAATATGGACTGCTTTGTTTTCTTCCTTGTGGAACTCTGGTGTTCATGC
TACTTTGTTCACCGGTGTGGCTGGCTGTTGCTAGCAAAGAGGCTCTTCACAGAAGTGGCTGA
ACCCAAAGTTCTGGTTGGGAAAGGCCTTTGTGGCAGCTCCTATCAAGCGCAAGTGCGAGGC
CACCCCCTCCTCGTGGGCTCTGGGGTCGATTTTGTTAGGGTTTGACATGAGTGGCTGCATTT
GGGTACTCACAGATTTCACAAAGGAAGGGTAAACTGGAGATTTTTGGCCGGGCACGGTGGC
TCATGACTATAATTTCAGCACTTTGGGAGGCTGGTGGGCAGATACTTTAGGTCAGGAGTTCA
AGACCAGCCTGGCCAACATGGCAAAATCCTGTCGCTACTAAAAATACAAAAGTTAGCCAGGT
GTGGTGGCGCACGCCTATAATCCCAGCTACTCGGGAGGCTGAGGCAGGAGAATCACTTGTA
CCCAGGAGGCGGAGGCTGCAGTTACCCAAAATTGTGCCACTGCACTCCAGCCTGGGTGACA
CAGCGAGACTTTTTCTCAAAACAGAAAAAAACGTGCTGTGGCTCACGCCTGTAATCCCAACC
CTTTGGGAGGCCAAGGCAGGCAGATCACAAGGTCATGAGATCAAGACCATCCTGGCTAATA
CAGTGAAACCCCATCTAAACTAAAAACACAAAAAAATTAGCCGGGCGTAGTGGTGGACGCCT
GTAGTCCCAGCTACTCGGGAGGCTGAGGCTCGCAGGATAATGGCGTTGAACCCGGGAGGT
GGGGCTTGCAGTGAGCCAAGATTGCGCCACTGCACTCCAGCCTGGGCGACAGAGCAAGAC
TCCGTCTCAAAAAAAAATAAAAATAAAAAAAATAGGGAGATTTCCCCAGTTACCAAGAACTCAG
GAAGCAACATTAAGAGCTTGGGGGAGGCCAGGCGCGGTGGCTCACGCCTGTAATCCCAGC
ACTTTGGGAGGCAGAGGCAGGCTGATCACGAGGTCAGGAGATTGAGACCATCCTGGCTAAC
ACGGTAAAACCCCGTCTCTACCGAAAATAAAAAAAAAATTAGCCGGGCGTGGTGGCAGGCG
CCTGTAGTCACAGGTACTCAGGAGCCTAATGCGGGCGAATGGAGTGGAGGCGGGAGAATG
GCGTGAATCCGGGTGGCGGAGCTTCCAGTGACCCGAGATCGCGCCACTGCACTCCAGCCT
GGGCAACAGAGCGAGACTCCGTCTCAAAAAAATAAAAATAAAAAAAGAGCTTGGGTACACAA
AGCAAGCAGCATTTCATTCCGGGATGAAAAAAATTCCGATACCCATCGCCCTTCTTGGGCCC
TTGTCAGTTTCTTGCCACATCTTTCATTTTCCCATTTCAGGCCCAGTAAATGCGGATGTTTATC
TTCCATTGTTTGTTTCCTGAGATTCAGATGTCTAAAGCATTTTTCTGTGACTTTTCAAGTCAAG
AGGAAAACCTGACATATGGAAAGGGAATTAATTGCTCGTTTTATCCTCTTCTCCTGCAATGCT
CTGAATCCATGGGTTTGGAGTGGGGCCCTGGGAGTTGGGGGAAGCACCATACCCAGTGAGT
CTGCACTTTGAGGACCCACTGCCAGTGTCAGCTTCAAAATCACATTGTAAAAGGCCGGGCGC
GGTGGCTCACGCCTGTAATCCCAGCACTTTAGGAGGACGAAGCGGGCGGATCACTTGAGGT
CAGGAGTTCGAGACCAGCCTGGCCAATATGGCGAAACCTCGTCTCTACCAAAAATATAAAAA
TTAGCCGGGCGTGGTGGCGCGGGCCTGTGGTTCCAGCTACTCGGGAGGCTGAGGCAGGAA
AATTCCTTGAACCCGGGAGGAGGCTGCAGTGAGCCAAGACCACGCCACTGCACTCCAACCT
GGGCGGCAGAGCAAGGCTCCGACTCAAAAGTAAATACATGAATAAATAAAATAAAATCACAT
CGTAAGAGCTCTCCCTGCCCTGTTTCTGAGTAAGGTTCAGAGTTAAATTCCGAGATCGGCCT
TTACAAGACACACAGACCTGAGGCGCCTCACGAGGTAACCAGCAGGTAAATGGAGCGCGCT
CCACCCACCCGCCACTAGGGGTCCCAGCGGTCAAGGGGGTGGAATGCGGGCGTCCATCGC
GAAGGCATTCTGCTCGCAAGCCTTGGCACAGGCGCGGGCTTCGCTACCGGAAAAGTCCCG
GTAGGATTCCGGAAGCCGGCCACGCGTTCCGCGCAGGCGCAAACTGCTCCAAAAGTGGGC
GTCGCTCCCCCGGAGTCCCGATTCCTGCGTCACAGCCCGCGCCGAAGTCGGAAGTGCGCT
CACCGGGCTGTTTCTTCTGGCGTCCTGGACCTGAGCAAGCGCTGTTTTATGCGTCATCATCC
CGCGCAGACACAGGAAGTGCCGCACAGAGCGAGCCCCTGTCCTTGTCTCGAGTTCTGGGC

-continued

DNA Sequences encoding circRNA's of Table 1

CGGAGGTCGGCTATTATATCATCATTACGCGCCAATACAGGAAGTGACGATACTTTTGGCGC
GCGCCGGTTGCTGTTTCTTCTCTGGCTCCGGGACCGGCGGCGGCGGCGGCGGCAGCGGC
GGCGGCGTAGGGGTGAGTTCCGACTGGGCGGACCAGGTGTGGGAGCGCGAGGAGAACTG
TGCACCGAGGTCTTTCTTCCGAGCAGGCCTCGGAGCGGGGCGGACCCGGGCCCGGGGGC
GAGCGACACCCTCGCTTCCGCGGACAGTCTCATCCCGCACGGAACTTTGGGTGGTGGAGG
CGGCGGGTCCAAACGCTGTCTGGAGCCAACGTCTGCCAGGCTGAACCTCAAGTGTGCGGG
ACTGAACCCGAGGAAATAGCCCAGTGCCCGGGTCAGGTGGCCTTGTTCGCGAGCACATCTC
GGAGCATCTCCCCGGTCTCAAGGTGCAGCTGTCCAGTGTGCTAGTGGCTTCACGTAGTCCA
AGCGGTCTTTCTAGCAGATTCTGACAGTAAAAGCAGTGTTTGATGAGTGGCAGGTCCTGAGT
TAAGAGCCTTTAAACGGATGATCTTTAATCCGCGATCGATACTATCACGTAGGTGTTGTTATT
CTGGTTGTACGGAAGACTAAACTGAGGTGAATTACGTTACCCAAGACCATACAAGAATGACA
GAAACGAGACTTGATTTCAAGCGGTCATTTTTCAGAACCCATCACTCTTTTTTGTCGCCCATG
CTGCAGCGCAGTGGCTGTTCACAAGCGCACTTCAGCCTGGAACTCCTGGGCTCAATCGGTC
TCCCATCTCAGCTTGCAGAGTATATGGGACTACAGGCGCTCGCCACCTTGCCTGGCTTACAA
CTTATCATTCTTGTTTTTTTTTCTTTTTTTTTTTTTTTTTTTTGAGACGGGGTCTTGCTGGAGT
GCAGTGACGCGACCTCGGCTCACTGGAACCTCCGCCTTTCGGATTCAAGCGATTCTGCTGC
CTCGGCCTCCCGAGTAGCTGGGATTACAGGCACCCGCCACCACGCCCAGCTAAGTTTTGTA
TTTTTAGTGGAGACAGGGTTTTCGCCGTGTTGGCCAGGCTGGTCTTGACCTCCTGACCTTGT
GATCCACCCGCCTCAGCCTAGAGCTTACCTTTTTTTTTTTTTTTTTTTTTAACCAAGTCTTAC
TTTGTTATGTAGGCTGGAGTGCAGTGGCGCAGTCTTGGCTCATTGCAGCCTTGACCTCTCTG
ATTCAAGTGATCCTCCTGCCTCTAGCAGCCTCCTTCCTGTAGCTAGGAATACAGGCACGCGC
CACCACACTGGGCTAACTTTTGTATTTTTTGTAGAGACGAGGTTTTGCCATGTTGCCCGGGCT
GGTGTTGAACTCCGGAACTCCAGCGATCTGCTCGCCTCGGCCTCCCAAAGTGCTAGGGTTA
CCGTCTTGAGCCACTGCGCCGGGCACAACTTCTTATTCTTAATGAGGATTTATTCTGAATCCC
TCAAAAGTGACTAGGTTCAAGTGTTCAGCACCATAGCTTGCTGTGTCCTGATGTAGGCTGAA
TTATTTTTCTTTTTGCAGTGTTTTAACTCAAATGGGTGATGAAAAGGACTCTTGGAAAGTGAAA
ACTTTAGATGAAATTCTTCAGGAAAAGAAACGAAGGAAGGAACAAGAGGAGAAAGCAGAGAT
AAAACGCTTAAAAAATGTAAGCCATATTTTTTAAGTAAGTGGTTTTCTTAAAGGAGATTTAATTT
CTTTGCCCTCATTTTTCCATTAGAACAACGCTTCTTCGGTGAAGTTCTTTTGTACTTCCAAATG
TCGCAGGTGAGCCCAAAATCTATTCTAAAAATTAACAAAAACATTCAAATATTCAGTTGACATT
AAAGGCAGATTTAACACACTAAAGCTGTGTCTAGATTGAGCATACATGGAGAATAAAATACGT
TGAATGTTAAGTCATTAGCAAAACTGGACTAATTTTTCTCGGTTCATTAGTATGTTCATAATAC
TATCTCTAAGTATTTTTAATATAGTGGGAACTTGCCTTGAAATTAATATAAATATTTTACATCTT
TCTTGGTTTGCATGGTAATGTACTCAGGAAACCTTTTTAGTAATTTGGTAAGAGGCATTGGCA
AAGTACCTCTTTTGCTAAGATCTTTAGCAGCATCATTTGGGATGTTAGTGAGTACAGGCATAC
CTTGTTGTATTGCACTTCACTTTATTATGCTTCACAGATATTGAAATTTTTCCAAATTAAAGGTT
TGTAGCAACTCTGCATTGAGCATTTTTCCAATAGCATGTGCTCACTTTGTTAGCTTTTTTTTTG
TTTTTGAGACGGAGTCTCGCACTGTCGCCCAGGGCCGGGTTCACGCCATTCTCCTGCCTCA
GCCTCCCAAGTAGCTGGGACTACAGGGGCCCACCAACATGCCAAGCTAATTTTTTGTATTTT
TTAGTAGAGATGGGGTCTCACGGTGTCAGCCAGGATGATCTTAATCTCCTGACCTCATGATC
CACCCACCTCGGCCTCCCAAAGTGCTGGGATTACAACAGGCATGAGCCTCCGCGCCCGGCC
TTTTTTGTTTGTTTTTGAGACAGTCTTGCTCCATTGCCCAGGCTGGAGTGCAGTGGCATGATC
TCAGCTAACTGCCACCTCTGCCTCCTGTGTTCAAGCAGTTCTCCTGTCTCAGCCTCCTGAGT
ACCTGGGACTACAGGCACCTGCCAGCACGCTCGGCTAATTTTTATATTTTTAGTAGAGACGA
GCTTTCACCTTGTTGGTCAGGCTGGTCTGGAACTCCTGACCTCAGGTGATTCACCTGCCTCA
CCCAGCCTCCCAAAGTGCTGGGATTACAGGCGTGAGCCACCATGCCTGACCTAAACCAAAC
TTTTATATGCGTTGGGAAACCAAAAAATCTGTGTGACTCACTTTATTGTGGTGTTTTGGAGCC
AAACCCAAAATATCTCCAAGGGATGCCTGTACCATATGAGGTATCACAAAGTATTTGGTTTGC
AAGATACGCCTTAAGATTCATTTTTGGCTCATATAAGCAACTAACATACTTGGCATAGAGTCTA
ATGTCCCTTGTCATATATGCTATTTTTAAATTTCTCATCTCAGGTTTCAGATTACAGAGAGTTG
TAATTTTAATGTGATAAGATTTGAATTAAAGTTTGTTTGTTTGTTTGTTTTCCCTGATACGGAGT
CTAACTCTGTTGCCAGGCTGGAGTGCAGTGGTGTGATCTCGGGTCACTGCAATGTCCGCCT
CCCGGGTTCAAGCAGTTCCGGTCACTACGCCCAGCTAATTTTTGTATTTTTAGTAGAGATGG
GGTTTCACTGTGTTGTCCAGGGTGGTCTCGAGCTCCTGACCTCGTGATCCGCCTGCCTGGG
CCTCCCAAAGTGCTGGGATTACAAGCGTGAGCCACCACACCCGGCCAAAAGTTCTTTATATT
TTATAACACTGGCTCATTCAGAGTATATATGAAAGTTTGTTTTGGGATGTTGCCCAGGTTTGA
TTATCATTAAAAATACTTTTATCTATGAAGAAAAAAAAACTTATAAAGAAAATGATTAACTTTCT
CTTTGCTTCTTAGTCTGATGACCGGGATTCCAAGCGGGATTCCCTTGAGGAGGGGGAGCTG
AGAGATCACCGCATGGAGATCACAATAAGGAACTCCCCGTATAGAAGAGAAGACTCTATGGA
AGACAG

>RSL1D1_hsa_circ_0000673 (SEQ ID NO: 3)
ATTATCTCCCTCCAAACTCTAAAGAAGGAATATAAATCCTATGAAGCCAAGCTCCGCCTTCTG
AGCAGTTTTGATTTCTTCCTTACTGATGCCAGAATTAGGCGGCTCTTACCCTCACTCATTGGG
AGACATTTCTATCAAAGAAAGAAAGTTCCAGTATCTGTAAACCTTCTGTCCAAGAATTTATCAA
GAGAGATCAATGACTGTATAGGTGGAACAGTCTTAAACATTTCTAAAAGTGGTTCTTGCAG >ZNF609_hsa_circ_0000615 (SEQ ID NO: 1)
CAATGATGTTGTCCACTGGGCATGTACTGACCAATGTGGCAGGTCTGAGAACATAGCTGAAG
CTGAAAATAGGAAAGCTGGGGGCAAGGAAGAGCCTTGAATCTTGAGGTGGGACGTTGACTC
TAAGATGTCCTTGAGCAGTGGAGCCTCCGGAGGGAAAGGAGTGGATGCAAACCCGGTTGAG
ACATACGACAGTGGGGATGAATGGGACATTGGAGTAGGGAATCTCATCATTGACCTGGACG
CCGATCTGGAAAAGGACCAGCAGAAACTGGAAATGTCAGGCTCAAAGGAGGTGGGGATACC
GGCTCCCAATGCTGTGGCCACACTACCAGACAACATCAAGTTTGTGACCCCAGTGCCAGGT
CCTCAAGGGAAGGAAGGCAAATCAAAATCCAAAAGGAGTAAGAGTGGCAAAGACACTAGCA
AACCCACTCCAGGGACTTCCCTGTTCACTCCAAGTGAGGGGGCAGCTAGCAAGAAAGAGGT
GCAGGGGCGCTCAGGAGATGGTGCCAATGCTGGAGGCCTGGTTGCTGCTATTGCTCCCAAG -continued

| DNA Sequences encoding circRNA's of Table 1 |
|---|
| GGCTCAGAGAAGGCGGCTAAGGCATCCCGCAGTGTAGCCGGTTCCAAAAAGGAGAAGGAG<br>AACAGCTCATCTAAGAGCAAGAAGGAGAGAAGCGAAGGAGTGGGGACTTGTTCAGAAAAGG<br>ATCCTGGGGTCCTCCAGCCAGTTCCCTTGGGAGGACGGGGTGGTCAGTATGATGGAAGTGC<br>AGGGGTGGATACAGGAGCTGTGGAGCCACTTGGGAGTATAGCTATTGAGCCTGGGGCAGC<br>GCTCAATCCTTTGGGAACTAAACCGGAGCCAGAGGAAGGGGAGAATGAGTGTCGCCTGCTA<br>AAGAAAGTCAAGTCTGAAAAG |
| >circNPPA (SEQ ID NO: 12)<br>AGAGGGGAACCAGAGAGGAACCAGAGGGGAGAGACAGAGCAGCAAGCAGTGGATTGCTCC<br>TTGACGACGCCAGCATGAGCTCCTTCTCCACCACCACCGTGAGCTTCCTCCTTTTACTGGCA<br>TTCCAGCTCCTAGGTCAGACCAGAGCTAATCCCATGTACAATGCCGTGTCCAACGCAGACCT<br>GATGGATTTCAAGG |
| >AFF1_hsa_circ_0001423 (SEQ ID NO: 8)<br>TTTGTACAATGACGACAGAAACCTGCTTCGAATTAGAGAGAAGGAAAGACGCAACCAGGAAG<br>CCCACCAAGAGAAAGAGGCATTTCCTGAAAAGATTCCCCTTTTTGGAGAGCCCTACAAGGTA<br>TTTACTGAACACTAGACATTGAAGTCCTGATTTATCACAATGTTGAACCCTATGATGAAACAAT<br>TCAGTATAATTGAGTTCGAACAAGGGTCACAGCTGTGAAAATAAGATAACTTATTCTAACTTAT<br>TCTAGAGATTTTTGAAAACAAAGTATGAAAATTCTCTGAAGGTTGTTAGAATTACCAAAGTTTG<br>TGGTTTTCTTTTGTAATGCTAGTCTTCTACAGTTAGTAATATGTATCCATGGTAGTCTTCTCAA<br>CAGGGGAATTGAGTTAAAATGGCACATTAAATTCTACATGTCGTACATTAAGTTCGGAGTTTT<br>TTCCTTAATAGTATTATATAACGTGGTTTGTTAAATGGTAGTTTTCCTTAGTTTTTTTTCATTCT<br>CAAATTCTCCTTTTTTTTCAGACAGCAAAAGGTGATGAGCTGTCTAGTCGAATACAGAACATG<br>TTGGGAAACTACGAAGAAGTGAAGGAGTTCCTTAGTACTAAGTCTCACACTCATCGCCTGGA<br>TGCTTCTGAAAATAGGTTGGGAAAGCCGAAATATCCTTTAATTCCTGACAAAGGGAGCAGCA<br>TTCCATCCAGCTCCTTCCACACTAGTGTCCACCACCAGTCCATTCACACTCCTGCGTCTGGA<br>CCACTTTCTGTTGGCAACATTAGCCACAATCCAAAGATGGCGCAGCCAAGAACTGAACCAAT<br>GCCAAGTCTCCATGCCAAAAGCTGCGGCCCACCGGACAGCCAGCACCTGACCCAGGATCG<br>CCTTGGTCAGGAGGGGTTCGGCTCTAGTCATCACAAGAAAGGTGACCGAAGAGCTGACGGA<br>GACCACTGTGCTTCGGTGACAGATTCGGCTCCAGAGAGGGAGCTTTCTCCCTTAATCTCTTT<br>GCCTTCCCCAGTTCCCCCTTTGTCACCTATACATTCCAACCAGCAAACTCTTCCCCGGACGC<br>AAGGAAGCAGCAAGGTTCATGGCAGCAGCAATAACAGTAAAGGCTATTGCCCAGCCAAATCT<br>CCCAAGGACCTAGCAGTGAAAGTCCATGATAAAGAGACCCCTCAAGACAGTTTGGTGGCCC<br>CTGCCCAGCCGCCTTCTCAGACATTTCCACCTCCCTCCCTCCCCTCAAAAAGTGTTGCAATG<br>CAGCAGAAGCCCACGGCTTATGTCCGGCCCATGGATGGTCAAGATCAGGCCCCTAGTGAAT<br>CCCCTGAACTGAAACCACTGCCGGAGGACTATCGACAGCAGACCTTTGAAAAAACAGACTTG<br>AAAGTGCCTGCCAAAGCCAAGCTCACCAAACTGAAGATGCCTTCTCAGTCAGTTGAG |

The invention claimed is:

1. A method for treating a patient at risk of developing heart failure after having suffered from myocardial infarction, said method comprising:

(a) determining the risk of said patient for developing heart failure by monitoring the expression level of one or more of circRNAs selected from ZNF609_hsa_circ_0000615 (MICRA) (SEQ ID NO: 1), SNORD116-19_hsa_circ_0000585 (SEQ ID NO: 4), AFF1_hsa_circ_0001423 (SEQ ID NO: 8), and SLC8A1_hsa_circ_0000994 (SEQ ID NO: 11) in a sample of said patient after said myocardial infarction and comparing said expression level to the expression level of said one or more circRNAs in a reference sample or in a sample of a control patient, wherein a sudden statistically significant deviation of said level is indicative for an increased risk of developing heart failure in said patient and wherein the deviation is statistically significant if the P value is $<0.05$;

(b) determining based on (a) that said patient has an increased risk of developing heart failure; and (c) administering to said patient an effective amount of a drug that treats heart failure.

2. The method of claim 1 wherein said sample is from a patient who has suffered from a myocardial infarction within less than 5 days before taking of the sample.

3. The method of claim 1 wherein the deviation of said level corresponds to a decrease of the level of circRNA by at least about 20% (about 0.8-fold or less).

4. The method according to claim 1, wherein said circRNA is ZNF609_hsa_circ_0000615 (MICRA) (SEQ ID NO:1).

5. The method according to claim 1, wherein said expression level is determined by RT-PCR assay, a sequencing-based assay, quantitative nuclease-protection assay (qNPA) or a microarray assay.

6. The method according to claim 1, which further comprises assessing one or more clinical factors in said patient and combining said assessment of said one or more clinical factors and the expression of said one or more circRNAs in said determination of the risk of a patient having suffered from myocardial infarction of developing heart failure.

7. The method according to claim 6, wherein said clinical factor is selected from age, body-mass index, gender, white blood cell count, ischemic time, antecedent of MI, diabetes, hypertension, hypercholesterolemia, and smoking.

8. The method according to claim 1, which further comprises assessing one or more other biomarkers in said patient and combining said assessment of said one or more other biomarkers and the expression of said one or more circRNAs in said determination of the risk of a patient having suffered from myocardial infarction of developing heart failure.

9. The method according to claim 8, wherein said one or more other biomarkers is selected from CPK, cTnT, Nt-pro-BNP, MMP9.

10. The method according to claim 1, which comprises determining expression of two, three, or all four of said circRNAs the circRNAs selected from ZNF609_hsa_circ_0000615 (MICRA) (SEQ ID NO: I), SNORD116-19_hsa_circ_0000585 (SEQ ID NO: 4) AFF1_hsa_circ_0001423 (SEQ ID NO: 8), and SLC8A1_hsa_circ_0000994 (SEQ ID NO: 11).

11. The method according to claim 1, wherein said sample is a whole blood cell sample.

12. The method of claim 1, wherein said drug attenuates tissue remodeling, reverses tissue remodeling, or both attenuates and reverses tissue remodeling.

13. The method of claim 1, wherein said drug is an angiotensin-converting enzyme (ACE) inhibitor, a drug which directly or indirectly inhibit aldosterone, or a beta-blocker.

14. The method of claim 1, wherein said drug is perindopril, captopril, enalapril, lisinopril, ramipril, or carvediol.

* * * * *

SEQUENCE LISTING

<160> NUMBER OF SEQ ID NOS: 20

<210> SEQ ID NO 1
<211> LENGTH: 874
<212> TYPE: DNA
<213> ORGANISM: Homo sapiens

<400> SEQUENCE: 1
caatgatgtt gtccactggg catgtactga ccaatgtggc aggtctgaga acatagctga 60
agctgaaaat aggaaagctg ggggcaagga agagccttga atcttgaggt gggacgttga 120
ctctaagatg tccttgagca gtggagcctc cggagggaaa ggagtggatg caaacccggt 180
tgagacatac gacagtgggg atgaatggga cattggagta gggaatctca tcattgacct 240
ggacgccgat ctggaaaagg accagcagaa actggaaatg tcaggctcaa aggaggtggg 300
gataccggct cccaatgctg tggccacact accagacaac atcaagtttg tgaccccagt 360
gccaggtcct caagggaagg aaggcaaatc aaaatccaaa aggagtaaga gtggcaaaga 420
cactagcaaa cccactccag ggacttccct gttcactcca agtgaggggg cagctagcaa 480
gaaagaggtg caggggcgct caggagatgg tgccaatgct ggaggcctgg ttgctgctat 540
tgctcccaag ggctcagaga aggcggctaa ggcatcccgc agtgtagccg gttccaaaaa 600
ggagaaggag aacagctcat ctaagagcaa gaaggagaga agcgaaggag tggggacttg 660
ttcagaaaag gatcctgggg tcctccagcc agttcccttg ggaggacggg gtggtcagta 720

-continued

```
tgatggaagt gcaggggtgg atacaggagc tgtggagcca cttgggagta tagctattga    780

gcctggggca gcgctcaatc ctttgggaac taaaccggag ccagaggaag ggagaatga    840

gtgtcgcctg ctaaagaaag tcaagtctga aaag                                874
```

<210> SEQ ID NO 2
<211> LENGTH: 49639
<212> TYPE: DNA
<213> ORGANISM: Homo sapiens

<400> SEQUENCE: 2

```
aggagaagaa gatgattctt tggccatcaa accaccccag caaatgtctc ggaaagaaaa      60

agttcatcac agaaaagatg aaaagagaaa agaaaaatgt aggcatcata gccattcagc     120

agaagggggg aagcatgcta gagtgaaaga aagagagcac gaacgtcgga aacgacatcg     180

agaagaacag gataaagctc gccgggaatg ggaaagacag aagagaaggg aaatggcaag     240

ggagcattcc aggagagaaa gggaccgctt ggagcagtta gaaaggaagc gggagcggga     300

gcgcaagatg cgggagcagc agaaggagca gcgggagcag aaggagcgcg agcggcgggc     360

ggaggagcgg cgcaaggagc gggaggcccg cagggaagtg tctgcacatc accgaacgat     420

gagagaggac tacagcgaca aagtgaaagc cagccactgg agtcgcagcc cgcctcggcc     480

gccgcgggag cggttcgagt tgggagacgg ccggaagcca gtaaaagaag agaaaatgga     540

agaaagggac ctgctgtccg acttacagga catcagcgac agcgagagga agaccagctc     600

ggccgagtcc tcgtcagcgg aatcaggctc aggttctgag gaagaagagg aggaggagga     660

agaggaggag gaggaaggga gcaccagtga agaatcagag gaggaggagg aggaagagga     720

agaggaggag gaggagaccg gcagcaactc tgaggaggca tcagagcagt ctgccgaaga     780

agtaagtgag gaagaaatga gtgaagatga agaacgagaa aatgaaaacc acctcttggt     840

tgttccagag tcacggttcg accgagattc cggggagagt gaagaagcag aggaagaagt     900

gggtgaggga acgccgcaga gcagcgccct gacagagggc gactatgtgc ccgactcccc     960

tgccctgttg cccatcgagc tcaagcagga gctgcccaag tacctgccgg ccctgcaggg    1020

ctgccggagc gtcgaggagt tccagtgcct gaacaggatc gaggagggca cctatggagt    1080

ggtctacaga gcaaaagaca agaaaacaga tgaaattgtg gctctaaagc ggctgaagat    1140

ggagaaggag aaggagggct tcccgatcac gtccctgagg gagatcaaca ccatcctcaa    1200

ggcccagcat cccaacattg tcaccgttag agagattgtg gtgggcagca acatggacaa    1260

gatctacatc gtgatgaact acgtggagca cgacctcaag agcctgatgg agaccatgaa    1320

acagcccttc ctgccagggg aggtgaagac cctgatgatc cagctgctgc ggggggtgaa    1380

acacctgcac gacaactgga tcctgcaccg tgacctcaag acgtccaacc tgctgctgag    1440

ccacgccggc atcctcaagg tgggtgattt tgggctggcg cgggagtacg gatcccctct    1500

gaaggcctac accccggtcg tggtgaccca gtggtaccgc gccccagagc tgctgcttgg    1560

tgccaaggaa tactccacgg ccgtggacat gtggtcagtg ggctgcatct tcggggagct    1620

gctgactcag aagcctctgt tccccgggaa ttcggaaatc gatcagatca acaaagtgtt    1680

caaggagctg gggaccccca gtgagaaaat ctggcccggc tacagtgagc tcccagtagt    1740

caaaaagatg accttcagcg agcacccccta caacaacctc cgcaagcgct tcggggctct    1800

gctctcagac cagggcttcg acctcatgaa caagttcctg acctacttcc ccgggaggag    1860

gatcagcgct gaggacggcc tcaagcatga gtatttccgc gagaccccccc tccccatcga    1920

cccctccatg ttccccacgt ggcccgccaa gagcgagcag cagcgtgtga agcggggcac    1980
```

cagcccgagg ccccctgagg gaggcctggg ctacagccag ctgggtgacg acgacctgaa 2040
ggagacgggc ttccacctta ccaccacgaa ccagggggcc tctgccgcgg gccccggctt 2100
cagcctcaag ttctgaaggt cagagtggac cccgtcatgg ggagaactca gccgggacca 2160
caggcgtggc tactgcggct ggagctgcga tgagactcgg aactcctcgt cttactttgt 2220
gctccatgtt ttgtttttgt attttggttt gtaaatttgt agaattaaat cattttcctt 2280
gttgtggagg aaagagctgt gttttctccg tgacttgcca gggcatcttc gggtgcccac 2340
gtggggcagc acaaacctcc acacaccctc tcccactctc gacacgcacg gggctggctg 2400
ggccgtgatt tggaaaggaa ctggtgggag ccgggtggat tgtttaatct tcggagctgg 2460
agacctgttt ctgtgttggg atgagcgatg ccctcttgcc ccaacccact cgtccagacc 2520
agccctgtcc acacaggccc ccggccccca acccccagcc ccagctgtgc cagcagactc 2580
gacaggtttt tatacaaggt tgttgagttt taaaatgtat taaaatattc ttcgaggaaa 2640
gctccccgtg tcgtcctttg agtgacccgg gaccatgtgt gggaggggag tcgcagacca 2700
ccgggctcta ggggaagagg gtggggtggg cggctgtggc ctctgacccc atgtgggcca 2760
gtgtcttccc caggcaggag gggagctcct acctcctggg gggcctccac tctggcaagg 2820
tggtccccca ccctgtgcca gtcctcccag cccccaccca catctccttg cagaagatcc 2880
tggaggccca tcccagccac atctttcagg aagcccccctt tgcctccctc ccccagctct 2940
gagcaagtcc tagacagaac ccaggcttct ggggctaccc caggtgctgc tccacgtgct 3000
gcccctgtca ctggggcctc ctcttatccc actttcccag gggccacctt agcaaagccc 3060
gtcccgtcct gtgctgtacc tgtggtccgc tgtgcgggga agcaggggtg cccagccccg 3120
aggacgccca gctctcggtg gaccaggggc tggggtgtcc acctgcccag actggctgcc 3180
cgctgccctc ccaagaatga gcgaggagcc atcagagaga aagtgcttta tcagccgggc 3240
tcagccccgc acacggactc gccaggagta ggtggtcagc acgcgctgct ggcggcgcac 3300
cacgcaggtg taggtgccct cattgacggc gttggcgatg atgctcaggt gcgcctcgcc 3360
cagggccagg tagccggggt aggagaactc caggggctcc tggtccttgt accagctgca 3420
ggggggcggg gcgtctcctg caggcacagc cccccccgc tgcctgcccc gcacccctgc 3480
cccaaggccg cccgcgggct gcccaccccg aggaccgccc ggggcgctca ctcactacac 3540
tttccctttc ttgtggagga tcttctggcc gcagcggaag gtcacgttcc tgccctcggg 3600
caccagcctg gttttggtcc tggggggcgg tggggtggtg gccaccgtgg ggaaggggaa 3660
ttctgctccg ggtgggggaa agagccccgt cagtgccccc tcagccccga ccatggccaa 3720
ggcccagctc ccacgcagcc ctgtcccggc cccgtgggca tcaccgtagc agaagtcgca 3780
gctgctgggg cagagcctct tcatgagccg ccggcgagcg tcgcagaagc ccctccgcgc 3840
ccaggacgcg cacacgaaca gcctgtcgag gcatcctgtc gggagcgtgg ggagcacggc 3900
ctggctcagg accgcccggt ccccgccctc ccgcccgaca aagggactca ccgtagagcc 3960
ggtgcagccc ccacagctcg tcctgggaca acgccttcca gccgcgcagc gtggcgttca 4020
ggtgcatgag cgcccggccg tgttgtgagt gcatcaggcc cagcgcgtgg ccgatctcgt 4080
gggccgccac gtgcaccagg tccgtgagcc acacgcctgc gggcccccggg ggtcagcgcc 4140
tgggagcccc gggcccagcc ccgccgcccg tgggccagct ccccgaggcc cggtgtatct 4200
gctggagcgc agccgcggag ccgccctcgg ccgcagccac ggaaagataa gaatgttctg 4260
ggcccaggcg gtgagctcgg cccccaggaa tgcagctcca gctcccgctc cagaggcgca 4320

-continued

```
gggggatggg aaagggagtt cagggctgcc gggatggggg ctcccacggg ctcccctcct   4380
tgcctgctag actccagtgg cagccaccac cccggaaggt ccctcctgcc gtctgcccca   4440
aagcccgacc gcggcagccc actgtgctgc agaggagagg cctccaggag gccagcctgg   4500
acggtcacct ttcttccagc tgtagcgcgt ggggcccagg acccagtact cgctgtcgtc   4560
gaagtggatg ccgccgtgcg gggggaagaa ggcgtgggcc agctcccccg tggggccgtc   4620
gaagcagtgg tgcagcgcgg agaccaggca gtccgtgtgg ttgatcgggt agaagcctgg   4680
ggggagcacg gggctgagag gccgggcgcg cagggccggg ccggggcggg ggcgggcgcc   4740
cacctatccg gaggtcgctg ggctgctcgg gggccacctc gcggaagctg aagggggaca   4800
cgtcgctcca catgcggaag gcggcagcta gggcccgccg cgtctcccgc gggctcagca   4860
ggttccgcgg gaaggagagg atcctgcagg gagagtgagc tcagcgggcg ccggccgcgc   4920
cccctccccc ggggcccagc cagggcgcac ctgtaggtga ggttgaagtg gtcccagcgc   4980
agcctggctg gagtcagcgt gtagcggcgt ctgcgggggg ccagtgggcc cgggacccgg   5040
gtgggggggga ccgccgagag gcccagcgca gcgacgtctc ccttcaggga agaaagcgtg   5100
cgtgggaggc atcggtgacg gtccccagga ccaaaaactg ccgcggaaaa tggactggaa   5160
ggaaacgggg gtgggggtgc ccagggctgg gagcgggcgt ggcgggtcct gtctgcctgt   5220
ggtttcgggt ctcctaacct gagcgccctg ttgcacgtcc ctgggaacgc ggcccagtgg   5280
aggggaaggg gctgaacagc agggcgaggc ctcccacccc tcccaacaac tggacacagg   5340
ggcgtccaac cctccgacct cgggacgcac atccggaccc tcaaacaccc cgcacacccc   5400
gcacaccctg cacaccccgc acacgtcctg tgggcccctt ttctgaagtg ctgatgtaca   5460
tactttctcg tacacacttt tgtgaagatt tcaaggggaa gggagtcgtc tgccattcaa   5520
tgtttacatt tatgttctgc aagacgctgt cctcagggac cattagggga ccattctgtt   5580
cagtgcgatc ctgatggtcc gggagatgag ggtttccggg gctagtgatc gtgatccctt   5640
ttatttgcaa ctgtaatgag aatttttcac actaacacag cgagggactc aacacgctga   5700
ttctcctcct gcctctcccg tgagtctcca gcctgcccag caccagcagc tgtggagcac   5760
gtggatgctg cctaccccgg cgcccgcgtc ttccacgggc acaggtgtgt ggaggccgtg   5820
gtcggaccct ggtgtcctgg ttactgctgc ccgggtgtct ttttttgag taactgctct   5880
ctgagttttg cacacaaagt tgccctcatc tgctggagat cgataaggaa ggcacaagac   5940
gttctcctct gcccgtgagg agcttcccgc agccgcctgg cccagcctgg gcacgttctc   6000
cgaggcatgt gtctccctgc tcaccctcgt ctgggcacct cagcatctgt ggacttgagc   6060
gtccaaaaac cctgagtgtg attctgggca gccggcctgg cttgaagtcc gccatgaccc   6120
tgggcacagg ggaagcccag ccgtgggctt aggagagagg gaccagcgcc cagcgttagg   6180
gctggaagac ggcagtgttc agaattccag ccgctcatct gaacacagaa ggtgtgaact   6240
gacctctaaa gcagcgtgag atgggaatga tctagaaaac tttggatttt tgaagtaaat   6300
tttaatgttt catattaatt tcttgaaaat gtattaaatg tcattgaaag ccttattacg   6360
cttttcagat cctttcaata aacaagactt gtagaaaata agctgggtta ataacagctt   6420
tcttctgacg ccgtggaacc aacatagagg ggtcgggcag ggtcaccccc attaaatcct   6480
agccccaaaa tgcccatcca ccgagtgtgg ggccggcagg gcatcctccc caaggggctg   6540
ggggtgccgc tgcctcttcc gggcaagggg gcagtgccct ggcgggggta ggggtagaca   6600
gaagggactc aaacccgagg ggtggtgtcg actcgggcag gctgtgttgc tcccggaaga   6660
gccactgaga ccagggggag ttgagtccct gcattcccgg ggccagcagg gctggaagag   6720
```

```
ccccctccatc cgggctgcct aacaggggca gccacaagcc aggtgaggac ccgctggccc   6780
ctgggcccag cctgggcacc gatatcggcc tccctccctc cactgacgtg gtcctgcgcc   6840
ccgcaacccc cccaccccgc accgtccctg ttgtcctaac aaggcccaga tgaatgtggc   6900
tcagggcttt gccggcagcc agtctgcact acacgcgtgc aagtccagga gagaccaaaa   6960
cgaccaccct gtggacacct gcccctccag caccctgccc cgttttgggg acgtgaaacc   7020
ctgggctgtg ggccccgccc taccgacctg gagcgcctct gcctccccgg cctggaagag   7080
gctgtgggtc aagcctaacc ttcttggctt tggggagcac agaggcccca agacatcctc   7140
gggggctgcc gggctcaggc tctggggcat ggaaaccttt tcgagcctga aacggcggca   7200
tccacggtcc ctgccgggcc agtgccagcc tgcaccctgg gcacctctgt gctgggcccg   7260
gcacccccac cctgcctccc acagccaggg tgtctcctca ggtcaggtcc aaaggggctg   7320
cagccaggcc caaagaccca gcccaagtcc cacggctcct gcggggtctg ggtgaggcct   7380
gtcctgctgg gagcccagga ggctgcgacc ctgcctggag ctggaagtct ggttgggggg   7440
tagtagggtc gggggaaagc agggtggggc aggtacaggg tagagaagcc agctggagga   7500
gcccagggaa ggctggcggt gctggggatg taggggacag caggagctgg tacatcacca   7560
catgtttcag ctgcttccag cacatcctgc cccagaagga tctcagccag ggcatgggct   7620
gccttcaggg tctggcaaca ccaaggagcc aaggcaggtg gtaaaccgag gccacaacct   7680
ccttaggagc ctccacaacc agggcgcaca gctgaaagag gaaggaggcc cctgcggaga   7740
gcagggtggg caggagtggg tggccaggac aggtggtgcc cagtgaccgg cggtggggac   7800
ccgggagcca cagaggagcc ggctcagcca cccctgtgca ggaggcacct ggggcctgta   7860
ctcaggcctc acccagggct gccccacgcc cacatcctgc tgacaagccc ccaggaccag   7920
catccccacc cagctgctct gtgcagaggg gacaggaggc cagacaaaaa gatggacaaa   7980
cacccacgta gattcacaca cacacaaaca gacacaccac acagaaaaat atgcatggac   8040
accactgaga cacacgcagg caccacacac tcagagacac acacacagac acatcacaca   8100
gaaaaatatg catggacgcc actgagacac acgctaacac cacacactca gacacaaaca   8160
caccacacac acagactcac acagatacac acacagaaaa atacacatgg acgccactga   8220
gacacataca ctcagagaca ggcagtgcgc tctgggaaac aggatggttc ctccaaacca   8280
gtgaagggcc caggaaagca tgagcggccc tgacatgtat ggagggtcca aaggctgcgg   8340
gaacttgccc gtgagtgacc ttggcctgga gaactccccg gcctcagttt ccccacctgc   8400
tgatgaggac aaattgcagg ggcatgagcg gctgctgctc ccctacctct gcgcaggtgg   8460
ccgagtggcc tgcaggctgg gtctccaggt ggggaccctt ccctcttcct ccccacccac   8520
tctatcccct tccggcgtca tgtggataga aattcattaa tatgcacaac aaatgactac   8580
atgcaagcag gaaaacattt gcaataatac agcaggtcga tgttctcaac tagcaaaaca   8640
gatgcaataa tacaattcgt ggatgttctc aatacagaca aagctcatat aatcgacaca   8700
aaacattcac agaaaaattg tcaaagggca gaaaccgatg actcaaggaa gaatataaat   8760
agctaagaag taaatgatca ataatcaaac tagaacataa tcaaagaact ttaaaattaa   8820
aattattaat acactcctcc caggcaaaat agcaaagaga ggggacatgg tggctcacac   8880
ctgtaatccc aacactttgg gaggacgagg tgggaggtcc ttctggggag aggaagagag   8940
gaaagcacac aggcttccag acactattcc aaaatcatta atacgcacac cccaggccca   9000
gcacggtgac agccacctgc agacccagct actcgggagg ctgaggccag agagccctga   9060
```

-continued gtttgagccc agcctgggca aagtagcgag atccccccatc tcaaaaaataa aataaaaatgc 9120
atggttcctc atgaaatgta aggctttgct ataaaaactt tgagaggcca ggcgtggtgg 9180
ctcacacctg taatcccagc actttgggag gccaaggtgg gtggatcatg aggtcaggag 9240
ttcaagagca tcctggctaa caacggtgaa accccgtctc tactaaaaat acaaaacaat 9300
tagctgggca tggtggcggg tgcctgtgat cccaactcct cgggaggctg aggcagaaga 9360
atctcttgaa cctgggaggt ggagcttgca gtgagccgag atcgcgccac tgcactccag 9420
cctgggcgac agagtgagac tccgtctcaa aaaaaaataa aggccgggcg tggggtagct 9480
cacgcctgta atcccagcac tttgggaggc tgaagcgggc agatcacaag gtcaggagat 9540
ggagaacatc ttggccaaca tggtgaaacc ctgtctctac taaaaatata aaaattagct 9600
gggcgtgagg gcacacatct gtaatcccag ctactcagga ggctgaggca ggagaatcac 9660
ttgaacccgg gaggcggagg ttgcagtgag ctgagatcgt gccactgcac tccaacctgg 9720
gcgatgagag cgaaattcca tctcaaaaaa aaaaggagta ctttttataa atctgctttt 9780
gaaatcattt ggataccaca gcggccctgc tgaccacaac agctgagact gttgggcaaa 9840
tcaccagaca tttctgggtt tcctggaaag taggagaatc tactttgtaa actgctctca 9900
aatttatgaa ctccgtgtgg atagtgaact caggcagcag gcaggtggca ctccactgcg 9960
ttaatttcac ttcattttat aattttcttt cttccttttt tttttttttt tttttttgac 10020
ggagtctcac tctgtcgcca ggctggagtg cagtggccca atcttggctc actgcaagct 10080
ctgcctcctg agttcaagtg attctcctgc ctcagcctcc caagtagctg ggattacagg 10140
cacgtgccac catgcccggc taattttttt tcgtattttt tgtagagacg gggtttcatc 10200
gtgttagcca ggatggtctc gatctcctga cctcgtgatc cgcccgcctc ggccacccaa 10260
agtgctggga ttacaggcgc gagccaacgc acccagcctt tttttttttt tttttttttt 10320
tttttttttt tttgtgagac aagggtctca ctctgtcgcc caggctggag tgtggtgctg 10380
tgattctagc tcactgcagc ctcaagctcc caggctcaag ccatcctccc acctcagcct 10440
cccgagtggt tggaaccaca gacaccatcg ctgcgctctg accggctccc gggggcgctc 10500
cgtgcccctc ctcctgcccc actcctctgg ggacatcccc accaaagacc ccacgggagg 10560
aaacagtccc agcctctggc ccaacccggc tgcgggcgcc acggggaagc ctggggaagg 10620
aggctgccat cagcctcctg aagctttacg aaggttcatg caacggaaac aaaaacaagt 10680
ggaagtttaa caaaacgtaa aagtaatatt tatttattta tttatttatg agatgaagtc 10740
tcccactgtc gcccaggtcg gagagcagcg gcgctatctc gcctcactgc aaccttcaac 10800
tccaaggttc aagcgattct cctgcctcaa cctcccgagt agcggggacc acaggcacgc 10860
gccacgagac ccgggtaatt ttttttgta tttttagtag agatgggggg gggttcacta 10920
tgttggccag gctggtctcg aactcctgac ctcaggcgat ccgcccgcct cagcctctca 10980
aaatgctggg attacagacg tgagccacct cgcccggcca aaagtaatct tttcttttt 11040
cttttgacag ggagtctcgc tctgtcgcca ggctggagtg cagtggcgcc atctcggctc 11100
actgcaacct ccgcctcccg ggttcaggtg atcctccttc ctcagcctcc ggagtagctg 11160
ggattacagg cgcccgccac cacgcccggc caatttttgt atttttagta gagacgacgt 11220
tttaccacgt tggccatacc aggctggtct caagctcctg acctcgtgat gcgccggcct 11280
cggcctccca aagtgttgag attacaggcg tgagccaccg ggcccggccc aaaagtaatc 11340
tctaaagagc cctttagccg taacttcatt cctgaaaatt atttgggaaa gtaacgctag 11400
gaaaacgctc gacgaagctc cggagccggg ggtcctcggg gccgcaggcg cgcccgcggg 11460
tgtctgctcc ggatgtcccg cggcagcccc gacgccagcc tggatacgaa ggccccgccc 11520
cggagcgcgc caccagccaa tcagcgccct gaggcgagtc ctcaccccgc gcggcggccc 11580 cgcccccgc agctccgggc ccagctgtca gagcagcttt ccctcaggct gggcggagcg 11640
tggccacttc cgccaggagg cgcctttgtg tcttctaagt taagcctatt cagtggattt 11700
cttattcctg gaacccaaac ctgggcagta aaccctccgg ggcttagagg ccgctgcctc 11760
cacagactgg ccgatcccgc cctgaagtgc cgctggtgga acagcccggg cggaaccgcc 11820
cgggcggaac caacgggctg ccgcgggggg tggggccacg gtcccccccc ttctgccttc 11880
agtggaacgg ccccggcgga accaacgggc cacggggatg cactacgcgc accgtcgtcc 11940
tctccctctg cctgcagtgg aacggcccgg gcggaaccaa cgtgcggccg cccggagcac 12000
tcggcgcgcc gtgtccctcc ccgtgtggct gcactgcaac ggcccgggct ggaccaccag 12060
gcggcagcgg agaggcactt aaaagccccg tgttacccta gaccttaaaa aaaaaaaaaa 12120
aactgcgtgt ttccaccccc gtcggcctgc agtggaaggg cccgagcaga accaacgggg 12180
gaggggacgc tgagcgcgcc gtgtttctcc tcccgtctgc ctggagtaga acggcccggg 12240
cggaaccaac gggcagccgc gggggcgttg tgggccgcgg cgcgtttccc cggctccgtg 12300
gctctggggc actgaggagc ggcgcccgcg gggcagcgag gagcccgatg cagggttctg 12360
cgcgtcattt ccggtcccgc gggcgccccg tgaagcccac ctggatccgc cagcgctgtg 12420
ccactcccca gtgccgagct ccgagctgtc tccgcggcct cgcgcccggc ccctccaccg 12480
cgcgcctctc aggccccgcc cgccagcgtc cctttgttgt gaaggcgccg gggcctagcg 12540
ctatgcctgc ggcggagact gcatcaggct ctcggtgggt tctgcgtgcg gggtgctctg 12600
ctcggtgatc ggtgctgggt gctgcgtgct cggtgctcgg tgctgggtgc tgggtgccgg 12660
tactgatgct gagtgtgcgg gcgtccgggg tttccctgcc cggattcgct cctgggggtc 12720
ctttcctatg gctggcgctg tgcgcggaaa acgctggtgg ggttttccca gctggcttta 12780
agcgttttca cgtccgggag tccacggcga cccccacgcc ctgaagcctg ggaacgcggt 12840
gtgcgtggcc gcaaaaagaa caacaacaac aaaaaaacac aaaacaaaac acgcaaaaaa 12900
ctaaagcaaa actcccgaca gccgagcccc gttcggtgcc ttttcttttt tttttctttt 12960
aatggagtga aatctacttt gctcaggaag cctgcaaatc acattttcag gccaaacgag 13020
gcagtatttt agaaggggtc gctgaggcag gagtaggaag gctttccact ccactcacgc 13080
attttcagtg taggcgaatc gtaaaacgga gggcagaacg aaaatgagcg gatctgggag 13140
tgcaggctgc gcttcgtcca catcgataac agatgtttcc tggtgaagat gtgtagggcg 13200
cagcgggtca cctggtcggg ggagggcaca gggcgtccct ccacggggtg cctttggcgt 13260
tgggcacttg tgtggtctcc agcttccggg ttttggaagc ggagtgtccc ctgcagcctg 13320
agcctcttgc aggtggtttc cttgggacga actcccaggg ggaggtctga gttctggggc 13380
atggtttgaa gatttgggac acattttgcc tgaaattccc tgctggccgt ttgaacccac 13440
ctggacttcc tgaccagggg cacggattct taacctctgg tgcaggggcc tggctaggag 13500
aggtctgcac agttggacga ggtgcaaagt gacgctttgt cagtaacccg gcgttgagat 13560
tcctgtggtg ggacgagcag ctcctatggc tttatcccat tttaaatcca agttttcttt 13620
tccttctagt cctcgggctc cacccgggga gctgtgccca gacagcagaa gggaaggatg 13680
tcacttctga gatgaggttc agaaaggtct gggctcctgt cctggctgct ctctcccact 13740
ccctgatgag cttgctggat gaaagctcct gtcaggctgt ggggcgtcct gtggagaagc 13800

-continued

```
tggcaagaaa ctggtggggg ccctttccac ctatagccag caaggaactg aacccagcca  13860
gcgtccacct gagtgagctc agaggtgggc ctcagcccca gttgagcctt cggatgaggt  13920
cacagccctg gtccatggtg tgactgcagc ttcaggaggg accttaagcc agaggtgcct  13980
ggctaagctt cccgcagatt gctgccccac aggagccaac atcaaaagca tttgttgttt  14040
tgaggtggta agtgtggaat gactgttaca gggcagtaga gaaggagcat gcacccttcc  14100
tgcttcttat ttgcctttta gaaattgtcc tctgtgaatc gcttgaacct gggaggttga  14160
ggttgcagtg agctgatatc tcaccactgc actccagcct gggcgacagg agcgaaactc  14220
cttctccaaa aacataaatt cttctctgtg aaatatgttg ttttgttttt ttttttttctt  14280
tactttttga gacggagtct tgctgtgtca cccaggctgg agcaggcgca gtctcagctc  14340
actgcaacct ccgcctccca ggttcaagtg attctgctgc ctcagcctcc tgcgtggctg  14400
ggattacagg cgcctgccac cacgcctggc taatttttgt atttttggta gagacggagt  14460
ttcatcatgt tggccaggct ggtctcgaac tcctgacctc aggtgatctg cccgccttgg  14520
cctcccaaag tgctgggatt acaagcatga gccaccatgc cccgccaaca tttttttttt  14580
tttgcctgtt tttctacttg gtttgtagga attctttata ctttctggat attaatcctt  14640
tgccatgttg caagtatttt ttcccaggtt gtggctgttg atttcacttt atggtatgta  14700
tatatatata tatatttttt tttgtttctt tttttttttt ttgagacaga gttttgttct  14760
tattgcccag gctgttgtgc aatggcgcga tcttggctca tcacaacctc tgcctcccgt  14820
gttcaagtga ttctcctgcc tcagcctcct gagcagctgg ggttaaaggc atgtgccacc  14880
atgccggcca actttgtatt tttagtagag atggggtttc tccatgttgg tcagactgat  14940
ctggaactcc caacctcagg tgatccaccc acctcagcct cccaaagtgc tgggattaca  15000
ggcgtgagcc aagtctggcc tttttttttt tttttgaga cagggtctca ccctgttgcc  15060
caggctggag tgcagcggcg cagtctgggc tcactgcaac ctccccgtcc tgggttcaag  15120
caattctcct gcctcaccct cccgagtagc tgggattaca ggtgcatacc accacacctg  15180
gttaattttt gtatttttag tagaaacagg gtttcaccat gttggtcagg ctggtctcga  15240
gctcccgacc tcaagtgatc cgcccacctt ggcctcccaa agtgctagga ttacaggcat  15300
gagccactgc gcccggccca ctttgtggtg tactttggtg aaacagaatt cttcatttag  15360
ccaagttagt ccacctgacc cttttttttaa tgggtcatgc ttttggggtt tggttagaga  15420
aattattgtc ctaccccaaa aagggtcagg aagacattct cttatatttt cctgagcata  15480
aagttttaca catttaagtt tatcataaga gcaggccacc tgggttcgaa tcgtgaccct  15540
gctgctgcaa agccgtgtct ttccttcgtg tgtctcacgt gggtgataac agcaccttcc  15600
ccagagggct attgtgggga ttcaccgctg tgcagagagt gcttcggacc ctccagcagc  15660
acagtcaggg ctgtgtcagt gttactaatt gtcgctgttt gtgtactgat aatgagatca  15720
gaatccagtt tttctttttg cctggcagca tggacaactg tcctggtatc atagactgaa  15780
taaagtttcc ttcttcagca actcgtggtg cctccattct gggtacacca gacctgtttg  15840
tttgtttttt tttgagacag tctcgctctg tcagccaggt tggagtgtag tggtgcaatc  15900
tcagctcact aaagcctccg tctcccaggt tcaagtgatc ctcgtgcctc agcctcctgt  15960
gtagttggga ctactggcac ccaccaccac gtccagctaa gttttttgta tttttggtag  16020
agacggggtt tcactgtgtt agccaggatg gtctcaatct cctgacctcg tgatgcgccc  16080
acctcggcct cccaaagtgc tgggattaca ggcttgagcc accgcgcccg acctcgaggt  16140
ccttattctt ttgcatttgt ttactcgccc agccctgcac caaggtctca gactgaacta  16200
```

gaagtcctca tgtcttggga ggacggctgc cgccccctcc ctgcgcctcc gtctccttgc 16260
aggacgtgtt tgtcttctac tcatcgtgcg tgcatagctt tctctctgat tcacacatgc 16320
tttgtgcgtg catagctttc cctctgtgat tgacatgtgc ctcatagggc tggatctatc 16380
tcgagactac atagcctctt gtttctaagc tttatttttt tctgggacag agtttcgctc 16440
tgccgcccag gctggagtgc aatggcgcga tctccgctca ctgcagcctc cacctcctgg 16500
gttcaagcga ttctcctggc tcagcctcct gagtagctgg gattacaggc acgcgccatc 16560
atgcccggct aatttttgt agtagaaatg gggtttgact gtgttggcca ggaggatctc 16620
gatgtcctga ccttgtgatc cgcccacctc agcctcccaa agtgctggga tggcaggtgt 16680
gagccagcgc gcccggccgt ttctaagctt ttactcagta gttttagtct cttggtgact 16740
cgtcgtgatt gtgatgatga tcgtgatggt ggccagatgg tggcttctca ttctgtcact 16800
ctgatgatca tggattgact ttgtgctggg aagaaagact tcccctcctt tgccattcgt 16860
tcatcagcat ggccttgtgg gctgttgttt tactgggggt tctgatcctt tactgtgtta 16920
cgtactctgc ctttcaagcc ccctgcgccc tccctcggcc aaccctgagt tcattcctag 16980
atcacaaact ttcggcgcag ccaacatgac cgctcctctg gtgtctttcc caccacagcc 17040
cgagagtcag tcatttttca aagaagcctg gttggctttg tggagaatga tatatgttat 17100
tattattttt tgttttgtta tgttgtgttt tttagacagt ctcgctcttt gcccagcctg 17160
tagtacagtg gtgcaatctt ggttccctgc aacctccgcc tccgggttca agcgattctc 17220
atgcctcagc ctcctaagtg gctgggacta caggcacccg ccaggattaa tcttttttt 17280 tttttttga gatggagtct ccctccatca cccaggctgg agtgcagtgg cccgatctag 17340
gctcactgca acctccgcct cccgggttca agagattctc ctgcctcagc atgccaagta 17400
gctgggacta caggcgcctg ccaccatgtc tggctaattt tttttgtatt tttagtagag 17460
atggggtttc attatgttgg ccaggctggt ctcctgacct catgatctgc ccgtctcggc 17520
ctcccaaagt gctgggatta caggcgtgag ccaccacgcc cggcctaatt ttttgttttt 17580
ttagtagaga ctaatttttt gtatttttag tagagacagg gtttcgccac attgcccagg 17640
ctcgtctaga actcctgagc tcgggtaatc cgcctgcctc agcctcccaa agtgctagga 17700
ttacaggcgt gagccattgc gcccagcccc tttagtggag aatgatattt agaaaccaag 17760
gttagggcgc tgggagcgcg ctgtgcaggt gtgactgtct ctgggcagat gtgctgtgtt 17820
ggggtgtgtg tgtgcgtgcg tgtcgcccgt ccgcccatcc gttcaagcct gtgcgctcgg 17880
gcccgacagc accctcacag gccgacaccg cgggggtcat tccatccatc ttctttcttc 17940
tttttattta tttatttatt tgtttttgag acggagtctc actctgtggc ccaggctgga 18000
gtgcagtggc acgatctcag ctcactgcaa gctccgcctc ctgggttctc gcccttctcc 18060
tgcctcaggc tcctgagtag ctgggagtac aggtgcccgt caccacgccc ggctaatttt 18120
ttgtattttt agtagagaca aggtttcaca gtgctagcca ggatgatctc gatctcctga 18180
cctcatgatc cgaccccctt ggactcccaa agtgctggga ttacaggcgt gagcctccgt 18240
gcctggcctt tttattttt tgagacagag tctctgtcgc ccaggctgga gtgtggtggc 18300
atgatctcgg ctcactgcga cctccgtctt ctaggttcaa gtgattcttc tgcctcagcc 18360
tcccgagtag ctgggattac aggcgcatgc cactgcaccc agctaacttt tgtattttta 18420
ctagggatgg ggtttcacca tgaactcctg acctcaggtg atccacccgc ctcggcctcc 18480
caaagtgctg ggatcacagg cgtgagtcac cgtgcccagc ctcttttttt catttttatt 18540

-continued

```
tttatttttt cactacaaga ctgccctgaa ggacttcctt tcgtgtttgc atctcgcttc  18600
actcacatga tgaaatctgc ctcccgtcat gtacaaaata tttatgtatt tgcccaatcc  18660
ggaattctaa cccatgagtc agcaaaaaaa aaaaaaaaaa agaaaaaaaa agaaaaggga  18720
ggctgggcgc agtggctgat gcctgtaaat cccagcactt tgggaggccg aggcaggcag  18780
atcacgaggt caggagttcg agaccagcct ggccaacatg gtgaaaaccc gtctctacta  18840
aaaatacaaa atcagcaggg tttggtggca cgtgcatgta atccccacta cccgggaggc  18900
tgaggcagga gaatcgcttg aacctgggag gcgaaggttg tggtgagcca agatcgtgcc  18960
attgcactcc agcctgggca acaagagtga aactccatct aaaaatgaaa tgaaaataca  19020
aaaattcact gggcgtggtg gcgggtgcct gtaatcccag ctactcagga ggctgaggca  19080
ggagaatcac ttgaacccgg gaggtagagg ttgcagtgag ctgagatcgc gccattgcac  19140
tccagcctgg gcgacagagc gagactccgt ctcaagaaaa gaaaagggaa aaaagcatgt  19200
ttagaactcg gtatttgttt ggagctcctg tgtctggagc tacttgtgtg tctggagccc  19260
ttgtgtccat cacctgcgta cccacatcca gcgtccatgc acccgagttc ccagggcttg  19320
ttctgcttct cccctcaggg tgattgtgtc gtttgtttga tctgtggtgt ggttcatgca  19380
ttcgtgttcg tgttccattt cagagaccct tttcccctac ccttgttgat ttaattattt  19440
ttgcttttta agcaagcgac atattttcat ggttctgaaa gtcagacctg gagccgcccc  19500
cacctcactg cactgcactc ctgcctgccc tgtcactgaa gagtctcctt attcttgggt  19560
atatccttcc tgtatttctt tttccttttc tttttttttt tttttttct gagaaaacgt  19620
ttcactgtgt cgcccaggct ggagtgcagt ggtgagatca cggtcactgc aggctcatcc  19680
tcccagactc aagcagtccc cccacctcag ctgggcacac aggcgcacac caccgtgccc  19740
aggcctaatt tttgtacttt tttggtagag atgaggtttc gtcatattac ccaggctggt  19800
attgaactcc tgggctcaag caatcctcct gcctcggtct cccaaagtgc taggattaca  19860
agcatgaacc aacacacctg ggcaaaaaat gctccaactt tttttttttt ttttgagacg  19920
gagtttttgc tcttgttgcc caggctggag tgcaatggcg caatcttggc tcactgcaac  19980
ctccacctcc caggttcaag tgattctcct gcctaagcct cccaagtagc tgggactaca  20040
ggcatgcgcc accacgcccg gctaattttg tatttttta gtagagacag ggtttcttca  20100
tgttgatcag gctggtctcg aactcccaac ctcaggtgat ctgcccgcct tgggctccca  20160
aagtgctggg attacaggtg ggaaccactg cacccgctgg ctgtcctgtt tttttttttt  20220
tttttttttt tttgagatgg agtctcgctc tgttgcccag gctggagtgc aatggcgcga  20280
tctcggctca ctgcaagctc tgtctcccag gttcacgcca ttcttctgcc tcagcctgcc  20340
aagtagctgg gactgcaggc acccaccacc acgcccagct aatttttgta tttttagtgg  20400
agacggggtt tcaccatgta ggccaggatg gtctcaatct cctgaccttg tgatccaccc  20460
gcctcggcct cccacagtgc tgggatgaca ggcgtgagcc actgtgccca gcctcctggg  20520
atgacaggcg tgagcccccg cgcccggcct cctattctta atttccaagg cccacttggg  20580
ttgtgggtgg tccccactta ccatggtctg agttgtgatt ttctgacttt atgatggtgg  20640
gaaagcaaac gccttcagca gaaacgctgc cctgagctca cagccgtcct ctctctcact  20700
tccggtgggg ttgtctgaat ttcacgagcg gctcagcgcg cttatagcca ctctgcatta  20760
ggcggcttag cccaaatgtc actgatgtgg gtgtcagcac gcggaggtgg atgaggcaca  20820
ttaagagcca aaggacgggc tgggggctgt ctgtggagat gtcagtggcc ttgaaaagac  20880
agtgcactgg ggcaagcgtc tcacgactgc tgagtgtcta ccctgcggcc cacgggtctc  20940
```

ctgggctgtg ccccagacgt gagtggacag caagcgatcc tccctcctcg gccttccaaa 21000
gtactggggt tctaggtgtg ggccaccgcc gctggccaaa catgaaggtt tgacttacaa 21060
ctttgtggtc tctggtctga acaggcacct gcacctggag gactctgaga ccctgtttcc 21120
aaccatgatg ttttgcactt gtgctctgat atgaaatgtg tttggtcttt gttcctggtt 21180
cctggcacag aagctcctcg aagccttgga atttcctgag tgacaggagt ggttcagatc 21240
accccggagc ttatgctgat cacacctgag cttatgctga tgaggcaggg ggtggggccc 21300
tggagagcgg gggtaggggg gactggtcgc cagaacacca ggtgacccca ggattggagg 21360
ctgggagctt tgagccccac ccgccaacct cagggacgca gcgagcgaag gtggagatta 21420
aacgctgtaa aaacccgtga atgagagatg aaagagtggg atggtcttcg gattgtggtg 21480
ctgggggcag ggggtggcgc ccagagaggg cctgaaaccc agcacctgcc caggccttgc 21540
ctgcgcgtct ctgcggccgg ctgctcctct gttttctttt aacgtaagtg ctttctgcag 21600
ttctgtaggg cagtcctgtc aaactcattg atcctcagga gggtgtcgtg ggaaccccga 21660
tgtatagctg ccggtcagaa gcacggccca caggctgacc agcatctgag gagggggcag 21720
tcttgtggga tccagccctc gccgcagggg acctggcact ctccccaggg ggacggcttc 21780
gggagggaat tgaaccagag gacacacagc tagtgtctgt ggagaattgc tcaacgtgga 21840
aataacctgc atctcctgtg ggaagtgttg tgtgggagtg cagagaaact gtgcattcct 21900
cacaggactt tatttatttg cttgtttatt tatttgtttg tttttggaga cagagtctcg 21960
ctctgtcccc caggctggag tgcaatgtct cgatgtcggc tcactgcgat ttccacctcc 22020
agggttcaag caattctcct gcctcaacct cttgagtagg tgggattaca ggtgcccaca 22080
accacacctg gctaattttt atatttttag tagagacggg gtttcacctt gttggccaga 22140
ttggtctcga actcctgacc tcaagtgatc cacctgcctc caaagtgctg ggattacagg 22200
cgtgagccac caagcccggc ctcccccatg taaaccttga actctcggaa ctacttagga 22260
aggaccccgg gctgtgatct ctcacaacta cttagggagg accccggaac cccctggctg 22320
ctcagctggg ttccagcacc tgaaggtgct gttgctttcc cctggggccc gtccccgaga 22380
tgagaggagc acgtgctgga attccctctt tcaggcactt tcatgctttt atttctacac 22440
gtggtgcttc ccgcacagct gacagcgcat ggtggagccg agtcgtgcgt ttctgtctgt 22500
gattcgtccc tcagtcttcc cccgctccgg tgggtttggg cttggggtcc gtccctttga 22560
cactgggact gagcccctca tttccatcgt agcttcagct ccatcaataa ggtgtttgtt 22620
tctactgttg acaggcacgt aggttggcat tcttttggtg tttgctttgt cttgttttgc 22680
tactaacaaa aaatgctcat taaacaccca cctccaagac ttctatgaga aggtgtgaag 22740
agcccaccca ttttcccggg accgtttggc cctctgtgac ccaagtcagc ctcggcgaag 22800
tgctttattt tcttgttttt tgtcgctccc tgtcacccgc atgacctctg aaaggttgca 22860
cccagccggg cacggtcact catgcctgta atcccagttc tatgggaggc caaggcgggc 22920
gaatcacatg aggtcaggag attgagacca acctgggcaa catggtgaaa ccctgtctct 22980
tctttttttt tttttttttt tttttttttt tttttttttt tttttttttt ttttgagaca 23040
gagtgttgct ctgtcgccca ggctggagtg agtgcagtgg cgcgatctcg gctcgctgca 23100
agctccacct cccgggttca caccgttctc ctgcctcagc ctcctgagta gctgggacta 23160
caggcgcccg ccaccacgcc tggctaattt tttgtatttt tagtagagac agaatttcac 23220
agtgttagtc aggatagtct ccatctcctg acctcgggat ccctctgcct cagcctccca 23280

-continued aagtgctggg attacaggcg tgagccacca cgcccggcct aaatcctatc tcttctaaaa 23340
gtacaaaaat tagccaggct tggtggcgca tgcctataat tccagctgcc cgagaggctg 23400
aggcatgcga atcccttgaa tccaagaagt gggggctacg gtgagctgag attgtgccac 23460
tgcactctag cctgggcgac agagtaagag tccctctcaa aaaagaaaag aaaagaggcc 23520
gggcgcggtg gctcacgcct gtagtcccag cactttggga ggcctaggtg ggtggatcac 23580
gaggtcagga gatcgagacc atcctgggta acatggtgaa accctgtctc tactaaaaaa 23640
atacaaaaaa aaacaaaatt agccaggcgt ggtggcgggc gcctgtagtc ccagctactt 23700
cagaggctga ggcaggagaa tggtgtgaac ccaggaggca gagcttgcag tgagccaaga 23760
tcatgccatt gcactccagt ctggctgaca gagcgagact ctatctcgaa aaaaagaaaa 23820
ggaaaaggaa agaaaggtct cactagacag tttcaggccg gaatctgttt gcatttgtac 23880
cgtcaggaat ttccagcctg ggaacagtca gtgacaggaa cgaaccgtgg gtgcctctgc 23940
aggggtggct cctgcctggc tgcccttgag ttggctgagg agctgagaac ttggacttca 24000
ggattctctg acttcactgg tctgacgtgg agctcccagt gtttgaataa gaagcggctg 24060
ggcgtggtgg caggcgcctg taatcccagt tactcgggag gctgaggcag gagaatccct 24120
tgaacctggg aggtggaggt tgcagtgagc cgagattatg ccactaaact ccagcctggg 24180
cgacagatcg agattccatc taaaaaaaaa aaaaaaagaa taagcagcca gcctcaggca 24240
tttacgcagg gacaggtgtt tacgtggggg gaagattaga tatcgcctcc tcctgcggcc 24300
ttggagctgt ggggacaggg atgctggggg tgaggacggt tcatggtagt gaagtcctgc 24360
agattgggag gggaatggag accccgggac cacgtgggct caactgcagg gacgggacag 24420
tcacccacac agagccgggg cagggctgtg ggagcacagg tcggtgtgac gttggctggg 24480
gctcagcatg cgtgtcccag ggctgggcag ttccactcct gcacgtagac acagacgagg 24540
atgctcctag tagcccgtcc caagtgcttc ttgccagaat gggtccattt gtccagtggg 24600
ctgctgtgca gtgatcggac agagaacccg cgtcccagcg cagctgcatg gagaggcctt 24660
tgtttgcagt cggcttcttg tttaagctct tttaattttt tttaactttt ttttaatttt 24720
tagagtcagg gtcttgctct gttgcccagg ctggagttca gtggcacaat cacggctcac 24780
tgcagccttg acctctcttg ttcaagcaat cctcccaccc cagcctccta agtagttagg 24840
actacagaca tgcaccacca tgcccggcta cattaaaaaa aaattttttt tttttgagac 24900
ggagtttcac tcttgttgcc caggctggag tacaacggtg tgatctcggc tcaccgcaac 24960
ctccgcctcc cgggttcaag cgattctcct gcctcagcct cctgagtagc tgggattaca 25020
ggcatccact acgcccggct aattttgtat ttttagtaga gacggggttt ctccacgttg 25080
gtcaggctgg tcttgaactc ctgacctcat gatccaccct cctcggcctc ccaaagtgct 25140
gggattacag gtgtgagcca tcgcgcccag catttttttt tttttttttt ttgacgggag 25200
tctcgctctg ttgctcaggc tggggtgcaa tggcgcgatc tcagctcact gcaagctctg 25260
ccttccaggt tcaagtgatt ctcctgcctc agcctcccga gtagctggga ttacaggtgc 25320
cagccaccac acccggctga tttttttttt gtacttttag tagagacggg gttttgctgt 25380
gtttgccagg ctggtcatga actcctgagc tcaggtgatc cgcccacctt ggcctcccaa 25440
agtgctggga ttccaggtgt gagccacggc gcctggccca gaaccttaag ttcttgatgt 25500
acagagaacg gcagcgtcag tgaagtgtga tttctgtttt tttgtttcca ctaattgtga 25560
gcaaacatta gggtggggac tgggctgctt gtgtgggtcc cacaggcttc ttggagcaca 25620
gtgtcagcag agaaggggaa tgggggtcct cattgcgggg agcagttttg cctgggatgc 25680

```
tgtgagtttc tcagagggaa gctaagtgga cagactgttc tggcaagagg gagatgcttg  25740
ccttttgaat tccaggtttg cctcgacgtc aggtgggacg tgactggcgt cgtctgcaca  25800
cgcccgagcc cacgtgctgt tccttgctcc tggaggggtt tcttgagcgt ggcctccttg  25860
ccatgtaaat gaatttggtt ttagaaactc gctggtggtg gcagagcctg tgtagcgggt  25920
gctgtgacag cgtccccagc caggggggcag ccttcgaggt gggagggaga ggtcaagggc  25980
cgtgaggcct agtgaggtgg ggagtgagat ccacgcctgc catgagctcc acccctgcct  26040
tgcggagccc tgtcgcgagt gctctgtcct tttgctctgc cgcacccttt gttgttggat  26100
tttcacctca ggaaagccag gtagctgctc cacccccagc cagggcccat cagtccggga  26160
aactggcaca aagtctccta gctccctggc tcagggccca gccagtccta gctccaggga  26220
ggctgcagcc catggaggtt tagctcccag cttgttgtca ccccaggcta agcagtggga  26280
ctgtgctgct gaacaggaag aagggaatgg tgtctttgtg gagatctggc actgtcagtg  26340
gcccgaggag tggatgagtc ctttgttatt ccgaggctgt gggaactggt ggaggggtcg  26400
gccttctcct cactgaggcc tggggtgccc ttggaggcag ctgtcctggt gcaccgaggg  26460
gtcagggcac acatgggtgg cctgggagcg tctgggtggc actgagctgg cggtgtgatg  26520
ggcagacggg gagacctggg tgcacagaca cacacagcag ggggagggga ggagagagag  26580
gaaggctgca gaggccctgg cattgccgcc actggggaga gggcagaagc gcctgttccc  26640
gggtatgggg aggccaagtt tcaggcacct ctgagcactg ctgggcaggt gagctggggg  26700
agaggccggc ctgagcaccc aggcgaggtc ttcatggggg agggggtggc gtgcgtccct  26760
cagtgtgaac acagaatatt tatgtataca tatggcacgc acgcaagtgc ataaacataa  26820
acacagaagg aggtcacgaa tgaggtggga accccagttt cccgggggag aagtgagacg  26880
aggaggggta ctgggtcggg cagcacggcc ggcaccacac gctcccagag cgccttggtg  26940
agacaggatg ggcgcccctt cagatgcaca gcctccccccg aagcaggaag agaaacccag  27000
gtgtgagaaa caggaaatcg ggctgcctga gcgctgggat tgagacctgg gggaggtggg  27060
gtctcggtgc tgcggagtca cagtggcgtc tgtgcaaagc cccagctggg gggatgattc  27120
ccactggacc tcaggaggaa acggctgttc tgaccttcct ggagctcgtg ggaagggagg  27180
gggtgtctcg ccccgaagcc acagtcgcct gagcgtgaag cgggtgtaag tgtggtttta  27240
taccacggag tctgtctaga aagtagcatg gaactttagg aggccgaggt gggcggttca  27300
cgaggtcagg agatcgagac catcctggct aacacggtga aacccgtct ctactaaaaa  27360
aaaaaaaatt acaaaaaatt agccggacgt ggtggcggac gcctgtcgtc ccagctactc  27420
gggagcctga ggcaggagaa tggcgagaac ccgggaggcg gagcttgcag tgagcccaga  27480
tcacgcctct gcacttcagc ctgggcgaca gagcaatact ccgtctcaaa aaaaaaaaaa  27540
aaaaggaaaa agaaagtagc atggaattag tcctgggcac ccgacagcgg cagccacaaa  27600
gcccatcgag aaggtgcagc tgccaggcag ggcgtgaagg acccacagcc ccaggtctgc  27660
caggacgaca gtcaagtgtg ccaggagacc gtctctcaag agcaaggatc cgccaacacg  27720
cgcagagaaa aacgggattc aattgctaaa aatctttgga cagtgaacga ttgcattttc  27780
tttttttctt ttcttgagac agagtctcac tctgtcactg aggctggagt gcagtggtat  27840
catgtcggct cactgcaacc tccgtctcct gggttcaagc aattcttctg cctcagcctc  27900
ccgagtagct gggattacag gcgccggcca ccatgccctg ctagttttta tatttttagt  27960
agagacgggg tttcgtcatg ttggccaggg tggtctcgaa ctcctgacct aaggtgatcc  28020
```

-continued

```
acctgcctcg gcctcccaaa gtgctgggat tacaggtgtg agccaccgtg cccggcccaa  28080
ttgcattttc aaagtgattt taaattggtg gttgaaacct ttgaggacat taaatgttca  28140
aaacgggtga tgtgtttcct tttcttaata ttttagcgtc tgcttctgcg ctttgcctgg  28200
gagaggccct ggtggcctcg ttcctggcgc ccggagtccc tgctgcggcc ccaccccegg  28260
gcggtcacgg tgacccatgc tgcccagcct ggaggtaaaa tcgttcgtgg ctgtggcttc  28320
agcatgtcgt cctcggtgaa aaccccagca ctggaagagc tggttcctgg ctccgaagag  28380
aagccgaaag gcaggtcgcc tctcagctgg ggctctctgt ttggtcaccg aagtgagaag  28440
attgtttttg ccaagagcga cggcggcaca gatgagaacg tactgaccgt caccatcacg  28500
gagaccacgg tcatcgagtc agacttgggt gtgtggagct cgcgggcgct gctctacctc  28560
acgctgtggt tcttcttcag cttctgcacg ctcttcctca acaagtacat cctgtccctg  28620
ctgggaggcg agcccagcat gctaggtagg cggcggctcg ggcagggtgg aagccggcca  28680
cctgccaccc cacagggagc agccagcaac cacccgggag ggccggggga gcccaggtca  28740
ggatgggagg ccgggggtgg agcccactgc aggcatggga ggggtgattc tccctcttgt  28800
cttcggcccc ctccctcccg caggtgcggt gcagatgctg tccaccacgg ttatcgggtg  28860
tgtgaaaacc ctcgttcctt gctgtttgta tcagcacaag gcccggcttt cctacccacc  28920
caacttcctt atgacgatgc tgtttgtggg tctgatgagg taaagaatct cctggttttg  28980
gttgagtgtc tctttttctt taaatgtaaa gtccctctcg ttactagagc ggggactctg  29040
ctggctggtg agttttcagt gcagacttta taaaagcacc agggctgtcc agatttcagg  29100
acaccaaatg aatgtggctt cgtggctctc actgccacgt gtgttcagtc agcttctttc  29160
cgggctggtg gtctcaggac agggtgcctc cttgtctctg ggacgttttc aaggggtggc  29220
agaagtcact tcccattgga cgcagtgccg tttcctgggg gctcgaccta aagcgtcaca  29280
gaagcgggtc caggcaccat gttggtgatg aggaggtggg cggagagggg ccgacgtgcc  29340
aaccgagcga gcgagcccct tggagagcct gcccggtggg tgcaggcaga cagactcgtt  29400
ctaaggtgat ggtgcttttg gctcattttt aggtttgcaa ctgtggtttt gggtttggtc  29460
agcctgaaaa atgtggcggt ttcgtttgct gagacggtga agagctccgc ccccatcttc  29520
acggtgatca tgtctcggat gattctgggg gagtacacag gtgaggcccc cgggccccgc  29580
ccctccgcct gcgccccacc atcccaggcc tccatccgtg gtgcccgtct ctgctgcctg  29640
ccatggggct ctgccgcgag gaccactcag agtggtgccc acactggcag tgccttcact  29700
tctctcacgg tcacatgtgc gggggtgtct tggagcctgg cgtctgccag gtattctcac  29760
actggcatgc ggaggtcagg gcagggttgt gtctgtggcc ctaactgggt ggggagacag  29820
gtgggggctg ggcagattcc tggcaagcaa gattactgca ggtgccaatc actgatccga  29880
agaggacggg tgggggccgc cttcggccag caccacacag gcggccgtgg ctcctggtcc  29940
gtgggccctc ctgtgccagc accccacagc ctctccagca cccgccacca caggcctgtc  30000
ctgggcccca gcccctgacc tcagctgcaa cccaggctcc tgcctctccc acctcttaat  30060
gactcacagg cgatttccag cgacatgtca gccccatgtc gcgtacccag tgtggctgca  30120
tgaaaaccag cgaggagcag aggcgcccac agagcgcggc gtcttgaacg gagtcggggg  30180
gtgcacacgt gttcgcttat ttaagaaact acaagatctt aaggccgagg gaagtgtctg  30240
tctgcctttg gggacgggag gaggccgagg gtccaggatg gggttgggct tgccccacat  30300
gcacttgaga cccgcacaca cgtttaggtg attataacaa aatcaaagcc taaaagtcaa  30360
ctctggtttt tttttgtttt tttttttttg tttttttat gtttttgaga caggtcttg  30420
```

ctctgtcgcc caggctgcag tgcagtggcg aggtcacgac tcactgcaac ctcggcctcc 30480
caggcttagg caatcctccc acctcagcct gttgggtagc tgggacctca ggcatgtgcc 30540
accatgccca gctaattttt gtatttttgtg tgtcttttttg ttttttcact gtgaatatac 30600
gttagtcatt tttcttaaca attgaaactt ggaactctgg ggattcagaa ttaacagcct 30660
tggctgtgag cttatcgata ccagaaaaag tttggacctt gcgttccacg ttattctgct 30720
gggctttgtc cgaatgaacc cttgtgagct gctgtgtcca tttcacgccg attctcctgc 30780
ccacaatttc acctgggaag accgagtcct cgaggattgc gacgtgcgca gctgtcggag 30840
cgtggatcct gggacgcttt tgcttatttt ttgtacacct tttttgagtt ggtttaggca 30900
gaattttcct ctaagcaata gacgacatac ttaccagtga actttttctc caattcacgt 30960
actagccaga cttggatgtt ctggaattat ttcagtggca gaacaggaac aaagattatg 31020
ataacttcct tttttttttc tttttttttt ttttcttttt tgagaggagt cttgctctct 31080
cgcccaggct ggagtgcagt ggcacgatct tggctcactg caagctccat ctcccgggtt 31140
ctcgccattc tcctgcttca gcctcctgag tagctgggac tacaggcgcc caccactgcg 31200
tccgtctaat tttttgtatt tttagtagag actgggtttc accgtgttag ccaggatggt 31260
ctcgatctcc tgacctcgtt gatccgcacg cctcagcctc ccaaagtgct gggattacag 31320
gtgttagcca ccacagccgg ccctcttttt tttgagatgg agtctcgctt tgttgcccag 31380
gctggagtgc agtggcgcaa tcttggctca ctgcagcctc tgcctcccgg gttcaagtga 31440
ttctcctgct tcggcctcct ctgagtagct gggattacag gcatgtggcc ccacacccag 31500
ctaatttttg tatttttagt agagatgggg tttcaccatg ttggccatgc tggtcttgag 31560
ctcctgacct cgtgatctgc ccgcctcagc ctcccacagt gctgggattc caggcgtgag 31620
ctgctgcacc tgcccataat aactttctca ccaccaccaa cttcagtttc cctcactgct 31680
gtaatattca gctccctgag ctgggccttg aggtccgagt tcatctccag ctccagaaga 31740
atctaagaag gcaagaacac cagggtcaac cctcagtgcg tgtatgagca cccccagcct 31800
catttttgtg ttttctatag agatggggtc tcgctgtgtt gcccatgctg gtcctgaact 31860
ccttatctca agtgatcctc ctgcctcggc ctcctaaagt gctgggatta cagccatcag 31920
ccgccgtgtc cggctttaaa aagcaatcct aaaaatcgta aacaaaatga cacagaggaa 31980
ccttattgcg catcgagcca tgcaagaaag gagccgttta tttccagcaa gtttaaacat 32040
cgatttgacc tccagccatg gtcgatgaga tgttagaaaa ccaactctct tgctgacaac 32100
aatgagaaaa tcttgatacc atttagcaaa aagaagtctg tgggggaggc gttggagagt 32160
gacggaactg ccagggcctg aggcacccgg cttccggtgc ctctggcagc ccagagaagt 32220
gactctgtct gtcttaaggc accaccctcc ccggtgcatt tgctgatggt ttctgagcag 32280
agcagtctcc tggggctgga ggggcacaag ctggaatggg cgccccacca tggggacccc 32340
cagatgccag accttcaact gagataggaa tctggtgctg gatataggcg tctatggcac 32400
cccagctgca tgtcaacagc agcagcaagc cctccttgaa gggtgaaacg gcattcacag 32460
tctccagttt tctctacaat tttcataaat gttgtccgtg attcaaccag agtttccagc 32520
agaggccgag accaggtgac ggcagacgag aggacgcccc tctggctgga gcctccccgc 32580
acagactcgg gtccctctgc tacgccaggg tctcgactgg gcagtatctg tgggtttccc 32640
acgttaactt gtctcaggtt tctctttctt cttttgagac aaggtctcac tctatcgtcc 32700
aggctggagc gcagtggcat ggtcacagcc cactgcagcc tcggcctccc ccgtgcaggt 32760

```
gatcttccca cctcagcctc cccagtagcc gggacacaca cccagctaat ttttgtattg  32820
tttgtagagg cggggtctca cctttgctca gccctgttct tgaacccctg ggctcaagtg  32880
atcctcctgc ctcagcctcc caaagtgctg ggattacagg tgtgagcggt gttccataga  32940
ttttttaaaa atccttcacg taaaagtttt ttgttacatt tcagaaggaa acagaaaagc  33000
ataaattcaa tgtgggcatc cccctcccgg cccacagggc ctctttctct gcagttccct  33060
ggggaccatc tccttcacac tcaccgtttc acaggagcgt tcacagaatc aggaaggttt  33120
ctgtggctca cctgcccatg gctggggctc agtctctggg ggacgcatct catgtagagt  33180
gaaaggcgcc acctttgccg tggggacggg acttatttgc agacacggac tttgatttgc  33240
tttatctcac aatgtgaaga aactgacaag tattgttttt gaattgaagg aagcatccgt  33300
tcctttcata agaggggatg gaaacagcct ggccctcggg agggagcgtc cgcccggcgg  33360
gtcagccact cacaggggct gtcctctcgc cagggctgct ggtcaacctc tccctcatcc  33420
cagtcatggg cgggctggcg ctgtgcacgg ccactgagat cagcttcaat gtcctggggt  33480
tctcggccgc actgtccacc aacatcatgg actggtgagt cacagagaag gtgggcgtga  33540
gggggacgag acccggtgct cacctgcatc tgggtgtgca gattctcagg tgagctgaga  33600
attcctcccg tgagccaaag caggtgcgtc caatgctgcc ctttcctaaa gagcaaaaca  33660
acaggtatcc ccggcaggta agtttctcaa aaataagccg aaatttcagg atggacggtc  33720
ttggtactta aaatgctaac catggagaca cggttagctg acaaatgctg aaatacgcag  33780
atacgctcag cagtgtgtct cgctcggtgt gtcttcatgc ggctgccaga gcagggacag  33840
tcccccagcg gcaggttctg cctgtttggg agctgcgcgg cctccaggtc gggcggatcc  33900
tctgcttcct tgtggccatc tgtgtcctgg tgtcacgatg gcaggaagga tgagaggccg  33960
actcccacag cgaggacagc gcgtggcagg ctcccagagg agagggccct gttatttacg  34020
tctttgtcac tcggtagaga agagcggtgg acgctgcact tcgggggccg ttcagattca  34080
cccagaattg ggcgtccacc tccctgccgt gctgttaatg gccacactcc agccccggca  34140
aaacctgccc tttgagaatg accggcttct aggcttttcc tgcttttgag gaaagaaagg  34200
aaaagacacc accactggtg tctgagagtt tatcattatt actgataatc aaaacaggtt  34260
tgtggtgaga ttttgaataa tacagaagta aaaataaaaa tatgttgggc acagtggctc  34320
acgcctgtaa tcccagcact ttgggaggcc aaggcgggtg gatcacgagg tcaggagatc  34380
gagaccatcc tggctaacat ggtgaaaccc cgtctctact aaaaatacaa aagattagtc  34440
gggcatagtg gcggacgcct gtagtcccag ctactgggga ggccgaggaa agagagtggc  34500
gtgaacctgg gaggcggagc ttgcagtgag ccgagattgc gccactgcac tccagcctgg  34560
gcgacagagc cagactctgt ctcaaaaaaa aaaaaaaaat ctgttgggcg tggtggctca  34620
cacttgtaat cccagcactt tgggaggctg aggcgggtgg atcacttgag gtcaggagtt  34680
ggagaccagc ctggccaaca cggtgaaacc ctatctctac taaaaataaa aaaagtaacc  34740
aggcgtggtg gcgggcacca ctgaggtctg gtcattgtcg ccatcgctcc gtgtgagcgc  34800
agacaccttc tccccctgat gttccgtgcc gaggactagt attgatgcat aacctctttt  34860
ctttattcta gtttgcaaaa tgttttttca aaaaagctgc tcagcgggga caaatacagg  34920
ttctcgtaag tattattcgt cagtgaaatc tccaagtcat aagacgaaga ggacttcctg  34980
ctcactgtaa gagtcagaac accccacagg cctgactccc ttcctgtctg gcttgggtgg  35040
cctttacaag taccctgtct aagctcggga gggacccgcc cgtttctcag ctactccctt  35100
gagcccctca gccagcctgg tgtgcgtttg cgttttcatt tctgggaagc tgcagcaccc  35160
```

```
tagtcctgtc tagagagaat gaacgtcttc tgggctgggg tgcctgggtg ttcttgctgt  35220
gagggagctg cgtgtgaact cggcctgtcc cgacacgggg ggcccagcgt gttctgtcac  35280
ccacagggcc ccggagctgc agttctacac cagcgccgct gcggtggcca tgctcgtccc  35340
ggcccgggtt ttctttacgg tgggtttcag acacaggcgt cccgtcctta cttgccgggc  35400
tgccttctcc ggtgattcag gagcagaatg acttccgttt ccaggccgtg tgctggctgg  35460
ttgggcccag ctccgctgcg ggtcctgctt agctgagttg ccctgggagc cactcggggt  35520
ttgcagctca gatttctgtg tgaagacttt tattttgttt attgtttgtt tgttttgttt  35580
tgattcttca tcattcaact tgagatgact tttaggttag cttaatttct tttttttatt  35640
agaaaaactt ttttttttta tttttataaa gagtctcgct ctgtatccca ggctggagtg  35700
caatggtgtg atctctgctc actgcaaagt ctgcctacca ggctcaagtt attctcctgc  35760
ctcagcttcc caagtagctg ggacctgcaa tttgtagact tccctagagt cccccacaca  35820
gagggttctc tgtgtgagat gcagtttcaa gttcttattg cggttttctg gattttaatc  35880
cattagctgt caaggctgac tgacttggcc attctccctg cagggaagtt gtggttgccg  35940
gccagggcca tcagttcttg tgcgtgtata cccagcagtg gaagtgctgg attatataat  36000
aattctatat ttaatttttt tttttttttt tggagatgat atctcactct gttgcccagg  36060
ctggggtaca gtggtgcgat ctcagctcac tgcaacctct gcctcccggg tttaagtgat  36120
tgtcctgcct cagcctcccg agtagctggg attacaggcg cccaccacca cgcctggcta  36180
gtttttatgt ttttagcaga gacgaggttt caccgtgttg gccagactgg ccatgcccgg  36240
ccccgcattg ggtttctgt tgcattttcc tgatgatggt gacgttcagc ctctttcatg  36300
tgcttgttgt ccatttgcat ctgcatggtg aaaattaatt agtgcaaaaa ataataaaaa  36360
caaacaaaca aaaaaaacag aaaatggatg agtgcacagt ccagctgtcc gctcgaggca  36420
ttttcagggc tgtcctcagt ggcagcagct ttacccagtt tctgggcagg agtggcgctg  36480
ggcgtttttg gtggatgatt agtaaatgga aaatggaaac cgatagagta cccttttgtt  36540
tgccacatag gacgtcccag tgatcgggag gagtgggaag agcttcagct acaaccagga  36600
cgtggtgctg ctgcttctga cagacggagt cctgttccac cttcagagcg tcacggcgta  36660
cgccctcatg ggaaaaatct ccccggtgac tttcaggtga gcagaggaac ttcccaagag  36720
ttgagtgtgt ccaggttgtt tacaaaggag accagaaatc taggtatttt tataagggac  36780
acatgtgatt ctcttccacg gggatgagtg tggctatgca gtgtaattac taggctattt  36840
tatacccatg ctgtttgaaa tgcaaacgat aggccgggcc cagtggctca tgcctgtaat  36900
cccagcactt gagaggacaa ggcaagtgga tcacttgagg tcagtagttc aagaccagcc  36960
tggctaacat ggtgaaaccc catctctact aaaaatacaa aaattagccg ggtgtgatgc  37020
tgggcacctg taatcccagc tactcgggag gctgaggcag gagaatcact tgaatccagg  37080
agccggaggt tacagtgagt tgagatctca ccactgcact ccagcctggg ggatgggagc  37140
gagagtcctt ctcaaaaaaa aaaaaacaga aaaacaaatg agaaactgta aaataaaccg  37200
taaactgtgt gaaataggta tttagggaaa tctccactag aagtctctgc gtttgaaggt  37260
ttttgaaatt gagtgctttt ctgtctagaa tagtcgggcg ttgcgactag tcttgtctgc  37320
aggaatggaa tggtctcttc tgggctgtcc agtgcaggag ccactggcca catacagctt  37380
ctgagcactt gaaatgtgga gaatataaca agaaccagat taggaattca agctgattgc  37440
tgtcagtttg aacttgaaca gacacctgtg gccactgctt cctgtgccgt gcggtgcagc  37500
```

-continued

```
tctagaaacg gggaggatcc ttcagcttct ttccacttct gtaactgggc agattgaatg  37560
aagctgcaat ttatttgttt atgtatttta ttttatttat ttattttttt gagacagagt  37620
ctcactcttt cacccaggct ggagttcagt atcgcagtct cggctcactg caagctccgc  37680
ctcccgggtt cacgccattc tcctgcctcc gcctcccgag tagctgggac tacaggcgac  37740
tgccaccacg cccggctaat tttttttttt tgtatttttt agtagagaca gggtttcacc  37800
gtgttagcca ggatggtctc gatctcctga ccttgtgatc tgcccgcctc agcctcccaa  37860
agtgctggga ttacaggcgt gagccaccgc gccctgccta tgtattttat ttttcccgaa  37920
acagagtctt gctctgtcac ccagagctgg atttctctgg tttgatctcg gctcactgca  37980
acctccgcct cccgggttga agtgattctc ctgcctcagc ctcccaagta gctgggatta  38040
caggcgtgtg ccaccatgcc cggctaattt ttgtattttt agtggagacg gggttcacca  38100
tattggccag gctggtctca aactcctgac ctcaggcgat ccgcccgcct cggcctccca  38160
cagtgctggg attacaggcg tgagccacgg cgcccggcct ccacagtgct gggatgacag  38220
gctgagcccc cgtgcccggc ctcccacagt gctggggtta cacacatgag cccccacgcc  38280
cagcctccca cagtgctggg gttacaagca tgagccccca cacccagcct cccacagtgc  38340
tggggttaca gacatgagcc cccacgccta gcctcccaca gtgctgggat tccaggctaa  38400
gccgctgcgc ccggtgatgt tcttgttctt tagagagcag gctgaagtac tcaggggtga  38460
gatgtcatga tacctgtaat ttacttaaaa atatttcatc tgggtgtggt ggctcacgcc  38520
tatgatccca gctctgtggg aggcccaggt gggaagatca cttgagccca ggatttgaag  38580
accagcctgg gctacatagt gagacccacc tcgattggat gaagctgatg aggcggatgt  38640
catgaattcc tgcgtctaga tcacaggacg tggccgttac ttaggtttct cctcctctgc  38700
ctttttttaat aatgaaaagt acccctcaaa aaagaaggga cgagggagca ggcaagcccc  38760
gctgaaagct cccaaacccc tgggctgatc tcaccaccac cgaggtcccg ttgagcaccc  38820
ccgccccatc ctggcctcca gacccggggt cagccgagct gctggccgca gggctgatgt  38880
caccgtgacg ctgagtcccc caaccccacc cagcctccag acccaggctc agccgagctg  38940
ctggccacgg gctgaggaga ccatagccct gagcgcccct gctgcctccc cttgcctccg  39000
cagcgtcgcc agcaccgtga aacatgcctt gtccatctgg ctcagcgtaa tcgttttcgg  39060
caacaagatc accagcttgt cggccgttgg cacagccctg gtgaccgttg ggtcctgct   39120
ctacaacaaa gccaggcaac accagcagga ggcgctgcag agcctggctg cagccactgg  39180
ccgggcccca gacgacacag tggagccgct gcttccacag gaccccaggc agcatccctg  39240
agagcaggaa gctgccagct gctgctgtcc tcgtgacact gcatccccca gaaatgggca  39300
gggacgccct cctccatggc cctgctgggg tgcaggacat ggggagctaa gttggccatt  39360
gcctgcggct ttctcggttt gtcggtgaag accagcagaa actcaaactg gggattccag  39420
gtatcagctt cctggagtag agaccagacc agtagctgac tgtgtccgcc gagcccatcc  39480
ccgtgtagtg tgaaaacagc ctctgaggct cccatgctgg gggtgcccac ttcctctctg  39540
ggcgacaccc cagggtccac cgggagccag aggtgggtcc agtgccaacg agagccgctc  39600
cctgccacag ccaagagagc cctcggcttc ccacaccagc catcgaaggc cctgaggccc  39660
tggaccggcg gcagactggc cctgggcatg aggccacaga gcagggccga agggagggga  39720
cagagggccc tggaaggaag ggtctcctgc tgccacggtg ggcactcaga acttctcccc  39780
acctgaccca gggctgtggg catcctcaga ctatcccaga ggcatcgcaa gcctcaagct  39840
gcagcattgc acggcactca agggctatga ccacggaggc cgttcagtcg cttctgttta  39900
```

```
gaggaaggcc ccctacctct tccacaccct gccctcctat cccttccaca ccctgggctg  39960
cgtgagctcc ccgcaacccc agggcaccct gccctcctac ctgtgggggt ttccagccct  40020
gaggttgagg acaaacctct cgtgtttaac ttgggaggag atgtgtacgt tccttttctt  40080
ttttggactc tgagtatgag gcaggctgtt ctgaggtccc cgtggggtga gcctgtctgt  40140
cctccctcag agcccaccgt tcctatcatc atctagcacc tgtccggttc cccacgtgag  40200
ccttgggcag gacgctgcag tgttgatggt ttgggttacg tggcgtttac ctgggcgccg  40260
tccttgctga aaaaggaaac gtccacactg aatgtttctg gggcgcgtgg tgtgtgtcag  40320
gcgcccaccc tgtcccactc tccccaaggg acagtagtac ggcacactgg ggccaccagc  40380
cagctcaact catcctcctg tgtcacgcac ccccgagggc gcaggaggcc tgaggagtgg  40440
ctactggagc cgtgtgttag gcagaggctt ctgaccatgt ctgagctctt tacccccaat  40500
ctcgcagctg gcggattccc atgcccggtg cagcctgttg ccagccagcc tttgagaccc  40560
agagctccag ggcttgtcag aggcagcatg gggcgccagt ggtcctgagt ctcatttccc  40620
tgcctgctct ttaggccttt ggcacccatg gtcacttcac tggctttcca tttggcttct  40680
cacctgggaa atacaaaaat agcccctcct gaagataaaa tcattcagaa acagagcaat  40740
aattctgact cattaacttc tacctactca aaaaagtctg ccatgatgat ggaccgaagt  40800
gaggcttttt aacccacaag taaccttttt atttttttga gacagtcttg ctctgtctgt  40860
cacccaggct ggagtacagt ggcatgatct tggctcactg cagcctcgac ttcctgggct  40920
caaatgatcc tcccacctca gcctcccatg tggctggaac cacaggcacg tgccaccatg  40980
cctggctatt tttttgttga gctgggctct cgctttgttg cccaggctgg tcttgaactc  41040
ctcggctcaa gcaatccttc ctactcagcc tcctgtagtg tcgagaatat aggcgtgggc  41100
tactacacct gcttcagccg cttctataaa accgctgacc tgtgtgtgga ggacaggcca  41160
ggtgtgtgct cactgcgctg cgaagatgtt ttgtcacgtg actttccccg gatttccatt  41220
tctttttttc tgctttcctc aaaaactaat agaagactgg gtgtggtggc tcacgcctct  41280
aatcgcagca ctttgggagg cagcagctgg cggatcacaa ggccaggagt tcgagaccag  41340
cctggccaac atgatgaaac cctgtctcta ccaaaaatac aaaaattagc tgggtgcgat  41400
ggtgggtgcc tgtaatccca gatactcagg aggctgaggc aggagaattg tttgaacccc  41460
ggagatggag gttgcagtga gccaagatcg tgccattgca ctccagcctg ggcaacaggg  41520
caagattccg tctcaaaaac aaacactatt agaaaatgcc ctggaggtgg cggggagttg  41580
ttgatttgtg aggacagatt gaaagcaact cccagggtgg taatgtggct gccggcctct  41640
ttgaagattg tggtctggca taaggagagg tgcaggcgcc tggttctgag caccttggaa  41700
tttccagccg cacagcatct ggtgccctcc cctccaccct cacaaggagc tgccatcctg  41760
tttggatttt ctgtttgtgg accagaaaca aacgtttttc caaaggatta gcaaataggg  41820
taatttcctg tgtaacgctg ctctggggcc tcttcctcat cctggcagaa ggagcctgga  41880
gcccatgagg cagccagcac tgtgccettg ctcagtcgtg ctgtcccctc cctctccctc  41940
agtctcctct ccatgcccaa gtcggtttcc agccgctggt cttcatggca ttcccagcac  42000
agccgggcac caagaggcaa aacccaaggc ctggcttggc cgtgttaacg attgtacaga  42060
catttttttaa aataactttg tgtaatactt ttctggaata gtaagttctt gttgaactgt  42120
cacaggtgag cttctaggaa cacaccgggt gtggttactt ccactgggtg tgtccatggt  42180
cgtggtctgt gcttttgtaa acgaacagaa cacttgaacc acctcccgaa ttgggtcatc  42240
```

-continued

```
ggcttcttta cgttgatact tagagatttg cagctctctt tcaaggaaac ttcccctact  42300
gaaaggcata aaaaggttaa aaaagaaaat ccgagagtcc caattccctg tataacagca  42360
ttaaaataat ctgcctgcct ggaaagatga gaacactgtt gcacaaccca aaatgtgtct  42420
ttaatttgtg aaaaattacc atggtgagtc agacagtcat tttaaacagc tgaacagaga  42480
ctatcatcag caaatagagc tcagctttgt agctgccttt aaaatccttg tcccaaatcc  42540
ggtgagctct gcttgctgcc gccgcgctcc tgggtgatca ctcagacggg tcagtgggaa  42600
taacaggcca acaagacagc tttttacatg tgtccaaagg atggcctttc gaaggcctgg  42660
aagtatttca ctgttggaag aagtaaacaa gaatgacatt ccagatggaa atagaattct  42720
ctctcttgcc tttgaccaac atggtactaa ggggtttctt ctttcccaat gtatgtacgt  42780
gccctgctgg gggccttact ttatagaatg agagcatccg agcttcccta atgaatctgg  42840
ctagttctgt gtctggctga ggatacagga gtgggacatc cactctcgga tccctcagag  42900
cacagaaacc ttcagctttg ctgtctctga agtatttcct ccagtttccc tgcgggcccc  42960
tatgtttgag tttgatggct gctggatcct cactcaacga aaactcggtt ggaaactgtt  43020
ccgcctggca gtcctttttt gttgttttcc atctcatttc ccttccatct gaaagtggca  43080
ttcagctgac ttgctcattt agactgttca cggagtctga atctgccaac gtggtgttgg  43140
aggctccacc ttgaaaaggg ccacagtcag ggcaactttc cccatacagg aaaacttgaa  43200
aattacatca acagtctacg tcacagccaa attatatttc ctttatacca aacaaaaacta  43260
tggagaacta aaagtacatc acacaaaacg tttatagtgt tttgcatgtg acctatttca  43320
gtatttatat aactagatta gtgctttcta gcaaacggtt ctgttaatta gcgagtcact  43380
gttgattctg ctgtggtggt aagttgatac cgtgtaacta atcccgtgga tgcctcctcg  43440
ttatttttgt ccaaacgaag cagccgtggt agtagctgtc tatgattctt gctcagcaaa  43500
gtaaaataaa tgttaaatat ggactgcttt gttttcttcc ttgtggaact ctggtgttca  43560
tgctactttg ttcaccggtg tggctggctg ttgctagcaa agaggctctt cacagaagtg  43620
gctgaaccca aagttctggt tgggaaaggc ctttgtggca gctcctatca agcgcaagtg  43680
cgaggccacc ccctcctcgt gggctctggg gtcgattttg ttagggtttg acatgagtgg  43740
ctgcatttgg gtactcacag atttcacaaa ggaagggtaa actggagatt tttggccggg  43800
cacggtggct catgactata atttcagcac tttgggaggc tggtgggcag atactttagg  43860
tcaggagttc aagaccagcc tggccaacat ggcaaaatcc tgtcgctact aaaaatacaa  43920
aagttagcca ggtgtggtgg cgcacgccta taatcccagc tactcgggag gctgaggcag  43980
gagaatcact tgtacccagg aggcggaggc tgcagttacc caaaattgtg ccactgcact  44040
ccagcctggg tgacacagcg agacttttc tcaaaacaga aaaaaacgtg ctgtggctca  44100
cgcctgtaat cccaaccctt tgggaggcca aggcaggcag atcacaaggt catgagatca  44160
agaccatcct ggctaataca gtgaaacccc atctaaacta aaaacacaaa aaaattagcc  44220
gggcgtagtg gtggacgcct gtagtcccag ctactcggga ggctgaggct cgcaggataa  44280
tggcgttgaa cccgggaggt ggggcttgca gtgagccaag attgcgccac tgcactccag  44340
cctgggcgac agagcaagac tccgtctcaa aaaaaaataa aaataaaaaa atagggagat  44400
ttccccagtt accaagaact caggaagcaa cattaagagc ttgggggagg ccaggcgcgg  44460
tggctcacgc ctgtaatccc agcactttgg gaggcagagg caggctgatc acgaggtcag  44520
gagattgaga ccatcctggc taacacggta aaaccccgtc tctaccgaaa ataaaaaaaa  44580
aattagccgg gcgtggtggc aggcgcctgt agtcacaggt actcaggagc ctaatgcggg  44640
```

```
cgaatggagt ggaggcggga gaatggcgtg aatccgggtg gcggagcttc cagtgacccg  44700
agatcgcgcc actgcactcc agcctgggca acagagcgag actccgtctc aaaaaaataa  44760
aaataaaaaa agagcttggg tacacaaagc aagcagcatt tcattccggg atgaaaaaaa  44820
ttccgatacc catcgccctt cttgggccct tgtcagtttc ttgccacatc tttcattttc  44880
ccatttcagg cccagtaaat gcggatgttt atcttccatt gtttgtttcc tgagattcag  44940
atgtctaaag catttttctg tgacttttca agtcaagagg aaaacctgac atatggaaag  45000
ggaattaatt gctcgtttta tcctcttctc ctgcaatgct ctgaatccat gggtttggag  45060
tggggccctg ggagttgggg gaagcaccat acccagtgag tctgcacttt gaggacccac  45120
tgccagtgtc agcttcaaaa tcacattgta aaaggccggg cgcggtggct cacgcctgta  45180
atcccagcac tttaggagga cgaagcgggc ggatcacttg aggtcaggag ttcgagacca  45240
gcctggccaa tatggcgaaa cctcgtctct accaaaaata taaaaattag ccgggcgtgg  45300
tggcgcgggc ctgtggttcc agctactcgg gaggctgagg caggaaaatt ccttgaaccc  45360
gggaggaggc tgcagtgagc caagaccacg ccactgcact ccaacctggg cggcagagca  45420
aggctccgac tcaaaagtaa atacatgaat aaataaaata aaatcacatc gtaagagctc  45480
tccctgccct gtttctgagt aaggttcaga gttaaattcc gagatcggcc tttacaagac  45540
acacagacct gaggcgcctc acgaggtaac cagcaggtaa atggagcgcg ctccacccac  45600
ccgccactag gggtcccagc ggtcaagggg gtggaatgcg ggcgtccatc gcgaaggcat  45660
tctgctcgca agccttggca caggcgcggg cttcgctacc ggaaaagtcc cggtaggatt  45720
ccggaagccg gccacgcgtt ccgcgcaggc gcaaactgct ccaaaagtgg gcgtcgctcc  45780
cccggagtcc cgattcctgc gtcacagccc gcgccgaagt cggaagtgcg ctcaccgggc  45840
tgtttcttct ggcgtcctgg acctgagcaa gcgctgtttt atgcgtcatc atcccgcgca  45900
gacacaggaa gtgccgcaca gagcgagccc ctgtccttgt ctcgagttct gggccggagg  45960
tcggctatta tatcatcatt acgcgccaat acaggaagtg acgatacttt tggcgcgcgc  46020
cggttgctgt ttcttctctg gctccgggac cggcggcggc ggcggcggca gcggcggcgg  46080
cgtaggggtg agttccgact gggcggacca ggtgtgggag cgcgaggaga actgtgcacc  46140
gaggtctttc ttccgagcag gcctcggagc ggggcggacc cgggcccggg ggcgagcgac  46200
accctcgctt ccgcggacag tctcatcccg cacggaactt tgggtggtgg aggcggcggg  46260
tccaaacgct gtctggagcc aacgtctgcc aggctgaacc tcaagtgtgc gggactgaac  46320
ccgaggaaat agcccagtgc ccgggtcagg tggccttgtt cgcgagcaca tctcggagca  46380
tctccccggt ctcaaggtgc agctgtccag tgtgctagtg gcttcacgta gtccaagcgg  46440
tctttctagc agattctgac agtaaaagca gtgtttgatg agtggcaggt cctgagttaa  46500
gagcctttaa acggatgatc tttaatccgc gatcgatact atcacgtagg tgttgttatt  46560
ctggttgtac ggaagactaa actgaggtga attacgttac ccaagaccat acaagaatga  46620
cagaaacgag acttgatttc aagcggtcat ttttcagaac ccatcactct tttttgtcgc  46680
ccatgctgca gcgcagtggc tgttcacaag cgcacttcag cctggaactc ctgggctcaa  46740
tcggtctccc atctcagctt gcagagtata tgggactaca ggcgctcgcc accttgcctg  46800
gcttacaact tatcattctt gttttttttt cttttttttt tttttttttt ttgagacggg  46860
gtcttgctgg agtgcagtga cgcgacctcg gctcactgga acctccgcct ttcggattca  46920
agcgattctg ctgcctcggc ctcccgagta gctgggatta caggcacccg ccaccacgcc  46980
```

cagctaagtt ttgtattttt agtggagaca gggttttcgc cgtgttggcc aggctggtct 47040
tgacctcctg accttgtgat ccacccgcct cagcctagag cttacctttt tttttttttt 47100
ttttttttta accaagtctt actttgttat gtaggctgga gtgcagtggc gcagtcttgg 47160
ctcattgcag ccttgacctc tctgattcaa gtgatcctcc tgcctctagc agcctccttc 47220
ctgtagctag gaatacaggc acgcgccacc acactgggct aacttttgta tttttttgtag 47280
agacgaggtt ttgccatgtt gcccgggctg gtgttgaact ccggaactcc agcgatctgc 47340
tcgcctcggc ctcccaaagt gctagggtta ccgtcttgag ccactgcgcc gggcacaact 47400
tcttattctt aatgaggatt tattctgaat ccctcaaaag tgactaggtt caagtgttca 47460
gcaccatagc ttgctgtgtc ctgatgtagg ctgaattatt tttctttttg cagtgtttta 47520
actcaaatgg gtgatgaaaa ggactcttgg aaagtgaaaa ctttagatga aattcttcag 47580
gaaaagaaac gaaggaagga acaagaggag aaagcagaga taaaacgctt aaaaaatgta 47640
agccatattt tttaagtaag tggttttctt aaaggagatt taatttcttt gccctcattt 47700
ttccattaga acaacgcttc ttcggtgaag ttcttttgta cttccaaatg tcgcaggtga 47760
gcccaaaatc tattctaaaa attaacaaaa acattcaaat attcagttga cattaaaggc 47820
agatttaaca cactaaagct gtgtctagat tgagcataca tggagaataa aatacgttga 47880
atgttaagtc attagcaaaa ctggactaat ttttctcggt tcattagtat gttcataata 47940
ctatctctaa gtatttttaa tatagtggga acttgccttg aaattaatat aaatatttta 48000
catctttctt ggtttgcatg gtaatgtact caggaaacct ttttagtaat ttggtaagag 48060
gcattggcaa agtacctctt ttgctaagat ctttagcagc atcatttggg atgttagtga 48120
gtacaggcat accttgttgt attgcacttc actttattat gcttcacaga tattgaaatt 48180
tttccaaatt aaaggtttgt agcaactctg cattgagcat ttttccaata gcatgtgctc 48240
actttgttag cttttttttt gtttttgaga cggagtctcg cactgtcgcc cagggccggg 48300
ttcacgccat tctcctgcct cagcctccca agtagctggg actacagggg cccaccaaca 48360
tgccaagcta attttttgta ttttttagta gagatggggt ctcacggtgt cagccaggat 48420
gatcttaatc tcctgacctc atgatccacc cacctcggcc tcccaaagtg ctgggattac 48480
aacaggcatg agcctccgcg cccggccttt tttgtttgtt tttgagacag tcttgctcca 48540
ttgcccaggc tggagtgcag tggcatgatc tcagctaact gccacctctg cctcctgtgt 48600
tcaagcagtt ctcctgtctc agcctcctga gtacctggga ctacaggcac ctgccagcac 48660
gctcggctaa tttttatatt tttagtagag acgagctttc accttgttgg tcaggctggt 48720
ctggaactcc tgacctcagg tgattcacct gcctcaccca gcctcccaaa gtgctgggat 48780
tacaggcgtg agccaccatg cctgacctaa accaaacttt tatatgcgtt gggaaaccaa 48840
aaaatctgtg tgactcactt tattgtggtg ttttggagcc aaacccaaaa tatctccaag 48900
ggatgcctgt accatatgag gtatcacaaa gtatttggtt tgcaagatac gccttaagat 48960
tcatttttgg ctcatataag caactaacat acttggcata gagtctaatg tcccttgtca 49020
tatatgctat ttttaaattt ctcatctcag gtttcagatt acagagagtt gtaattttaa 49080
tgtgataaga tttgaattaa agtttgtttg tttgtttgtt ttccctgata cggagtctaa 49140
ctctgttgcc aggctggagt gcagtggtgt gatctcgggt cactgcaatg tccgcctccc 49200
gggttcaagc agttccggtc actacgccca gctaattttt gtatttttag tagagatggg 49260
gtttcactgt gttgtccagg gtggtctcga gctcctgacc tcgtgatccg cctgcctggg 49320
cctcccaaag tgctgggatt acaagcgtga gccaccacac ccggccaaaa gttctttata 49380
ttttataaca ctggctcatt cagagtatat atgaaagttt gttttgggat gttgcccagg 49440
tttgattatc attaaaaata cttttatcta tgaagaaaaa aaaacttata aagaaaatga 49500
ttaactttct ctttgcttct tagtctgatg accgggattc caagcgggat tcccttgagg 49560
agggggagct gagagatcac cgcatggaga tcacaataag gaactccccg tatagaagag 49620
aagactctat ggaagacag 49639

<210> SEQ ID NO 3
<211> LENGTH: 251
<212> TYPE: DNA
<213> ORGANISM: Homo sapiens

<400> SEQUENCE: 3
attatctccc tccaaactct aaagaaggaa tataaatcct atgaagccaa gctccgcctt 60
ctgagcagtt ttgatttctt ccttactgat gccagaatta ggcggctctt accctcactc 120
attgggagac atttctatca aagaaagaaa gttccagtat ctgtaaacct tctgtccaag 180
aatttatcaa gagagatcaa tgactgtata ggtggaacag tcttaaacat ttctaaaagt 240
ggttcttgca g 251

<210> SEQ ID NO 4
<211> LENGTH: 10562
<212> TYPE: DNA
<213> ORGANISM: Homo sapiens

<400> SEQUENCE: 4
gtggtgttgg catgaggaaa ggaggtatct tcgagggaca atcttcttct tgtgcgatcc 60
ttggagatgc catgaggccc ctggacacat gtggtgtggg ctcctttgga ggctgttgta 120
tcccttctga atgtaagtgt ccactttcca aagtcctgat tttcctcatt tttgggcatg 180
aataatgtgc atggatcgat gatgacttcc atatatacat tccttggaaa gctgaacaaa 240
atgagtgaaa actctatacc gtcatcctcg tcgaactgag gtccagcaca ctgttcatca 300
ggggctagag agagagacaa catccatttg ttgacacagg ctgcatcaat gcttgggatg 360
ggatcgtctt tgggtgaagt ggagtagctg ggcattttgg acttctgtgg ctgagagaca 420
gcttggttga agctcttccc tctgtgtggc tatgtgtgtt atcgattcat accccttggc 480
tcctgcactc cccagaggaa gacagttact gctgcatggg gacacagcac aatgttgttc 540
ccaggcactt cttcggctca cttttatcct aagtcgggga catgggagtt cctgtggtgt 600
atgggtatca tcaagggcag gcagtcgtga ggagggtggc aatactgatt tgctttctgc 660
agagaagccc agagagggta tccacgttga attgtatgtc cataggaggg ggaaacccaa 720
gtcccgtggc ccctgaagca tcctggcagt ggaaggggag agggccgtgc atgcgtgtac 780
cacacagcct tctgtctggg tcacagagcg acgactgtga gcctctttcg ggcattgtag 840
ggtgcccata gtccatttca tgatgacctc agggtgctgg gatgggaatg taattgtagg 900
tccacgtgct cctgcatctc tgcagactga cttggtttgg aaggtctgtg ttgaggaacc 960
tctgtgggat acttttcctt ggtgcatttg aggtgtctga taatgagtgt gtgggtttct 1020
gtatcctggt gacttctact cagaaatgtg acccagcaag gtctctgtgc ttaaatacct 1080
tagtggcttg tgatgttagg ttattttcaa attcctccta attgtgtgtg acaattcaca 1140
caagtctttg tgaaattgtc cttgaattgt atgacagggc tagtgtctgt aggccagtga 1200
tggataagtt ttggactcca cagccatgtt cacagccaag tggcttaaga tgtatggtgt 1260

-continued

```
tcttagtcat agtgccttgg aagccctgta ggattcagca tgtcttgtgc tcttctgggt   1320
ccccgagctg tacctttgag gaaaacccag aggtggaggt tgatttgtga ttgagcatgt   1380
ttctcagtgg gaagagtgtc aaaggagcct ggggtgaaag tacttcagga ccaaaggaaa   1440
attgcccttc actcaagaag aggctttcct tgaacctgtc cccactgaaa tatcctcatg   1500
ggcttcatct tctctgatgg ccaaaagcag gacttttgat tcagaggtgg caaatgaatg   1560
gtgttgagag agtttgttat gcttggtgct ctgtagctgg aaggagccct caaaattatt   1620
gtgtgcatga tagcttcatg cctgcttaca cccatgcaca tgtcccagta agaggggctg   1680
cctgtgggag atacatacac gatacaccac agtgggatga attgtatggc ccttgcaatg   1740
tgtgtacctg cctgctgttg tcaaacacac ctgtttttcc tctgaacttt ccaggtggcg   1800
tgggcataga aggaaggcca gtggccacga gggacaatct tggtcttggg agatcctgga   1860
aatgataggg agtcccttga tatgtgtggc atgggctcct tcaggtgcta gtggattcct   1920
taggatggta agtgtccatt tctcagaagc tccagatatt cctcctctgc agggacaaag   1980
actgtgcctg gatcgatgat gacttcctta tatacattcc ttggaaagct gaacaaaatg   2040
agtgaaaact ctataccgtc atcctcgtcg aactgaggtc cagcacattg ctcttacagg   2100
ggctagagag agagggacaa atttcatttg atgatgccca ttgcaccaag ggttctgtc    2160
caggcttagg atggggtctc gtttgggcaa aggagaatgg caggggagtg gaggctatgt   2220
acacaggaga ttccttgttt gaaggactct atttgtgagg ccagggtacc acacatgctg   2280
tccgcaggag taggtgaatg tgcagttgcc caggaagagt tagcctgtag cctgcctctg   2340
catggcagtt tgtccttggg tcctggctct ggatttccat gttccttgga ggaggatagg   2400
tgattttgct tgagaagaca gcacagtacc atacttttgt tgtttttctg ctcatttcat   2460
cgtccattga ggacaatgaa gttgtggtca gcaggcatag ctttcaggcc agcgtgccca   2520
tgttgtgtcc catgcattgt gagcacatgc atgtggcatg aacacatagg ctgccactcc   2580
aagctgagtc tgataggcaa tgagactctg gcttatcctg atcccggtgt agatcaaagt   2640
cttcccagta ggattgcatg gccccgaggc tattgtgagc tgcattgcag gtgtggaagc   2700
aagggtgttg agagggatgc tcaacattag tgctctttag cgagatgatg cactataagg   2760
gcaccctgaa cccagacgtg catccctatg tacgtgcatt tctgtgtcca taaatagttg   2820
aagccagaca gccagattcc agatgtatcg cagggggctg gatgacatgg cccttgtcac   2880
ctgtgtacct gtctgccttt ctgaagcacg cttgtgtttc ctctacacct cccaggtagc   2940
attggcatgg aaggcaggcc catgttggtg agggacaatt gttatcttgt gtgagccgca   3000
gggataccag gaaacccctg gacacaaatg gcaaaggctt ctttggaagt tgttggatcc   3060
cttctgcatg taagcagttc tttcccagag cgctctgatt ttcctcattt gcagggacaa   3120
acactgtgcg tggatcgatg atgacttcca tatatacatt ccttggaaag ctgaacaaaa   3180
tgagtgaaaa ctctataccg tcatcctcgt cgaactgagg tccagcacat tactccatca   3240
ggggctagac agagagggcc aacattcgtt tgttgatatg ggttgcatca aggggtccat   3300
ccaggcttag gatggggtcc ctttgggcaa ttggaagtca cagggaagtg ggagctccca   3360
tgcacaggaa attccttatt tgaaggactt ctttctccct gggcgggata actcacctac   3420
tgtctgaagg actaggtgaa tggcaggtgg catggaaaga gtttgtgggt agtctgcctc   3480
tggtggccaa gtttgttctt gagtccaagc tctggattcc cagaggaaga cagatcccct   3540
ggttgcgggg agagcacaag cctacactat tctcacttgt tagcttgttt tgtccttggc   3600
ggaggacgtt gtatttccag gcacccagca tagcctcttt gccgcatttc catgtcatat   3660
```

```
cccatatgtt atgaggattt gtgtattgca tgatcaggca ggcttctgct ccaagctggg   3720
gctgtcaggc aaggagtctc tgggttattc caaacctgat ttaggtcagt ggcttcctct   3780
ttcaggattc atggccccaa ggcttttgtg agcaccattg caggtgttga agcaacgatg   3840
ttgagaggga tgcccaacat cagtgctctt tagcaggatg gtgcacctcg agggcccctg   3900
gccctgggac gagcatctgc gtgtccatgc atttctgtgt ccatgaacag gcgaggccat   3960
agacaggcaa atagcagatg tgtcacaggg gactggataa catggccctc gtgacgtgtg   4020
caacctgtct gcctttctga agcacgcctg tgtttcctct gcacttcaca ggtggtgttg   4080
gcatgaaagg caggcttgta tcatgaggaa tgattgtcat cttgtctgat tcttggagat   4140
ggcaggaagc ccctggaaac acatggtgtg gactctttca caggctgttg aaaccctcct   4200
gaatgtaagt gatttcattc caaagcaccc tgagtttcct catttgcagg gatgaaacct   4260
gtgtgtggat cgatgatgac ttccatatat acattccttg gaaagctgaa caaaatgagt   4320
gaaaactcta tactgtcatc ctcgtcgaac tgaggtccag cacattactc caacaggggc   4380
tagacagaga aggccaacat ccgtttgttg acatgggtta tatcaaggcg tctgttcagg   4440
cttagaatgt ggtctcttat gggtgatggg ggtcacagga gagtggtggc tcccatgtat   4500
aggaaatttc ttgtttgaag gactgtcagt gagggtgggt aacacatgca ttgtctgcag   4560
gactaggtga atgtccatgt ggcctagcaa gagttagctg gtagcccgcc tctggttgcc   4620
aatttgttct tgagtccttg ttctgggttc tcaggtccca cggaggaaaa cagatctgtg   4680
tggttgagag gtgggtacaa ggccgcatct ttgtcatttg ttggctaact ttgtccttgg   4740
ttgaggacat tagagttttg gtcaccaggc atagcctatg tgcctttgtg cccgtgttgt   4800
atcccacgtg ttttgaggac atgtattttg cacgtaaagg tgagctcctg ctccaagctg   4860
gttctgatac caaaggagtc cctggcttat cctaaactca tggtaggtta aagccttcct   4920
ccttaggggt tcagggccgc aaggcttttg tgagtggcat tgcaggcgtt gaagcagtga   4980
tgttgagagg gatggtcaat gtcagtgctc tttagcagga tggtgtactg caggggcccc   5040
cagccccgag acgagcatcc ctgcatccat gcatttctgc ctccatgaac aggggaggcc   5100
agagacaggc agatagtaga taaattgcag gggactggat gacatggccc tcgtgacctg   5160
tgcacctgtc tgtctttctg aagcacgcct gtgttaactc tgcacctccc aggtagcact   5220
ggcatggagg gcaggcacat gttggtgagg gacaattgtt accttgtgtg agctgcggag   5280
ataccaggaa gcccctggac acaaatggca aaggctcctt cggaagttgt tggatccctt   5340
ctgaatgtaa gcacttcttt cccagagcac tctgagtttc ctcatttgca gggacaaata   5400
ctgtgcgtgg atcgatgatg acttccacat atacattcct tggaaagctg aacaaaatga   5460
gtgaaaactc tataccgtca tcctcgtcga actgaggtcc agcacattac tccaacaggg   5520
gctagacaga gagggccaac atctgttttt tgacatgggt tataccaagg catccgttca   5580
ggcttaggat ggggtctttt atgggtgatg ggggtcacag gagagtggtg gctcccatgt   5640
ataggaaatt tcttgtttga aggactgtca gtgagggtgg gtaacacatg cattgtctgc   5700
aggactaggt gaatgtccat gtggcctagc aagagttagc tggtagcccg cctctggttg   5760
ccaatttgtt cttgagtcct tgttctgagt tcctggaagg aaacagattt gtctggttgg   5820
gaggagaata caaggccaca tctttgtcgt ttgttggcta actttgtcct tggttgagga   5880
cattagagtt ttggtcacca ggcatagcct atgtgcctgt gtgcccgtgt tgtatcccat   5940
gtgtttgggg gacatgtaca ttgcatgaac tagtgagctc ctgctcattg cttctgatac   6000
```

ccaaggagtc cctggcttat cctaaaccca atataggtta aagcctttct cattaggggc 6060
ccagggtccc aaggcttttg tgagtatcat tgtaggtatt gaagcaacga tgttgagaag 6120
gatgctgaac atgctcttta gtgggatgac gtactctgaa ggctcctgac ccccagatga 6180
gcatccttgt gtccgttaac ttctgtgttt atgaacaggt gaggccagag acaggcagac 6240
agcagatgta ttgcagggag ctggatgaca tggcccttgg aacctgtgca catgcctgcc 6300
tttctgatgc acgtccatgt tttctctgca cctccccggt ggtgttggta taaaaagcag 6360
gcttacatca gcaagggatg attgtcgtct catgcgatcc tgggagatgg cagaagtccc 6420
gggacacatg gagtgtgggc tctttcggag gctgttggat ccctcctgaa tgtaagtgat 6480
tccttcttaa agcatgctga ttttcctcat ttgcaggggc aaggactgga tcgatgatga 6540
cttccatatg tacattcctt ggaaagctga acaaaatgag tgaaaactct ataccgtcat 6600
cctcgtcgaa ctgaggtcca gcatactgct catcaggggc tagagagagg gacaacatcc 6660
gtttgttgac aagggctgtg tcaacacttg ggatggggtc gtctttgggt gaagtggagt 6720
agctgggcat tttggacttc tgtggctgag agacagctta gttgaagcac ttccctctgc 6780
gcagctatgt gtgtccttga ttcaaactcc ttggctcctg cactccccag aggaagacag 6840
tggcttctgc atggggacac cacacaatgt tgttcctgtg cacttctttg gttcactttc 6900
accctcattt ggggacgtgg cagttcccat ggtgtttagg tagcattgag ggcaggcagt 6960
cctcaggagg atgttgatgc tgatttgctt tctgcagagg agccagagag ggtatccatg 7020
ttgaacttgt atatccatag gaggaaacca gtcccatggc cctgaaggg tcctggcagt 7080
gggaagggga gaggtctgca tgtgcatgta ctggacagca tattccatgt gggtcatgga 7140
gtgatgactg tgggcctctt tcgggcattg tagcaggccc ccatttcatt tcatgatgac 7200
ctcggggtgc tgggacagga atgtgattgc gggtccacgt gcttctgcaa ctcctcagac 7260
tgacttggtt tggaaggtct gtgttcagga ccctctgtga gatgcttgtc tccattaggc 7320
atttgagctt atatcggccc agggtttcta cctatcgtag gttgtgcata ctttgcctct 7380
gaaccactca ggcacctcga tgcagtcaac gtgcccgatt ataagagtgt gacttcccat 7440
atcctggtga tctctactcg gaaacatggt ccaggaaggt ctctgtgctt aaatacctta 7500
gtagctcgtg atgttaggtt attttctaat tcctcctaat tcttcccagg agtcttcttt 7560
gtgaaatagt catcttgttg taggacaggg ctggtatcca caggcagtga tgcataggtt 7620
ttgcactgcg cggccatgtt caaaggcaag tgccttaaaa tgtatggtgt tctcagccac 7680
agtgccttag aagccatgtg ggattcagtg tgtctggtgg tcctctgagc tgcacctgtg 7740
aggaagacgc tgaggtagag gttaagttgt tattgaacgt ttttctcaat ctgaaaagtg 7800
ttcaagcagc ccagggtgaa aagtcttcaa gactgaagga aaattgcctt ttgtactgga 7860
agagtttttc cccaaaactc tcctcattta aatagccctg tggcttgtgt cttctctgat 7920
gaccaagagg agggcttttg agtcagtgat ggcaaatgag tggttttgag agagttctta 7980
cacttagggc tctgtagctt gatggtgcct tcaaaattaa cacgtgcctg ctatcttcat 8040
tcctgggtag acccatacac ccatcccaaa aggggagtag cctgtgggaa gcacatatgg 8100
gatataccac agtgagtcga gtggaatggc ccttttgaca tgtgtacctg cctcccgttc 8160
ttaagcacac ccgtttttcc tctgcacttc ccaggtgttg tggccatgga agtaaggcca 8220
gtggctacga gggacagtct tcatcttggg agatccctag agagggcagg gagccccttg 8280
acatgtggaa tgtgatctct gttgggtgct ggtggatccc acaggttggt aaatgtccat 8340
tttccaaaag cccctgatgt tccttctttg cagggataaa gactgtgcat ggatcgatga 8400

```
tgacctcaat acatgcattc cttggaaagc tgaacaaaat gagtgaaaac tctataccgt   8460

cgtcctcgtc aaactgaggt ccagcacgtg gctccaactg gagctggaga gagagagaca   8520

acttccattg gttgatgtgg gttgcactaa gccatccatc caggcttagg atggggtcca   8580

ctttggatca aagggagtca cagggcagta ggtgctcctg tgcagaggag attccttgtg   8640

tgaaggactt ctctttgtga ggctgggtag cacgcacaat gtctgcagga ctgggtgaat   8700

gtgcaggtgg cacagaagag ttagccggta acccgcctct gtgtggccag gtttgtcctt   8760

gagtgctggc tctgggttcc cttgttcccc agaggtagat agctccttgt ggttgggaag   8820

agagcccaag gccacatctt tgttgttctt tggctcattt tttttcatgg ctgaggactt   8880

tttagtgccc atggtgtttt cgtagcagca gtggaagtca gttgtgagga ggttggtgat   8940

gcttattttc tttctggaga gtaccctgta gatcggctcc atttatgatt tgtgtgtctc   9000

cagggagaaa ctgaaatccc atggctggtg atggatactc caggtgggaa tgagaaagcg   9060

ccatacatgt gttgacttgg taccctaaga tggggatggt ccgccacatt tgcgcgtctg   9120

ttttgcatgg tgtgtactgc acatcacaaa tgccatgttg gccttagggt gctgggaatg   9180

gaatatgatc tgatgtctac atgggagggc ctttcagcag attgcttttg tttcctgaca   9240

gtctttgctc catccccagt cacacgtgtt tttctccagg gaacatttta ttggagtata   9300

tcaggtcgat atcagaaaaa aaaatgttgt ggttatccca acattaagtg tggtgatgta   9360

acagcagtgt ggatggtagc tcaagtgaac agtggcaaaa ccaaaatata ttggtttacg   9420

taagtgaccc tattctctcc tatgtttgaa gtctggtatg catctctttc tgcaataatc   9480

tcagtgatct ggaaactttc aggaggtctt ttttagatat tttatgtcct tgtggttgta   9540

ctcatactcc ctgcagtgct aagtctgagt cattctgcta tcctagtgct actggaattt   9600

ctattgtttt gggggcactg tctggtcatt gtggatacct ctcttggggc cctttaataa   9660

gaagtatgtt agaggtcggt tttggggcag tgttgacctc ctgcctaagg tcaaaggcag   9720

ttttcttcct aaatcttatt gcaggattca ctgcctgggg gttgtgtgac agggagagca   9780

caaaattagg gtatcccatg tggacttgtg tccagtatca aggcagtgtt ggataatttt   9840

ctatatccac aaggctccca ctggactctt tatgtccagc agacattcac aggccaactt   9900

ttctcttaca cagggggcct cattcctgcc atgtgtagct tccatggaac catccttcag   9960

gttttaagtg caaggatttc tctcaagagt ttaatttgtt tctttaagac accgttttct  10020

tttctataaa ttctgctttc tgtggtttgt agcacagatg aaattgccag gtcatattct  10080

acatttctgc ccaatcttgg attagtgagc ctttgaaata tgttccttga tcactggcaa  10140

tggttcttgg aataccagaa cttagttaca agcattgcag acctacagag gtttgttgtt  10200

atttttaact gcatgaagca gtgggtttgt ttgtatcttg tcactcacgg ctgtcagcaa  10260

aacttaggtg ttgctaaacc agaccacacc catgaattat agtgcctctg gttccttctg  10320

tagtagcctg tgggaagtag atacaggatg caccacaagg gaatgaatgg catggccctt  10380

gagacctgtg tacctgcttg cctttctcaa gcacacctgt tttgcctcta attcctaggt  10440

ggtctggcat ggaagaaggc cagaggctgc gatggatcat ctttgtcttg ggagattcct  10500

ggagatggtg gggagcccct gggcacgtgc agcatatgtg gcgtgggctt cttcaggtgc  10560

tg                                                                10562
```

<210> SEQ ID NO 5
<211> LENGTH: 343
<212> TYPE: DNA

<213> ORGANISM: Homo sapiens

<400> SEQUENCE: 5

```
gtgcacattc aggttcccga gcacaaacat caagataacg ttcactgccc tgtccagcga     60

gaagagagag aagcaggagg cgtctgagtc tccagtgaag gccgtacagc cacacatctc    120

gcccctgacc atcaacattc cagacaccat ggcccacctc atcagccctc tgccctcccc    180

cacgggaacc atcagcgctg caaactcctg cccctccagc ccccggggag cggggtcttc    240

agggtacaag gtgggccgag tgatgccatc tgacctcaat ttaatggctg acaactcaca    300

gcctgaaaat gaaaaggaag cttcaggtgg agacagcccg aag                      343
```

<210> SEQ ID NO 6
<211> LENGTH: 490
<212> TYPE: DNA
<213> ORGANISM: Homo sapiens

<400> SEQUENCE: 6

```
gtgcacattc aggttcccga gcacaaacat caagataacg ttcactgccc tgtccagcga     60

gaagagagag aagcaggagg cgtctgagtc tccagtgaag gccgtacagc cacacatctc    120

gcccctgacc atcaacattc cagacaccat ggcccacctc atcagccctc tgccctcccc    180

cacgggaacc atcagcgctg caaactcctg cccctccagc ccccggggag cggggtcttc    240

agggtacaag gtgggccgag tgatgccatc tgacctcaat ttaatggctg acaactcaca    300

gcctgaaaat gaaaaggaag cttcaggtgg agacagcccg aaggatgatt caaagccgcc    360

ttactcctac gcgcagctga tagttcaggc gattacgatg gctcccgaca aacagctcac    420

cctgaacggg atttatacac acatcactaa aaattatccc tactacagga ctgcggacaa    480

gggctggcag                                                           490
```

<210> SEQ ID NO 7
<211> LENGTH: 655
<212> TYPE: DNA
<213> ORGANISM: Homo sapiens

<400> SEQUENCE: 7

```
tgacatgaag tccgagagga gaccccccctc acctgacgtg attgtgctct ccgacaacga     60

gcagccctcg agcccgagag tgaatgggct gaccacggtg gccttgaagg agactagcac    120

cgaggccctc atgaaaagca gtcctgaaga acgagaaagg atgatcaagc agctgaagga    180

agaattgagg ttagaagaag caaaactcgt gttgttgaaa aagttgcggc agagtcaaat    240

acaaaaggaa gccaccgccc agaagcccac aggttctgtt gggagcaccg tgaccacccc    300

tccccccgctt gttcggggca ctcagaacat tcctgctggc aagccatcac tccagacctc    360

ttcagctcgg atgcccggca gtgtcatacc cccgcccctg gtccgaggtg ggcagcaggc    420

gtcctcgaag ctggggccac aggcgagctc acaggtcgtc atgcccccac tcgtcagggg    480

ggctcagcaa atccacagca ttaggcaaca ttccagcaca gggccaccgc ccctcctcct    540

ggcccccccgg gcgtcggtgc ccagtgtgca gattcaggga cagaggatca tccagcaggg    600

cctcatccgc gtcgccaatg ttcccaacac cagcctgctc gtcaacatcc cacag         655
```

<210> SEQ ID NO 8
<211> LENGTH: 1429
<212> TYPE: DNA
<213> ORGANISM: Homo sapiens

<400> SEQUENCE: 8

```
tttgtacaat gacgacagaa acctgcttcg aattagagag aaggaaagac gcaaccagga     60
agcccaccaa gagaaagagg catttcctga aaagattccc ctttttggag agccctacaa    120
ggtatttact gaacactaga cattgaagtc ctgatttatc acaatgttga accctatgat    180
gaaacaattc agtataattg agttcgaaca agggtcacag ctgtgaaaat aagataactt    240
attctaactt attctagaga tttttgaaaa caaagtatga aaattctctg aaggttgtta    300
gaattaccaa agtttgtggt tttcttttgt aatgctagtc ttctacagtt agtaatatgt    360
atccatggta gtcttctcaa caggggaatt gagttaaaat ggcacattaa attctacatg    420
tcgtacatta agttcggagt tttttcctta atagtattat ataacgtggt ttgttaaatg    480
gtagttttcc ttagtttttt ttcattctca aattctcctt ttttttcaga cagcaaaagg    540
tgatgagctg tctagtcgaa tacagaacat gttgggaaac tacgaagaag tgaaggagtt    600
ccttagtact aagtctcaca ctcatcgcct ggatgcttct gaaaataggt tgggaaagcc    660
gaaatatcct ttaattcctg acaaagggag cagcattcca tccagctcct tccacactag    720
tgtccaccac cagtccattc acactcctgc gtctggacca ctttctgttg gcaacattag    780
ccacaatcca aagatggcgc agccaagaac tgaaccaatg ccaagtctcc atgccaaaag    840
ctgcggccca ccggacagcc agcacctgac ccaggatcgc cttggtcagg aggggttcgg    900
ctctagtcat cacaagaaag gtgaccgaag agctgacgga gaccactgtg cttcggtgac    960
agattcggct ccagagaggg agctttctcc cttaatctct ttgccttccc cagttccccc   1020
tttgtcacct atacattcca accagcaaac tcttccccgg acgcaaggaa gcagcaaggt   1080
tcatggcagc agcaataaca gtaaaggcta ttgcccagcc aaatctccca aggacctagc   1140
agtgaaagtc catgataaag agacccctca agacagtttg gtggcccctg cccagccgcc   1200
ttctcagaca tttccacctc cctccctccc ctcaaaaagt gttgcaatgc agcagaagcc   1260
cacggcttat gtccggccca tggatggtca agatcaggcc cctagtgaat cccctgaact   1320
gaaaccactg ccggaggact atcgacagca gacctttgaa aaaacagact tgaaagtgcc   1380
tgccaaagcc aagctcacca aactgaagat gccttctcag tcagttgag                1429
```

<210> SEQ ID NO 9
<211> LENGTH: 22406
<212> TYPE: DNA
<213> ORGANISM: Homo sapiens

<400> SEQUENCE: 9

```
tggttgcagg ttgtgaggta tggagatact gaggggtacg aggcactgtt tgtggtgaca     60
tgagagccac tagcggacag agactgggga gaaggattga tcagctggcg cattagcccc    120
aagatgcagg tgaatttggg aacagaaaga gggccaaatg agatgtttgt gaaaatactt    180
tgtcgattta aaacattcct tccagctcag gtgctgttat gtttagggaa gatgtgcgtg    240
ttttctcttt ctagtgggct attgttagct acaaggtgac cttgcctcct gctttgaggg    300
agaaggaaaa agctggaccc acaagacaca aatcccagca gtctgtggtt actgctggaa    360
tgattactgt tctttatttg tactattagt tgtctctaag attggtaaca ggaaagtgag    420
aataagctta ctctcagaaa tttttgttga gggagttttg tataatttct gactattacc    480
acattcccct ttacttcgac cctcttggtt ttgctgtttg ctgtgctcta gttttaccat    540
ctaataaccc agcactaaaa tctgatcttg ggtatcagat tctcctttgt ggtttggttt    600
gttaataatt gaagtaccta atggttctgg gtgtgaactg tgcatacttg acaatctaga    660
```

-continued

```
accagggaag tgagtttcct attgaagtaa ttaataaaac cttgtggctc ttaaaaatat    720
ataaaaactg ttacacagaa ataaccaaaa tgtaaactta acaggatata gtttaattat    780
gtttttataa cataaacctt aaagatagaa gtatttttaa gcttgttggt gtcctgttcc    840
tttctagttt gggtgtgtag gagtcttttt tatcaggaat tttgttagtg ctaatgctgg    900
ggtggctttt ttttttaaa tctatgtaaa catgacccta ttagacagct gtgtttaatg    960
tagtaaagac tcatggggag actttatagt gtttcttgtt gggacttagt gtctgtatat   1020
tttagtattt aaaggatgtg gtttggtgct ttgaaaatga gagggaggtc acctaactca   1080
tagctgaatg cctgcgtgtc tagattgttc cgtcctggag gttattaaca acatgaaagt   1140
tgtttttatt ctagttaaac tgatagtatt aagttaaata actttattgt ggaagtgttt   1200
gtttacacat ggctgctgag tagaattttc cttaaaatct gattacatag gaatgtttta   1260
gtaaatagag tgctggaaaa aagctgctac acaagccaga gcctgttgtg ctttgcagaa   1320
cagtaaccaa gatgaagagt ggcctctttt tctccacctt ttccaccgct catctcagag   1380
aaagcagggc gctaatcagg tggagctgct taattgcatt aagttcatgg gctgctcaag   1440
ggttgattag tcagactcat aaacttccag ttatgagatg cttgctgact ggctggttta   1500
agtccttagg gtttgatgca cattcactct aatgagtact tacatgtaca gggcactgtg   1560
ctgtgtgccc tgtgatggac acagaaaaga ataagattac ttctatcttg aagacagggt   1620
agaacctggg aagtgtccca gggtagaaac tgggaaggca cagttctggg aattcaacgg   1680
aggcatgtag ttagtagcca ttgggtaata ttgatggggt gggggtgggg cagtagatgt   1740
gatctgggca acgaggagcc agttggagaa gtggtttcag tagttgcagt gggtaaagca   1800
tgataaagat gctcacaaag cagagaggaa aagtaaaatt gacaggatca ggccactgtg   1860
aacatgaagg gcaagttaga ggaactcagg cggaagctct tcatcaggag ccctggagct   1920
ttccccaaaa tcctaccaaa atcacttatg tatgtgcttt ggtatttttg ggtggcagag   1980
aacttagacc ttttctcaca tgttcggaag ggtccagcat ccaaaaaaga ttgaccactg   2040
ctgcgctgag ttttcatcca ttggtgacaa gatggtcaga cttctagaga aataaggtag   2100
ttttgtggta gaacaaactc ttccttgtgg gaggtatagt gggatttggg gaatagggtt   2160
tatgaaatgg tccccagagt gggatggctt gccttttcaa actgggtttc ccacccagca   2220
agttaagttg acccattgca gtggattgag tggagggcag gtgaagggca ggtgttttca   2280
agtcaaagga gttcaggtga agggcaggtg cttttagtca aaggagttcc ttagcattat   2340
ttcctccttt atttggagat cagattgaag atgtagggga ctagaatgca gttgtagttt   2400
gtggtgttta ctttttatgg aaaagtgcct cttatgtgaa aagtcttctg tgcttgatcc   2460
tgggggtagg ggggttataa aaatgtcata cctgggatcc tgcccttaag gagttgatgg   2520
taggtaatgc tttcctttgg ctttttgttc atcttgagtc tgtgtatgtt cagttatctt   2580
cagccatttc ctgggcaatg ggaaacattt ctgttaaaac aaacttctga ctttgatctg   2640
tgacttatat ttctttttag ataatgaaga accactggga ttagagggtg tataaaatac   2700
aataataagt atagtgtatg taggaacctc tgtacaacca atttggtgac ttttaggcaa   2760
ctcatttgac tatttgactg tttgttacat gagtgtgcat ttggctttgt ttaaaattcc   2820
tctataaagc acattttaaa aaatgaccca gtacttagta tataagatga actgccattt   2880
gtataattga tcatttaaaa atgcttatta tacttttaat caatcagttt ccatgtttat   2940
gaaatgggaa taattattat atctagctca tagaattgtc ctgaagatga aatttatatc   3000
catatataca taatgaagct ctttagagca atgtataact acatgccaac tgttcaaaaa   3060
```

-continued

```
atattaatgg ctacatcact attaatattt taaaattagt actgtcattt tcccttccta   3120
catgactgaa tgtaggaggt gactattttt gttataaaag gatttccaat gagatacctt   3180
tgaatggtaa aatttcctat gcatttattt aaatgtttat atatatatgt ctttaaagta   3240
tgaaagttaa gtgcacttat acaaggcaga ttcaggtact aattaaactg ctcatttaga   3300
ttacagaatg agggactgaa aattatatgt atttaattag gaattggatt gattggtctt   3360
gactgctgtt gtctttcagt tctttttat tgttatactt cccatgtgtt tgtctccttt   3420
tctttttatc ttttaaaaat tgctttctga tttatttcct gttcagtttt cagtaatggg   3480
tgtagaatag ggcaagaact tatgttggtg cccgttgttt gaaccaggaa ggagcaactg   3540
catcagacag cctggggctc agttgggagg gacttcagat cagtccctgc agagctgcct   3600
ggcccaggga accactgaat tccagtttcc taactccaaa tcggacagtt tgtgggtcta   3660
cactgtatgt acataatgaa cattttaagg ctcattcatc cagtgttttc cacatgctcc   3720
catttgttta gttctccttt ttaaaaacca ataattatgg aaaaatttag ctatgtacag   3780
aaatagtagt gagaaacccc ccacttagcc atcatgcagc ttcagcagtt gatcatctca   3840
tagccagtct tgtttgctca atactcccaa ccatttcttt tctcccattt tattttgcag   3900
gaaatcccag acattatatc atttaatcta aaagtatttc aggatgtatc tgtaagagat   3960
gaggactcaa aaatgcatac acacattttg agaacttccc agaaatgtaa aaaaaaaaaa   4020
tgctatacac atatagaata tatacatgca cgcacacaca cacacacaca cacacacata   4080
tatactattt tatggtctgt ctgactcaga atcctatgtg gtgtgtttgg ttggtaggtc   4140
tcttcactct ttttttattt ttattttttt tttttttttg agacagtctc actctgtcgc   4200
ccaggctaga gtgcaatgac actatcttgg ctcactgcaa cctccacctc ctggactcga   4260
gatcctcttg ccttagcctc ctgagtagct gggaccacag atgtccacca ctgtgcctgg   4320
ctaatttttg tatttttagt agagacaggg tctcaccatg ttgcccaggc tggtctctaa   4380
ctcctgaact caagggattc actcacctta gcctcccaaa gtgctgggat tacaggcatg   4440
agccactgca cctggtccat gcttatggtt atattttaat gctattttct tctattctct   4500
agcatttctc attctatgga acaatttttt gtaaataaat ccgttataaa ttgacaccac   4560
aacagtatat ctgtgcatgt tctcttccat gtgttctgta tagttgtacc agccttactc   4620
tttgataatg tcatcgtcct caggcctccg ctcaagacta tcatattcaa tttttgaagt   4680
ctctttttgc caaaaataaa acttgaatgt ttctaatgat ggctgctttt attgctaagt   4740
tgatttcaat acattagaaa attacagatt tggaaatgaa aagactaagg aattgatgca   4800
tctctctcaa atgtgccttg agggcagaaa ttcctcagtt ttgttcatgc tgaagccgca   4860
ggctagcaca atatccgaca cttagaggga agttaaatat ttgataaaca aatgaattta   4920
attttaagta aggtgtcaaa cttgaggcat ccagaattga acctgaagcc acagttctgc   4980
ctcctttcac agtcacacat cttatactcc acttaccact tgaagataag cttgctgagg   5040
agtaccctgc catgggccct tcagaatctc ctttcctcat tgcatagtgt agtggtaaga   5100
gcgtaggctt tgactcctga ccgcacacat attgagctct atgatatgct tcctgtgcga   5160
acttagcaag tttcttaact tgcctctgat tcagtttctc catctacaat tggagataag   5220
agtatgtact tctttttttt tttttttttt tgagatggag tctcgctctg tcgcccaggc   5280
tggagtgcag tggcacgatc tcagctcact gcaacctctg cctcccggat tcaagcaatt   5340
ctcctgcctc agtctcctgg gtagctggga ctacaggcac gtgccaccac acccagctaa   5400
```

-continued

```
tttttgtat ttttagtaga gacggggttt cactgtgtta gccaggatgg tctcgatctc   5460
ctgaccccat gatctgcccg cctcggcctc ccaaagtgtt aggattacag gcatgagcca   5520
ctgcggccag cgagtatgga cttcttttat gggtattgtg accttgatct ttgtaagttc   5580
cttaagccat ctctgattca gtttcttcat ctacagttgt agataagagt atgtacttct   5640
tggggtttta tgggtatttt gagcttaaaa cagtacctgg cacatagtaa acattgtaga   5700
ggtattagag ctgttattat tctagaataa aaacaagtta ttctcctctt actcattttt   5760
accttttatc tctagctcta ccttggtttc ttttcttagg cctaaaaaca ggccaggcgt   5820
ggtgcctcac gcctgtaatc ccagcacttt gggaggccaa ggtgggtgca tcacaaggtc   5880
aggagatcga gaccatcctg gctaacacgg tgaaacccca tctactaaaa atacaaaaaa   5940
ttagctgggc atggtggcag gcgcctctag tcccagctac tcgggaggct gaggcaggag   6000
aatggcgtga atctgggagg cggagcttgc agtgagctga gattgcgcca ctgcactcca   6060
gcctgggcga cagagcgaga ctccatctca aaaacaaaaa aaaacaaaaa aaaaaaagcc   6120
aaaaaaaacc ccccaaaaaa accagttctc taagatacaa aatccttgcc ataaaacttg   6180
cacgcttgtc ttgctggtag cagtgaaaat tagcattatc cctttggaga gtggttgggc   6240
aagatatatc cagttgtgaa aatacactct gactcaataa tttcactttt ggaaatattt   6300
tctaaggaca taccettaaa tgcataggag acagtattca tgaaaatgtt acaatgtcca   6360
ggtttagagg gaatggttaa atatattctg gtacttacac atttacaata ttggttttga   6420
agactatgta atatggaaaa tgtctccctg tgataaaaag tacattgtat gtacaatatg   6480
atcataacca tattaagtaa tatatactga cattcaggaa tttccctagg gtaggacttg   6540
taactgctcc tttaatcacc tgcccccccc cccaatcctg gatctatgct aacctggttc   6600
caaaggccca aattttacct tgaaactagg tgctctgtat cctttgtcga agccattatc   6660
ctttttatat ggctttagga attccaagtt ttgtcagatt cttgcagaat aatacacaac   6720
aatgaagatt ccctctgtgt acttaaggaa tagttgtgtt tggaggataa gacaaataca   6780
ccagataaca ttacagtttg ggctcttggt gcccaatgat tgatttatct atagtataga   6840
tttatttctc acagtacctc ttggaatgct catttttaac cccaatagtt aaatttgcct   6900
tggtaagcta caaaaacagg caccaaagca gcaatgtttt ttagttttct gttgaccata   6960
aatctcgttt ctttacaagt agtaattcta aacagagtat accttaacca gccagtgcac   7020
atactgctac ttcagtcttg gttcagcaga tcttagaggc atgtggtaga aggaagaata   7080
gttactcaac aggtgagcag gcaggacagt ggttttggct ttctttggta aacactatgg   7140
ggcctatttc tgaagtaatt ccccaccccc ttcactccca ctcagtattg ctgacagaag   7200
tcttaacttg ccaagtcttt tgtctacatt gatgctataa gcaaactatt atttttagag   7260
accaggtctt gctgtgttgc tcaggctgga ctcaaacaac tgggcttgta gctacccttc   7320
cacctcagcc tcccaagttg ctgggagtac gggggtgtgc cactgtgcct ggcttgcaag   7380
caaactcttt tgcttggtgc actaatactt gttatcctga atttttacca acgtttgctt   7440
gcttttgaga ccaggtctct ctgtttcgcc ctagctggag tgcagtggca tgatcatagc   7500
tcactgcaac ctctaactcc tgggctcagg caatcccatg gtcacctccc aaataggact   7560
acaaatacag gccatcatgc ttggcttttt tttttttttt gaatgggggt ggtacatagg   7620
gaacctccct gtattgctca gtctgatctc gaacttttgt gctcaagtga tcctcctgcc   7680
ttggtatccc aaagtgctgg gattacacat gtgagccacc atgcctggct ggctcgtaat   7740
ttttatttta gcctcttttt ttctttccct ggggtcaagc cattttaaaa ttcagttacg   7800
```

-continued

```
tataactgtg ttaatgggcc agcctgtgcc caggtggcat gtgttaggta cttggcctaa   7860
gatcattgtc cagccaggga tttgtgtgtg tggtggcaga tgtgtgcggt gtcaggttgc   7920
atttatactc tagaattagt agctgtactc ttatttttca tatcaaatgt tatttgacac   7980
ataatggatt tttgaactgg attcaaggct agccttggaa tcttgaatat tatcccttaa   8040
gagagagcct tttgtttgag ttacattttg gtcaaatagg gcacatatta aagcactgat   8100
caactctttg aaagtactgc aagtgatgtc agaaattgct attgccttaa aaatattttt   8160
aaaaaattta tgtttacata aaaatacatg ttaaagaaaa aactgatact tgttaaaggt   8220
gggcaaaaaa gactattcag gaccatcgcg ataagtatag ggatcactgc agcggggtct   8280
tgcagcaaag gaaagaggtt gggctcaact ccaaatacat catgggcaag gagcaggata   8340
ggggtcagtt gaaggtaaac tactaagagg aaacatttgg agtaaggggg attctggcta   8400
aacccatcta acaggattct tgctgaagac aagccagggt gatcagacat cacctggggg   8460
atggtggaaa atgaagaacc tgatcagata ttgaagatgg gagggggtct tttgctaaaa   8520
ctggattttg tgagaaagtg cacagatggg cctagaagaa agtttagaat ccttactcaa   8580
gtttggccaa gcaaaggatc tttgtcatat ggaaaaatga ttggtttcaa agtaaaagca   8640
agcatcagcc cactcaagga agtagtggtt tgctatgcaa agggatagga gttttatttt   8700
ccttcagttt ctgtaaaaaa tattagaata ggtaaaatat gcaagagagt tgttaatagg   8760
aactccgaat atctgaaaat ccttggaaat taaatttttcc tggtaatgct caatgtattt   8820
ttcaaaatgt attaattttt ttggacttta actttttatg aggtttcatc tgcattttgt   8880
tgttcattct agtggcattt accactggta ggcttttcat ttgcctgctt agcagtaaat   8940
gtgatatgct ggagttttgt gggtgtttgg cattatgtca taggagcaat aggaaatgac   9000
tacggattaa cttaaacatc attaagttta acaaaatgga atgctttatt ttgtctctat   9060
cctgaagtgt tatttaataa ttcacaacag cttaagcaga agttctttcc tccaggccct   9120
tctcttccct ccctactcca acaaaagtgg gctggggaac tgtgtaaatt tgcataatat   9180
tactaattca ctattttgta atactgtcaa actattaggt gttgcattta ttgcgagcac   9240
aaaagaaaac caaagtgtag tggctgtcat tcccaacttg tcaatattcc tttttaatat   9300
gttctggata ctttgttgtc ccatcaaact tatcatagac ctttctctac cttctggaag   9360
ttagcttcat ttggtcaata ttatagataa ctttgaagca ggtaggtgct gtatttaaat   9420
cccattgtga attctaagat ggaagccgtg agcagttttt gaaaaccata catgtgtttc   9480
caaaggccat tctattactc agtatccatt aacagacaat aaaggacttt tctgtcgttc   9540
gccactaacc ctaaccaccc agtcctcata aggcaaaatt aagaagttac atgaattgat   9600
tttagagaat attccctaaa aataaaaggg agtggactgc ctccccgaaa aagtcatccc   9660
ccaatatttt gaaagttaat ttgagaaata ctgcattttc tgaccgatag ggttattttt   9720
tctccctttt ttccttttt aaaaaaggca tgctgtggga gttggatgca ttttttctgt   9780
cagtgcttag agacatggag ggggaagtct tttcttgtgc ctctgcctat attcacaccc   9840
tcctggtctt ggcatttttt ccaatttaat agccattgaa acagcctttt atatgctttt   9900
agattagtat ggtttatgtg atctgtctgc cataatgcat cacagctctg tgtagtagtt   9960
ttatgtggca cttattaaaa actgacctag tttgaaagat aaaagctctt ggaatagatg  10020
ctgtcagaat tatttaattt tatttgcgtc ataatttatc gtaggttttc gatatatcat  10080
ccttcatagt ggggaaagta tagatccagg agactgtatt tcctatctaa ttctaatctt  10140
```

-continued

```
aattttacca ctgtctagct gtggggcttc agaagtcact ttatttgtgc ttcctcattt  10200
gtaaaaacaa ggatttcatt atatatatct gcagcacttt gctgaagttg ctaatcattt  10260
gtacaatggt ccagtgaaga aggctgtcat aagatggtct ctggaagctt ttacagtttt  10320
taagacacaa atgatgaatt ttcttactgt atactttttt cctctctaaa ggtattatat  10380
aatgagaagg ggcctttgta tactattcta tttttattcc tccgattttt tttttttttt  10440
ttttggtctc ccaagacgga gtcttgctct gtcgcccaga actagagtgc agtgacgtgg  10500
cctcagctca ctgcaacctc tgcctcccgc attcagcaat tctcctgcct tagcctcctg  10560
agtagctggg attacaggcg catgccacca cacccggcta atttttatat ttttagtaga  10620
gatggtgttt catcatgttg gccaggctgg tctcgaactc ctgacctcgt gatctgcctg  10680
cctcggcctc ccaaagtgct gggattacta gcgtgagcca tgcccccagc cattattcct  10740
ccgattttta taaataaaga gtggctctta tgctaataag tgactccttt ttggaattag  10800
cattcctgtg cctttactga agcagaaaga aacatgaact gtcgtatctt ctaacttgtt  10860
ttgataagca aggctgaaga ctagcaagtt agaaaactgg catctgcctt tgatattgtg  10920
gcttcctatt agcactaaga gaaatatcgt cctttctcct tttctgacca cgtattgtca  10980
ttcgattctt catcaggttt acccctctgt ggacaagagt tagtatgact ctttaggtgt  11040
taggatttat ccaagtacat tttttaaaaa ggaaagttta gttgtctttt atggcttcat  11100
tttggggagt gtatactgtc tttaggtgag agttttcttt tctttacttt tttaagctga  11160
acttagagtc taaaaggaat actggaatta ttgaatgcag gatttgggcc tttactggaa  11220
taaagttgct caaattatac ctggttcact attctatctc cccatagacc tggaaaggat  11280
ttaagctgac aggtatgttg agactgtcct tcatagccaa gcttagtgag agagtcgctg  11340
tagttggtgc tcaccctctc accttctagt cacccctcca tcatgaactt ttgacttctt  11400
gtccactgta cttcctcaca gcagggtcac caggggtctt tatcaccaag tgggcacaat  11460
tctttatttg accttgctgc tgactgtgcc ttccttttac agactttttt tttttcctga  11520
ttatgaaagt aatacatggt cattgtgaaa aattttggaa aaagagttgt tatctctatc  11580
cagaaaactt tctcctcatt gaaatgtttc tgtgacaact gtcttcttcc tttcctcctg  11640
tttctcttga ccagacctga gtcatttcgc ctcctggata tctctgtctt gtaggcactc  11700
aagcccaatg ttaattttg tgtatgtgta tttttttttt ttttttttact ttaagttctg  11760
ggatacatgt gcagaatttg caggtttgtt acacaggtat acacgtgcca tggtggtttg  11820
ctgcatctat caacctgtca tctaggtttt aagccctgca tgcattaggt atttgtccta  11880
atgctctccc tccccttgtc ctccaccccc accacccacc aacatcccca gtgtgtgatg  11940
ttcccctccc tgtatccatg tgttctcatt gttcaactcc cacagtgaga acatgcggtg  12000
tttggttttc tgttcctgtg ttagtttgct ctccccatgg gctctcacag caccctgtgc  12060
tatccttctg acacgtataa catttgttgt aattgtctgt ttgcttttct gtctcaaggg  12120
cagcaacgat gttttactca tatttatacc agtgtctagc ccagagcggc taggacattt  12180
ctgataataa acgggtaggg ctgggtgtgg tgactcactc ctgtaatccc aatactttgg  12240
gaggccaagg tgggaggctt acctgagtcc aggagttcag gatgatgatg gggtcaaatg  12300
atgaccccaa catttattaa agtgaattta cctctgcctc ccctgctcca agtatgctca  12360
gccacctgtt gccatctcac tgggaggcat cactcttcat gtagttgctg aagccataga  12420
tgaggaccca tccttgactc ctctccctca tcctccattt tcagtcagta gttagaaacc  12480
ttcttgttat tcctgtgaac ccatttactt gtcatctctc tactcttagc accttaactt  12540
```

```
agactctctt tatttcccac ctacctgaat ttcctaaaag catcatccac ttttgaaggc  12600
ttaggacttt gcgtatcttc cctcagggct tagcttagaa aatcaggact tctctgacct  12660
gttcctatac cctcaggtga gcttggtgct gatgtcccct tctccctctt catccatacc  12720
tcttccttct tctccccgtc tccccatggg ctctcacagc accctgtgct atccttctga  12780
cacatataac atttgttgta attgtttgct tttctgtctc aagggcagca actatgtttt  12840
actcatattt ataccagtgt ctagcccaga gcggttagga catttctgat aataaacagg  12900
tagggctggg tgtggtggct cactcctgta atcccaatac tttgggaggc caaggtggga  12960
ggcttacctg agcccaggag ttcaggacca gcctgggcaa cttagtgaga ccctgtctct  13020
acaaaaaatt tttaaaaaga ttagctggcc attgtggcat gtgcttgtgg ttgcagctac  13080
ttgggaagct gaggtaggag gattgcttga gcctgggagg ttgaggctgc agtgagccaa  13140
gatcacgcca ctcactgtag cctgggtgac agaggaaggc cctgcctcag aaagaacgaa  13200
attaaataaa taaaaaatga gtagaaggaa atgaacattt gtaggttgga ggttagtata  13260
aaaaatctga tgctacatgt tttatggtct tggtcttggc tgccttcaaa ttgtatctta  13320
atataattgg ctttcactac ctagtctagt agtcatggtt ctgtgaacaa gctttcaaag  13380
tgtgaagtat ggtagagcaa agcaggagta aagctgtcag gttggctgga atgggcctca  13440
gcactttgct tgtattgata gaggttaggt tttccaataa ctgatgacag tgtagcagag  13500
atgactaggg cagttgtgct agggataaag agtggcacag tttagtgact tggcgatgag  13560
atgtggggat cagaaaggag gaatctaagt gactcaagct tctggcttaa tggactaggt  13620
atacttgagg ctatcattaa ctagtagtgt tgattttgag attctttttg atatccaggt  13680
gagtatgtct accaggctgt gggatatgaa gttggggaga gtgtgtcact ggaaatgttt  13740
gagttaaaac tacaagaaat cacttagata tatagcttaa gaagagtagt ggtctagaaa  13800
cagaaagaac tctgaagaac actgatgttt aggggctggg gaagaagaga gctgggaagt  13860
ctatgtcaaa gaaactgagg agctggtggt tgaagaggga atttggcaat aaaaaggcca  13920
tttgaccttc agctctagaa gccaggaaat taagagaaaa aaggccgttg agtttattgt  13980
gttttaaaaa gaaaatatca agaaaacggg tgtgttttta cccagccctt agatgagatg  14040
cttcagtatg gactgtctgc ttggcatttt gttgggcagt tccaccttac ccgttagtag  14100
cccagcaccc cagtccacat ccagaatcct actcttacat tagatctaac acatgacctc  14160
taaagtccct tccaatttca acctaacatt aaaaacagat tctgggccca gtctgagaaa  14220
ttgtgattca gcgggcctag gggatcttaa tttcttctaa gggcctttct gagaatctga  14280
agaacattga tgtgtaggtg ctataaacct gcattttact ttattgcaag agagcaggac  14340
tttattatag caacagttta aaatacaatt gtgatgaaga ggttggcaac catggaaacc  14400
tagctggagc tttaccccac ccatgcctgc ctttgtgtgt gggggtgact tgggggtggg  14460
aaagtgccac catctgttgt aatctgttgg agatttaaag tttttgcttt atggattttt  14520
gcagcagatg ccctttgctc cctgcattat atcctctcag gccatcactg gtttcaaaca  14580
aaacttagat ttttgtagtt tctctgtgtc ttgccaacag ctttctattt tctgcctcag  14640
ggctctcaaa cccagcaaat gatggggaaa ggctaacctc aggcaacctt caaccagtga  14700
gggattggag ctggtgccta aatgtcctgc ttctttcagg ggtctcacag aatcacccca  14760
ctttgcagca gtcaccctgt gtgtccttac tggctatttt ccttccctca cgtctgttcc  14820
ctgggatcac ctcctatttt aatcttgcta aaatcttgca cacaaagtgt tagttgagct  14880
```

-continued

```
gactttaaag ctggaatgca aataaaagcc ttctgtaatt acattagttt ctttttaatg  14940
tccctctcta tcaataatag cacctaaaat aatatatggg ggaagaagtc aaagagaaca  15000
tattgtgcaa tgcacaatgg cgcacatatt gctaaagttt aaatttattc atagatactg  15060
tgtaatgaga tcattatgtg agaatttatt gggtttttca acacttccat ttctttcatt  15120
taggaatggg gttgaacgga tatgaaaatg tagaaaatag ttggcacaga gagcactagg  15180
tgtgcctctt ttattcattt atatgtcatc cgttcttgaa ttctgggtag ctctatttgt  15240
aagactatac agtataatga tagaaagcta ttaaaaatgt cacagtgcag aaagggggaa  15300
gatctctaca gatgattagg ctataaattg ccaaagatca gaaagaccct gataagatct  15360
gtttcaaagg ttttgtttgg ttggttggtt gggtttgttt ggttgggttt ttttgttgtt  15420
gttgtttttg gagacagggt cttgctgtgt tgcccaggct agagtatagc agtgtgatca  15480
tagcttactg taaccttaaa ctcttgggct caatagatcc ttctgcctca accaccccat  15540
tagctgagac tacaggcacg tgccgtcaca cctggctaat taaaaaaaaa ttttttttag  15600
agatgaggtc ttgccgcgtt gcccaggctt tcctagttga agcatacatc ttggacagct  15660
cagtgtattc atcctcgttt gctccacatt tactgagtgc ctgccatatg gcagcctcta  15720
tggtaactgt tttcagatac cagttttaat cactaggaat aaacttggtc ccaaactcct  15780
ggcctcaaag ggtcctccca cctatgcctc ccaaagcact gggattatag gtgtgagcca  15840
ccatgcctgg ctcctatttc aggggtaact tttaaaaaac actttgtatg ctttaaatgc  15900
aaaatttctc tttatctggc tagaagatat caatatccat aattctttta tctgagacta  15960
gaatgtagga tttaaaagtt gaaggtgaaa ggtaaacttg ttccagacga tcactttcat  16020
tcttggtgat taaaactgat aacctgaaat cagttaccac agaggctgcc atatggcagg  16080
tacccagtaa atgtggagca aaggaggatg aatatactga gctgtctgag atgtatgtgt  16140
tcagctgctg tcccagtgag caagagtagg tgaaacttca cgtgcttaga cctgtaggta  16200
ctattgcctc actcccacca aactgggact gcagatcttt agtttctagg tttattttgc  16260
aggagtccag ccatccctag aaaacactct ttcctcaatc cagggtgttt tgtgtagcag  16320
tgggctgttt tatgtaaatt gtacattgac aagttcatta ggttatctag tatttcagcc  16380
cctcagttaa catttcagct gagaccgaga gaggaagtga cttgcccaag gtaaaatcac  16440
catgtctaga taatcactga tatggcaggg actggaacac tagtctctgc atgtaatcat  16500
ctttttgtct cgtttctgaa atagctccca tctctacccc tggccaagga ccaaaacaag  16560
gcaccatctt tctgaactag tttaaaatgg ttttagaatt aataaggact gtagggtcta  16620
tatttaagat ggttacagga aattcgacag ttaaatgttt ctacacatag attatttaga  16680
aaatcaagac taatagatgg gcaaagtaca caggaagcaa atgaaaaatt gtaaacatct  16740
aaatattcag tattcagtgg tatgggaata gtttaggaag caataatttt cttttttttt  16800
tttttttttg agacaaagtc tcgctctgtt gcccaggttg gagggcagtg gtgtgtgcga  16860
tcttggctgc agcctctgcc cctaggttaa agcaattctt gtgcctcagc ctctcgagta  16920
gctgggatta caggcacgcc ccactacgcc cggctgattt ttgtactttt agtaaagaca  16980
gggttttccc atgttggccg ggctggtctt caactcctgt ccccacgtga tacgcctgcc  17040
ttgtcctccc aaagtgctgg gattacagac gtcagtcacc atgcccggcc aggaagcaat  17100
aattttgatg ggctgtttgc aactaataaa atgcgaattg tgatgattta gaaagggtgt  17160
ttaaaaatct agtagggatc ttggaggagt tctttttata ctttcctttc ttctgtacta  17220
tgcctaatac ttagttgttt tcaggaagtt cagatttttt tttaatttaa aaggttaaag  17280
```

```
tttaccaaat gttaactgaa gtcagtttct gaagttcttc agtcaaaacc aatttatttt  17340
ctgtaaaaaa aaaaaaaaag tactacacac catataaact ggtagctgtt tgttattctt  17400
gatatgtgca gtaaaaacta tcatgagaga gttggtaaag atttaatgaa ctggtagaac  17460
atgtttttct tagttgctaa gaaccatctg agcttaaatt taaaaacatt tttttctaaa  17520
aacaaaattg gtttctgaat caaatgtgta tttctttcct ataggggctt tgttatgcac  17580
ctaaagccat attggaagct ccagaagaaa gagcaccccc cggaagtcag cagggaaacg  17640
cagagaactc ctatgaacca ccaaaaggct gtaaatgatg aaacatgcaa agctagccac  17700
ataacatcaa gtgtctttcc ttcagcctct ctcggtaaag catcatctcg aaagccattt  17760
gggatccttt ctccaaatgt tctgtgcagt atgagtggga agagtcctgt agagagcagc  17820
ttgaatgtta aaaccaaaaa gaatgcacca tctgcaacga tccaccaggg cgaagaagaa  17880
ggaccacttg atatctgggc tgttgtgaaa cctggaaata ccaaggaaaa aattgcattc  17940
tttgcatccc accagtgtag taacaggata ggatctatga aataaaaaag ttcctgggat  18000
attgatggga gagctactaa gagaaggaaa aaatcagggg atcttaaaaa agccaaggta  18060
caggtggaaa ggatgaggga ggttaacagc aggtgctacc aacctgagcc ttttgcatgt  18120
ggcattgagc actgttctgt gcactatgtg agtgacagtg gggatggagt ctatgctggg  18180
aggcctctgt cagttataca gatggttgcc ttcttggagc aaagagccag tgctctgcta  18240
gctagctgtt caaaaaactg cacaaactca cctgcaattg tgaggttttc tggccaatcc  18300
agaggtgtgc ctgcagtgtc tgagtcctat tctgccccag gagcttgtga agaacccaca  18360
gaaaggggaa atcttgaggt tggtgaacca cagagcgaac cagtccgtgt ccttgacatg  18420
gtagccaagt tggagtctga gtgcctgaag cggcagggcc agcgtgagcc tgggagcctc  18480
tcaaggaata acagcttccg tcgaaatgtg ggcagagtat tgcttgcaaa tagcactcag  18540
gctgatgaag gcaaaacaaa gaaaggcgtc ttggaggcac ctgacactca ggtgaatcct  18600
gtggggtctg tatctgtgga ttgtggccct tcaagagctg atcgttgttc tcctaaggag  18660
gaccaggcct gggacggtgc ttctcaggac tgccccccat tgccagcagg agtgagtttc  18720
cacatagaca gtgcagagtt agagccgggt tcgcaaactg ccgtgaaaaa cagcaacaga  18780
tatgatgtgg aaatgacaga tgaactcgtt gggttacctt tttcctctca tacctattcc  18840
caagcctctg aattgcccac agatgctgtt gattgtatga gcagagagct tgtgtccctt  18900
actagccgaa atcctgatca aagaaaagaa tctttgtgca ttagtatcac tgtgtccaag  18960
gtagacaaag accagccttc cattttaaac tcctgtgaag acccagttcc agggatgttg  19020
tttttttgc cacctggtca gcacttgtca gactattccc agttgaatga aagcacaaca  19080
aaagagtctt cagaggccag ccagcttgaa gatgctgctg ggggtgacag tgcatctgag  19140
gaaaaaagtg ggtctgctga gccatttgta ctgccagcct cttctgtgga aagtacatta  19200
ccagtgcttg aggcatccag ttggaagaag caggtgtcgc atgacttcct ggagaccagg  19260
tttaaaatcc agcagctttt ggagcctcag cagtacatgg cttttctgcc ccaccacatt  19320
atggtaaaaa tcttcaggtt acttcccacc aagagtttag tggcccttaa atgtacctgc  19380
tgctatttca agtttatcat tgagtactac aatatcaggc cagcagattc tcgctgggtt  19440
cgagatccac gctatagaga ggatccttgc aaacagtgca agaaaaagta tgtgaaaggg  19500
gatgtgtccc tgtgccgatg gcaccccaag ccctattgcc aggcattgcc ctatgggcca  19560
gggtattgga tgtgctgcca ccggtctcag aaaggattcc ctggctgtaa gctggggctt  19620
```

catgacaatc actgggttcc tgcctgccac agctttaatc gggcaatcca taagaaagca 19680
aaagggactg aagctgaaga ggaatactaa agtccatgtg agaggcaaca aaaggaccgg 19740
tttctaaagc tgcaaaacac ctagatacac cgttcaaatg agcgtagccc cctgagtcat 19800
cactctagaa gaatctgtac atcatcagga ctgcattgct caggcatttt ctaaactcta 19860
aatttacgag ctgtacaaaa aaattggtct tgttgtttat agtggcatct catgtttgaa 19920
cccgggtggt atcccacagt tggattcagt tggctgtgaa taactgcctg ttttcctaaa 19980
tcaaacccat cctcaaagga tgaagactca ccaccatcca ggacattcag aagagttcac 20040
tgcagatgct gcaggtagtc ctcaaaaatg ggttccagaa atgttttgag cactggcaac 20100
atatttgaaa taagtgaata ttgtcctgtg aaaagaatag caggactttt agatgaaaag 20160
tattcttaaa aagaaaagtc aggcacccca ccttagacct cgtatgcttg atcctgtgag 20220
attgatgttt gtggctggag gtggatttca tgccctgtgg tgtttacagt gtatataatg 20280
gttgtgtttt catggggcta tgaaagtgca cgttaaacct gagcgccttt acctttagat 20340
gagtgctttg gcccctctgt gaatagcacg attaaaatcc agttgtatat aatggacagc 20400
taacggaaca atataatcac cacaatgcag ctaggatagt gttgcggcta taattttgtg 20460
ttttttttt ttaattgtct agtcttaaat ttgtacatct tgtataaaat atgaatgttt 20520
cccaaataaa ctatgaatgt ttcctgtata atatatgaat gtttctgaga agaaactcta 20580
aatagttgaa aggctaacct gctcaaagga taccaaataa tggtttaact ggacaacctg 20640
aaaattagca tagaaaacaa tcctttgtta tattttagtg atccacaaga ttgagaaaat 20700
attatatagt tagataataa cattcttgtc tactttatcc tgtctggtta caaaattttt 20760
taaaacttaa ataaaaacat gcatcttaaa tggaacccaa gttttgcaaa gatttttttct 20820
cctgttttga tacaatgttg aagaaggttc ttgtgaattg aatcataaga atttttttaaa 20880
ttgttttgaa ttgttggaga taaagtgttt ttttctgcca cggaagaggc catcttcact 20940
taacattgaa gtttaaattt ttgcaacctg tcagttcttc cgtttgttgt ctgttcacaa 21000
ccattgtatt tcctgttcga gtgacgtatt atctaggaga ttcttacagc ttatctaggc 21060
gtcatcattt gggagtcact aaggatctat tcaagcctgt agctgcttag tgcttggtgg 21120
ggttgggagg tgttggaccc cagaaagctg ctgtgggtgg aagatctaaa aactaggctg 21180
gcttgaaatc gagtacccac caaaaagcct tgagaccagt gtcggctgca ggctgtggag 21240
aaggatggta cgtgctctag gggaggcgct gtgctgggct gatgtgcttg gtgacatggt 21300
aggctgcagc ctccaggctc atcagatttg tctgtgacac gggatcaaga ggaggctgag 21360
aatagctttt ccttcaagag tgtttttcct tatgactcac ccaggtgagg catgttggaa 21420
aatgcttcta aatcctagct gtccccttgg ttgaggtttc cagtgtttgt cctactcccc 21480
ttgtatttgc tgtaaactgg ccatctcagt agtgccttct taattggttt gttatgattc 21540
ataatttagg tttaaaggag atcaacataa aggacctaga gtacagcttg cctgtagacg 21600
tcagctatgg ctgacattga ctatggctct acactggccc agcctggaca ctggataaac 21660
aactctcttg gttggttttc acagatcagc cactcttgat ctggttttca tgtgggacac 21720
aaagctgtga ctgcgtgagg ggttaaagtg accaagagca gagggcacag taagtatgtc 21780
ccagccccag ttggcatgca gtacttgggt ccctcagaaa tcgccggtta tctgttttga 21840
actatgtggc aggacctggt tcccggtgct gtctgcatga aaggtggagg attagcaggt 21900
ggcatcagag gacacccccct cccagggctt catttctagg caagtgtagc tttcctctta 21960
ggtgaaagat gctgttcttc agggccccct agtgccaagc tggtgaaaac agcaggcttt 22020
taaaatgtct ccagtagtgt gccgcactac ctgctttcct gcattgctgt aggatcacag 22080
aattcaagaa aggacatgat agtgtgtcag tgtgggcacc agcaccctag cctctcccca 22140
ctgcacccct gcccccacca aaaaagagaa aacctccccc ctcagctttt cttcagggac 22200
tcagtacacc tggcttagtt tttttctctc ctacctccta cttcaagccc ttacttgatc 22260
atctgaagca aaaaccagaa ccagggaaac tagaggagga gtcagggagc tgctgctcct 22320
attcctggag tggttcacct ctcccctgcc cagtggatgg tccagaccca aggaaggagt 22380
gaattgaaag ctaaggaggg gctcag 22406

<210> SEQ ID NO 10
<211> LENGTH: 1748
<212> TYPE: DNA
<213> ORGANISM: Homo sapiens

<400> SEQUENCE: 10
ggactgaatt gactgtacca agaagcatct tctgggggaa catgagtggg ttgaagggga 60
gtatgcttaa ttttttccac tttgggattg tagaccagat tatagaggtt atgtatggaa 120
aacccaaaat atattcctag gggaaagaga tgaaaactaa tacacttatt aagtactatc 180
tatgaaatca tatttaaatt tctcagtaac cgttgaaata agtattgtca tcctttacca 240
tagacaagga aactaaggct aaaagcaggc acgtgatatc cctaagttca tacaataagt 300
tggacaggtg gactttaacc cattttggct tagtccaaag cctgtttact tgatattaca 360
caatgctact ttactgtttt gaaagaagac cacatggaac ctgatgattg ataccccctga 420 actgttagct ggccttaaat ttttgtaata aaatgaatag atgtatacat agtactttat 480
ggcccaggtg agcattttta ctcgacaaca cttagctgtc attggctatt ggtgtttggt 540
ttttggacat ggaataatga ttgattagtc ctccacaagc accttgaacc catcaccttc 600
actggaaaca tagttcttac ttaacagcat gttttataca aagttctaag gaaagtaatt 660
tttagatttg gcttggagtc tatgagtttc atggatgaag tttaatctct ttactggcat 720
gtctattttt tatgtcctag gtacttttaa attcaataca gatgctgctg aattcattcc 780
tcaggagaaa aaaaattctg gtctaaattg tgggactcaa aggagactag actctaatag 840
gattggtaga agaaattaca gttcaccacc tccctgtcac ctttccaggc aggtccctta 900
tgatgaaatc tctgctgttc atcagcatag ttatcatccg tcaggaagca aacctaagag 960
tcagcagacg tctttccagt cctctccttg taataaatcg cccaagagcc atggccttca 1020
gaatcaacct tggcagaaat tgaggaatga gaagcaccat atcagagtca agaaagcaca 1080
gagtcttgct gagcagacct cagatacagc tggattagag agctcgacca gatcagagag 1140
tgggacagac ctcagagagc atagtccttc tgagagtgag aaggaagttg tgggtgcaga 1200
tcccagggga gcaaaaccca aaaaagcaac acagtttgta tacagctatg gtagaggacc 1260
aaaagtcaag gggaaactca aatgtgaatg gagtaaccga acaactccaa aaccggagga 1320
tgctggaccc gaaagtacca aacctgtggg ggttttccac cctgactctt cagaggcatc 1380
ctctagaaaa ggagtattgg atgggtatgg agccagacga aatgagcaga gaagataccc 1440
acagaaaagg cctccctggg aagtggaggg ggccaggcca cgaccaggca gaaatccacc 1500
aaaacaggag ggccaccgac atacaaacgc aggacacaga aacaacatgg gccccattcc 1560
aaaggatgac ctcaatgaaa gaccagcaaa atctacctgt gacagtgaga acttggcagt 1620
catcaacaag tcttccagga gggttgacca agagaaatgc actgtacgga ggcaggatcc 1680
tcaagtagta tctcctttct cccgaggcaa acagaaccat gtgctaaaga atgtggaaac 1740
gcacacag 1748

<210> SEQ ID NO 11
<211> LENGTH: 1832
<212> TYPE: DNA
<213> ORGANISM: Homo sapiens

<400> SEQUENCE: 11
taggttgtga cagttggaag tgtcatgtac aacatgcggc gattaagtct ttcacccacc 60
ttttcaatgg gatttcatct gttagttact gtgagtctct tattttccca tgtggaccat 120
gtaattgctg agacagaaat ggaaggagaa ggaaatgaaa ctggtgaatg tactggatca 180
tattactgta agaaaggggt gattttgccc atttgggaac cccaagaccc ttcttttggg 240
gacaaaattg ctagagctac tgtgtatttt gtggccatgg tctacatgtt tcttggagtc 300
tctatcatag ctgatcggtt catgtcctct atagaagtca tcacatctca agaaaaagaa 360
ataaccataa agaaacccaa tggagagacc accaagacaa ctgtgaggat ctggaatgaa 420
acagtttcta acctgacctt gatggccctg ggatcttctg ctcctgagat tctcctttca 480
gtaattgaag tgtgtggcca taacttcact gcaggagacc tcggtcctag caccatcgtg 540
ggaagtgctg cattcaatat gttcatcatt attgcactct gtgtttatgt ggtgcctgac 600
ggagagacaa ggaagattaa gcatttgcgt gtcttctttg tgacagcagc ctggagcatc 660
tttgcctaca cctggcttta cattattttg tctgtcatat ctcctggtgt tgtggaggtc 720
tgggaaggtt tgcttacttt cttcttcttt cccatctgtg ttgtgttcgc ttgggtagcg 780
gataggagac ttctgtttta caagtatgtc tacaagaggt atcgagctgg caagcagagg 840
gggatgatta ttgaacatga aggagacagg ccatcttcta agactgaaat tgaaatggac 900
gggaaagtgg tcaattctca tgttgaaaat ttcttagatg gtgctctggt tctggaggtg 960
gatgagaggg accaagatga tgaagaagct aggcgagaaa tggctaggat tctgaaggaa 1020
cttaagcaga agcatccaga taaagaaata gagcaattaa tagaattagc taactaccaa 1080
gtcctaagtc agcagcaaaa aagtagagca ttttatcgca ttcaagctac tcgcctcatg 1140
actggagctg gcaacatttt aaagaggcat gcagctgacc aagcaaggaa ggctgtcagc 1200
atgcacgagg tcaacactga agtgactgaa aatgaccctg ttagtaagat cttctttgaa 1260
caagggacat atcagtgtct ggagaactgt ggtactgtgg cccttaccat tatccgcaga 1320
ggtggtgatt tgactaacac tgtgtttgtt gacttcagaa cagaggatgg cacagcaaat 1380
gctgggtctg attatgaatt tactgaagga actgtggtgt ttaagcctgg tgatacccag 1440
aaggaaatca gagtgggtat catagatgat gatatctttg aggaggatga aaatttcctt 1500
gtgcatctca gcaatgtcaa agtatcttct gaagcttcag aagatggcat actggaagcc 1560
aatcatgttt ctacacttgc ttgcctcgga tctccctcca ctgccactgt aactattttt 1620
gatgatgacc acgcaggcat tttttacttt gaggaacctg tgactcatgt gagtgagagc 1680
attggcatca tggaggtgaa agtattgaga acatctggag ctcgaggaaa tgttatcgtt 1740
ccatataaaa ccatcgaagg gactgccaga ggtggagggg aggattttga ggacacttgt 1800
ggagagctcg aattccagaa tgatgaaatt gt 1832

<210> SEQ ID NO 12
<211> LENGTH: 874
<212> TYPE: DNA
<213> ORGANISM: Homo sapiens

<400> SEQUENCE: 12
caatgatgtt gtccactggg catgtactga ccaatgtggc aggtctgaga acatagctga 60
agctgaaaat aggaaagctg ggggcaagga agagccttga atcttgaggt gggacgttga 120
ctctaagatg tccttgagca gtggagcctc cggagggaaa ggagtggatg caaacccggt 180
tgagacatac gacagtgggg atgaatggga cattggagta gggaatctca tcattgacct 240
ggacgccgat ctggaaaagg accagcagaa actggaaatg tcaggctcaa aggaggtggg 300
gataccggct cccaatgctg tggccacact accagacaac atcaagtttg tgaccccagt 360
gccaggtcct caagggaagg aaggcaaatc aaaatccaaa aggagtaaga gtggcaaaga 420
cactagcaaa cccactccag ggacttccct gttcactcca agtgaggggg cagctagcaa 480
gaaagaggtg caggggcgct caggagatgg tgccaatgct ggaggcctgg ttgctgctat 540
tgctcccaag ggctcagaga aggcggctaa ggcatcccgc agtgtagccg gttccaaaaa 600
ggagaaggag aacagctcat ctaagagcaa gaaggagaga agcgaaggag tggggacttg 660
ttcagaaaag gatcctgggg tcctccagcc agttcccttg ggaggacggg gtggtcagta 720
tgatggaagt gcaggggtgg atacaggagc tgtggagcca cttgggagta tagctattga 780
gcctggggca gcgctcaatc ctttgggaac taaaccggag ccagaggaag gggagaatga 840
gtgtcgcctg ctaaagaaag tcaagtctga aaag 874

<210> SEQ ID NO 13
<211> LENGTH: 18
<212> TYPE: DNA
<213> ORGANISM: Artificial Sequence
<220> FEATURE:
<223> OTHER INFORMATION: primer

<400> SEQUENCE: 13
gctaaagaaa gtcaagtc 18

<210> SEQ ID NO 14
<211> LENGTH: 18
<212> TYPE: DNA
<213> ORGANISM: Artificial Sequence
<220> FEATURE:
<223> OTHER INFORMATION: primer

<400> SEQUENCE: 14
tcaaggacat cttagagt 18

<210> SEQ ID NO 15
<211> LENGTH: 18
<212> TYPE: DNA
<213> ORGANISM: Artificial Sequence
<220> FEATURE:
<223> OTHER INFORMATION: primer

<400> SEQUENCE: 15
gattggcccc agcaagcc 18

<210> SEQ ID NO 16
<211> LENGTH: 21
<212> TYPE: DNA
<213> ORGANISM: Artificial Sequence
<220> FEATURE:
<223> OTHER INFORMATION: primer

<400> SEQUENCE: 16

-continued

```
tgcggagaca actgtagtac g                                          21


<210> SEQ ID NO 17
<211> LENGTH: 21
<212> TYPE: DNA
<213> ORGANISM: Artificial Sequence
<220> FEATURE:
<223> OTHER INFORMATION: primer

<400> SEQUENCE: 17

cagtggacaa catcattgct t                                          21


<210> SEQ ID NO 18
<211> LENGTH: 21
<212> TYPE: DNA
<213> ORGANISM: Artificial Sequence
<220> FEATURE:
<223> OTHER INFORMATION: primer

<400> SEQUENCE: 18

cagtggacaa catcattgct t                                          21


<210> SEQ ID NO 19
<211> LENGTH: 66
<212> TYPE: DNA
<213> ORGANISM: Artificial Sequence
<220> FEATURE:
<223> OTHER INFORMATION: synthetic

<400> SEQUENCE: 19

cctgctaaag aaagtcaagt ctgaaaagca atgatgttgt ccactgggca tgtactgacc 60

aatgtg                                                           66


<210> SEQ ID NO 20
<211> LENGTH: 34
<212> TYPE: DNA
<213> ORGANISM: Artificial Sequence
<220> FEATURE:
<223> OTHER INFORMATION: synthetic

<400> SEQUENCE: 20

aggtgggacg ttgactctaa gatgtccttg agca                            34
```